(12) United States Patent
Hudson et al.

(10) Patent No.: US 9,290,577 B2
(45) Date of Patent: Mar. 22, 2016

(54) IMMUNO-CONJUGATES AND METHODS FOR PRODUCING THEM

(75) Inventors: Peter J. Hudson, Blackburn (AU); Paul R. Sanders, Moonee Ponds (AU); Debra Tamvakis, Camberwell (AU); Fabio Turatti, Docklands (AU); Michael P. Wheatcroft, Southbank (AU); David Leong, Preston (AU)

(73) Assignee: AVIPEP PTY LIMITED, Parkville, Victoria (AU)

( * ) Notice: Subject to any disclaimer, the term of this patent is extended or adjusted under 35 U.S.C. 154(b) by 440 days.

(21) Appl. No.: 13/383,578

(22) PCT Filed: Jul. 2, 2010

(86) PCT No.: PCT/AU2010/000847
§ 371 (c)(1),
(2), (4) Date: Mar. 16, 2012

(87) PCT Pub. No.: WO2011/000054
PCT Pub. Date: Jan. 6, 2011

(65) Prior Publication Data
US 2012/0164068 A1    Jun. 28, 2012

Related U.S. Application Data

(60) Provisional application No. 61/223,353, filed on Jul. 6, 2009, provisional application No. 61/256,703, filed on Oct. 30, 2009.

(30) Foreign Application Priority Data
Jul. 3, 2009  (AU) .................... 2009903127

(51) Int. Cl.
  A61K 51/10   (2006.01)
  C07K 16/30   (2006.01)
  A61K 47/48   (2006.01)
  C07K 16/32   (2006.01)
  A61K 39/00   (2006.01)

(52) U.S. Cl.
  CPC .......... *C07K 16/30* (2013.01); *A61K 47/48676* (2013.01); *A61K 51/10* (2013.01); *A61K 51/1093* (2013.01); *C07K 16/3092* (2013.01); *C07K 16/32* (2013.01); *A61K 2039/505* (2013.01); *C07K 2317/21* (2013.01); *C07K 2317/56* (2013.01); *C07K 2317/565* (2013.01); *C07K 2317/567* (2013.01); *C07K 2317/622* (2013.01); *C07K 2317/624* (2013.01); *C07K 2317/626* (2013.01); *C07K 2319/31* (2013.01)

(58) Field of Classification Search
  CPC .............. A61K 51/1093; A61K 51/10; A61K 2039/505; C07K 2319/31; C07K 2317/56; C07K 2317/565; C07K 2317/567; C07K 2317/624

USPC ............ 424/133.1, 9.1; 435/69.6; 530/387.1, 530/387.3
See application file for complete search history.

(56) References Cited

U.S. PATENT DOCUMENTS

| 2009/0028856 A1 | 1/2009 | Chen |
| 2010/0004429 A1 | 1/2010 | Kai et al. |

FOREIGN PATENT DOCUMENTS

| WO | 03050531 A2 | 6/2003 |
| WO | WO 2004/003019 | * 6/2004 |
| WO | 2006008096 A1 | 1/2006 |
| WO | 2006034488 A2 | 3/2006 |
| WO | WO 2006/116076 | 11/2006 |
| WO | 2008052187 A3 | 7/2008 |
| WO | 2009012256 A1 | 1/2009 |
| WO | 2009012268 A1 | 1/2009 |
| WO | 2009099728 A1 | 8/2009 |
| WO | 2010141902 A2 | 12/2010 |

OTHER PUBLICATIONS

De Pascalis et al. (The Journal of Immunology (2002) 169, 3076-3084).*
Vajdos et al. ((2002) J. Mol. Biol. 320, 415-428).*
Wu et al. (J. Mol. Biol. (1999) 294, 151-162).*
Dufner (Trends Biotechnol. 24(11):523-29 (2006)).*
Coleman (Research in Immunol. 145:33-36 (1994)).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Webber, K.O. et al. Preparation and Characterization of a Disulfide-Stabilized Fv Fragment of the Anti-TAC Antibody: Comparison with its Single-Chain Analog. Molecular Immunology. 1995, vol. 2 (4), pp. 249-258.
International Search Report issued in International Patent Application No. PCT/AU2010/000847.
Written Opinion issued in International Patent Application No. PCT/AU2010/000847.

(Continued)

*Primary Examiner* — Lynn Bristol
(74) *Attorney, Agent, or Firm* — Perkins Coie LLP

(57) ABSTRACT

The present invention provides an isolated protein comprising an immunoglobulin variable region comprising at least two cysteine residues positioned within framework region 1 such that if at least two of the cysteine residues are not conjugated to another compound a disulphide bond forms between the cysteine residues. Preferably the protein comprises an immunoglobulin heavy chain variable region and an immunoglobulin light chain variable region, wherein at least one of the variable regions comprises the two cysteine residues. The present invention also provides a protein that binds to TAG72. The present invention also provides conjugates of the protein and another compound.

20 Claims, 52 Drawing Sheets

(56) References Cited

OTHER PUBLICATIONS

Saerens et al., "Disulfide Bond Introduction for General Stabilization of Immunoglobulin Heavy-Chain Variable Domains"; Journal of Molecular Biology; Mar. 21, 2008; pp. 478-488; vol. 377, No. 2; Elsevier Ltd.

Junutula et al. "Rapid identification of reactive cysteine residues for site-specific labelling of antibody-Fabs", Journal of Immunological Methods, Available online Jan. 14, 2008; pp. 2-13; Genentech Inc., San Francisco, California.

Sirk et al. "Site-Specific, Thiol-Mediated Conjugation of Fluorescent Probes to Cysteine-Modified Diabodies Targeting CD20 or HER2", Bioconjugate Chem 2008; Published on Web Nov. 18, 2008; pp. 2-9; vol. 19; American Chemical Society.

Voynov et al. "Design and Application of Antibody Cysteine Variants", Published on Web Jan. 21, 2010; BioConjugate Chem 2010; pp. 385-392; vol. 21; American Chemical Society.

* cited by examiner

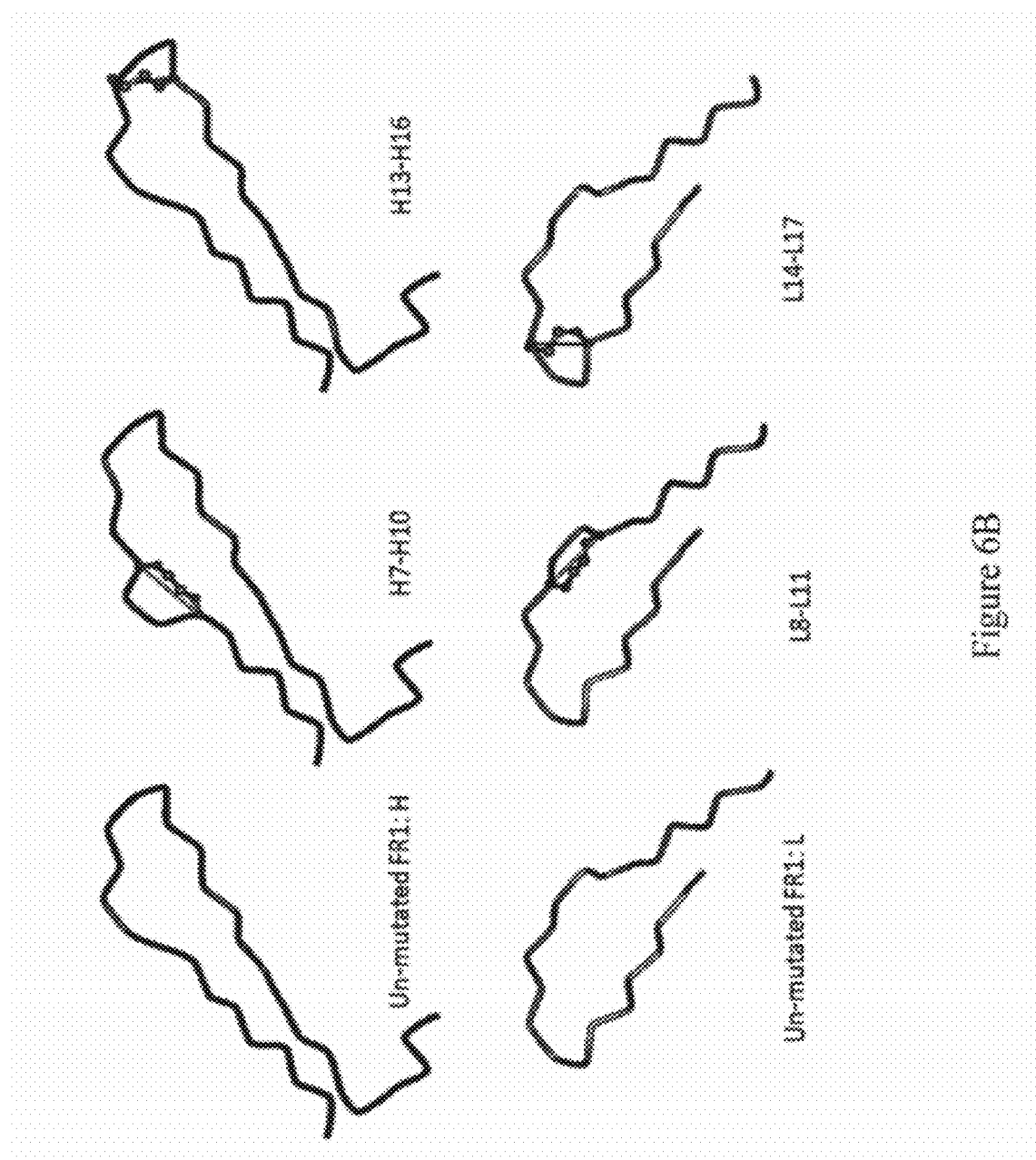

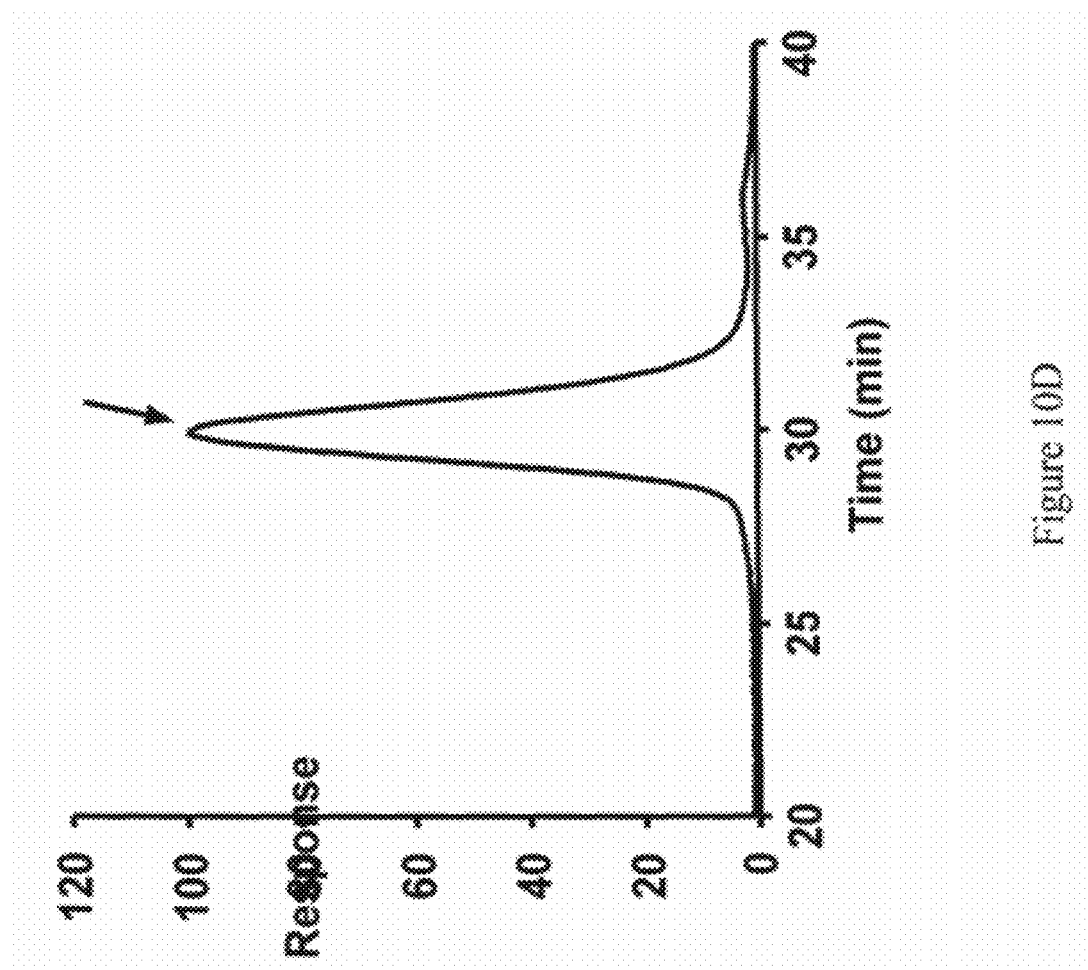

IMMUNO-CONJUGATES AND METHODS FOR PRODUCING THEM

CROSS-REFERENCE TO RELATED APPLICATIONS

This application is a 371 application of PCT/AU2010/00847 which claims priority from Australian Patent Application No. 2009903127 entitled "Immuno-conjugates and methods for producing them" filed on 3 Jul. 2009; U.S. Patent Application No. 61/223,353 entitled "Immuno-conjugates and methods for producing them" filed on 6 Jul. 2009; and U.S. Patent Application No. 61/256,703 entitled "Variable domain molecules and methods of use" filed on 30 Oct. 2009, each of which is herein incorporated by reference in its entirety.

FIELD OF INVENTION

The present invention relates to proteins comprising immunoglobulin variable regions modified to facilitate conjugation of a compound thereto or having a compound conjugated thereto.

BACKGROUND OF THE INVENTION

The highly specific binding nature of immunoglobulins, e.g., antibodies and antibody-like molecules (e.g., camelid immunoglobulin or immunoglobulin new antigen receptors (IgNARs) from cartilaginous fish) or proteins comprising antigen binding domains thereof makes them particularly suitable for delivering molecules to specific targets in a subject. For example, immunoglobulins or proteins comprising antigen binding domains thereof can be conjugated to cytotoxic or cytostatic compounds e.g., drugs, to kill or inhibit growth of cells, such as tumour cells (Lambert, 2005). Such a conjugate facilitates targeted delivery of the cytotoxic or cytostatic compounds to cells expressing the antigen to which the immunoglobulin or fragment binds, rather than non-specifically throughout a subject. Such conjugates can permit use of compounds that are generally toxic to a subject by ensuring the delivery of toxic levels of the compound to the site at which it is required rather than systemically within a subject. Furthermore, conjugation of antibodies or proteins comprising antigen binding domains thereof to detectable compounds, such as fluorophores or radioisotopes facilitates detection of target molecules within a subject, for example to facilitate detection of diseased cells such as cancer cells, e.g., using in vivo, imaging-based methods.

Conventional means of linking a compound to an antibody or a protein comprising antigen binding domain generally leads to a heterogeneous mixture of molecules where the compounds are attached at a number of sites on the antibody. For example, compounds have typically been conjugated to an antibody or protein comprising antigen binding domains thereof through the often-numerous lysine residues in the antibody or antigen binding domain, generating a heterogeneous antibody-compound conjugate mixture. Depending on reaction conditions used, the heterogeneous mixture typically contains a distribution of conjugates with from 0 to about 8, or more, attached compounds. In addition, within each subgroup of conjugates with a particular integer ratio of compounds to antibody or protein there is a potentially heterogeneous mixture where the compound is attached at various sites on the antibody or protein. Analytical and preparative methods are inadequate to separate and characterize the various conjugate species within the heterogeneous mixture resulting from a conjugation reaction.

Furthermore, non-specific conjugation of a compound to an antibody or protein comprising an antigen binding domain thereof may reduce or completely prevent binding of the antibody/protein to an antigen, for example, if the compound is conjugated to a region required for antigen binding. This risk is increased in proteins that comprise antigen binding domains that are far smaller than an intact antibody in which there may be few residues suitable for conjugation that are not important for antigen binding. For example, proteins comprising little more than antigen binding domains of an antibody have few sites to which a compound can be conjugated without reducing or preventing antigen binding.

Carbohydrate(s) on the Fc region of an antibody is a natural site for attaching compounds. Generally, the carbohydrate is modified by periodate oxidation to generate reactive aldehydes, which can then be used to attach reactive amine containing compounds by Schiff base formation. As the aldehydes can react with amine groups, reactions are carried out at low pH so that lysine residues in the antibody or antigen binding domain are protonated and unreactive. Hydrazide groups are most suitable for attachment to the aldehydes generated since they are reactive at low pH to form a hydrazone linkage. The linkage can then be further stabilized by reduction with sodium cyanoborohydride to form a hydrazine linkage (Rodwell et al, 1986). Disadvantages of this approach include the harsh conditions required for linkage which can damage and aggregate some antibody molecules. For example, methionine residues present in some antibody variable regions may be particularly susceptible to oxidation by periodate which can lead to loss of antigen binding avidity. Histidine and/or tryptophan residues are also susceptible to oxidation. Furthermore, many proteins comprising antigen binding domains of an antibody do not necessarily comprise a Fc region, meaning that they cannot be conjugated to a compound using the foregoing process.

Cysteine thiols are reactive at neutral pH, unlike most amines which are protonated and less nucleophilic near pH 7. Since free thiol groups are relatively reactive, proteins with cysteine residues often exist in their oxidized form as disulfide-linked oligomers or have internally bridged disulfide groups. Extracellular proteins generally do not have free thiols (Garman, 1997). Cysteine residues have been introduced into proteins by genetic engineering techniques to form covalent attachments to ligands or to form new intramolecular disulfide bonds. However, inserting or substituting cysteine thiol groups into a protein is potentially problematic, particularly in the case of those which are relatively accessible for reaction or oxidation, i.e., positioned at sites useful for conjugation of a compound. This is because, in concentrated solutions of the protein, whether in the periplasm of *Escherichia coli*, culture supernatants, or partially or completely purified protein, cysteine residues on the surface of the protein can pair and oxidize to form intermolecular disulfides, and hence protein aggregates. Such protein aggregation often leads to poor yields of isolated protein that is in a useful form, e.g., having a desired biological activity. Furthermore, the protein oxidatively can form an intramolecular disulfide bond between the newly engineered cysteine and an existing cysteine residue, which can render the protein inactive or non-specific by misfolding or loss of tertiary structure. Each of the foregoing problems are exacerbated in antibodies and proteins comprising antigen binding domains thereof which generally comprise several cysteine residues that bond with one another to ensure correct folding and stability and, as a consequence antigen binding activity.

It will be clear to the skilled artisan from the foregoing that there is a need in the art for proteins comprising antigen binding domains of immunoglobulins that are modified so as to permit simple conjugation of a compound thereto. Preferred proteins will facilitate recombinant production in a variety of systems, preferably without resulting in considerably levels of multimeric aggregates linked by intermolecular bonds.

SUMMARY OF INVENTION

In work leading up to the present invention, the inventors sought to identify sites within a variable region of an immunoglobulin, e.g., an antibody that permit conjugation of a compound thereto without preventing binding of the variable region to an antigen. As exemplified herein, the inventors have determined that numerous sites within framework region 1 (FR1) of a variable region that are accessible for conjugation, and are sufficiently removed from the antigen binding site of the variable region that a compound conjugated thereto is unlikely to interfere with or prevent antigen binding. These sites are conserved in both heavy chain variable regions ($V_H$) and light chain variable regions ($V_L$). Based on this determination, the inventors produced various proteins comprising mutated variable regions in which two cysteine residues are inserted into FR1. These cysteine residues are positioned such that a disulfide bond can form between them. During recombinant production and/or purification, the cysteine residues are linked by a disulphide bond thereby reducing or preventing those residues bonding with other cysteine residues either within the same protein or in another protein. This reduces the likelihood of production of linked multimers and/or an aberrantly folded variable region, and permits production and/or isolation of functional protein. Following isolation, the cysteine residues are reduced or otherwise broken permitting conjugation of a compound to the protein. The inventors have also demonstrated that conjugation of numerous compounds to these proteins, including bulky compounds such as polyethylene glycol (PEG) and imaging compounds, such as radioisotopes does not prevent binding of the variable region to an antigen.

In one example, the present invention provides an isolated protein comprising an immunoglobulin variable region comprising at least two cysteine residues positioned within framework region (FR)1, wherein if at least one of the cysteine residues is not conjugated to a compound a disulphide bond is capable of forming between the cysteine residues.

In another example, the present invention provides an isolated protein comprising an immunoglobulin variable region comprising at least two cysteine residues positioned within framework region (FR)1, wherein if at least two of the cysteine residues are not conjugated to a compound a disulphide bond is capable of forming between the cysteine residues.

In an alternative or additional example, the present invention provides an isolated protein comprising an immunoglobulin heavy chain variable region ($V_H$) and an immunoglobulin light chain variable region ($V_L$), wherein at least one of the variable regions comprises at least two cysteine residues positioned within framework region (FR)1, wherein if at least one of the cysteine residues is not conjugated to another compound a disulphide bond is capable of forming between the cysteine residues.

In an alternative or additional example, the present invention provides an isolated protein comprising an immunoglobulin heavy chain variable region ($V_H$) and an immunoglobulin light chain variable region ($V_L$), wherein at least one of the variable regions comprises at least two cysteine residues positioned within framework region (FR)1, wherein if at least two of the cysteine residues are not conjugated to another compound a disulphide bond is capable of forming between the cysteine residues.

Preferably, the protein comprises at least one of $V_L$ and at least one of $V_H$ in a single polypeptide chain.

Preferably, the cysteine residues are positioned such that the disulphide bond is present under non-reducing conditions.

Preferably, the cysteine residues are positioned between residue 2 numbered according to the Kabat numbering system and complementary determining region (CDR)1.

In one example, the cysteine residues are positioned within one or more loop regions of FR1.

In an alternative or additional example, the cysteine residues are within the $V_H$ and are positioned between residues 2 to 30 numbered according to the Kabat numbering system. Preferably, the cysteine residues are positioned between residues 7-20 and/or residues 24-30 numbered according to the Kabat numbering system, and more preferably positioned between residues 7-20. In a further example, the residues are positioned between residues 6-16 numbered according to the Kabat numbering system. In a further example, the residues are positioned between residues 7-16 numbered according to the Kabat numbering system.

In an alternative or additional example, the cysteine residues are within the $V_L$ and are positioned between residues 2 to 22 numbered according to the Kabat numbering system. Preferably, the cysteine residues are positioned between residues 7-20 numbered according to the Kabat numbering system. In a further example, the residues are positioned between residues 7-19 numbered according to the Kabat numbering system. In a further example, the residues are positioned between residues 7-17 numbered according to the Kabat numbering system.

In an exemplified form of the invention the cysteine residues are additional to a conserved cysteine residue in the $V_H$ and/or $V_L$. The skilled artisan will be aware that the conserved cysteine residue is at residue 23 in the $V_L$ and/or residue 22 in the $V_H$ numbered according to the Kabat numbering system in at least a majority of naturally occurring antibodies.

In one preferred form of the invention the cysteine residues are positioned N-terminal to the conserved cysteine residue. Preferably, the cysteine residues are positioned at one or more of the following:
 (i) residue 8 and residue 11 of a κ $V_L$ numbered according to the Kabat numbering system;
 (ii) residue 14 and residue 17 of a κ $V_L$ numbered according to the Kabat numbering system;
 (iii) residue 7 and residue 11 of a λ $V_L$ numbered according to the Kabat numbering system;
 (iv) residue 14 and residue 17 of a λ $V_L$ numbered according to the Kabat numbering system;
 (v) residue 8 and residue 12 of a λ $V_L$ numbered according to the Kabat numbering system;
 (vi) residue 7 and residue 10 of a $V_H$ numbered according to the Kabat numbering system; and/or
 (vii) residue 13 and residue 16 of a $V_H$ numbered according to the Kabat numbering system.

In another preferred example of the invention, the cysteine residues are positioned at one or more of the following:
 (i) residue 13 and residue 19 of a κ $V_L$ numbered according to the Kabat numbering system;
 (ii) residue 13 and residue 19 of a λ $V_L$ numbered according to the Kabat numbering system;
 (iii) residue 6 and residue 9 of a $V_H$ numbered according to the Kabat numbering system; and/or (iv) residue 12 and residue 18 of a $V_H$ numbered according to the Kabat numbering system.

The present invention clearly contemplates modifying additional residues within the variable region or protein comprising same. For example, the present inventors have clearly demonstrated that substituting residues positioned between cysteine residues or even replacing cysteine residues naturally occurring within CDRs does not prevent a protein of the invention binding to an antigen.

The present invention also provides an isolated protein comprising a Fv comprising at least one protein of the invention in which at least one $V_L$ binds to at least one $V_H$ to form an antigen binding site.

One form of the protein comprises the $V_L$ and the $V_H$ which form the antigen binding site being in a single polypeptide chain. For example, the protein is:
(i) a single chain Fv fragment (scFv);
(ii) a dimeric scFv (di-scFv); or
(iii) at least one of (i) and/or (ii) linked to a Fc or a heavy chain constant domain ($C_H$)2 and/or $C_H$3.

Alternatively, the protein comprises the $V_L$ and the $V_H$ which form the antigen binding site being in different polypeptide chains. In one example, each polypeptide chain in the protein comprises a $V_L$ and a $V_H$. Preferably, such a protein is:
(i) a diabody;
(ii) a triabody; or
(iii) a tetrabody.

In another example, the protein of the present invention is an immunoglobulin, preferably an antibody. Exemplary forms of immunoglobulins are described herein and are to be taken to apply *mutatis mutandis* to the present example of the invention.

In some examples of the invention, the protein of the invention comprises the cysteine residues being linked by a disulphide bond. Alternatively, the protein of the invention comprises a compound conjugated to at least one of the cysteine residues, wherein conjugation of the compound does not prevent binding of the protein to an antigen. Exemplary compounds include a compound selected from the group consisting of a radioisotope, a detectable label, a therapeutic compound, a colloid, a toxin, a nucleic acid, a peptide, a protein, a compound that increases the half life of the protein in a subject and mixtures thereof. The skilled artisan will appreciate that the term protein encompasses proteins comprising one or more immunoglobulin variable regions, for example, an antibody or fragment thereof including an Fv containing protein such as is described herein.

In one example, a protein of the invention is conjugated to polyethylene glycol (PEG). For example, the PEG is monodisperse PEG.

In one example, the PEG has a molecular weight no greater than about 4000 Da, for example, a molecular weight no greater than about 2000 Da, such as a molecular weight no greater than about 1,500 Da. In one example, the PEG has a molecular weight no greater than 1,000 Da, such as, no greater than 900 Da, for example, no greater than 800 Da, such as, no greater than 600 Da. In one example, the PEG has a molecular weight from about 550 Da to about 1,000 Da.

In another example, the PEG has no more than about 70 or 75 or 77 ethylene glycol units. For example, the PEG has no more than about 50 ethylene glycol units. Preferably, the PEG has no more than 48 ethylene glycole units. For example, the PEG has no more than about 40 ethylene glycol units. For example, the PEG has no more than about 30 ethylene glycol units. For example, the PEG has no more than about 27 ethylene glycol units. For example, the PEG has no more than about 24 ethylene glycol units. For example, the PEG has no more than about 15 ethylene glycol units. For example, the PEG has no more than about 12 ethylene glycol units. Preferably, the PEG comprises about 12 to 27 ethylene glycol units.

In one example, a protein of the invention comprises at least one polypeptide comprising a sequence at least about 80% or 90% or 95% or 96% or 97% or 98% or 99% or 100% identical to the sequence set forth in SEQ ID NO: 57 and having conjugated to at least one of the cysteine residues in FR1 a short monodispersed PEG. Preferably, the PEG comprises 15 to 30 ethylene glycol units and preferably 24 ethylene glycol units. The protein can comprise one or more and preferably less than 10 or 5 or 4 or 3 or 2 substitutions, preferably conservative amino acid substitutions or deletions or insertions. Exemplary changes to the recited sequence include deleting the N-terminal serine or substituting the serine for another amino acid residue (preferably a conservative amino acid substitution) and/or deleting or substituting the C terminal lysine and/or arginine.

The inventors have also modified proteins comprising variable regions to include a serine or threonine residue at the N-terminus. This residue permits site-specific conjugation of a compound thereto. By combining the N-terminal serine/threonine mutation with the cysteine mutations discussed above, the inventors have produced proteins to which they can site-specifically conjugate at least two different compounds.

Accordingly, an example of the invention provides a protein of the invention additionally comprises at least one N-terminal threonine or serine residue. The serine or threonine residue may be added to the N-terminus of the protein (i.e., is additional to the sequence of the protein). Preferably, the serine or threonine residue replaces a naturally occurring amino acid residue at the N-terminus of the protein, i.e., is the result of a substitutional mutation. Optionally, the threonine or serine residue is linked to a compound such as a compound described above.

In one example, a protein of the invention comprises a first compound conjugated to at least one of the cysteine residues and a second compound conjugated to the threonine or serine residue, wherein the second compound is different to the first compound.

The present invention contemplates a protein that can bind specifically to any antigen. Preferred proteins of the invention bind specifically to an antigen selected from the group consisting of human epidermal growth factor (Her)2, tumour associated glycoprotein Tag72, MUC1 or prostate specific membrane antigen (PSMA). Other proteins bind to a plurality of antigens, e.g. the previously listed antigens, by virtue of cross-reactivity or the protein being multi-specific.

Examples of proteins of the invention comprise a sequence 80% or 90% or 95% or 96% or 97% or 98% or 99% or 100% identical to the sequence set forth in any one of SEQ ID NOs: 55, 59, 61, 109, 115 or 117, modified to include the two or more positioned within FR1. Suitable sites for modification are described herein and are to be taken to apply *mutatis mutandis* to this example of the invention. For example, the protein comprises a sequence at least about 80% or 90% or 95% or 96% or 97% or 98% or 99% or 100% identical to the sequence set forth in set forth in any one of SEQ ID NOs: 57, 63, 65, 75, 77, 79, 81, 83, 85, 87, 89, 91, 93, 95, 97, 99, 101, 103 or 105, 119, 121, 123, 125, 127, 129, 131 or 133, provided that the protein comprises the cysteine residues in FR1.

As discussed above, the inventors have also produced proteins comprising a N-terminal threonine or serine residue. This site is also useful for conjugation of a compound, even in the absence of cysteine residues in FR1.

Accordingly, the present invention also provides an isolated protein comprising an immunoglobulin heavy chain variable region ($V_H$) and an immunoglobulin light chain variable region ($V_L$), wherein at least one of the variable regions comprises a N-terminal threonine residue or serine residue. The serine or threonine residue may be added to the N-terminus of the protein. Preferably, the serine or threonine residue replaces a naturally occurring amino acid residue at the N-terminus of the protein, i.e., is the result of a substitutional mutation.

Preferred proteins comprise a Fv comprising at least one protein of the invention comprising a N-terminal threonine or serine residue, wherein at least one $V_L$ binds to at least one $V_H$ to form an antigen binding site.

In one example, the $V_L$ and the $V_H$ which form the antigen binding site are in a single polypeptide chain. For example, the protein is:
(i) a single chain Fv fragment (scFv);
(ii) a dimeric scFv (di-scFv); or
(iii) at least one of (i) and/or (ii) linked to a Fc or a heavy chain constant domain ($C_H$)2 and/or $C_H$3.

Alternatively, the $V_L$ and the $V_H$ which form the antigen binding site are in different polypeptide chains. In one example, each polypeptide chain in the protein comprises a $V_L$ and a $V_H$. Preferably, such a protein is:
(i) a diabody;
(ii) a triabody; or
(iii) a tetrabody.

In another example, the protein of the present invention is an immunoglobulin, preferably an antibody. Exemplary forms of immunoglobulins are described herein and are to be taken to apply *mutatis mutandis* to the present example of the invention.

In one example, the protein additionally comprises a compound conjugated to the threonine or serine residue. Exemplary compounds are described herein and are to be taken to apply *mutatis mutandis* to the present example of the invention.

In one example, a protein comprises a sequence at least about 80% or 90% or 95% or 96% or 97% or 98% or 99% or 100% identical to the sequence set forth in any one of SEQ ID NOs: 55, 59, 61, 109, 115 or 117, modified to include the N-terminal threonine or serine residue. For example, the protein comprises a sequence at least about 80% or 90% or 95% or 96% or 97% or 98% or 99% or 100% identical to the sequence set forth in any one of SEQ ID NOs: 57, 63, 65, 75, 77, 79, 81, 83, 85, 87, 89, 91, 93, 95, 97, 99, 101, 103, 105, 119, 121, 123, 125, 127, 129, 131 or 133, provided that the protein comprises a N-terminal threonine or serine residue.

The present invention also provides the present invention additionally provides a protein comprising a modified immunoglobulin variable region comprising at least two cysteine residues positioned within framework region (FR) 1 and/or a N-terminal threonine or serine residue, and wherein the unmodified form of the variable region does not comprise at least one of the cysteine residues (preferably at least two of or all of the cysteine residues) and/or the threonine or serine residue. Suitable sites for positioning the cysteine residues and/or threonine or serine residue are described herein and are to be taken to apply *mutatis mutandis* to the present example of invention.

In one example, a protein of the invention is human, humanized, deimmunized or chimeric.

The present invention also provides a composition comprising a protein of the invention and a pharmaceutically acceptable carrier.

The present invention also encompasses an isolated nucleic acid encoding a protein of the invention. Exemplary nucleic acids include those having a sequence at least about 80% or 90% or 95% or 96% or 97% or 98% or 99% or 100% identical to the sequence set forth in any one or more of SEQ ID NOs: 54, 58, 60, 108, 114 or 116 altered to include codons encoding at least two cysteine residues in FR1 of the encoded protein and/or to include a N-terminal serine or threonine residue. In one example, a nucleic acid of the invention comprises a sequence at least about 80% or 90% or 95% or 96% or 97% or 98% or 99% or 100% identical to the sequence set forth in any one or more of SEQ ID NOs: 56, 62, 64, 74, 76, 78, 80, 82, 84, 86, 88, 90, 92, 94, 96, 98, 100, 102, 104, 118, 120, 122, 124, 126, 128, 130, 132, provided that the sequence encodes a protein comprising at least two cysteine residues in FR1 and/or a N-terminal serine or threonine residue. The skilled artisan will be aware that due to the degeneracy of codon usage, numerous nucleotide sequences can encode a protein of the invention. All such nucleotide sequences are encompassed by the present invention. For example, a codon optimized nucleic acid can be produced to facilitate expression in a specific cell type or organism.

A nucleic acid of the invention can be operably linked to a promoter to thereby produce an expression construct. Such an expression construct or the nucleic acid is preferably included in a vector, preferably a vector replicable in a cell, e.g., a plasmid or phagemid or cosmid or artificial chromosome.

The present invention also provides an isolated cell comprising an exogenous nucleic acid or expression construct of the invention, preferably wherein the cell expresses a protein of the invention. Exemplary cells include, but are not limited to, bacterial cells, yeast cells, mammalian cells or insect cells.

The nucleic acids and/or expression constructs and/or cells provided by the invention also provide a basis for methods for producing proteins of the invention. Accordingly, the present invention also provides a method for producing a protein of the invention, the method comprising maintaining an expression construct of the invention under conditions sufficient for the encoded protein to be produced. For example, the method comprises culturing a cell of the invention under conditions sufficient the encoded for the protein to be produced. In one example, the method additionally comprises isolating the protein. The method can additionally comprise testing the protein, e.g., for binding activity or affinity. The method can additionally comprise formulating the protein into a pharmaceutical composition.

The present invention also provides a method for producing a conjugate comprising a protein of the invention, the method comprising:
(i) obtaining a protein of the invention comprising at least two cysteine residues positioned within framework region (FR) 1; and
(ii) conjugating a compound to at least one of the cysteine residues to thereby produce the conjugate.

In one example, the cysteine residues in the protein obtained at (i) are linked by a disulphide bond and the method additionally comprises reducing or otherwise breaking the disulphide bond prior to linking the compound to the cysteine residue(s). Preferably, reducing or otherwise breaking the disulphide bond generates a free thiol group in the protein and the compound has a thiol reactive group. By reacting the compound with the thiol reactive group, the conjugate is produced.

In one example, the compound is conjugated to the protein using a maleimide. For example, the protein is contacted with a compound comprising a maleimide functional group such that conjugation occurs.

In a further example of the invention, the protein additionally comprises at least one N-terminal serine or threonine residue and the method additionally comprises conjugating a compound to the serine or threonine residue. Preferably, the compound conjugated to the serine or threonine residue is different to the compound conjugated to the cysteine residue(s).

The present invention provides an alternative method for producing a conjugate comprising a protein of the invention, the method comprising:
(i) obtaining a protein of the invention comprising a N-terminal threonine or serine residue; and
(ii) conjugating a compound to at least one serine or threonine residue at the N-terminus of the protein to thereby produce the conjugate.

Optionally, a method of the invention for producing a conjugate additionally comprises isolating the conjugate and/or formulating the conjugate into a pharmaceutical composition.

It will be apparent to the skilled artisan based on the foregoing that the inventors have produced reagents that are useful in a variety of applications, including, delivery of a toxic compound or a radioisotope to a diseased cell, tissue or organ (e.g., a cancer) and/or in vivo imaging and/or for increasing the stability of a protein.

Accordingly, the present invention also provides for use of a protein or a composition of the invention in medicine. For example, the present invention provides for use of a protein of the invention in the manufacture of a medicament for treating or preventing a condition. The present invention also provides a method of treating or preventing a condition in a subject, the method comprising administering a protein or composition of the invention to a subject in need thereof. Exemplary conditions are described herein and are to be taken to apply *mutatis mutandis* to the present example of the invention. Furthermore exemplary conjugated forms of a protein of the invention are described herein and shall be taken to apply *mutatis mutandis* to the present example of the invention.

The present invention additionally provides a method for delivering a compound to a cell, the method comprising contacting the cell with a protein of the invention that is conjugated to the compound or a composition comprising same. In one example, the cell is contacted by administering the protein or composition to a subject.

The present invention also provides imaging methods, such as a method for localizing or detecting an antigen in a subject, said method comprising:
(i) administering to a subject a protein of the invention for a time and under conditions sufficient for the protein to bind to the antigen, wherein the protein is conjugated to a detectable label; and
(ii) localizing or detecting the detectable label in vivo.

The skilled artisan will recognize that the foregoing method is useful for localizing or detecting cells, groups of cells such as tumours, tissues and organs or parts thereof expressing the antigen. Exemplary antigens are described throughout this specification and are to be taken to apply *mutatis mutandis* to the present example of the invention.

The present invention also provides a method for diagnosing or prognosing a condition in a subject, the method comprising contacting a sample from the subject with a protein or composition of the invention for a time and under conditions sufficient for the protein to bind to an antigen and form a complex and detecting the complex, wherein detection of the complex is diagnostic or prognostic of the condition. Preferably, the protein is conjugated to a detectable label and detection of the label is indicative of the complex.

In one example, the method comprises determining the level of the complex, wherein an enhanced or reduced level of said complex compared to a control sample is diagnostic or prognostic of the condition.

The present invention additionally provides a library comprising a plurality of proteins of the invention. In one example, the proteins are displayed on the surface of a particle (e.g., a phage or a ribosome) or a cell. Clearly, the present invention also provides a library of nucleic acids encoding said library comprising a plurality of proteins of the invention.

The present invention additionally provides a method for isolating a protein of the invention, the method comprising contacting a library of the invention with an antigen for a time and under conditions sufficient for (or such that) a protein binds to the antigen and isolating the protein.

The present invention additionally provides a method for producing a library comprising a plurality of proteins of the invention, the method comprising:
(i) obtaining or producing nucleic acids encoding a plurality of proteins comprising an immunoglobulin variable region, wherein the variable regions comprising at least two cysteine residues positioned within framework region (FR) 1 and/or a N-terminal threonine or serine residue;
(ii) producing a library of expression constructs comprising the following operably linked nucleic acids:
  a) a promoter;
  b) a nucleic acid obtained or produced at (i); and
  c) a nucleic acid encoding a polypeptide that facilitates display of the variable region containing protein in/on the cells or particles; and
(iii) expressing proteins encoded by the expression constructs such that they are displayed in/on the cells or particles.

Suitable sites for positioning the cysteine residues and/or threonine or serine residue are described herein and are to be taken to apply *mutatis mutandis* to the present example of invention.

In one example, the amino acids in the CDRs of the protein are random or semi-random or are derived from a human antibody.

In one example, the method additionally comprises isolating nucleic acid encoding the protein. Such a nucleic acid can be introduced into an expression construct. Optionally, the protein can be expressed.

The present inventors also produced a protein comprising an immunoglobulin variable region capable of specifically binding to tumour antigen TAG72. The inventors found that this protein is stable in vivo.

Accordingly, the present invention additionally provides an isolated protein comprising a plurality of polypeptides each comprising an immunoglobulin $V_H$ and an immunoglobulin $V_L$ linked by a region comprising an insufficient number of amino acids to permit the $V_H$ and the $V_L$ to associate with one another, wherein:
(i) at least one of the polypeptides comprises a $V_H$ comprising a sequence set forth in SEQ ID NO: 111 or a sequence at least about 60% identical thereto; and
(ii) at least another of the polypeptides comprises a $V_L$ comprising a sequence set forth in SEQ ID NO: 113 or a sequence at least about 60% identical thereto,
wherein the $V_H$ of the polypeptide at (i) and the $V_L$ of the polypeptide at (ii) associate to form a Fv capable of specifically binding to tumour antigen TAG72. In the description herein, this protein is referred to as an anti-TAG72 protein. However, any description herein in relation to a "protein of the invention" equally applies to this protein unless the context indicates otherwise.

In one example, the anti-TAG72 protein comprises a region linking the $V_H$ and the $V_L$ having 6 or fewer amino acids, for example 5 or fewer amino acids, such as 4 or fewer amino acids, e.g., 3 or fewer amino acids, such as 2 or fewer amino acids, for example, 1 or 0 amino acids.

In an example, the anti-TAG72 protein of the invention comprises a $V_L$ comprising a threonine at position 5 numbered according to the Kabat numbering system and/or a threonine at position 53 according to the Kabat numbering system and/or a glutamic acid at position 79 numbered according to the Kabat numbering system.

In an alternative or additional embodiment, the anti-TAG72 protein of the invention comprises a $V_H$ comprising a leucine at position 80 numbered according to the Kabat numbering system.

In one example, an anti-TAG72 protein comprises at least two polypeptides, each comprising:
(i) a $V_H$ comprising a sequence set forth in SEQ ID NO: 111 or a sequence at least about 60% identical thereto; and
(ii) a $V_L$ comprising a sequence set forth in SEQ ID NO: 113 or a sequence at least about 60% identical thereto,
wherein the $V_H$ of one polypeptide and the $V_L$ of another polypeptide associate to form a Fv capable of specifically binding to TAG72.

An exemplary anti-TAG72 protein is a diabody, a triabody or a tetrabody.

In one example of the invention:
(i) at least one of the polypeptides comprises a $V_H$ comprising complementarity determining regions (CDRs) of a $V_H$ comprising a sequence set forth in SEQ ID NO: 111; and
(ii) at least another of the polypeptides comprises a $V_L$ comprising CDRs of a $V_L$ comprising a sequence set forth in SEQ ID NO: 113.

Exemplary CDRs are as follows:
(i) CDRH1 comprises a sequence set forth in amino acids 31 to 35 of SEQ ID NO: 111;
(ii) CDRH2 comprises a sequence set forth in amino acids 50 to 66 of SEQ ID NO: 111;
(iii) CDRH3 comprises a sequence set forth in amino acids 99 to 104 of SEQ ID NO: 111;
(iv) CDRL1 comprises a sequence set forth in amino acids 24 to 40 of SEQ ID NO: 113;
(v) CDRL2 comprises a sequence set forth in amino acids 56 to 62 of SEQ ID NO: 113; and
(vi) CDRL3 comprises a sequence set forth in amino acids 95 to 103 of SEQ ID NO: 113.

In one example, an anti-TAG72 protein of the invention comprises at least two polypeptides both of which comprise:
(i) a $V_H$ comprising a sequence set forth in SEQ ID NO: 111 or a humanized or de-immunized form thereof; and
(ii) a $V_L$ comprising a sequence set forth in SEQ ID NO: 113 or a humanized or de-immunized form thereof.

An example of the invention provides an anti-TAG72 protein comprising at least two polypeptides each comprising a sequence set forth in SEQ ID NO: 55, 115 or 117.

In one example at least one of the polypeptides in the anti-TAG72 protein comprises at least two cysteine residues positioned within framework region (FR) 1 as described herein-above. Exemplary sequences are set out above. For example, the sequence is at least about 80% or 90% or 95% or 96% or 97% or 98% or 99% or 100% identical to the sequence set forth in any one or more of SEQ ID NOs: 57, 63, 75, 77, 99, 103, 119, 121, 123, 125, 127, 129, 131 or 133 and comprises the cysteine residues. Preferably, the sequence is at least about 80% or 90% or 95% or 96% or 97% or 98% or 99% or 100% identical to the sequence set forth in SEQ ID NO: 57 and comprises the cysteine residues.

In one example, the protein comprises a single polypeptide and comprises a sequence at least about 80% or 90% or 95% or 96% or 97% or 98% or 99% or 100% identical to the sequence set forth in SEQ ID NO: 101.

In one example, an anti-TAG72 protein of the invention comprises a compound conjugated thereto. For example, the compound is conjugated to a cysteine residue or a serine residue or a lysine residue in at least one of the polypeptides in the protein.

In one example, at least one of the polypeptides in the anti-TAG72 protein comprises at least two cysteine residues positioned within FR1, wherein if at least two of the cysteine residues is not conjugated to a compound then a disulphide bond is capable of forming between the cysteine residues and/or a N-terminal serine and/or threonine residue, and wherein the compound is conjugated to at least one of the cysteine residues and/or to the serine residue. For example, the polypeptide comprises the cysteine residues and the N-terminal serine and/or threonine residue, and wherein the compound is conjugated to at least one of the cysteine residues and a different compound is conjugated to the serine residue.

An exemplary compound is selected from the group consisting of a radioisotope, a detectable label, a therapeutic compound, a colloid, a toxin, a nucleic acid, a peptide, a protein, a compound that increases the half life of the protein in a subject and mixtures thereof.

The inventors have found that conjugation of polyethylene glycol (PEG) to a protein of the invention substantially increased its stability and tumour uptake. The inventors found that monodisperse PEGs and/or PEG having small molecular weights increased stability and/or tumour uptake to substantially the same degree as higher molecular weight PEGs. This appears counter-intuitive since larger molecules are generally cleared from a subject slower than smaller molecules. Since larger PEGs generally comprise mixtures of molecules of various molecular weights, the use of smaller and/or monodisperse PEGs provides an advantage in so far as it facilitates production of protein conjugates similar at the molecular level. Such conjugates are desirable for in vivo applications.

Accordingly, in one example, an anti-TAG72 protein of the invention is conjugated to polyethylene glycol (PEG). For example, the PEG is monodisperse PEG.

In one example, the PEG has a molecular weight no greater than about 4000 Da, for example, a molecular weight no greater than about 2000 Da, such as a molecular weight no greater than about 1,500 Da. In one example, the PEG has a molecular weight no greater than 1,000 Da, such as, no greater than 900 Da, for example, no greater than 800 Da, such as, no greater than 600 Da. In one example, the PEG has a molecular weight from about 550 Da to about 1,000 Da.

In another example, the PEG has no more than about 70 or 75 or 77 ethylene glycol units. For example, the PEG has no more than about 50 ethylene glycol units. Preferably, the PEG has no more than 48 ethylene glycole units. For example, the PEG has no more than about 40 ethylene glycol units. For example, the PEG has no more than about 30 ethylene glycol units. For example, the PEG has no more than about 27 ethylene glycol units. For example, the PEG has no more than about 24 ethylene glycol units. For example, the PEG has no more than about 15 ethylene glycol units. For example, the PEG has no more than about 12 ethylene glycol units. Preferably, the PEG comprises about 12 to 27 ethylene glycol units.

In one example, the PEG is conjugated to an additional compound, such as a chelating agent, e.g., a macrocyclic chelating agent, such as 1,4,7,10-tetraazacyclododecane-1,4,7,10-tetraacetic acid (DOTA).

The present invention also provides an anti-TAG72 protein of the invention and a pharmaceutically acceptable carrier.

The present invention additionally provides an isolated nucleic acid encoding one or more of the polypeptides in an anti-TAG72 protein of the invention.

The present invention further provides an expression construct comprising a nucleic acid encoding an anti-TAG72 protein of the invention or a polypeptide therefrom.

The present invention additionally provides an isolated cell expressing an anti-TAG72 protein of the invention. For example, the cell comprises a nucleic acid encoding an anti-TAG72 protein of the invention or polypeptide therefrom and/or expression construct comprising same.

The present invention additionally provides a method for producing an anti-TAG72 protein of the invention, the method comprising maintaining an expression construct encoding same such that the encoded polypeptide and for the protein are produced.

In one example, the method comprises culturing the cell under conditions sufficient the encoded for the protein to be produced.

In one example, the method additionally comprises isolating the protein.

The present invention additionally provides a method for producing an anti-TAG72 protein of the invention comprising a compound conjugated to at least one of the cysteine residue, the method comprising:
(i) obtaining an anti-TAG72 protein of the invention comprising cysteine residues in FR1; and
(ii) conjugating a compound to at least one of the cysteine residues in the FR1 of the polypeptide(s) to thereby produce the protein.

In one example, the cysteine residues in the polypeptide(s) in the protein obtained at (i) are linked by a disulphide bond and the method additionally comprises reducing or otherwise breaking the disulphide bond prior to conjugating the compound to the cysteine residue(s). For example, reducing or otherwise breaking the disulphide bond generates a free thiol group in the protein and the compound has a thiol reactive group permitting conjugation of the compound to the protein.

In one example, at least one polypeptide in the protein comprises at least one N-terminal serine or threonine residue and the method additionally comprises conjugating a compound to the serine or threonine residue.

In another example, the present invention provides a method for producing an anti-TAG72 protein of the invention comprising a compound conjugated to a N-terminal serine or threonine residue, the method comprising:
(i) obtaining an anti-TAG72 protein of the invention comprising a N-terminal serine and/or threonine residue; and
(ii) conjugating a compound to at least one serine or threonine residue at the N-terminus of the polypeptide to thereby produce the protein.

In one example, a method for producing a protein conjugated to a compound comprises conjugating the protein to PEG.

The present invention additionally provides a method for localizing and/or detecting and/or diagnosing and/or prognosing a cancer in a subject, said method comprising:
(i) administering to a subject an anti-TAG72 protein of the invention or composition comprising same such that it binds to tumour antigen TAG72, if present; and
(ii) detecting the protein bound to the TAG72 in vivo, wherein detection of the bound protein localizes and/or detects and/or diagnoses and/or prognoses the cancer.

The present invention additionally provides a method of diagnosing or prognosing a cancer in a subject, the method comprising:
(i) contacting a sample from the subject with an anti-TAG72 protein of the invention or a composition comprising same such that it binds to tumour antigen TAG72, if present; and
(ii) detecting the protein bound to the TAG72, wherein detection of the bound protein is diagnostic or prognostic of the cancer.

In one example of either of the previous two examples, the protein is conjugated to a detectable label and the method comprises detecting the label to detect the protein bound to TAG72.

The present invention additionally provides a method of treating a cancer, the method comprising administering an anti-TAG72 protein of the invention or a compositions comprising same such that it binds to tumour antigen TAG72 on cancer cells and treats the cancer.

In one example, the protein or a compound conjugated thereto induces death of the cancer cells.

In one example, the protein is conjugated to a compound induces death of the cancer cells.

BRIEF DESCRIPTION OF THE DRAWINGS

FIG. 6B is a diagrammatic representation showing the in silico homology modeled intra-Framework 1 disulphide insertion mutations in the $V_L$ and $V_H$ of the AVP02-60 diabody (comprising a polypeptide comprising a sequence set forth in SEQ ID NO: 61). Depicted are models of FR1 comprising various mutations as indicated. H=heavy chain. L=light chain. Numbers indicate positions of cysteine residues (if present). Un-mutated FR1 H/Un-mutated FR1 L=AVP02-60, H7-H10=AVP02-104, L8-L11=AVP02-101, H13-H16=AVP02-105, L14-L17=AVP02-102.

FIG. 10D is a graphical representation showing results of post-purification size exclusion chromatography of AVP04-50 (comprising polypeptide comprising a sequence set forth in SEQ ID NO: 57). Arrow indicates elution peak of interest.

MeOH by SDS-PAGE. Lane 1: Benchmark pre-stained molecular weight standard, Lane 2: AVP04-74-PEG$_{24}$ conjugate. Lane 3: AVP04-78-PEG$_{24}$ conjugate.

Figure 14A:
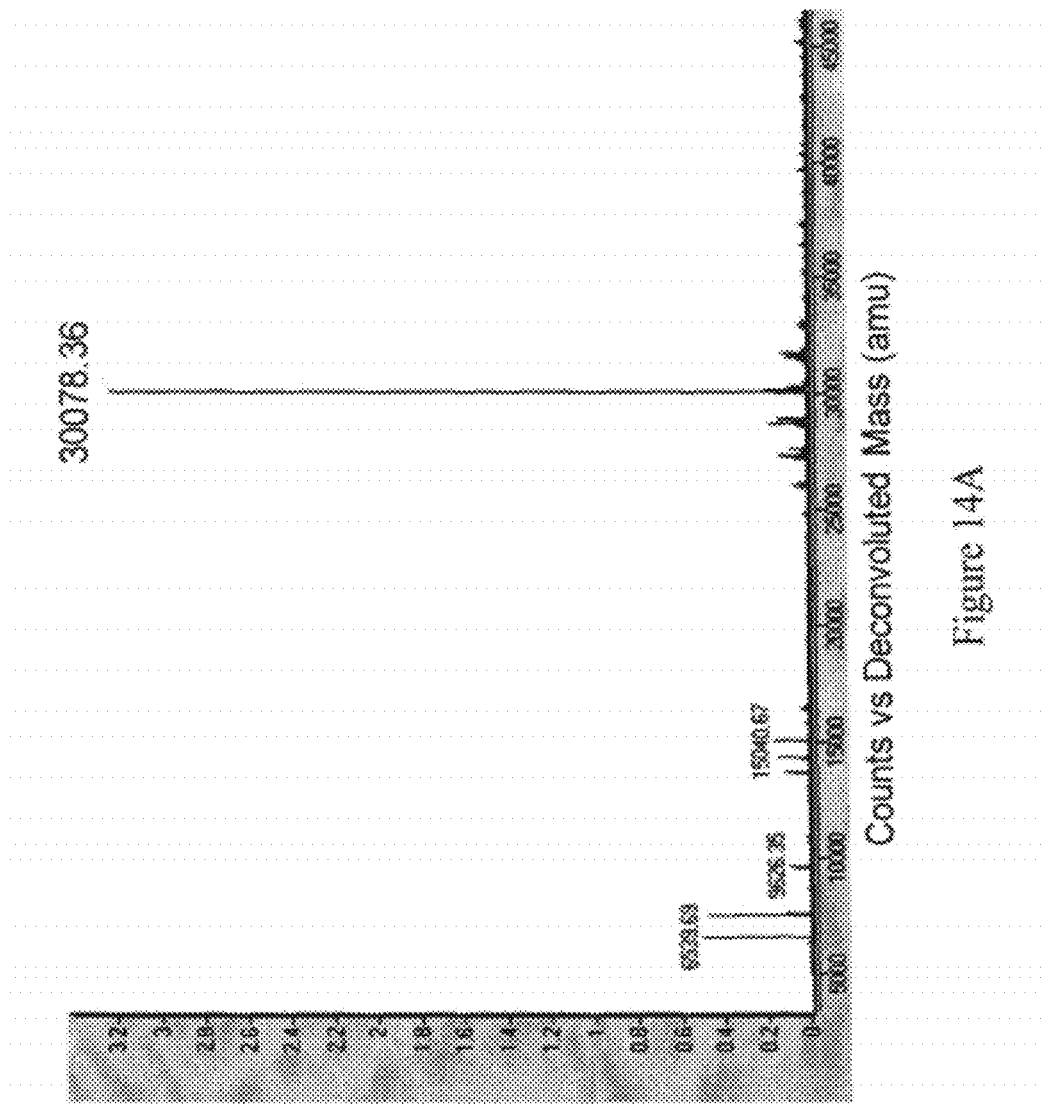

FIG. 14A includes a graphical representation of the atomic mass unit (AMU) of anti-HER2 scFv AVP07-71 (SEQ ID NO: 105) showing a mass proportional to the protein plus the addition of two molecules of PEG$_{24}$ following conjugation (30078.36 amu).

Figure 14B:

FIG. 14B includes a graphical representation of the AMU of anti-TAG72 AVP04-50 (SEQ ID NO: 57) showing a mass proportional to the protein plus the addition of two molecules of PEG$_{24}$ following conjugation (28166.84 amu) per monomer-chain.

Figure 14C:
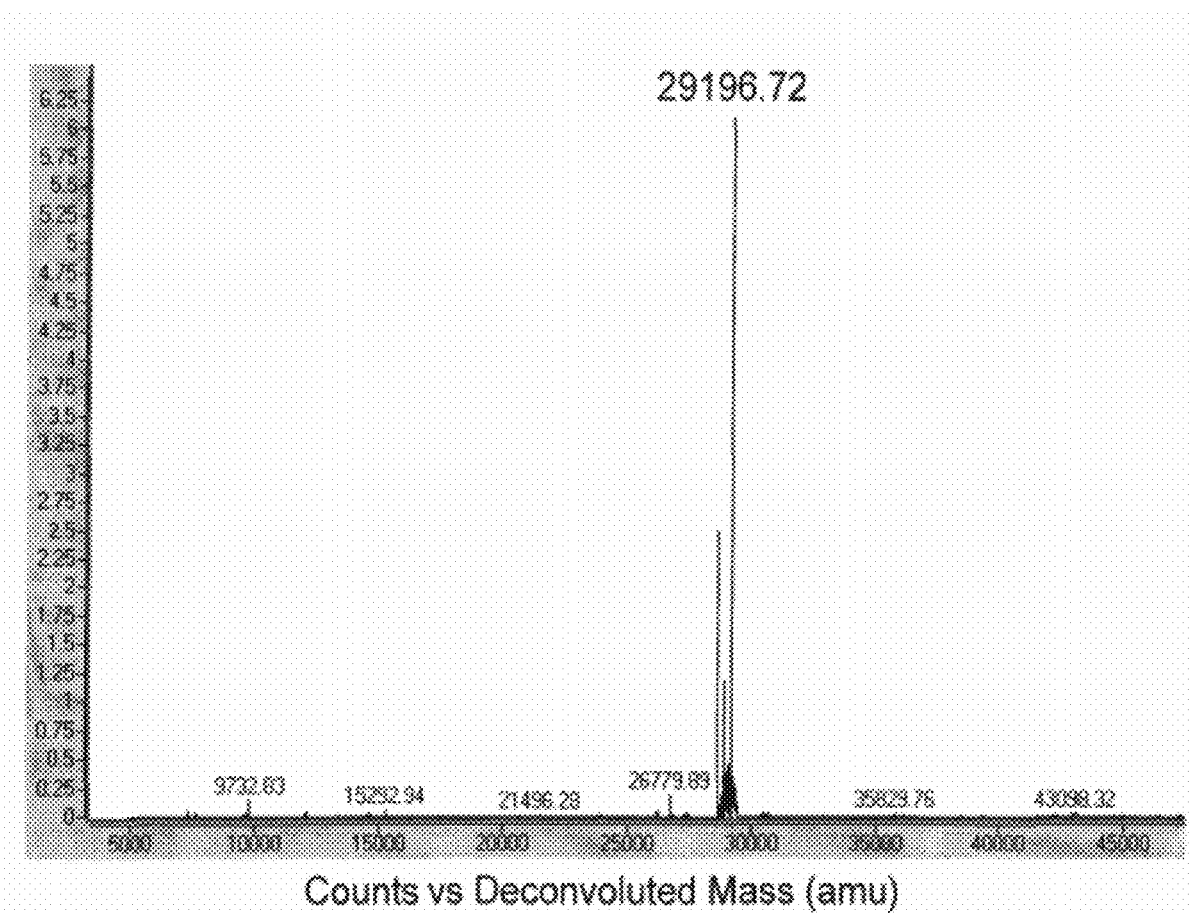

FIG. 14C includes a graphical representation of the AMU of anti-HER2 diabody AVP07-88 (SEQ ID NO: 87) a mass proportional to the protein plus the addition of two molecules of PEG$_{24}$ following conjugation (29196.72 amu) per monomer-chain.

Figure 14D:
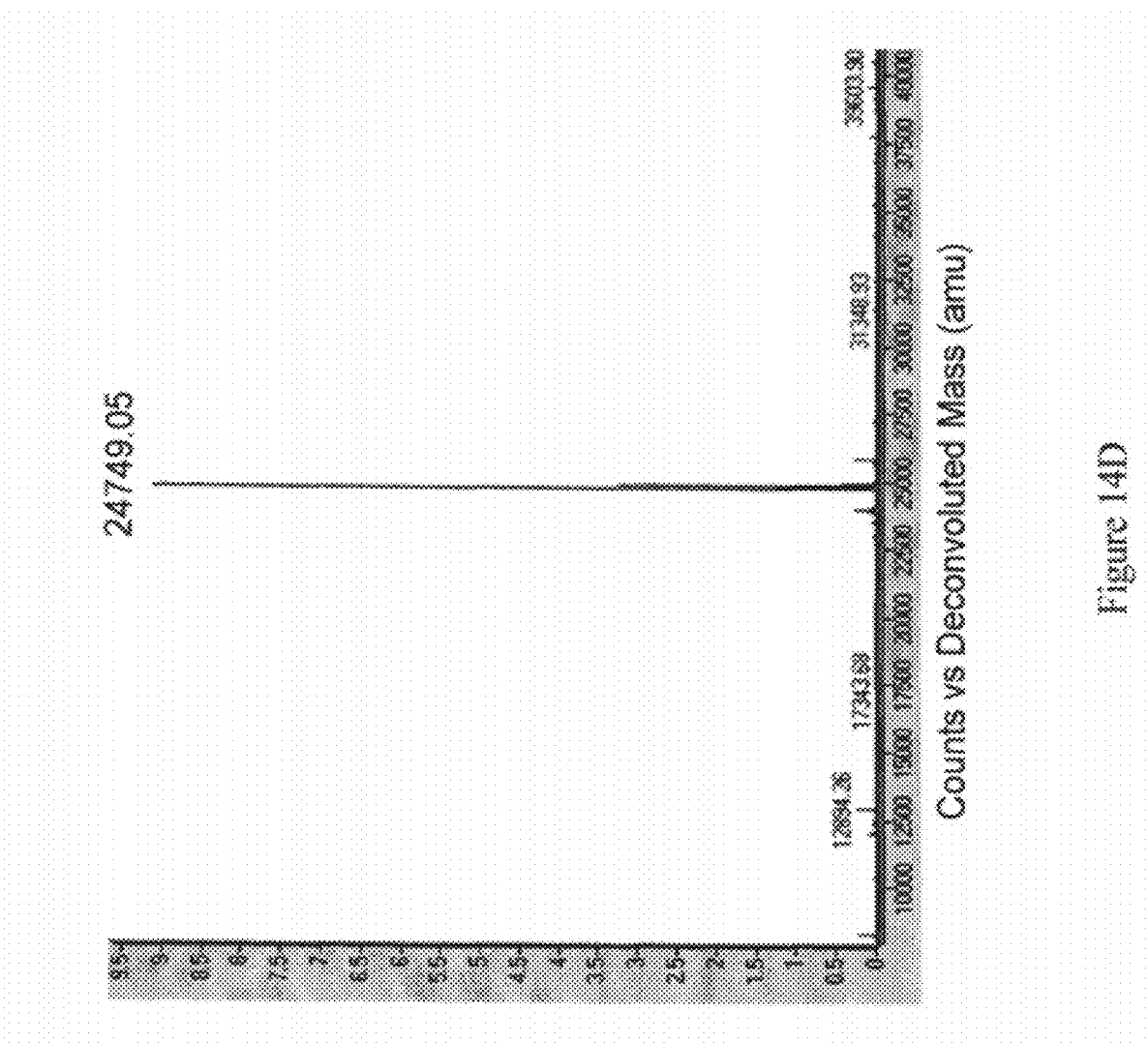

FIG. 14D includes a graphical representation of the AMU of anti-MUC1 diabody AVP02-101 (SEQ ID NO: 79) showing one molecule of PEG$_{24}$ conjugated (24749.05 amu) per monomer-chain.

Figure 15A:
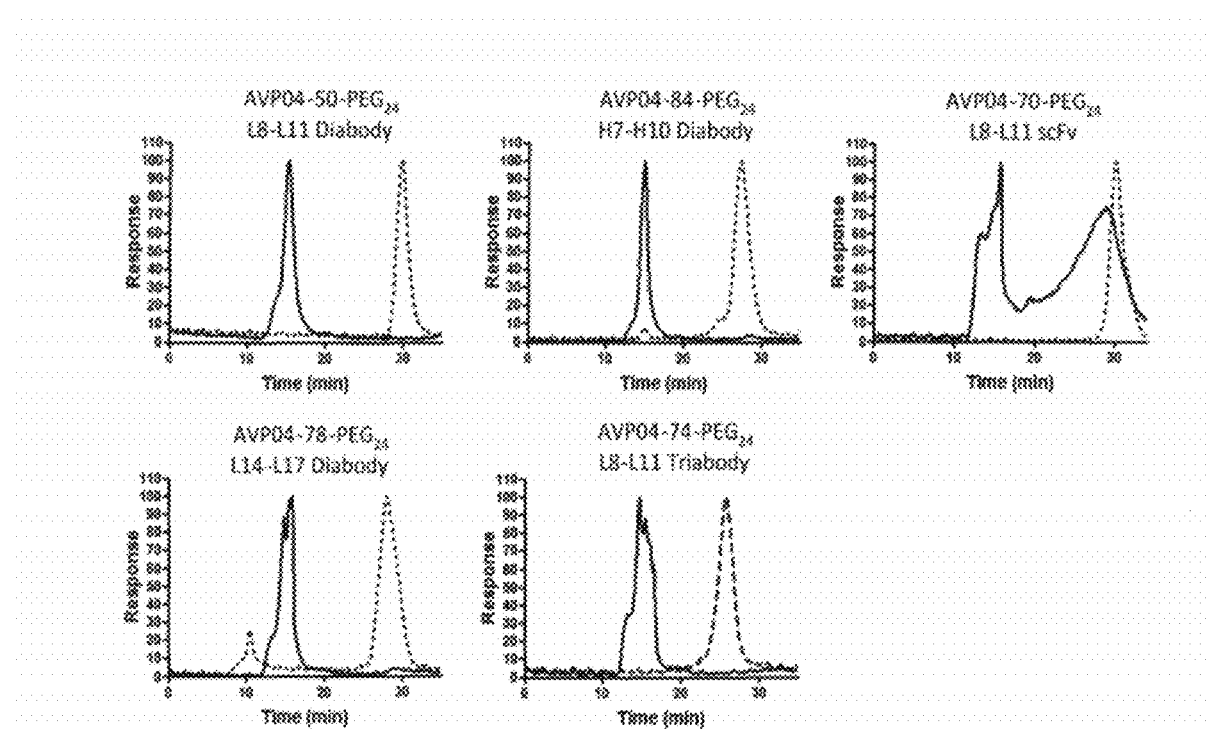
Figure 15B:
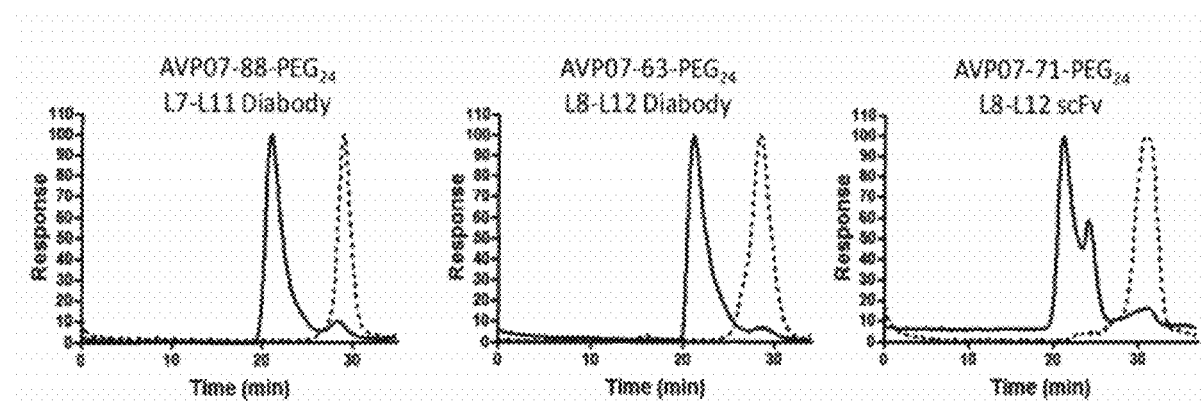
Figure 15C:
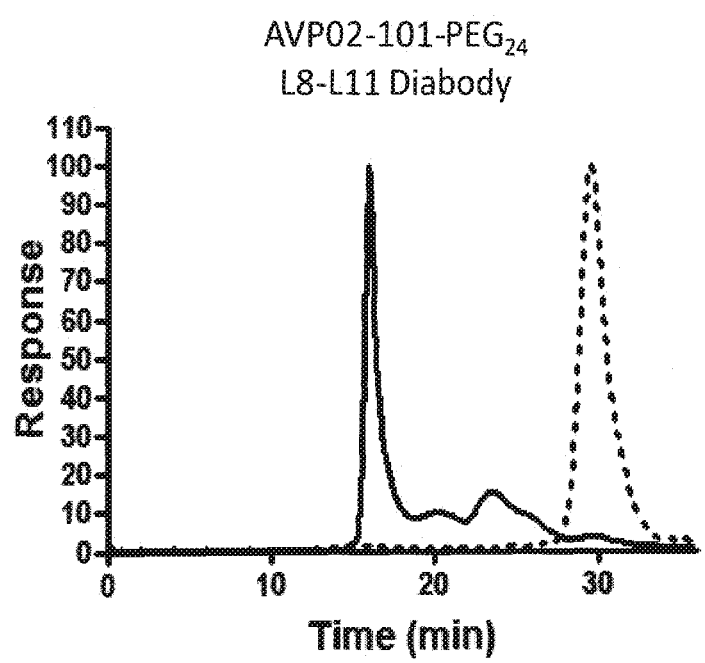

FIGS. 15A-C include graphical representations of a column shift assay used to determine immunoreactivity of PEGylated Avibodies mentioned herein (as indicated, nomenclature corresponds to that used throughout the text and in the sequence listing). Each graph comprises two overlaid size exclusion chromatography profiles; of the Avibody-PEG conjugate either in the presence (solid line) or absence (dotted line) of antigen.

Figure 16:
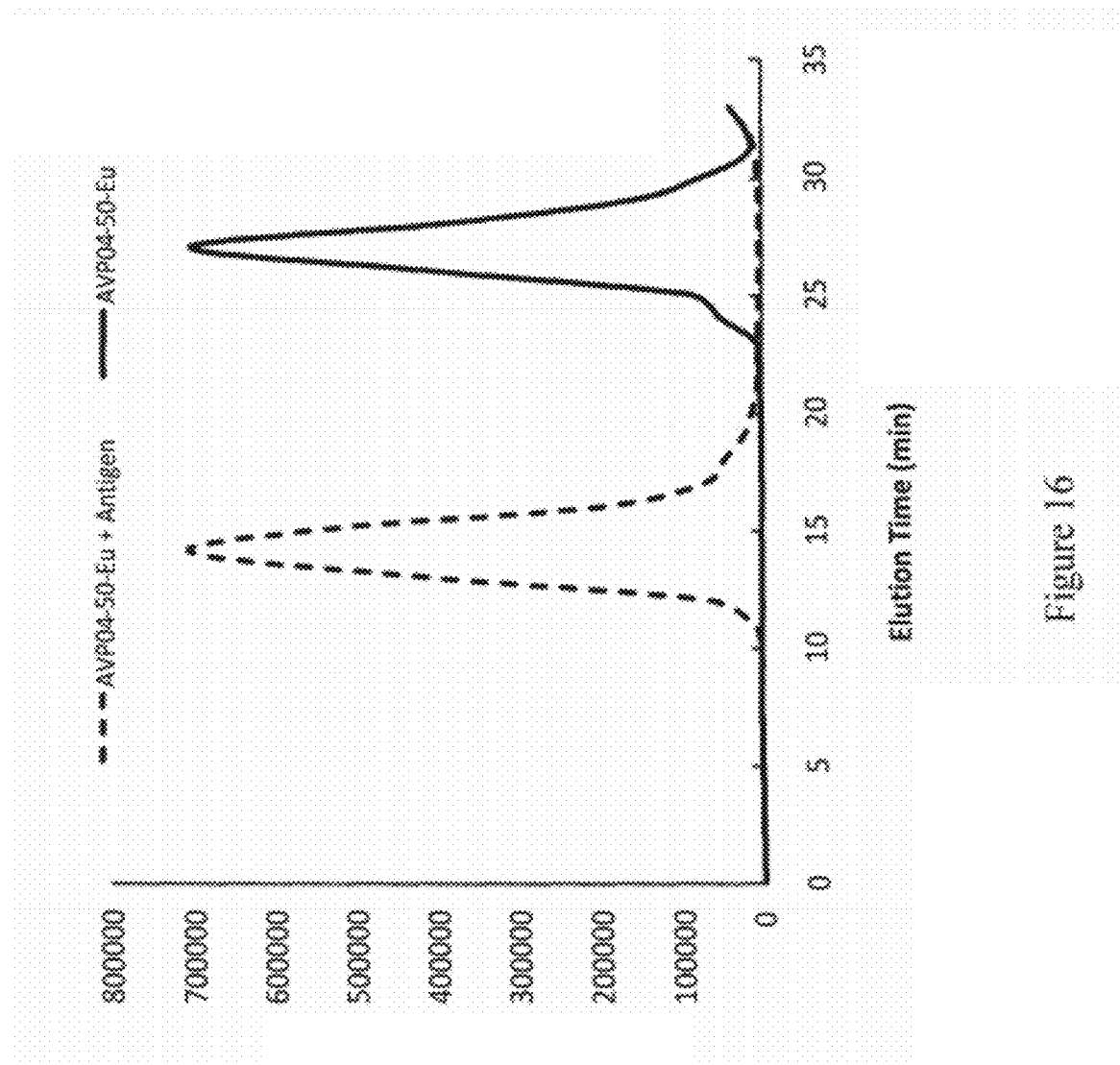

FIG. 16 includes a graphical representation of a column shift assay used to determine immunoreactivity of europium-conjugated AVP04-50 (SEQ ID NO: 57) Avibody. The representation comprises two overlaid size exclusion chromatography profiles; of the Avibody-Europium conjugate either in the presence (dotted line) or absence (solid line) of antigen.

Figure 17:
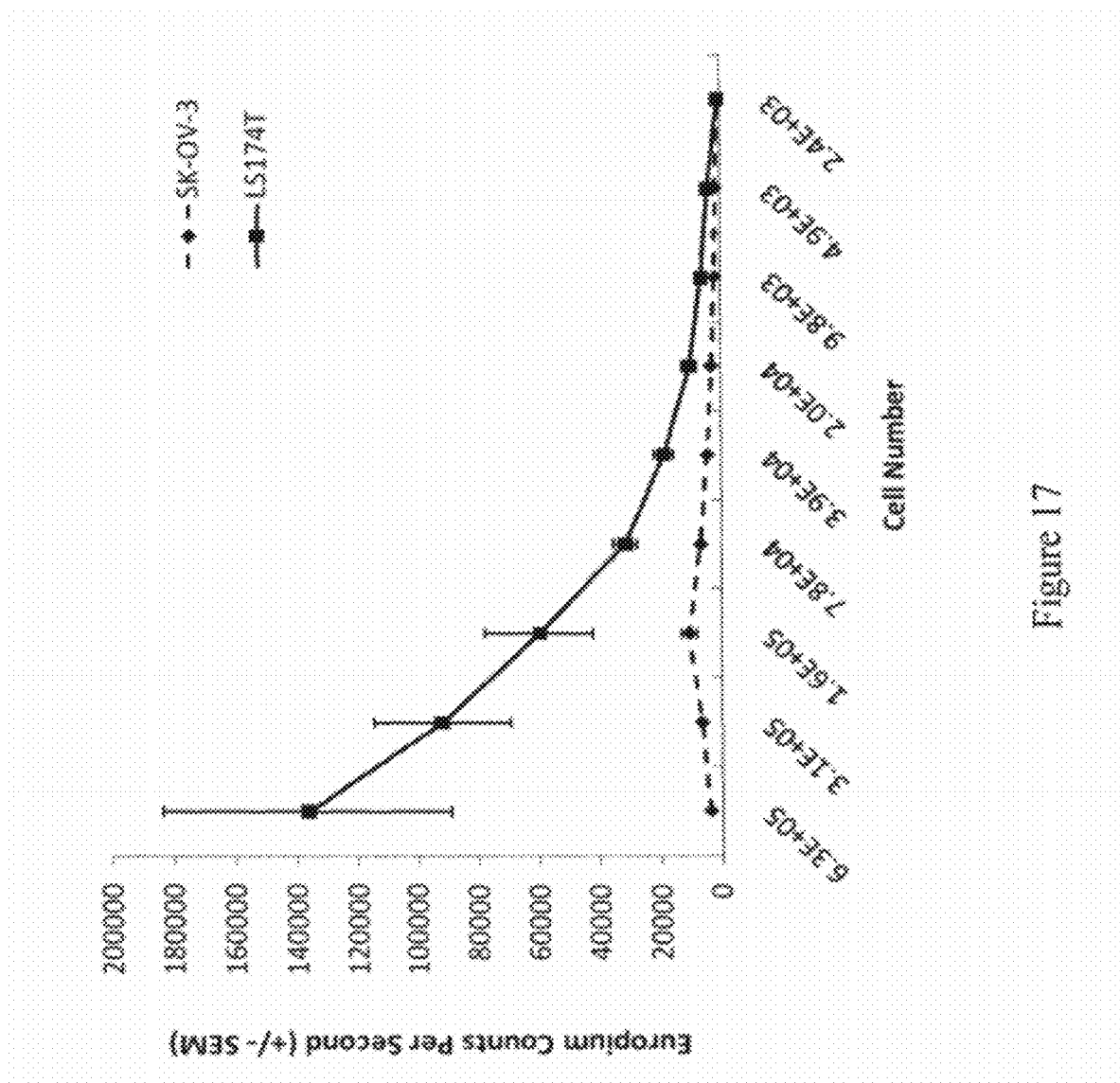

FIG. 17 includes a graphical representation of immunoreactivity of europium-conjugated AVP04-50 (SEQ ID NO: 57) as determined by cell binding assay on antigen positive (LS174T, solid line) and negative (SK-OV-3, dotted line) cell lines.

Figure 18A:
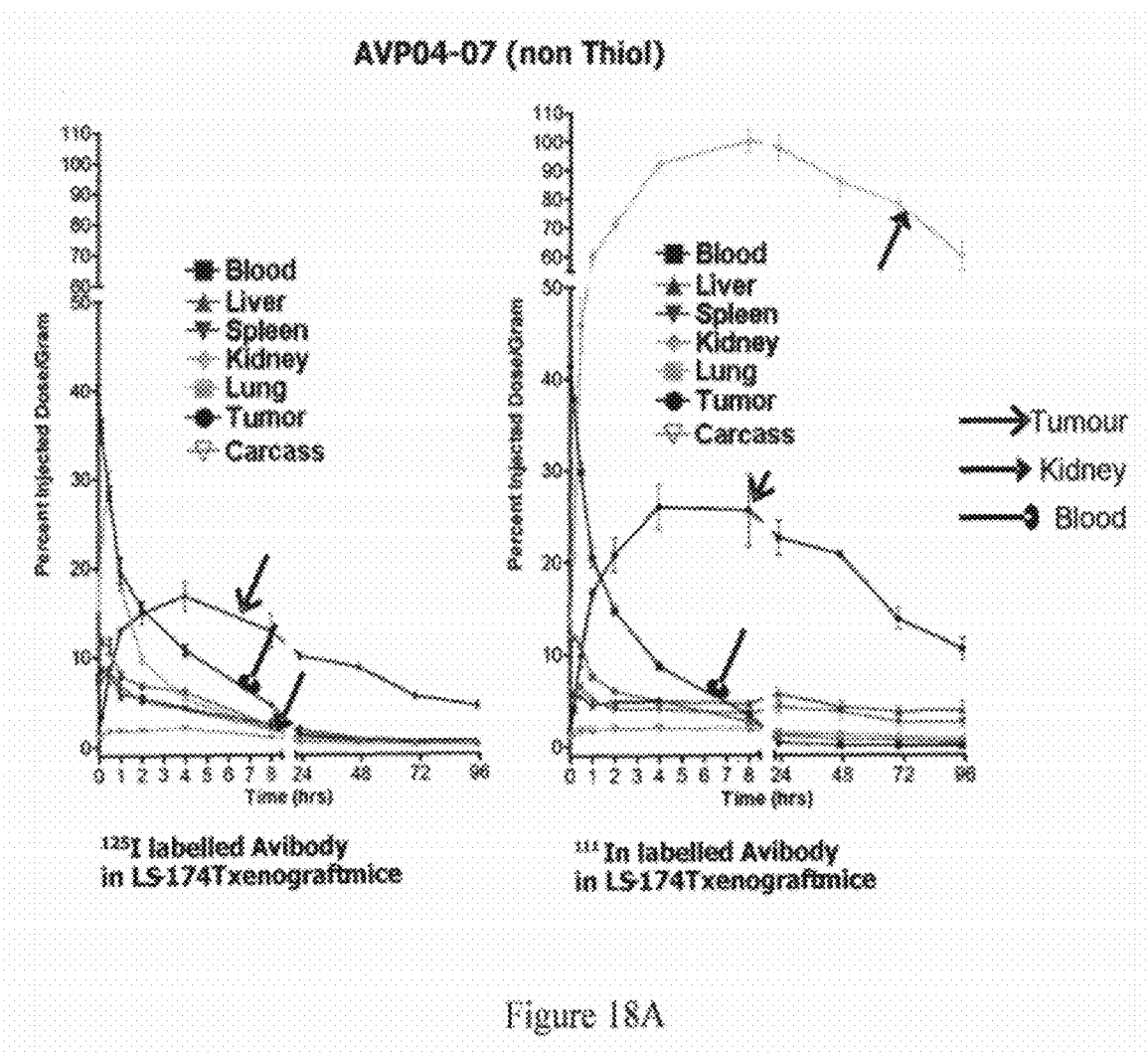

FIG. 18A is a graph showing the biodistribution of $^{125}$I and $^{111}$In-labelled AVP04-07 (comprising polypeptide comprising a sequence set forth in SEQ ID NO: 55) in established LS-174T xenograft mice. Open arrow=Tumour uptake curve, closed arrow=kidney uptake curve, circle arrow=blood clearance curve.

Figure 18B:
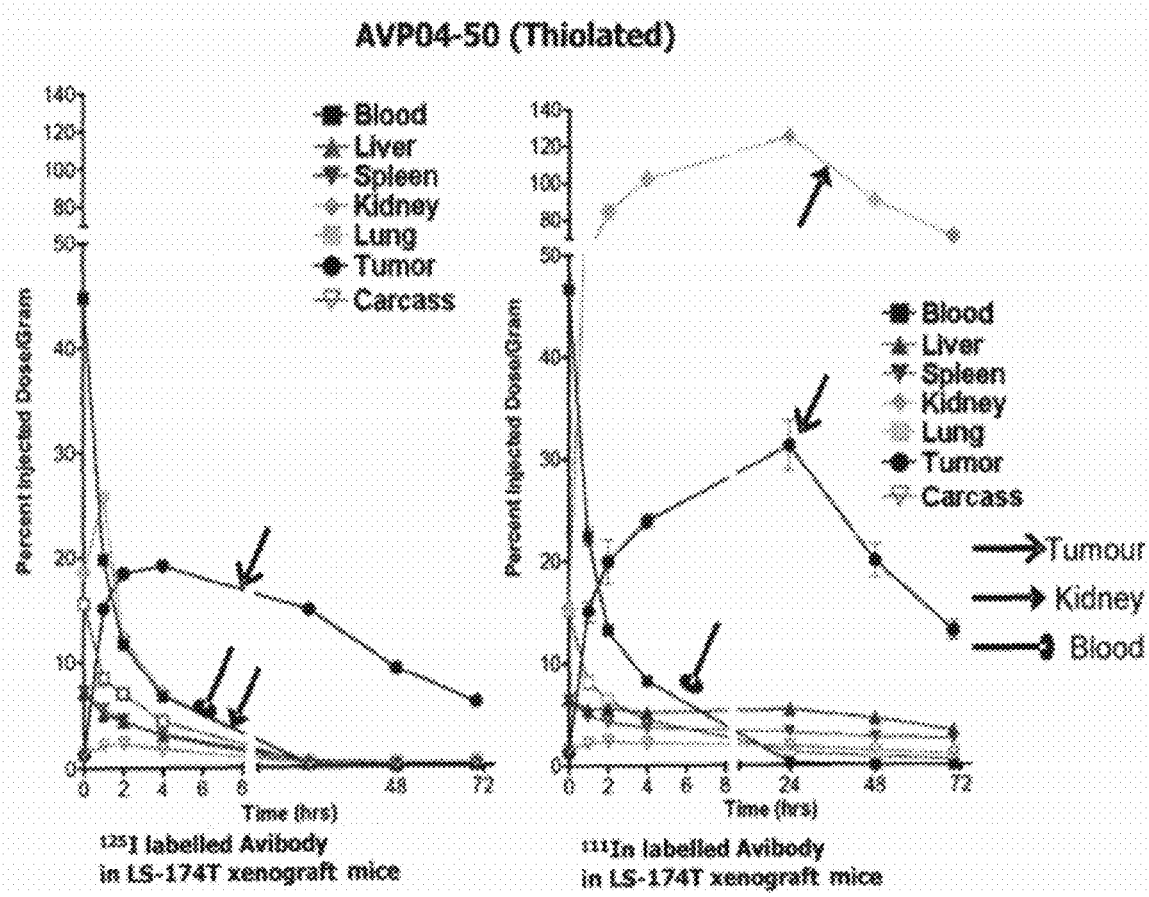

FIG. 18B is a graph showing the biodistribution of $^{125}$I and $^{111}$In labelled AVP04-50 (comprising polypeptide comprising a sequence set forth in SEQ ID NO: 57) in established LS-174T xenograft mice. Open arrow=Tumour uptake curve, closed arrow=kidney uptake curve, circle arrow=blood clearance curve.

Figure 19:
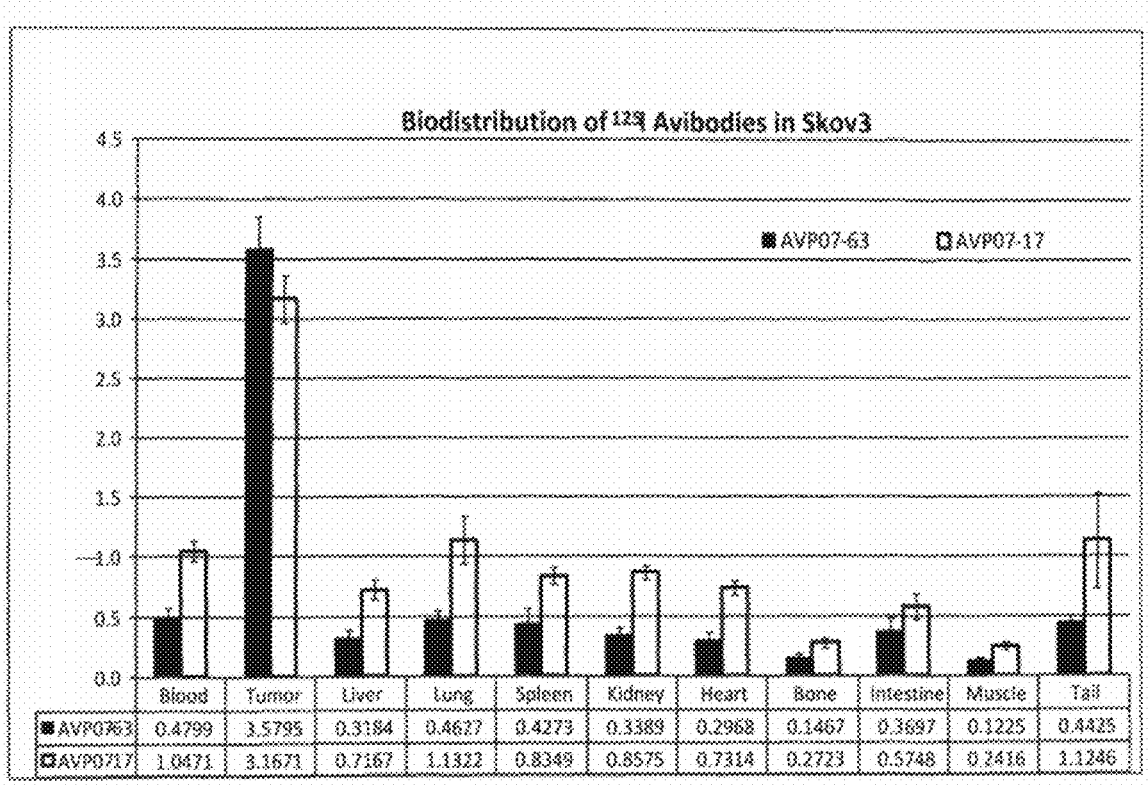

FIG. 19 is a graph showing the biodistribution of $^{125}$I labelled AVP07-17 (comprising polypeptide comprising a sequence set forth in SEQ ID NO: 59) and AVP07-63 (comprising polypeptide comprising a sequence set forth in SEQ ID NO: 65) in established SKOV3 xenograft mice. Dark grey bars=AVP07-63, open bars=AVP07-17.

Figure 20:
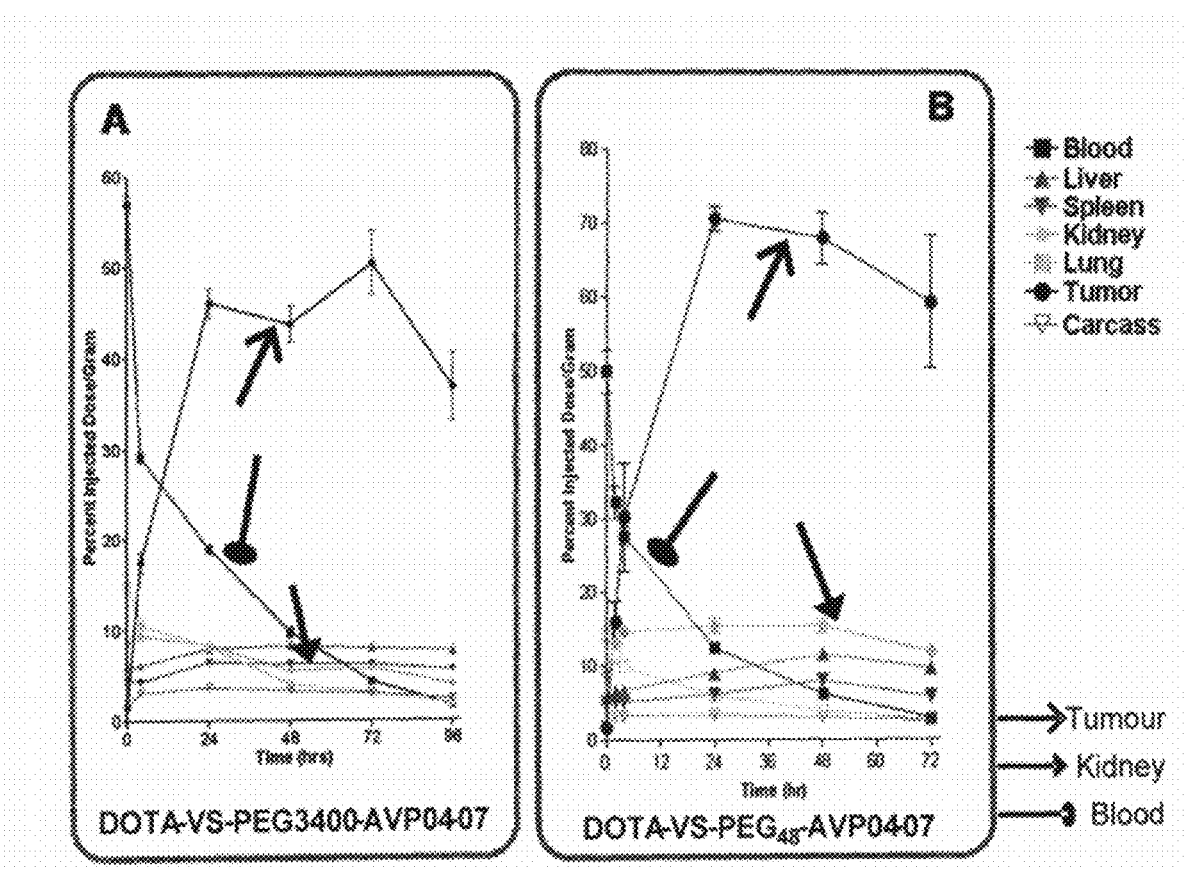

FIG. 20 is a graph showing the biodistribution of Panel A: $^{111}$In-labelled AVP04-07 (comprising polypeptide comprising a sequence set forth in SEQ ID NO: 55) conjugated with PEG3400 to random surface lysines and Panel B: $^{111}$In-labelled AVP04-50 (comprising polypeptide comprising a sequence set forth in SEQ ID NO: 57) conjugated with size-monodispersed PEG$_{48}$ conjugated to engineered intra-Framework 1 disulphide mutations in established LS-174T xenograft mice. Open arrow=Tumour uptake curve, closed arrow=kidney uptake curve, circle arrow=blood clearance curve.

Figure 21A:
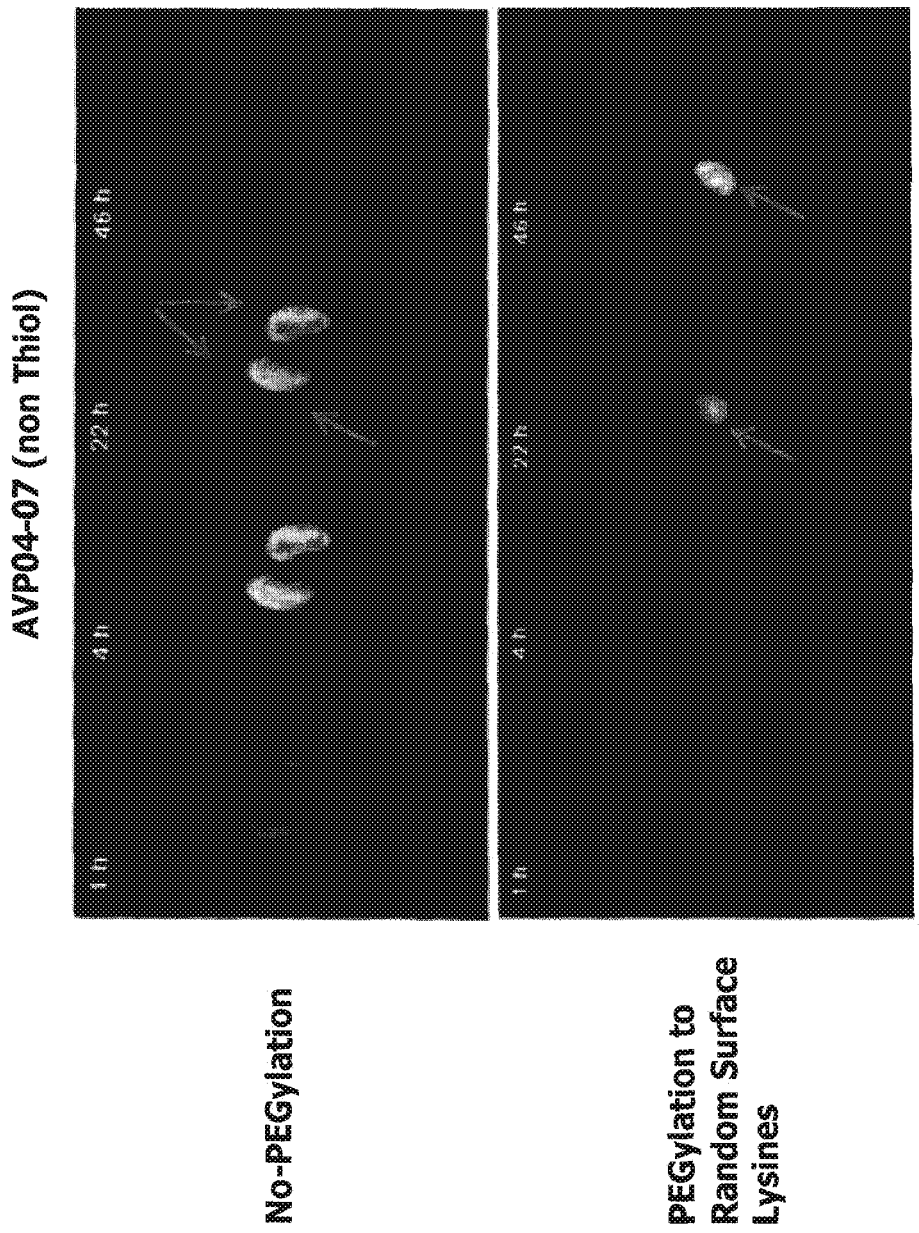

FIGS. 21A and B are graphical representations showing the PET biodistribution of $^{64}$Cu-labelled, unpegylated AVP04-07 (comprising polypeptide comprising a sequence set forth in SEQ ID NO: 55) AVP04-07 conjugated with size-monodispersed PEG$_{27}$ to random surface lysines and AVP04-50 (comprising polypeptide comprising a sequence set forth in SEQ ID NO: 57) conjugated with size-monodispersed PEG$_{48}$ conjugated to engineered intra-Framework 1 disulphide mutations in established LS-174T xenograft mice. Upward facing arrows=location of tumour, Downward facing arrows=location of kidney.

Figure 22A:
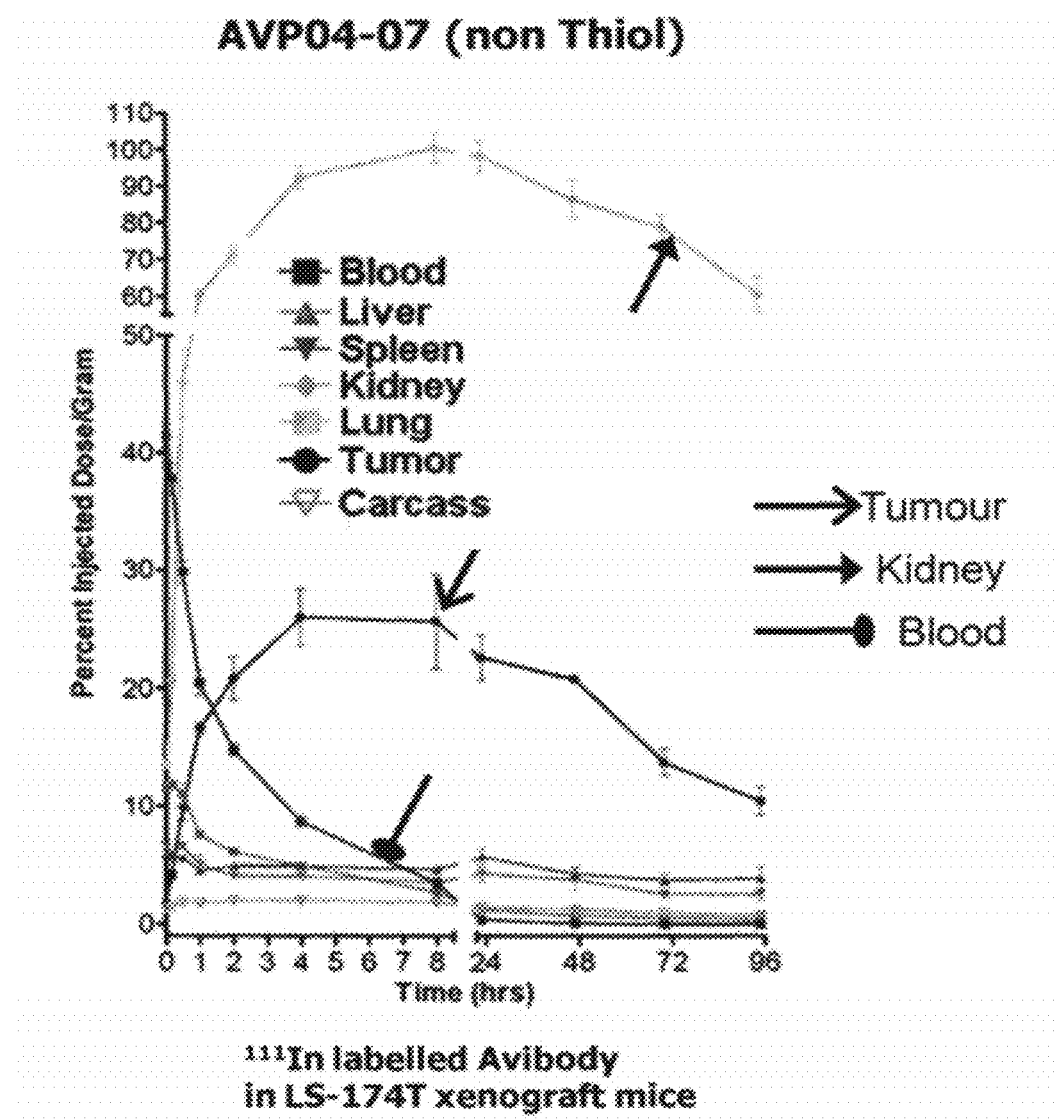

FIG. 22A is a graphical representation showing biodistribution of $^{111}$In-labelled intact AVP04-07 diabody in nude mice bearing LS174T xenografts. Open arrow=Tumour uptake curve, closed arrow=kidney uptake curve, circle arrow=blood clearance curve.

Figure 22B:
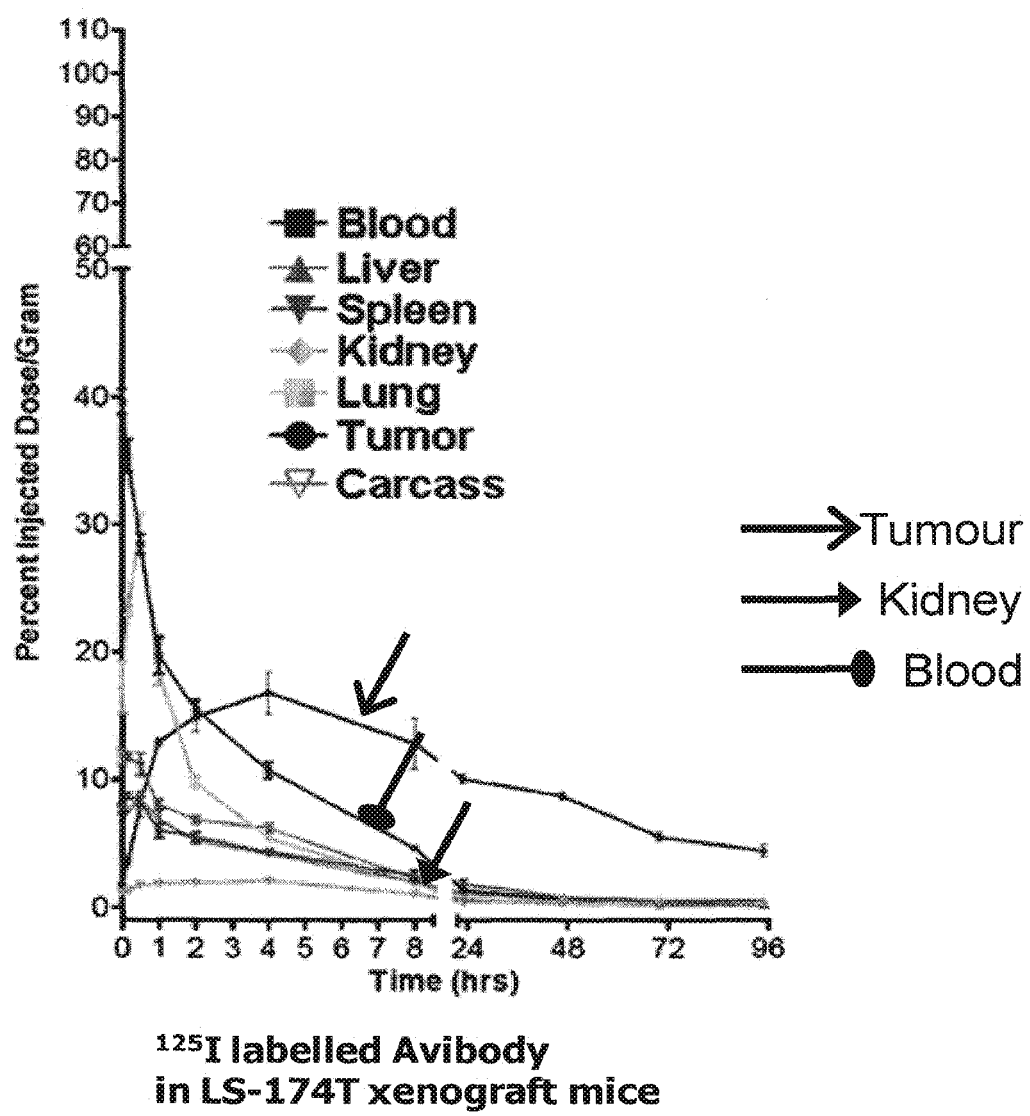

FIG. 22B is a graphical representation showing biodistribution of $^{125}$I-labelled intact AVP04-07 diabody in nude mice bearing LS174T xenografts. Open arrow=Tumour uptake curve, closed arrow=kidney uptake curve, circle arrow=blood clearance curve.

Figure 22C:
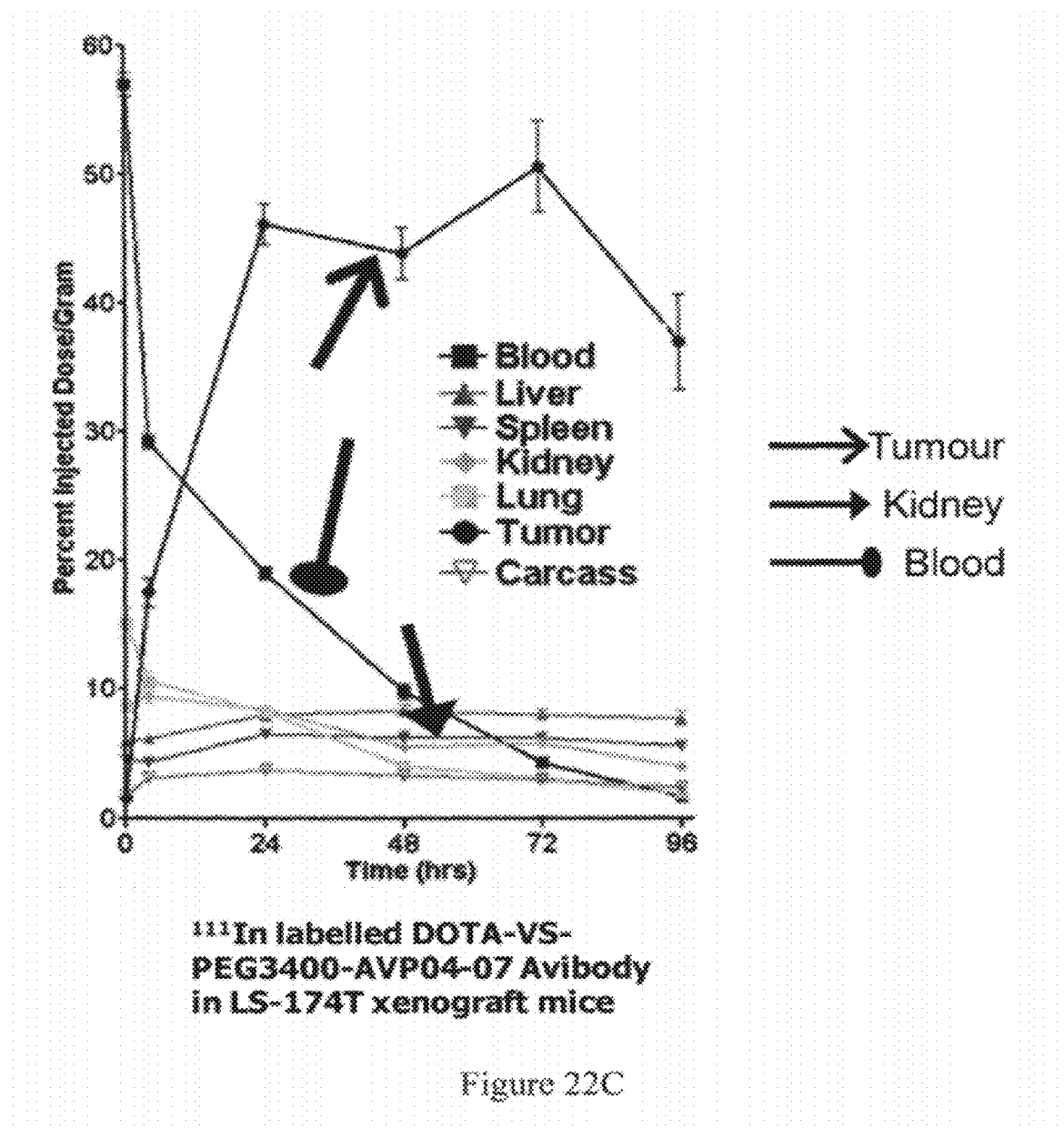

FIG. 22C is a graphical representation showing biodistribution of $^{111}$In-labelled AVP04-07 diabody conjugated to PEG3400 in nude mice bearing LS174T xenografts. Open arrow=Tumour uptake curve, closed arrow=kidney uptake curve, circle arrow=blood clearance curve.

Figure 23A:
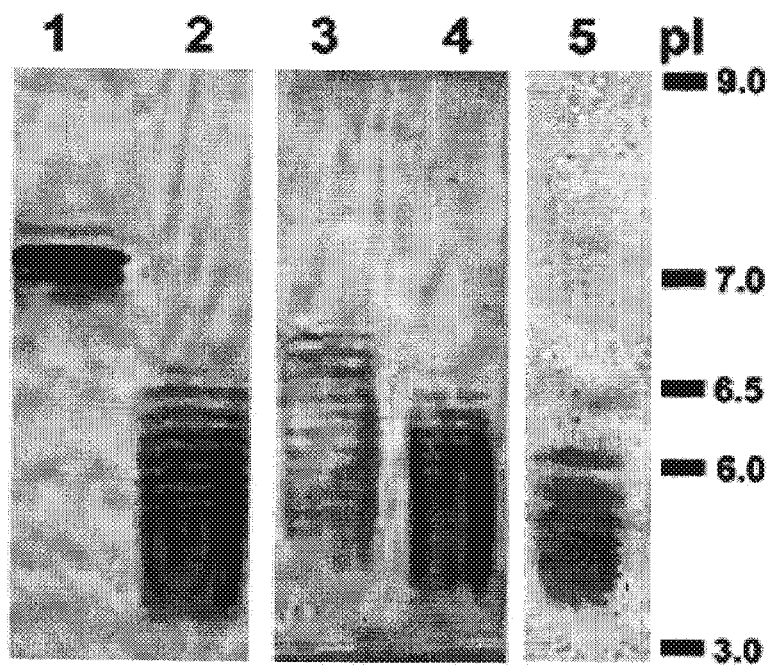

FIG. 23A is a copy of a photographic representation showing results of isoelectric focusing of 1, intact AVP04-07 diabody; 2, AVP04-07-PEG$_{27}$ conjugate; 3, AVP04-07-PEG$_{12}$ conjugate (20:1 ratio); 4, AVP04-07-PEG$_{12}$ conjugate (50:1 ratio); 5, AVP04-07-PEG3400 conjugate.

Figure 23B:
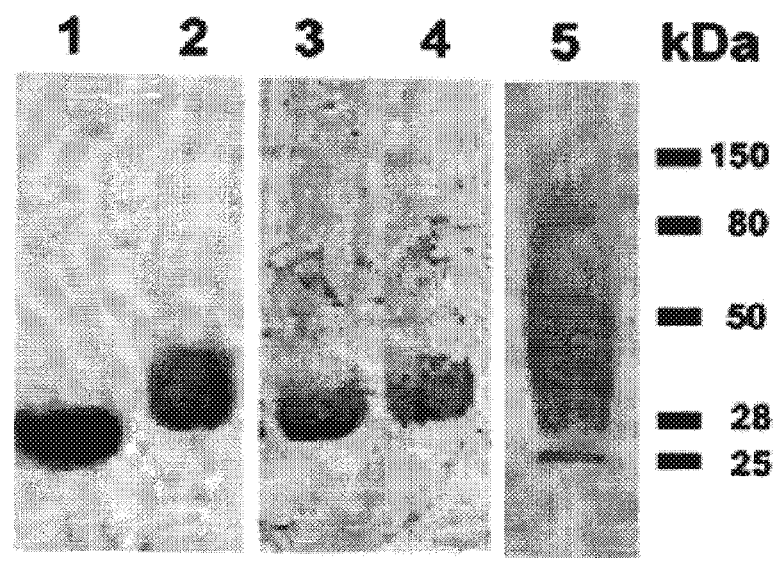

FIG. 23B is a copy of a photographic representation showing results of SDS gel electrophoresis of 1, intact AVP04-07 diabody; 2, AVP04-07-PEG$_{27}$ conjugate; 3, AVP04-07-PEG$_{12}$ conjugate (20:1 ratio); 4, AVP04-07-PEG$_{12}$ conjugate (50:1 ratio); 5, AVP04-07-PEG3400 conjugate.

Figure 24:
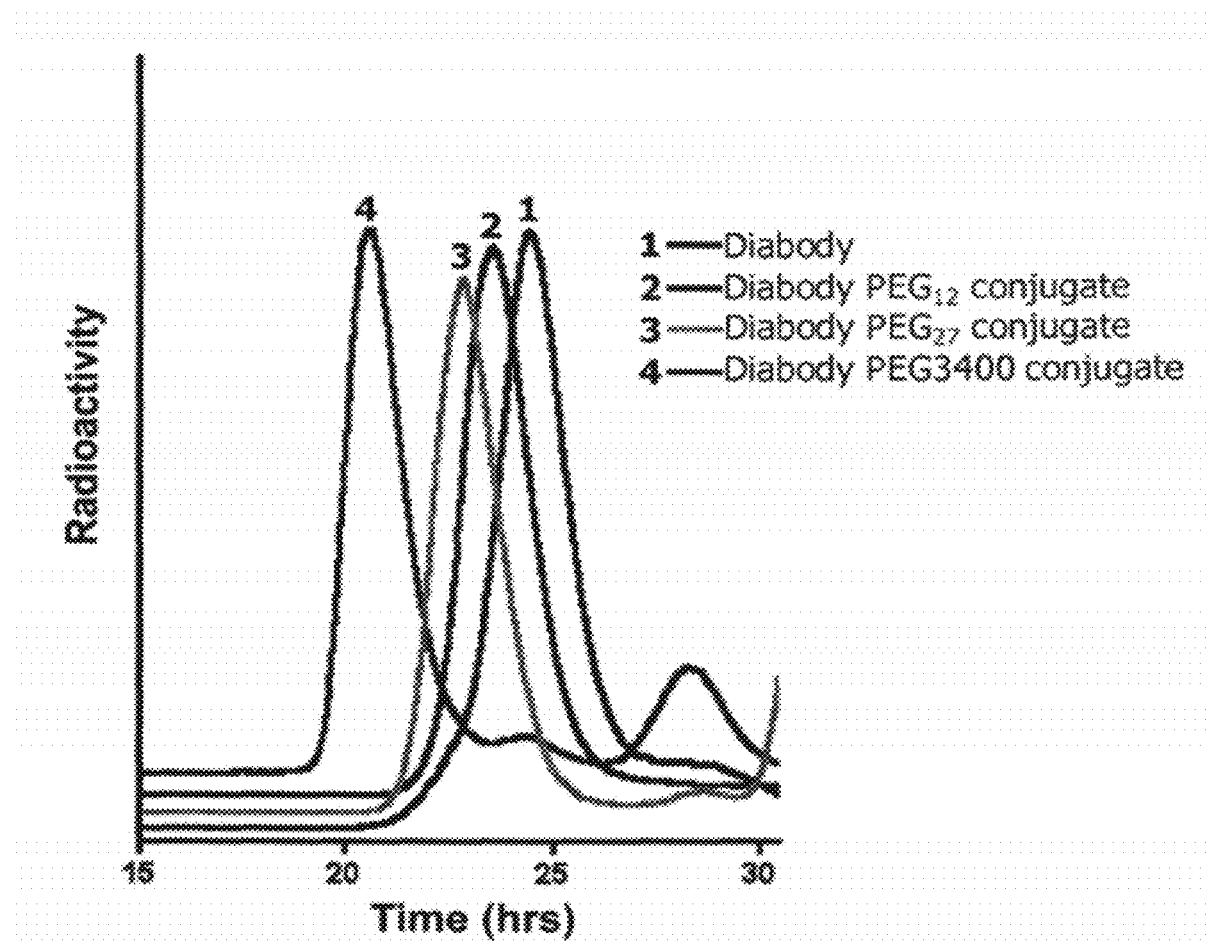

FIG. 24 is a graphical representation showing results of size exclusion chromatography of $^{111}$In-radiolabelled intact AVP04-07 diabody and PEG conjugates (radioactivity shown as arbitrary units). Peaks from Right to Left: labelled no. 1: DOTA-intact diabody, no. 2: DOTA-PEG$_{12}$-Cys-VS-diabody conjugate, no. 3: DOTA-PEG$_{27}$-Cys-VS-diabody conjugate, no. 4: DOTA-Cys-VS-PEG3400-diabody conjugate.

Figure 25:
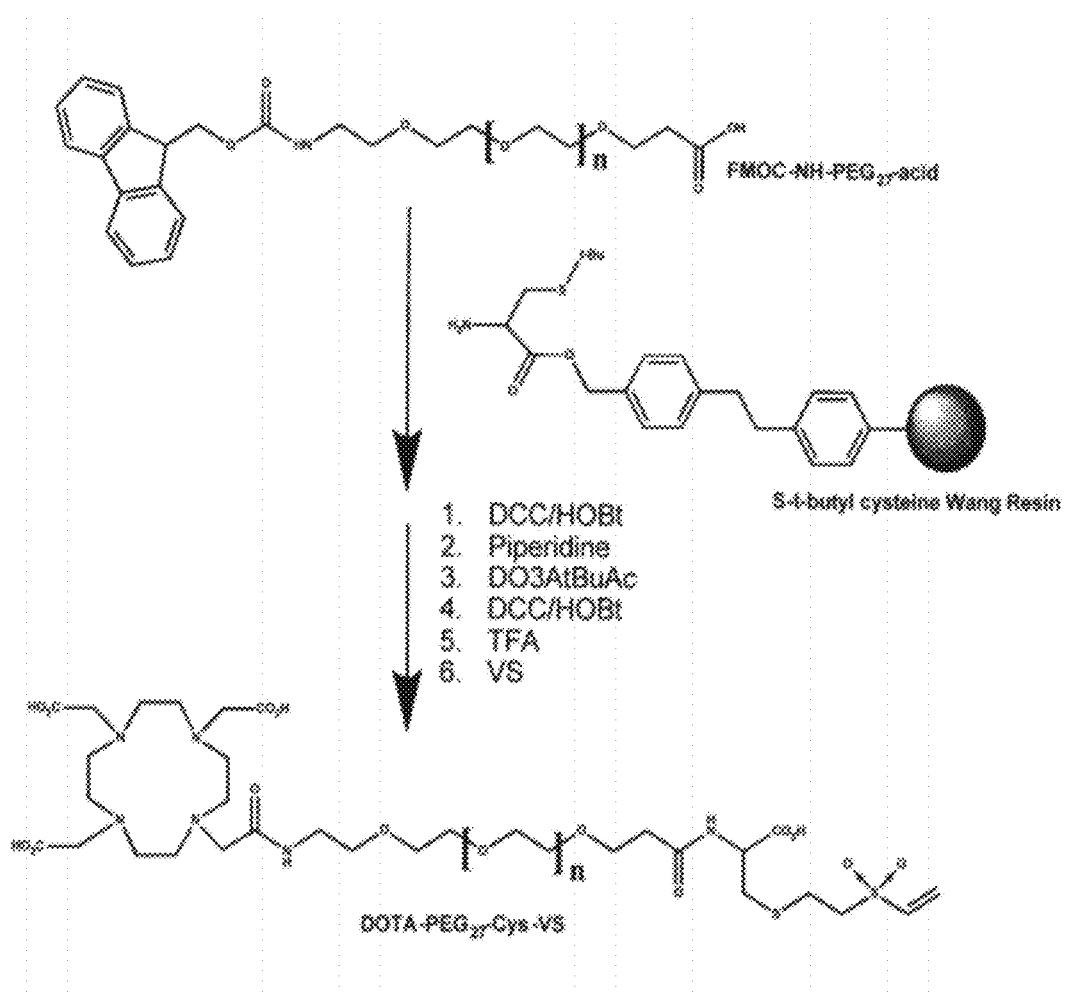

FIG. 25 is a diagrammatic representation of the scheme for synthesizing DOTA-PEG-Cys-VS. FMOC-amido-PEG-acid was conjugated to S-t-butyl cysteine on Wang resin using standard activation chemistry (DCC/HOBt). The FMOC was removed with piperidine and conjugated to DO3AtBuAc using standard activation chemistry (DCC/HOBt). The product was removed from the resin with TFA, purified by reverse phase HPLC, reacted with excess vinyl sulfone in DMF, and repurified by reverse phase HPLC.

Figure 26A:
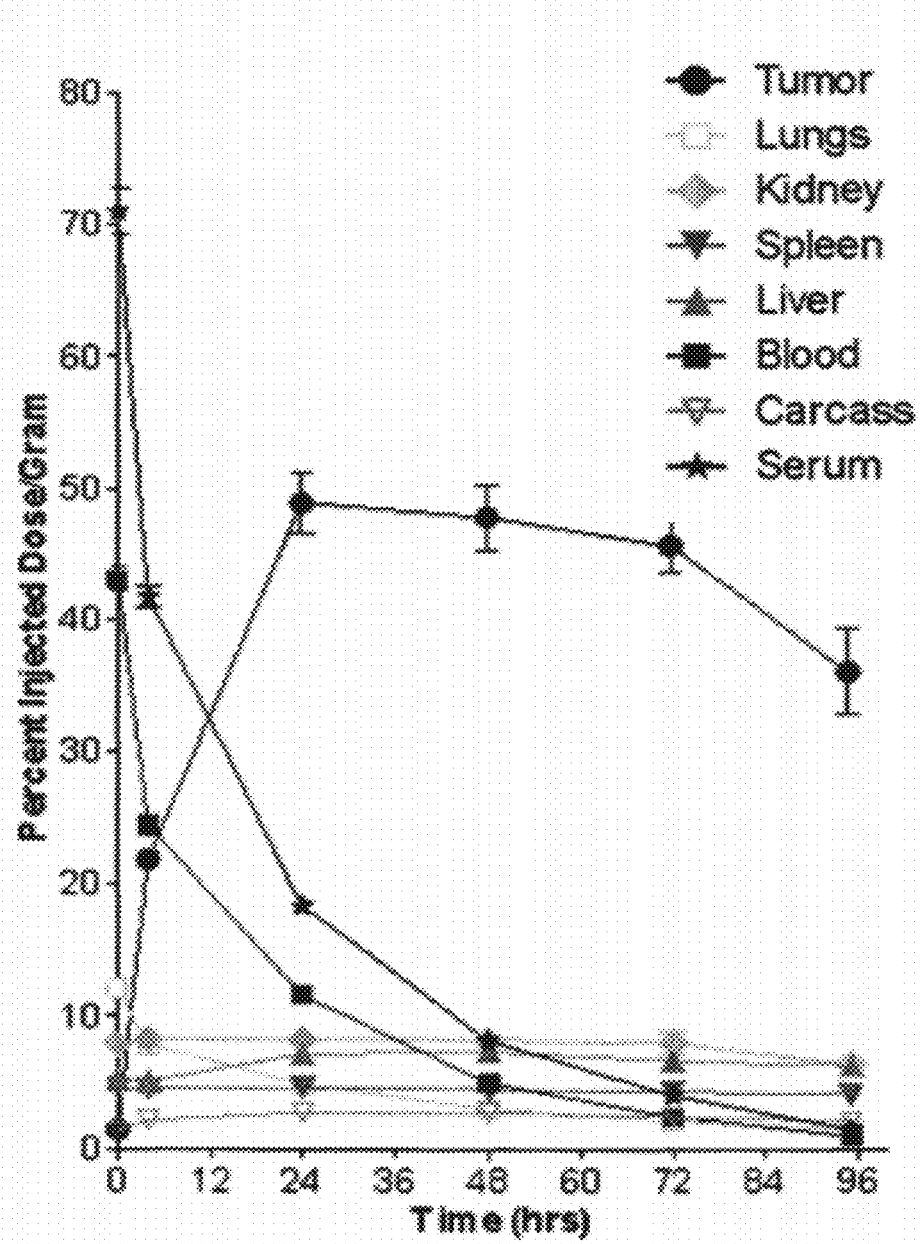

FIG. 26A is a graphical representation showing biodistribution of $^{111}$In-labelled PEG$_{27}$ conjugated AVP04-07 diabody in nude mice bearing LS174T xenografts.

Figure 26B:
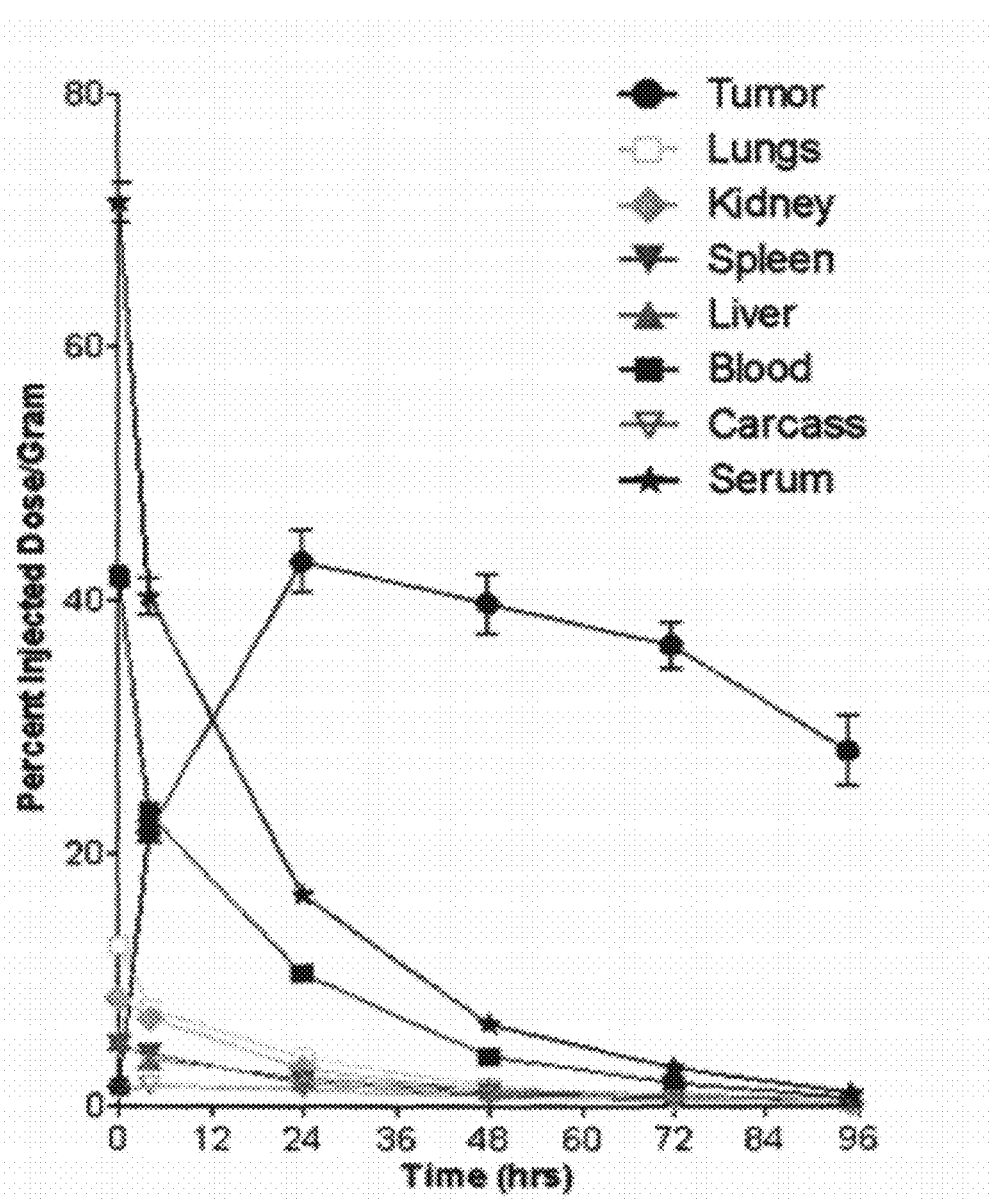

FIG. 26B is a graphical representation showing biodistribution of $^{125}$I-labelled PEG$_{27}$ conjugated AVP04-07 diabody in nude mice bearing LS174T xenografts.

Figure 26C:
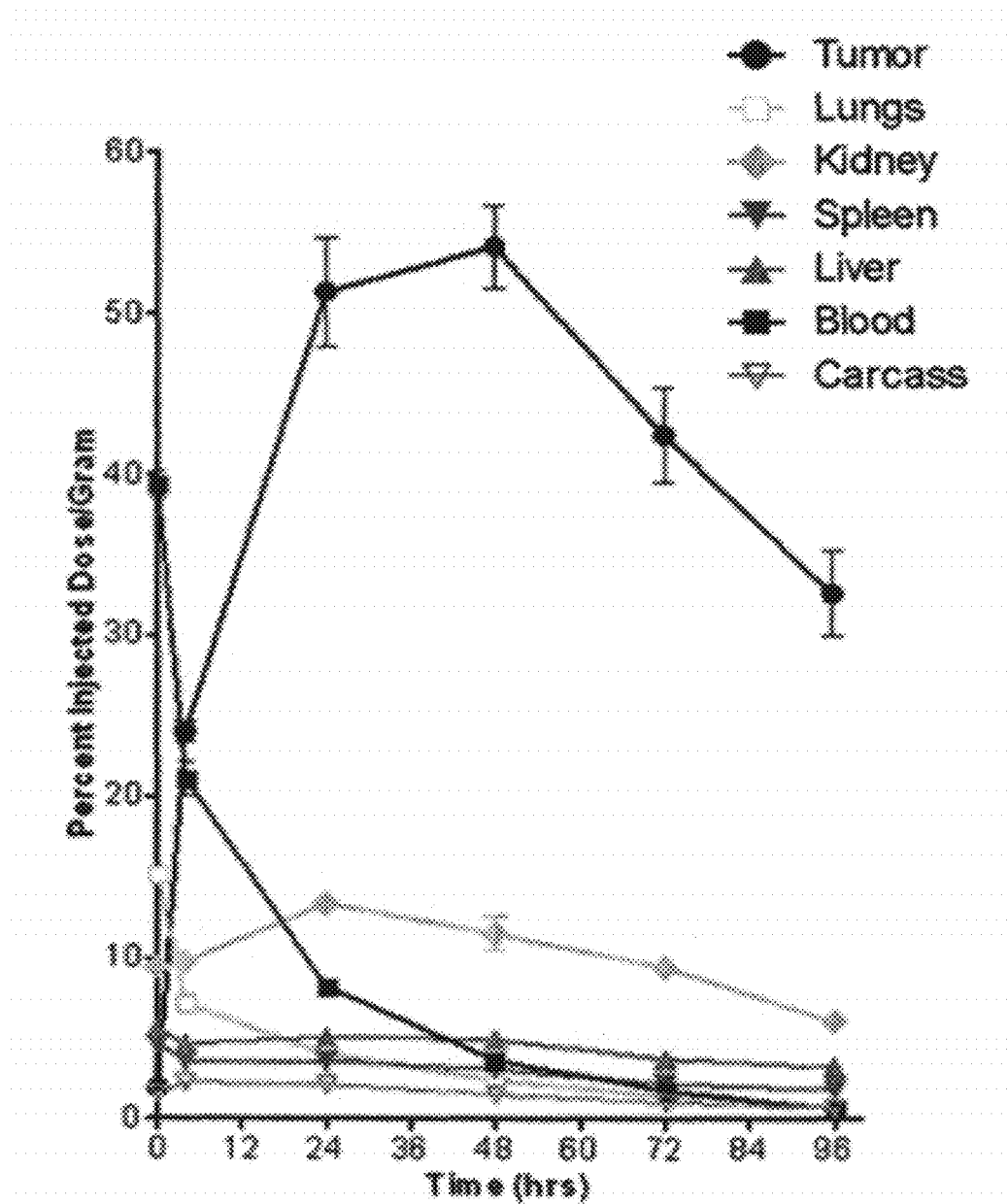

FIG. 26C is a graphical representation showing biodistribution of $^{111}$In labelled PEG$_{12}$ conjugated AVP04-07 diabody in nude mice bearing LS174T xenografts.

Figure 26D:
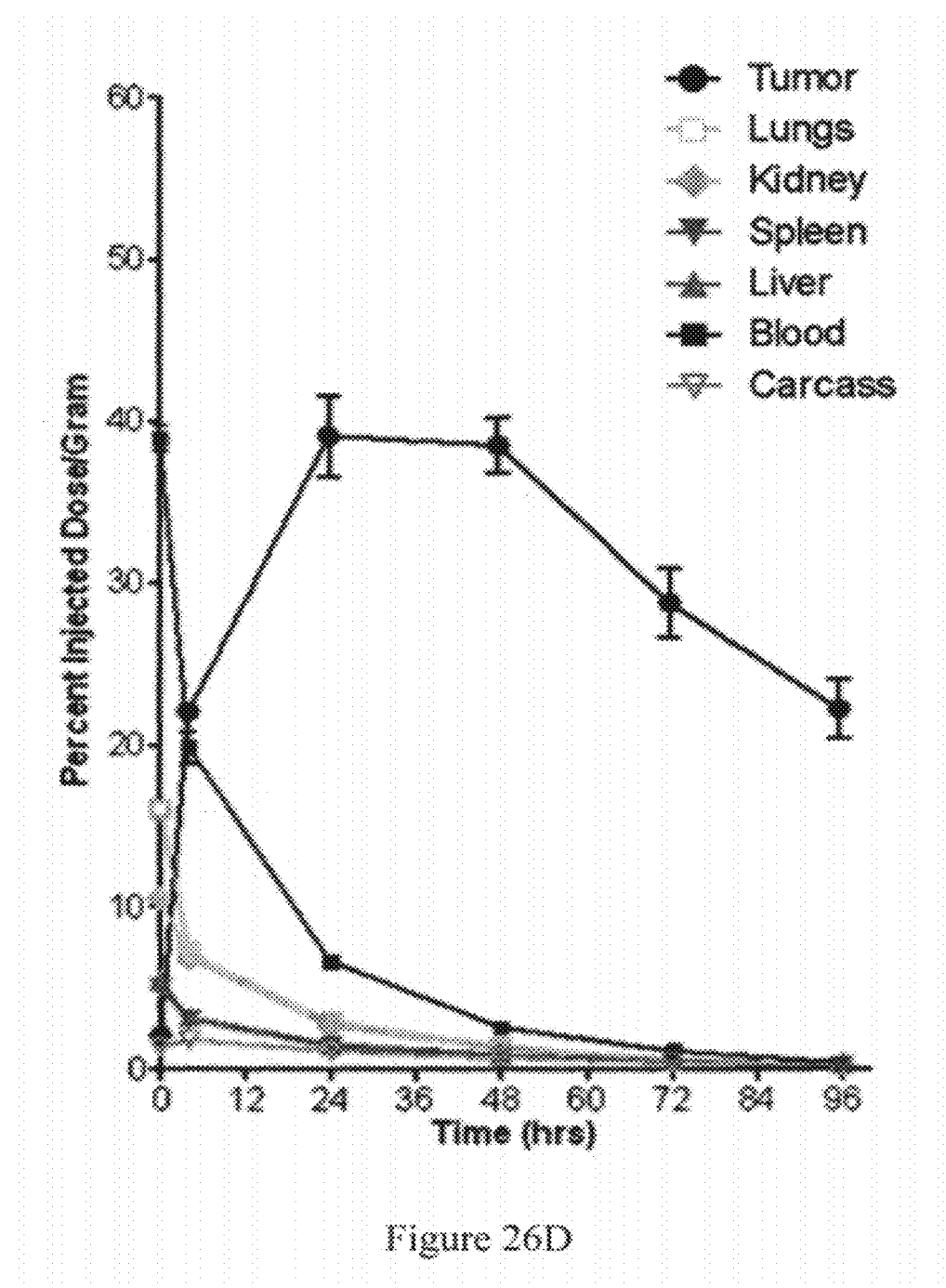

FIG. 26D is a graphical representation showing biodistribution of $^{125}$I-labelled PEG$_{12}$ conjugate conjugated AVP04-07 diabody in nude mice bearing LS174T xenografts.

Figure 27A:
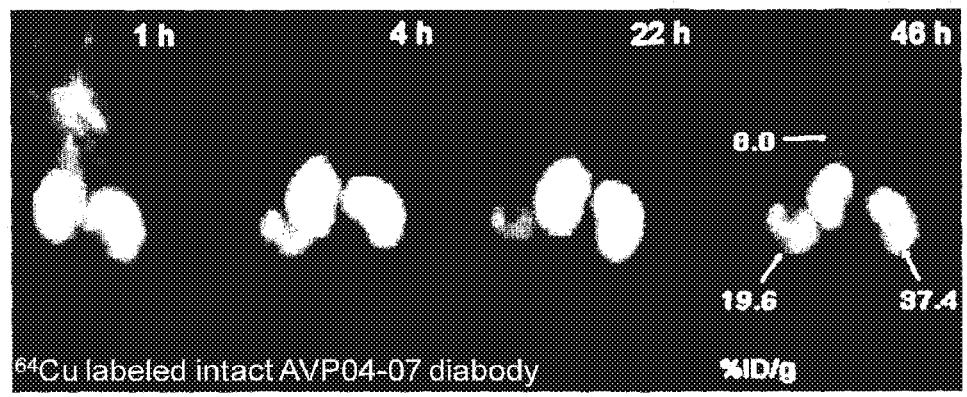

FIG. 27A is a graphical representation showing PET images of a time course of imaging for a single mouse injected with $^{64}$Cu-labelled intact AVP04-07 diabody at 1 h, 4 h, 2 h and 46 h post-injection.

Figure 27B:
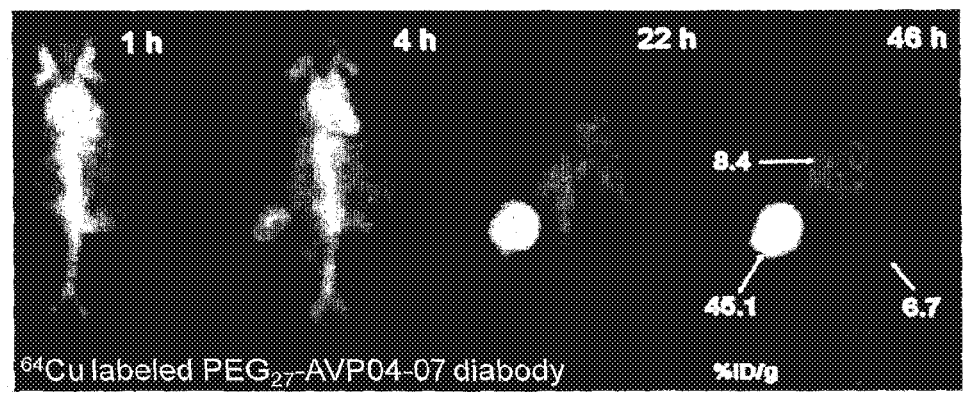

FIG. 27B is a graphical representation showing PET images of a time course of imaging for a single mouse injected with $^{64}$Cu-labelled PEG$_{27}$ AVP04-07 diabody.

Figure 27C:
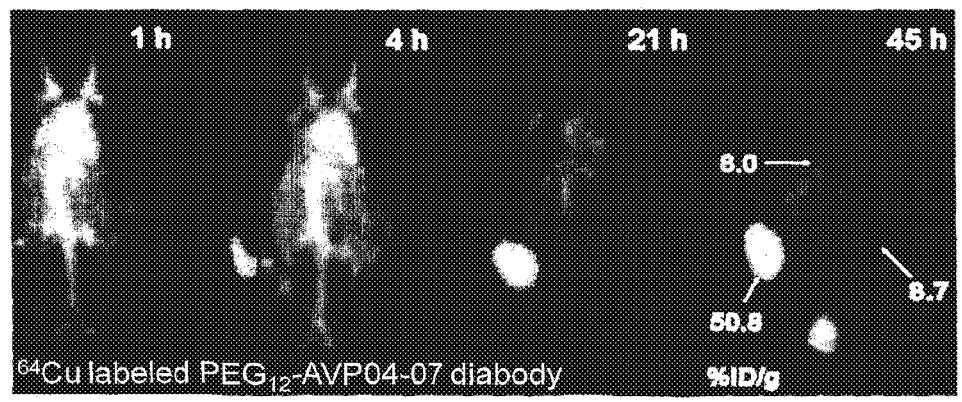

FIG. 27C is a graphical representation showing PET images of a time course of imaging for a single mouse injected with $^{64}$Cu-labelled PEG$_{12}$ AVP04-07 diabody.

KEY TO SEQUENCE LISTING

SEQ ID NO: 1—amino acid sequence of FR1 of a human antibody heavy chain;
SEQ ID NO: 2—amino acid sequence of FR1 of a human antibody heavy chain;
SEQ ID NO: 3—amino acid sequence of FR1 of a human antibody heavy chain;
SEQ ID NO: 4—amino acid sequence of FR1 of a human antibody heavy chain;
SEQ ID NO: 5—amino acid sequence of FR1 of a human antibody heavy chain;
SEQ ID NO: 6—amino acid sequence of FR1 of a human antibody heavy chain;
SEQ ID NO: 7—amino acid sequence of FR1 of a human antibody heavy chain;
SEQ ID NO: 8—amino acid sequence of FR1 of a human antibody heavy chain;
SEQ ID NO: 9—amino acid sequence of FR1 of a human antibody heavy chain;
SEQ ID NO: 10—amino acid sequence of FR1 of a human antibody heavy chain;
SEQ ID NO: 11—amino acid sequence of FR1 of a human antibody heavy chain;
SEQ ID NO: 12—amino acid sequence of FR1 of a human antibody heavy chain;
SEQ ID NO: 13—amino acid sequence of FR1 of a human antibody heavy chain;
SEQ ID NO: 14—amino acid sequence of FR1 of a human antibody κ light chain;
SEQ ID NO: 15—amino acid sequence of FR1 of a human antibody κ light chain;
SEQ ID NO: 16—amino acid sequence of FR1 of a human antibody κ light chain;
SEQ ID NO: 17—amino acid sequence of FR1 of a human antibody κ light chain;
SEQ ID NO: 18—amino acid sequence of FR1 of a human antibody κ light chain;
SEQ ID NO: 19—amino acid sequence of FR1 of a human antibody κ light chain;
SEQ ID NO: 20—amino acid sequence of FR1 of a human antibody κ light chain;
SEQ ID NO: 21—amino acid sequence of FR1 of a human antibody κ light chain;
SEQ ID NO: 22—amino acid sequence of FR1 of a human antibody κ light chain;
SEQ ID NO: 23—amino acid sequence of FR1 of a human antibody κ light chain;
SEQ ID NO: 24—amino acid sequence of FR1 of a human antibody κ light chain;
SEQ ID NO: 25—amino acid sequence of FR1 of a human antibody κ light chain;
SEQ ID NO: 26—amino acid sequence of FR1 of a human antibody κ light chain;
SEQ ID NO: 27—amino acid sequence of FR1 of a human antibody κ light chain;
SEQ ID NO: 28—amino acid sequence of FR1 of a human antibody κ light chain;
SEQ ID NO: 29—amino acid sequence of FR1 of a human antibody κ light chain;
SEQ ID NO: 30—amino acid sequence of FR1 of a human antibody κ light chain;
SEQ ID NO: 31—amino acid sequence of FR1 of a human antibody κ light chain;
SEQ ID NO: 32—amino acid sequence of FR1 of a human antibody κ light chain;
SEQ ID NO: 33—amino acid sequence of FR1 of a human antibody κ light chain;
SEQ ID NO: 34—amino acid sequence of FR1 of a human antibody κ light chain;
SEQ ID NO: 35—amino acid sequence of FR1 of a human antibody κ light chain;
SEQ ID NO: 36—amino acid sequence of FR1 of a human antibody κ light chain;
SEQ ID NO: 36—amino acid sequence of FR1 of a human antibody κ light chain;
SEQ ID NO: 37—amino acid sequence of FR1 of a human antibody λ light chain;
SEQ ID NO: 38—amino acid sequence of FR1 of a human antibody λ light chain;
SEQ ID NO: 39—amino acid sequence of FR1 of a human antibody λ light chain;
SEQ ID NO: 40—amino acid sequence of FR1 of a human antibody λ light chain;
SEQ ID NO: 41—amino acid sequence of FR1 of a human antibody λ light chain;
SEQ ID NO: 42—amino acid sequence of FR1 of a human antibody λ light chain;
SEQ ID NO: 43—amino acid sequence of FR1 of a human antibody λ light chain;
SEQ ID NO: 44—amino acid sequence of FR1 of a camelid immunoglobulin;
SEQ ID NO: 45—amino acid sequence of FR1 of a camelid immunoglobulin;
SEQ ID NO: 46—amino acid sequence of FR1 of a camelid immunoglobulin;
SEQ ID NO: 47—amino acid sequence of FR1 of a camelid immunoglobulin;
SEQ ID NO: 48—amino acid sequence of FR1 of a camelid immunoglobulin;
SEQ ID NO: 49—amino acid sequence of FR1 of a camelid immunoglobulin;
SEQ ID NO: 50—amino acid sequence of FR1 of a camelid immunoglobulin;
SEQ ID NO: 51—amino acid sequence of FR1 of a spiny dogfish shark IgNAR;
SEQ ID NO: 52—amino acid sequence of FR1 of a nurse shark IgNAR;
SEQ ID NO: 53—amino acid sequence of a linker;
SEQ ID NO: 54—nucleotide sequence encoding AVP04-07 anti-TAG72 diabody;
SEQ ID NO: 55—amino acid sequence of AVP04-07 anti-TAG72 diabody;
SEQ ID NO: 56—nucleotide sequence encoding modified AVP04-07 anti-TAG72 diabody designated AVP04-50 comprising cysteine residues in FR1 and a N-terminal serine;
SEQ ID NO: 57—amino acid sequence of modified AVP04-07 anti-TAG72 diabody designated AVP04-50 comprising cysteine residues in FR1 and a N-terminal serine;
SEQ ID NO: 58—nucleotide sequence encoding AVP07-17 anti-Her2 diabody;
SEQ ID NO: 59—amino acid sequence of AVP07-17 anti-Her2 diabody;

SEQ ID NO: 60—nucleotide sequence encoding AVP02-60 anti-MUC1 diabody;
SEQ ID NO: 61—amino acid sequence of AVP02-60 anti-MUC1 diabody SEQ ID NO: 62—nucleotide sequence encoding modified AVP04-07 anti-TAG72 diabody designated AVP04-84 comprising cysteine residues in FR1 and a N-terminal serine;
SEQ ID NO: 63—amino acid sequence of modified AVP04-07 anti-TAG72 diabody designated AVP04-84 comprising cysteine residues in FR1 and a N-terminal serine;
SEQ ID NO: 64—nucleotide sequence encoding modified AVP07-17 anti-Her2 diabody designated AVP07-63 comprising cysteine residues in FR1, removal of cysteine residues in CDR3H and a N-terminal serine;
SEQ ID NO: 65—amino acid sequence of modified AVP07-17 anti-Her2 diabody designated AVP07-63 comprising cysteine residues in FR1, removal of cysteine residues in CDR3H and a N-terminal serine;
SEQ ID NO: 66—nucleotide sequence of mutagenic primer for substituting the N-terminal Gln residue with a Ser residue in AVP04-07;
SEQ ID NO: 67—nucleotide sequence of mutagenic primer for substituting the N-terminal Gln residue with a Ser residue in AVP04-07;
SEQ ID NO: 68—nucleotide sequence of mutagenic primer for replacing cysteine for alanines residues into AVP07-17;
SEQ ID NO: 69—nucleotide sequence of mutagenic primer for replacing cysteine for alanines residues into AVP07-17;
SEQ ID NO: 70—amino acid sequence of human Her2;
SEQ ID NO: 71—amino acid sequence of human PSMA;
SEQ ID NO: 72—amino acid sequence of an isoform of human MUC1; and
SEQ ID NO: 73—amino acid sequence of an isoform of human MUC1 expressed in several forms of cancer.
SEQ ID NO: 74—nucleotide sequence encoding modified AVP04-07 anti-TAG72 diabody designated AVP04-85 comprising cysteine residues in FR1 and a N-terminal serine;
SEQ ID NO: 75—amino acid sequence of modified AVP04-07 anti-TAG72 diabody designated AVP04-85 comprising cysteine residues in FR1 and a N-terminal serine;
SEQ ID NO: 76—nucleotide sequence encoding modified AVP04-07 anti-TAG72 diabody designated AVP04-78 comprising cysteine residues in FR1 and a N-terminal serine;
SEQ ID NO: 77—amino acid sequence of modified AVP04-07 anti-TAG72 diabody designated AVP04-78 comprising cysteine residues in FR1 and a N-terminal serine;
SEQ ID NO: 78—nucleotide sequence encoding modified AVP02-60 anti-MUC1 diabody designated AVP02-101 comprising cysteine residues in FR1 and a N-terminal serine;
SEQ ID NO: 79—amino acid sequence of modified AVP02-60 anti-MUC1 diabody designated AVP02-101 comprising cysteine residues in FR1 and a N-terminal serine;
SEQ ID NO: 80—nucleotide sequence encoding modified AVP02-60 anti-MUC1 diabody designated AVP02-104 comprising cysteine residues in FR1 and a N-terminal serine;
SEQ ID NO: 81—amino acid sequence of modified AVP02-60 anti-MUC1 diabody designated AVP02-104 comprising cysteine residues in FR1 and a N-terminal serine;
SEQ ID NO: 82—nucleotide sequence encoding modified AVP02-60 anti-MUC1 diabody designated AVP02-102 comprising cysteine residues in FR1 and a N-terminal serine;
SEQ ID NO: 83—amino acid sequence of modified AVP02-60 anti-MUC1 diabody designated AVP02-102 comprising cysteine residues in FR1 and a N-terminal serine;
SEQ ID NO: 84—nucleotide sequence encoding modified AVP02-60 anti-MUC1 diabody designated AVP02-105 comprising cysteine residues in FR1 and a N-terminal serine;
SEQ ID NO: 85—amino acid sequence of modified AVP02-60 anti-MUC1 diabody designated AVP02-105 comprising cysteine residues in FR1 and a N-terminal serine;
SEQ ID NO: 86—nucleotide sequence encoding modified AVP07-17 anti-HER2 diabody designated AVP07-88 comprising cysteine residues in FR1, removal of cysteine residues in CDR3H and a N-terminal serine;
SEQ ID NO: 87—amino acid sequence of modified AVP07-17 anti-HER2 diabody designated AVP07-88 comprising cysteine residues in FR1, removal of cysteine residues in CDR3H and a N-terminal serine;
SEQ ID NO: 88—nucleotide sequence encoding modified AVP07-17 anti-HER2 diabody designated AVP07-90 comprising cysteine residues in FR1, removal of cysteine residues in CDR3H and a N-terminal serine;
SEQ ID NO: 89—amino acid sequence of modified AVP07-17 anti-HER2 diabody designated AVP07-90 comprising cysteine residues in FR1, removal of cysteine residues in CDR3H and a N-terminal serine;
SEQ ID NO: 90—nucleotide sequence encoding modified AVP07-17 anti-HER2 diabody designated AVP07-89 comprising cysteine residues in FR1, removal of cysteine residues in CDR3H and a N-terminal serine;
SEQ ID NO: 91—amino acid sequence of modified AVP07-17 anti-HER2 diabody designated AVP07-89 comprising cysteine residues in FR1, removal of cysteine residues in CDR3H and a N-terminal serine;
SEQ ID NO: 92—nucleotide sequence encoding modified AVP07-17 anti-HER2 diabody designated AVP07-91 comprising cysteine residues in FR1, removal of cysteine residues in CDR3H and a N-terminal serine;
SEQ ID NO: 93—amino acid sequence of modified AVP07-17 anti-HER2 diabody designated AVP07-91 comprising cysteine residues in FR1, removal of cysteine residues in CDR3H and a N-terminal serine;
SEQ ID NO: 94—nucleotide sequence encoding modified AVP02-60 anti-MUC1 diabody designated AVP02-103 comprising cysteine residues in FR1 and a N-terminal serine;
SEQ ID NO: 95—amino acid sequence of modified AVP02-60 anti-MUC1 diabody designated AVP02-103 comprising cysteine residues in FR1 and a N-terminal serine;
SEQ ID NO: 96—nucleotide sequence encoding modified AVP07-17 anti-HER2 diabody designated AVP07-68 comprising cysteine residues in FR1, removal of cysteine residues in CDR3H and a N-terminal serine;
SEQ ID NO: 97—amino acid sequence of modified AVP07-17 anti-HER2 diabody designated AVP07-68 comprising cysteine residues in FR1, removal of cysteine residues in CDR3H and a N-terminal serine;
SEQ ID NO: 98—nucleotide sequence encoding modified AVP04-07 anti-TAG72 diabody designated AVP04-51 comprising cysteine residues in FR1 and a N-terminal serine;
SEQ ID NO: 99—amino acid sequence of modified AVP04-07 anti-TAG72 diabody designated AVP04-51 comprising cysteine residues in FR1 and a N-terminal serine;
SEQ ID NO: 100—nucleotide sequence encoding modified AVP04-07 anti-TAG72 scFv designated AVP04-70 comprising cysteine residues in FR1 and a N-terminal serine;
SEQ ID NO: 101—amino acid sequence of modified AVP04-07 anti-TAG72 scFv designated AVP04-70 comprising cysteine residues in FR1 and a N-terminal serine;
SEQ ID NO: 102—nucleotide sequence encoding modified AVP04-07 anti-TAG72 triabody designated AVP04-74 comprising cysteine residues in FR1 and a N-terminal serine;
SEQ ID NO: 103—amino acid sequence of modified AVP04-07 anti-TAG72 triabody designated AVP04-74 comprising cysteine residues in FR1 and a N-terminal serine;

SEQ ID NO: 104—nucleotide sequence encoding modified AVP07-17 anti-HER2 scFv designated AVP07-71 comprising cysteine residues in FR1, removal of cysteine residues in CDR3H and a N-terminal serine;
SEQ ID NO: 105—amino acid sequence of modified AVP07-17 anti-HER2 scFv designated AVP07-71 comprising cysteine residues in FR1, removal of cysteine residues in CDR3H and a N-terminal serine;
SEQ ID NO: 106—nucleotide sequence of mutagenic primer for introducing cysteine residues at Kabat positions L8 and L11 of the FR1 region of the VL chain in AVP04-07;
SEQ ID NO: 107—nucleotide sequence of mutagenic primer for introducing cysteine residues at Kabat positions L8 and L11 of the FR1 region of the VL chain in AVP04-07;
SEQ ID NO: 108—nucleotide sequence encoding modified AVP07-17 anti-HER2 diabody designated AVP07-86 replacing CDR3H Cysteine residues Cys104 (Kabat numbering H100) and Cys109 (H100E) with Alanines and comprising a N-terminal serine;
SEQ ID NO: 109—amino acid sequence of modified AVP07-17 anti-HER2 diabody designated AVP07-86 replacing CDR3H Cysteine residues Cys104 (Kabat numbering H100) and Cys109 (H100E) with Alanines and comprising a N-terminal serine;
SEQ ID NO: 110—nucleotide sequence encoding $V_H$ of AVP04-07 anti-TAG72 diabody;
SEQ ID NO: 111—amino acid sequence of $V_H$ of AVP04-07 anti-TAG72 diabody;
SEQ ID NO: 112—nucleotide sequence encoding $V_L$ of AVP04-07 anti-TAG72 diabody;
SEQ ID NO:113—amino acid sequence of $V_L$ of AVP04-07 anti-TAG72 diabody;
SEQ ID NO: 114—nucleotide sequence encoding AVP04-07 anti-TAG72 diabody lacking a linker sequence (designated AVP04-69);
SEQ ID NO: 115—amino acid sequence of AVP04-07 anti-TAG72 diabody lacking a linker sequence (designated AVP04-69);
SEQ ID NO: 116—nucleotide sequence encoding AVP04-07 anti-TAG72 diabody lacking a linker sequence and amino acid N-terminal to linker in $V_H$ (designated AVP04-09);
SEQ ID NO: 117—amino acid sequence of AVP04-07 anti-TAG72 diabody lacking a linker sequence and amino acid N-terminal to linker in $V_H$ (designated AVP04-09);
SEQ ID NO: 118—nucleotide sequence encoding modified AVP04-07 anti-TAG72 diabody designated AVP04-50 comprising cysteine residues in FR1 of $V_L$;
SEQ ID NO: 119—amino acid sequence of modified AVP04-07 anti-TAG72 diabody designated AVP04-50 comprising cysteine residues in FR1 of $V_L$;
SEQ ID NO: 120—nucleotide sequence encoding modified AVP04-69 anti-TAG72 diabody designated AVP04-50 comprising cysteine residues in FR1 of $V_L$ and lacking a linker sequence;
SEQ ID NO: 121—amino acid sequence of modified AVP04-69 anti-TAG72 diabody designated AVP04-50 comprising cysteine residues in FR1 of $V_L$ and lacking a linker sequence;
SEQ ID NO: 122—nucleotide sequence encoding modified AVP04-09 anti-TAG72 diabody designated AVP04-50 comprising cysteine residues in FR1 of $V_L$ and lacking a linker sequence and amino acid N-terminal to linker in $V_H$;
SEQ ID NO: 123—amino acid sequence of modified AVP04-09 anti-TAG72 diabody designated AVP04-50 comprising cysteine residues in FR1 and lacking a linker sequence and amino acid N-terminal to linker in $V_H$;
SEQ ID NO: 124—nucleotide sequence encoding modified AVP04-07 anti-TAG72 diabody with a N-terminal serine residue in $V_H$;
SEQ ID NO: 125—amino acid sequence of modified AVP04-07 anti-TAG72 diabody with a N-terminal serine residue in $V_H$;
SEQ ID NO: 126—nucleotide sequence encoding modified AVP04-69 anti-TAG72 diabody lacking a linker sequence and comprising a N-terminal serine residue in $V_H$;
SEQ ID NO: 127—amino acid sequence of modified AVP04-69 anti-TAG72 diabody lacking a linker sequence and comprising a N-terminal serine residue in $V_H$;
SEQ ID NO: 128—nucleotide sequence encoding modified AVP04-09 anti-TAG72 diabody lacking a linker sequence and amino acid N-terminal to linker in $V_H$ and comprising a N terminal serine residue in $V_H$;
SEQ ID NO: 129—amino acid sequence of modified AVP04-09 anti-TAG72 diabody lacking a linker sequence and amino acid N-terminal to linker in $V_H$ and comprising a N terminal serine residue in $V_H$;
SEQ ID NO: 130—nucleotide sequence encoding modified AVP04-50 anti-TAG72 diabody comprising cysteine residues in FR1 of $V_L$ and a N-terminal serine residue in $V_H$ and lacking a linker sequence;
SEQ ID NO: 131—amino acid sequence of modified AVP04-50 anti-TAG72 diabody comprising cysteine residues in FR1 of $V_L$ and a N-terminal serine residue in $V_H$ and lacking a linker sequence;
SEQ ID NO: 132—nucleotide sequence encoding modified AVP04-50 anti-TAG72 diabody comprising cysteine residues in FR1 in $V_L$ and a N-terminal serine residue in $V_H$ and lacking a linker sequence and amino acid N-terminal to linker in $V_H$;
SEQ ID NO: 133—amino acid sequence of modified AVP04-50 anti-TAG72 diabody comprising cysteine residues in FR1 in $V_L$ and a N-terminal serine residue in $V_H$ and lacking a linker sequence and amino acid N-terminal to linker in $V_H$;
SEQ ID NO: 134 is an amino acid sequence of a linker; and
SEQ ID NO: 135 is an amino acid sequence of a linker.

DETAILED DESCRIPTION OF PREFERRED EMBODIMENTS

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

Any embodiment herein shall be taken to apply *mutatis mutandis* to any other embodiment unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, biochemistry and homology modeling).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in, for example, Kabat (1987 and/or 1991), Bork et at (1994) and/or Chothia and Lesk (1987 and 1989) or Al-Lazikani et at (1997).

The term "and/or", e.g., "X and/or Y" shall be understood to mean either "X and Y" or "X or Y" and shall be taken to provide explicit support for both meanings or for either meaning As used herein, the term "between" in the context of defining the positioning of an amino acid residue or nucleotide residue shall be taken to mean any residues located between the two recited residues and the two recited residues. For example, the term "between residues 8-11" shall be understood to include residues 8, 9, 10 and 11 in the context of a κ $V_L$ or a $V_H$ and/or the term "between residues 8-12" in the context of a λ $V_L$ shall be understood to mean residues 8, 9, 11 and 12 since a λ $V_L$ does not contain residue 10 in the Kabat numbering system.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

Selected Definitions

As used herein, the term "immunoglobulin" shall be taken to mean an antibody or any antibody-related protein. The skilled artisan will be aware that an antibody is generally considered to be a protein that comprises a variable region made up of a plurality of polypeptide chains, e.g., a light chain variable region ($V_L$) and a heavy chain variable region ($V_H$). An antibody also generally comprises constant domains, which can be arranged into a constant region or constant fragment or fragment crystallisable (Fc). Antibodies can bind specifically to one or a few closely related antigens. Generally, antibodies comprise a four-chain structure as their basic unit. Full-length antibodies comprise two heavy chains (~50-70 kD) covalently linked and two light chains (~23 kD each). A light chain generally comprises a variable region and a constant domain and in mammals is either a κ light chain or a λ light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region ($V_H$ or $V_L$ wherein each are ~110 amino acids in length) and one or more constant domains at the C-terminus. The constant domain of the light chain ($C_L$ which is ~110 amino acids in length) is aligned with and disulfide bonded to the first constant domain of the heavy chain ($C_H$ which is ~330-440 amino acids in length). The light chain variable region is aligned with the variable region of the heavy chain. The antibody heavy chain can comprise 2 or more additional $C_H$ domains (such as, $C_H2$, $C_H3$ and the like) and can comprise a hinge region can be identified between the $C_H1$ and Cm constant domains. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. Preferably, the antibody is a murine (mouse or rat) antibody or a primate (preferably human) antibody. The term "antibody" also encompasses humanized antibodies, primatized antibodies, human antibodies and chimeric antibodies. Proteins related to antibodies, and thus encompassed by the term "immunoglobulin" include domain antibodies, camelid antibodies and antibodies from cartilaginous fish (i.e., immunoglobulin new antigen receptors (IgNARs)). Generally, camelid antibodies and IgNARs comprise a $V_H$, however lack a $V_L$ and are often referred to as heavy chain immunoglobulins. As used herein, the term "immunoglobulin" does not encompass T cell receptors and other immunoglobulin-like domain containing proteins that are not capable of binding to an antigen, e.g., by virtue of an antigen binding site comprising a variable region. Furthermore, the term "immunoglobulin" does not encompass a protein comprising an immunoglobulin domain that does not comprise a FR1, since the invention cannot be performed with such a protein.

As used herein, "variable region" refers to the portions of the light and heavy chains of an antibody or immunoglobulin as defined herein that includes amino acid sequences of CDRs; i.e., CDR1, CDR2, and CDR3, and FRs. In the case of IgNARs the term "variable region" does not require the presence of a CDR2. $V_H$ refers to the variable region of the heavy chain. $V_L$ refers to the variable region of the light chain. According to the methods used in this invention, the amino acid positions assigned to CDRs and FRs are defined according to Kabat (1987 and 1991). The skilled artisan will be readily able to use other numbering systems in the performance of this invention, e.g., the hypervariable loop numbering system of Chothia and Lesk (1987 and/or 1989) and/or Al-Lazikani et al (1997).

As used herein, the term "heavy chain variable region" or "$V_H$" shall be taken to mean a protein capable of binding to one or more antigens, preferably specifically binding to one or more antigens and at least comprising a FR1 comprising at least about 30 amino acids. Sequences of exemplary FR1 from a heavy chain are provided herein (see, for example, SEQ ID NOs: 1 to 13). Preferably, the heavy chain comprises three or four FRs (e.g., FR1, FR2, FR3 and optionally FR4)

together with three CDRs. Preferably, a heavy chain comprises FRs and CDRs positioned as follows residues 1-25 or 1-30 (FR1), 31-25 (CDR1), 36-49 (FR2), 50-65 (CDR2), 66-94 (FR3), 95-102 (CDR3) and 103-113 (FR4), numbered according to the Kabat numbering system. In one example, the heavy chain is derived from an immunoglobulin comprising said heavy chain and a plurality of (preferably 3 or 4) constant domains or linked to a constant fragment (Fc).

As used herein, the term "light chain variable region" or "$V_L$" shall be taken to mean a protein capable of binding to one or more antigens, preferably specifically binding to one or more antigens and at least comprising a FR1 comprising about 23 amino acids. Sequences of exemplary FR1 from a light chain are provided herein (see, for example, SEQ ID NOs: 14 to 43). Preferably, the light chain comprises three or four FRs (e.g., FR1, FR2, FR3 and optionally FR4) together with three CDRs. Preferably, a light chain comprises FRs and CDRs positioned as follows residues 1-23 (FR1), 24-34 (CDR1), 35-49 (FR2), 50-56 (CDR2), 57-88 (FR3), 89-97 (CDR3) and 98-107 (FR4), numbered according to the Kabat numbering system. In one example, the light chain is derived from an immunoglobulin comprising said light chain linked to one constant domain and/or not linked to a constant fragment (Fc).

In some examples of the invention the term "framework regions" will be understood to mean those variable region residues other than the CDR residues. Each variable region of a naturally-occurring immunoglobulin (e.g., antibody) typically has four FRs identified as FR1, FR2, FR3 and FR4. If the CDRs are defined according to Kabat, exemplary light chain FR (LCFR) residues are positioned at about residues 1-23 (LCFR1), 35-49 (LCFR2), 57-88 (LCFR3), and 98-107 (LCFR4). Note that λLCFR1 does not comprise residue 10, which is included in κLCFR1. Exemplary heavy chain FR(HCFR) residues are positioned at about residues 1-30 (HCFR1), 36-49 (HCFR2), 66-94 (HCFR3), and 103-113 (HCFR4).

For all immunoglobulin variable regions of the invention, "framework region 1" (FR1) is defined as the residues between the natural N-terminal residue and the start of the complementarity determining region No. 1 (CDR1). These residues have been numbered by at least two nomenclatures being 1) Kabat (1987 and/or 2001) and 2) Chothia and Lesk (1987, 1989 and Al-Lazikani et at 1997). The Chothia and Lesk numbering system was based on the well established Kabat system and attempted to correct the numbering of light chain CDR1 and heavy chain CDR1 sequence length variability in the immunoglobulin variable regions to better fit their actual position in the three-dimensional structure. The CDR-specific numbering adopted by Chothia and Lesk was later modified in 1989 but then reverted in 1997. There are subtle differences between these numbering systems when dealing with residues found within CDR loops.

As the skilled person will appreciate, within framework region 1, and thus prior to CDR1, a single highly-conserved cysteine residue (Cys) is generally present. Within both kappa and lambda variable light chains, this conserved cysteine is invariantly in Kabat position 23 and forms a disulphide bond with another highly conserved cysteine residue, invariantly in Kabat position 88, within the region defined as framework region 3, between CDR2 and CDR3. However, the present invention contemplates indels, generally man made indels, e.g., of one, two or three amino acids, which may alter the position of the conserved cysteine relative to other amino acids of FR1.

The pairing of highly conserved cysteines is subtly different in variable heavy chains, occurring between conserved cysteines in invariant Kabat positions 22 (within FR1) and 92 (within FR3). However, this pairing is almost perfectly conserved in all immunoglobulins, suggesting this disulfide bond was probably already present at the beginning of Ig-loop diversification and was maintained under selective pressure. The almost perfect conservation of the disulfide bond further suggests that it contributes significantly to the stability of the Ig-loop.

As used herein, the term "complementarity determining regions" (syn. CDRs; i.e., CDR1, CDR2, and CDR3 or hypervariable region) refers to the amino acid residues of an immunoglobulin variable region the presence of which are necessary for antigen binding. Each variable region typically has three CDR regions identified as CDR1, CDR2 and CDR3. Each CDR may comprise amino acid residues from a "complementarity determining region" as defined by Kabat (1987 and/or 1991). For example, in a heavy chain variable region CDRH1 is between residues 31-35, CDRH2 is between residues 50-65 and CDRH3 is between residues 95-102. In a light chain CDRL1 is between residues 24-34, CDRL2 is between residues 50-56 and CDRL3 is between residues 89-97. These CDRs can also comprise numerous insertions, e.g., as described in Kabat (1987 and/or 1991).

The term "constant region" (syn. CR or fragment crystallizable or Fc) as used herein, refers to a portion of an immunoglobulin comprising at least one constant domain and which is generally (though not necessarily) glycosylated and which binds to one or more F receptors and/or components of the complement cascade (e.g., confers effector functions). The heavy chain constant region can be selected from any of the five isotypes: α, δ, ε, γ, or µ. Furthermore, heavy chains of various subclasses (such as the IgG subclasses of heavy chains) are responsible for different effector functions and thus, by choosing the desired heavy chain constant region, proteins with desired effector function can be produced. Preferred heavy chain constant regions are gamma 1 (IgG1), gamma 2 (IgG2) and gamma 3 (IgG3).

A "constant domain" is a domain in an immunoglobulin the sequence of which is highly similar in immunoglobulins/antibodies of the same type, e.g., IgG or IgM or IgE. A constant region of an immunoglobulin generally comprises a plurality of constant domains, e.g., the constant region of γ, α and δ heavy chains comprise three constant domains and the Fc of γ, α and δ heavy chains comprise two constant domains. A constant region of µ and ε heavy chains comprises four constant domains and the Fc region comprises two constant domains.

As used herein, the term "Fv" shall be taken to mean any protein, whether comprised of multiple polypeptides or a single polypeptide, in which a $V_L$ and a $V_H$ associate and form a complex having an antigen binding site, i.e., capable of specifically binding to an antigen. The $V_H$ and the $V_L$ which form the antigen binding site can be in a single polypeptide chain or in different polypeptide chains. Furthermore an Fv of the invention (as well as any protein of the invention) may have multiple antigen binding sites which may or may not bind the same antigen. This term shall be understood to encompass fragments directly derived from an immunoglobulin as well as proteins corresponding to such a fragment produced using recombinant means. In some examples, the $V_H$ is not linked to a heavy chain constant domain ($C_H$)1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain. A "Fab fragment"

consists of a monovalent antigen-binding fragment of an immunoglobulin, and can be produced by digestion of a whole immunoglobulin with the enzyme papain, to yield a fragment consisting of an intact light chain and a portion of a heavy chain or can be produced using recombinant means. A "Fab' fragment" of an immunoglobulin can be obtained by treating a whole immunoglobulin with pepsin, followed by reduction, to yield a molecule consisting of an intact light chain and a portion of a heavy chain. Two Fab' fragments are obtained per immunoglobulin treated in this manner. A Fab' fragment can also be produced by recombinant means. A "F(ab')2 fragment" of an immunoglobulin consists of a dimer of two Fab' fragments held together by two disulfide bonds, and is obtained by treating a whole immunoglobulin molecule with the enzyme pepsin, without subsequent reduction. A "$Fab_2$" fragment is a recombinant fragment comprising two Fab fragments linked using, for example a leucine zipper or a $C_H3$ domain. A "single chain Fv" or "scFv" is a recombinant molecule containing the variable region fragment (Fv) of an immunoglobulin in which the variable region of the light chain and the variable region of the heavy chain are covalently linked by a suitable, flexible polypeptide linker. A detailed discussion of exemplary Fv containing proteins falling within the scope of this term is provided herein below.

As used herein, the term "antigen binding site" shall be taken to mean a structure formed by a protein that is capable of specifically binding to an antigen. The antigen binding site need not be a series of contiguous amino acids, or even amino acids in a single polypeptide chain. For example, in a Fv produced from two different polypeptide chains the antigen binding site is made up of a series of regions of a $V_L$ and a $V_H$ that interact with the antigen and that are generally, however not always in the one or more of the CDRs in each variable region.

By "Kabat numbering system" is meant the numbering system to determining the position of FRs and CDRs in a variable region of an immunoglobulin as set out in Kabat (1987 and/or 1991).

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulphide bond. Examples of non-covalent bonds include hydrogen bonds, ionic bonds, Van der Waals forces, and hydrophobic interactions. A non-covalent bond contemplated by the present invention is the interaction between a $V_H$ and a $V_L$, e.g., in some forms of diabody or a triabody or a tetrabody.

The term "polypeptide chain" will be understood to mean from the foregoing paragraph to mean a series of contiguous amino acids linked by peptide bonds.

The skilled artisan will be aware that a "disulphide bond" is a covalent bond formed by coupling of thiol groups. The bond is also called an SS-bond or disulfide bridge. In proteins, a disulphide bond generally occurs between the thiol groups of two cysteine residues to produce cystine.

The skilled artisan will also be aware that the term "non-reducing conditions" includes conditions sufficient for oxidation of sulfhydryl (—SH) groups in a protein, e.g., permissive for disulphide bond formation.

As used herein, the term "antigen" shall be understood to mean any composition of matter against which an immunoglobulin response (e.g., an antibody response) can be raised. Exemplary antigens include proteins, peptides, polypeptides, carbohydrates, phosphate groups, phosphor-peptides or polypeptides, glyscosylated peptides or peptides, etc.

As used herein, the term "specifically binds" shall be taken to mean a protein of the invention reacts or associates more frequently, more rapidly, with greater duration and/or with greater affinity with a particular antigen or antigens or cell expressing same than it does with alternative antigens or cells. For example, a protein that specifically binds to an antigen binds that antigen with greater affinity, avidity, more readily, and/or with greater duration than it binds to other antigens. It is also understood by reading this definition that, for example, a protein that specifically binds to a first antigen may or may not specifically bind to a second antigen. As such, "specific binding" does not necessarily require exclusive binding or non-detectable binding of another antigen, this is meant by the term "selective binding". Generally, but not necessarily, reference to binding means specific binding, and each term shall be understood to provide explicit support for the other term.

The term the terms "preventing", "prevent" or "prevention" in the context of binding of a protein of the invention to an antigen shall be taken to mean complete abrogation or complete inhibition of binding to the antigen.

Variable Region Containing Proteins

The present invention contemplates any protein that comprises an immunoglobulin variable region that specifically or selectively binds to one or more antigens and that is modified as described herein according to any embodiment. Preferred proteins comprise at least one $V_H$ and at least one $V_L$. Exemplary immunoglobulin variable regions are variable regions from antibodies and modified forms thereof (e.g., humanized antibodies) and heavy chain antibodies, such as, camelid immunoglobulin and IgNAR.

Immunoglobulin Variable Regions

Antibody Variable Regions

As will be apparent to the skilled artisan based on the description herein, the proteins of the invention can comprise one or more variable regions from an antibody modified to comprise at least two cysteine residues in FR1. The present invention also provides antibody molecules. Such antibodies may be produced by first producing an antibody against an antigen of interest and modifying that antibody (e.g., using recombinant means) or by modifying a previously produced antibody.

Methods for producing antibodies are known in the art. For example, methods for producing monoclonal antibodies, such as the hybridoma technique, are by Kohler and Milstein, (1975). In a hybridoma method, a mouse, hamster, or other appropriate host animal, is typically immunized with an immunogen or antigen or cell expressing same to elicit lymphocytes that produce or are capable of producing antibodies that will specifically bind to the immunogen or antigen. Lymphocytes or spleen cells from the immunized animals are then fused with an immortalized cell line using a suitable fusing agent, such as polyethylene glycol, to form a hybridoma cell (Goding, 1986). The resulting hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Other methods for producing antibodies are also contemplated by the present invention, e.g., using ABL-MYC technology described generically in detail in Largaespada (1990) or Weissinger et al. (1991).

Alternatively, the antibody, or sequence encoding same is generated from a previously produced cell expressing an antibody of interest, e.g., a hybridoma or transfectoma. Various sources of such hybridomas and/or transfectomas will be apparent to the skilled artisan and include, for example, American Type Culture Collection (ATCC) and/or European Collection of Cell Cultures (ECACC). Methods for isolating and/or modifying sequences encoding variable regions from antibodies will be apparent to the skilled artisan and/or described herein.

Following antibody production and/or isolation of a sequence encoding same, the antibody is modified to include cysteine residues in FR1 at sites as described herein according to any embodiment. Generally, this involves isolating the nucleic acid encoding the antibody, modifying the sequence thereof to include codons encoding cysteine residues (i.e., TGT or TGC) at the requisite sites in a FR1 encoding region and expressing the modified antibody.

Exemplary human antibody heavy chain FR1 sequences comprise a sequence selected from the group consisting of
QVQLVQSGAEVKKPGASVKVSCKASGYTFT (SEQ ID NO: 1);
QVQLVQSGAEVKKPGASVKVSCKVSGYTLT (SEQ ID NO: 2);
QMQLVQSGAEVKKTGSSVKVSCKASGYTFT (SEQ ID NO: 3);
QMQLVQSGPEVKKPGTSVKVSCKASGFTFT (SEQ ID NO: 4);
QVQLVQSGAEVKKPGSSVKVSCKASGGTFS (SEQ ID NO: 5);
QVTLKESGPVLVKPTETLTLTCTVSGFSLS (SEQ ID NO: 6);
QITLKESGPTLVKPTQTLTLTCTFSGFSLS (SEQ ID NO: 7);
QVTLRESGPALVKPTQTLTLTCTFSGFSLS (SEQ ID NO: 8);
QVQLVESGGGLVKPGGSLRLSCAASGFTFS (SEQ ID NO: 9);
EVQLVESGGGLVQPGGSLRLSCAASGFTFS (SEQ ID NO: 10);
EVQLVESGGGLVKPGGSLRLSCAASGFTFS (SEQ ID NO: 11);
EVQLVESGGGVVRPGGSLRLSCAASGFTFD (SEQ ID NO: 12); and
EVQLLESGGGLVQPGGSLRLSCAASGFTFS (SEQ ID NO: 13).

Exemplary human antibody κ light chain FR1 sequences comprise a sequence selected from the group consisting of
DIQMTQSPSSLSASVGDRVTITC (SEQ ID NO: 14);
DIQMTQSPSTLSASVGDRVTITC (SEQ ID NO: 15);
EIVMTQSPATLSVSPGERATLSC (SEQ ID NO: 16);
EIVLTQSPATLSLSPGERATLSC (SEQ ID NO: 17);
EIVLTQSPGTLSLSPGERATLSC (SEQ ID NO: 18);
DIVMTQSPDSLAVSLGERATINC (SEQ ID NO: 19);
DIVMTQSPLSLPVTPGEPASISC (SEQ ID NO: 20);
DIVMTQSPSSLSASVGDRVTITC (SEQ ID NO: 21);
EIVMTQSPATLSLSPGERATLSC (SEQ ID NO: 22);
DIQMTQSPDFLAVSLGERATINC (SEQ ID NO: 23);
EIVLTQSPSSLSASVGDRVTITC (SEQ ID NO: 24);
DIVMTQTPLSLPVTPGEPASISC (SEQ ID NO: 25);
DIVMTQTPLSLSVTPGQPASISC (SEQ ID NO: 26);
EIVLTQSPDFQSVTPKEKVTITC (SEQ ID NO: 27);
ETTLTQSPAFMSATPGDKVNISC (SEQ ID NO: 28);
AIRMTQSPFSLSASVGDRVTITC (SEQ ID NO: 29);
AIQLTQSPSSLSASVGDRVTITC (SEQ ID NO: 30);
NIQMTQSPSAMSASVGDRVTITC (SEQ ID NO: 31);
DVVMTQSPLSLPVTLGQPASISC (SEQ ID NO: 32);
DIVMTQTPLSSPVTLGQPASISC (SEQ ID NO: 33);
DVVMTQSPAFLSVTPGEKVTITC (SEQ ID NO: 34);
VIWMTQSPSLLSASTGDRVTISC (SEQ ID NO: 35); and
AIRMTQSPSSFSASTGDRVTITC (SEQ ID NO: 36).

Exemplary human antibody λ light chain FR1 sequences comprise a sequence selected from the group consisting of
QSVLTQPPSVSAAPGQKVTISC (SEQ ID NO: 37);
QSVLTQPPSASGTPGQRVTISC (SEQ ID NO: 38);
QSALTQPASVSGSPGQSITISC (SEQ ID NO: 39);
QSALTQPRSVSGSPGQSVTISC (SEQ ID NO: 40);
SYVLTQPPSVSVAPGKTARITC (SEQ ID NO: 41);
SYELTQPPSVSVSPGQTASITC (SEQ ID NO: 42); and
QLVLTQSPSASASLGASVKLTC (SEQ ID NO: 43).

The foregoing sequences are merely exemplary of sequences that may be used to perform the invention and are not an exhaustive list of such sequences. These examples are provided for the purposes of describing the invention and not limiting the invention. It is within the capability of the skilled artisan to determine the sequence of an additional FR1 using known methods and/or based on the disclosure in, for example, Kabat (1987 and/or 2001).

The foregoing examples of FR1 regions are readily modified to include two or more cysteine residues at positions as described herein in any example or embodiment.

The skilled artisan will be readily able to determine the sequence of nucleic acid encoding a FR1 based on knowledge in the art and/or sequences set forth herein.

Chimeric, Deimmunized, Humanized and Human Antibodies

The proteins of the present invention may be derived from or may be humanized antibodies or human antibodies or variable regions derived therefrom. The term "humanized antibody" shall be understood to refer to a chimeric molecule, generally prepared using recombinant techniques, having an antigen binding site derived from an antibody from a non-human species and the remaining antibody structure of the molecule based upon the structure and/or sequence of a human antibody. The antigen-binding site preferably comprises CDRs from the non-human antibody grafted onto appropriate FRs in the variable regions of a human antibody and the remaining regions from a human antibody. Antigen binding sites may be wild type or modified by one or more amino acid substitutions. In some instances, framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable regions, in which all or substantially all of the CDR regions correspond to those of a non-human immunoglobulin and all or substantially all of the FR regions are those of a human immunoglobulin consensus sequence. Methods for humanizing non-human antibodies are known in the art. Humanization can be essentially performed following the method of U.S. Pat. No. 5,225,539, U.S. Pat. No. 6,054,297 or U.S. Pat. No. 5,585,089. Other methods for humanizing an antibody are not excluded. The skilled artisan will understand that a protein of the invention that is not a complete antibody can also be humanized, e.g., a variable domain can be humanized.

The term "human antibody" as used herein in connection with antibody molecules and binding proteins refers to antibodies having variable and, optionally, constant antibody regions derived from or corresponding to sequences found in humans, e.g. in the human germline or somatic cells. The "human" antibodies can include amino acid residues not encoded by human sequences, e.g. mutations introduced by random or site directed mutations in vitro (in particular mutations which involve conservative substitutions or mutations in a small number of residues of the antibody, e.g. in 1, 2, 3, 4 or 5 of the residues of the antibody, preferably e.g. in 1, 2, 3, 4 or 5 of the residues making up one or more of the CDRs of the antibody). These "human antibodies" do not actually need to be produced by a human, rather, they can be produced using recombinant means and/or isolated from a transgenic animal (e.g., a mouse) comprising nucleic acid encoding human antibody constant and/or variable regions. Human antibodies or fragments thereof can be produced using various techniques known in the art, including phage display libraries (e.g., as described in U.S. Pat. No. 6,300,064; U.S. Pat. No. 5,885,793; U.S. Pat. No. 6,204,023; U.S. Pat. No. 6,291,158; or U.S. Pat. No. 6,248,516), or using transgenic animals expressing human immunoglobulin genes (e.g., as described in WO2002/066630; Lonberg et al. (1994) or Jakobovits et al. (2007)).

In one example an protein of the invention is a chimeric antibody or part thereof, e.g., a Fab fragment. The term "chimeric antibody" refers to antibodies in which a portion of the heavy and/or light chain is identical with or homologous to corresponding sequences in antibodies derived from a particular species (e.g., murine, such as mouse) or belonging to a particular antibody class or subclass, while the remainder of the chain(s) is identical with or homologous to corresponding sequences in antibodies derived from another species (e.g., primate, such as human) or belonging to another antibody class or subclass, as well as fragments of such antibodies, so long as they exhibit the desired biological activity (U.S. Pat. No. 4,816,567). Typically chimeric antibodies utilize rodent or rabbit variable regions and human constant regions, in order to produce an antibody with predominantly human domains. For example, a chimeric antibody comprises a variable region from a mouse antibody modified according to the present invention any embodiment fused to a human constant domain and/or a human constant region. The production of such chimeric antibodies is known in the art, and may be achieved by standard means (as described, e.g., in U.S. Pat. No. 5,807,715; U.S. Pat. No. 4,816,567 and U.S. Pat. No. 4,816,397).

The present invention also contemplates a deimmunized protein. De-immunized proteins have one or more epitopes, e.g., B cell epitopes or T cell epitopes removed (i.e., mutated) to thereby reduce the likelihood that a subject will raise an immune response against the protein. Methods for producing deimmunized proteins are known in the art and described, for example, in WO00/34317, WO2004/108158 and WO2004/064724. For example, the method comprises performing an in silico analysis to predict an epitope in a protein and mutating one or more residues in the predicted epitope to thereby reduce its immunogenicity. The protein is then analyzed, e.g., in silico or in vitro or in vivo to ensure that it retains its ability to bind to an antigen. Preferable an epitope that occurs within a CDR is not mutated unless the mutation is unlikely to reduce antigen binding. Methods for predicting antigens are known in the art and described, for example, in Saha (2004). Exemplary potential epitopes in AVP04-07 occur at the following positions of SEQ ID NO: 55: 35-41; 68-77; 84-90; 109-119; 122-128; 160-169; and 185-194. Residues that may be mutated to potentially reduce immunogenicity include K38, T71, A72, K74, T87, T112, V113, S114, S115, G116, T125, Q163, Q164, P166, F188, T189, G190 or S191.

Heavy Chain Immunoglobulins

Heavy chain immunoglobulins differ structurally from many other forms of immunoglobulin (e.g., antibodies), in so far as they comprise a heavy chain, but do not comprise a light chain. Accordingly, these immunoglobulins are also referred to as "heavy chain only antibodies". Heavy chain immunoglobulins are found in, for example, camelids and cartilaginous fish (also called IgNAR).

The variable regions present in naturally occurring heavy chain immunoglobulins are generally referred to as "$V_{HH}$ domains" in camelid Ig and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

Heavy chain immunoglobulins do not require the presence of light chains to bind with high affinity and with high specificity to a relevant antigen. This feature distinguishes heavy chain immunoglobulins from some conventional 4-chain antibodies, which comprise both $V_H$ and $V_L$ domains. This means that single domain binding fragments can be derived from heavy chain immunoglobulins, which are easy to express and are generally stable and soluble. Heavy chain immunoglobulins and variable regions domains thereof domains derived therefrom can also comprise long surface loops (particularly CDR3), which facilitate penetration of and binding to cavities often found in antigens such as enzymes and on the surface of proteins of viruses and agents causative of infectious diseases.

A general description of heavy chain immunoglobulins from camelids and the variable regions thereof and methods for their production and/or isolation and/or use is found inter alia in the following references WO94/04678, WO97/49805 and WO 97/49805.

Exemplary sequences of framework 1 domains from heavy chain immunoglobulins from camelids include the following, GGSVQTGGSLRLSCEISGLTFD (SEQ ID NO: 44); GGSVQTGGSLRLSCAVSGFSFS (SEQ ID NO: 45); GGSEQGGGSLRLSCAISGYTYG (SEQ ID NO: 46); GGSVQPGGSLTLSCTVSGATYS (SEQ ID NO: 47); GGSVQAGGSLRLSCTGSGFPYS (SEQ ID NO: 48); GGSVQAGGSLRLSCVAGFGTS (SEQ ID NO: 49); and GGSVQAGGSLRLSCVSFSPSS (SEQ ID NO: 50).

A general description of heavy chain immunoglobulins from cartilaginous fish and the variable regions thereof and methods for their production and/or isolation and/or use is found inter alia in WO2005/118629. An exemplary consensus sequence for a Type 3 spiny dogfish shark IgNAR FR1 comprises the sequence AWVEQTPRTAKETGESLTINCVLT (SEQ ID NO: 51). An exemplary consensus sequence for a Type 3 nurse shark IgNAR FR1 comprises the sequence ARVDQTPKTITKETGESLTINCVLS (SEQ ID NO: 52).

Variable Region Containing Proteins
Diabodies, Triabodies, Tetrabodies

Exemplary preferred proteins comprising an immunoglobulin variable region are diabodies, triabodies, tetrabodies and higher order protein complexes such as those described in WO98/044001 and WO94/007921.

As used herein, the term "diabody" shall be taken to mean a protein comprising two associated polypeptide chains, each polypeptide chain comprising the structure $V_L$—X—$V_H$ or $V_H$—X—$V_L$, wherein $V_L$ is an immunoglobulin light chain variable region, $V_H$ is an immunoglobulin heavy chain variable region, X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding site, i.e., to form a Fv molecule capable of specifically binding to one or more antigens. The $V_L$ and $V_H$ can be the same in each polypeptide chain or the $V_L$ and $V_H$ can be different in each polypeptide chain so as to form a bispecific diabody (i.e., comprising two Fvs having different specificity).

As used herein, the term "triabody" shall be taken to mean a protein comprising three associated polypeptide chains, each polypeptide chain comprising the structure $V_L$—X—$V_H$ or $V_H$—X—$V_L$, wherein $V_L$ is an immunoglobulin light chain variable region, $V_H$ is an immunoglobulin heavy chain variable region, X is a linker comprising insufficient residues to permit the $V_H$ and $V_L$ in a single polypeptide chain to associate (or form an Fv) or is absent, and wherein the $V_H$ of one polypeptide chain is associated with the $V_L$ of another polypeptide chain to thereby form a trimeric protein (a triabody). For example, a $V_H$ of a first polypeptide chain is associated with the $V_L$ of a second polypeptide chain, the $V_H$ of the second polypeptide chain is associated with the $V_L$ of a third polypeptide chain and the $V_H$ of the third polypeptide is associated with the $V_L$ of the first polypeptide chain. The $V_L$ and $V_H$ associate so as to form an antigen binding site, i.e., a Fv capable of specifically binding to one or more antigens. The $V_L$ and $V_H$ can be the same in each polypeptide chain (i.e., to produce a monospecific triabody) or two of the $V_L$ and two of the $V_H$ can be the same and the third of each different in the third polypeptide chain to produce a bispecific protein or the $V_L$ and $V_H$ can be different in each polypeptide chain so as to form a trivalent protein.

As used herein, the term "tetrabody" shall be taken to mean a protein comprising four associated polypeptide chains, each polypeptide chain comprising the structure $V_L$—X—$V_H$ or $V_H$—X—$V_L$, wherein $V_L$ is an immunoglobulin light chain variable region, $V_H$ is an immunoglobulin heavy chain variable region, X is a linker comprising insufficient residues to permit the $V_H$ and $V_L$ in a single polypeptide chain to associate (or form an Fv) or is absent, and wherein the $V_H$ of one polypeptide chain is associated with the $V_L$ of another polypeptide chain to thereby form a tetrameric protein (a tetrabody). The $V_L$ and $V_H$ associate so as to form an antigen binding site, i.e., a Fv capable of specifically binding to one or more antigens. For example, the $V_H$ of a first polypeptide chain is associated with the $V_L$ of a second polypeptide chain, the $V_H$ of the second polypeptide chain is associated with the $V_L$ of a third polypeptide chain, the $V_H$ of the third polypeptide chain is associated with the $V_L$ of a fourth polypeptide chain and the $V_H$ of the fourth polypeptide chain is associated with the $V_L$ of the first polypeptide chain. The $V_L$ and $V_H$ can be the same in each polypeptide chain (i.e., to produce a monospecific tetrabody) or the $V_L$ and $V_H$ can be of one type in two polypeptide chains and a different type in the other two polypeptide chains to produce a bispecific tetrabody or the $V_L$ and $V_H$ can be different in each polypeptide chain so as to form a tetraspecific tetrabody.

The skilled artisan will be aware of diabodies, triabodies and/or tetrabodies and methods for their production. Generally, these proteins comprise a polypeptide chain in which a $V_H$ and a $V_L$ are linked directly or using a linker that is of insufficient length to permit the $V_H$ and $V_L$ to associate. The $V_H$ and $V_L$ can be positioned in any order, i.e., $V_L$—$V_H$ or $V_H$—$V_L$. The $V_H$ and $V_L$ are readily obtained, e.g., by isolating nucleic acid encoding these polypeptide chains from a cell expressing an immunoglobulin comprising one or more variable region(s) of interest (including an antibody or a chimeric antibody or a humanized antibody or a human antibody) or from a recombinant library expressing $V_H$ and $V_L$ polypeptide chains (e.g., a scFv library, e.g., as described in EP0239400 or U.S. Pat. No. 4,946,778). The $V_H$ and/or $V_L$ can then readily be modified to include the requisite cysteine residues as described herein according to any embodiment.

Proteins comprising $V_H$ and $V_L$ associate to form diabodies, triabodies and/or tetrabodies depending on the length of the linker (if present) and/or the order of the $V_H$ and $V_L$ domains. Preferably, the linker comprises 12 or fewer amino acids. For example, in the case of polypeptide chains having the following structure arranged in N to C order $V_H$—X—$V_L$, wherein X is a linker, a linker having 3-12 residues generally results in formation of diabodies, a linker having 1 or 2 residues or where a linker is absent generally results in formation of triabodies. In the case of polypeptide chains having the following structure arranged in N to C order $V_L$—X—$V_H$, wherein X is a linker, a linker having 3-12 residues generally results in formation of diabodies, a linker having 1 or 2 residues generally results in formation of diabodies, triabodies and tetrabodies and a polypeptide lacking a linker generally forms triabodies or tetrabodies.

Linkers for use in fusion proteins are known in the art. Linker sequence composition could affect the folding stability of a fusion protein. By indirect fusion of proteins through a linker not related to the fused proteins, the steric hindrance between the two proteins is avoided and the freedom degree for the linking is achieved.

It is often unfavorable to have a linker sequence with high propensity to adopt α-helix or β-strand structures, which could limit the flexibility of the protein and consequently its functional activity. Rather, a more desirable linker is a sequence with a preference to adopt extended conformation. In practice, most currently designed linker sequences have a high content of glycine residues that force the linker to adopt loop conformation. Glycine is generally used in designed linkers because the absence of a β-carbon permits the polypeptide backbone to access dihedral angles that are energetically forbidden for other amino acids.

In one embodiment, the linker is a glycine rich linker. Preferably, the linker is a glycine linker that additionally comprises alanine and/or serine. Such linkers provide flexibility, enhance hydrophilicity and are relatively protease resistant, see, e.g., Kortt et al., 2001.

The conformational flexibility imparted by glycine may be important at the junction between C terminus of the protein and the N terminus of the linker. Accordingly, linkers that comprise glycine in the region adjacent to the C terminus of the protein are preferred. In this regard, this does not impart a requirement that the first amino acid residue of the linker need be a glycine.

Proline residues can be incorporated into the linker to prevent the formation of significant secondary structural elements by the linker. For example, a linker comprises the sequence $Gly_n$-Pro-$Gly_n$ where n is a number between about 1 and about 5.

Preferred linkers include a sequence selected from the group consisting of G; GG; GGG; GGGG (SEQ ID NO: 134); GGGGS (SEQ ID NO: 135); S; SG; SGG; and SGGG.

Diabodies and higher order multimers can also comprise proteins that are covalently linked, e.g., by virtue of a disulphide bond between the proteins, e.g., as described in WO2006/113665.

Multispecific diabodies and higher order multimers can be produced through the noncovalent association of two single chain fusion products comprising $V_H$ domain from one immunoglobulin connected by a short linker to the $V_L$ domain of another immunoglobulin, thereby forming two Fvs, each from a different immunoglobulin, see, for example, Hudson and Kortt (1999). Similarly, multispecific triabodies can be produced by noncovalent association of three single chain fusion proteins as follows:

(i) a first protein comprising a $V_H$ domain from a first immunoglobulin connected by a short linker to the $V_L$ domain of a second immunoglobulin;
(ii) a second protein comprising a $V_H$ domain from the second immunoglobulin connected by a short linker to the $V_L$ domain of a third immunoglobulin; and
(iii) a third protein comprising a $V_H$ domain from the third immunoglobulin connected by a short linker to the $V_L$ domain of the first immunoglobulin.

The skilled artisan will readily be able to determine suitable modifications to the foregoing to produce bispecific triabodies, bispecific tetrabodies, trispecific tetrabodies and tetraspecific tetrabodies.

The present invention contemplates a diabody, triabody, tetrabody or higher order multimer against any antigen or combination thereof, and is not to be construed to be limited to those that bind to a specific antigen. Exemplary antigens are described herein for the purposes of illustration and not limitation.

Exemplary diabodies, triabodies and/or tetrabodies comprise a $V_H$ sequence set forth in amino acids 1-115 of SEQ ID NO: 55 or amino acids 1-129 of SEQ ID NO: 59 or amino acids 1-120 of SEQ ID NO: 61 or amino acids 1-129 of SEQ ID NO: 109, which are modified to include two or more cysteine residues in FR1 and/or a N-terminal threonine/serine residue. For example, the $V_H$ comprises a sequence set forth in:
(i) amino acids 1-115 of SEQ ID NO: 57;
(ii) amino acids 1-115 of SEQ ID NO: 63;
(iii) amino acids 1-115 of SEQ ID NO: 75;
(iv) amino acids 1-115 of SEQ ID NO: 77;
(v) amino acids 1-115 of SEQ ID NO: 99;
(vi) amino acids 1-129 of SEQ ID NO: 65;
(vii) amino acids 1-129 of SEQ ID NO: 87;
(viii) amino acids 1-129 of SEQ ID NO: 89;
(ix) amino acids 1-129 of SEQ ID NO: 91;
(x) amino acids 1-129 of SEQ ID NO: 93;
(xi) amino acids 1-129 of SEQ ID NO: 97;
(xii) amino acids 1-120 of SEQ ID NO: 79;
(xiii) amino acids 1-120 of SEQ ID NO: 81;
(xiv) amino acids 1-120 of SEQ ID NO: 83;
(xv) amino acids 1-120 of SEQ ID NO: 85; and/or
(xvi) amino acids 1-120 of SEQ ID NO: 95.

The diabodies, triabodies and/or tetrabodies comprise a $V_L$ sequence set forth in amino acids 121-234 of SEQ ID NO: 55 or amino acids 135-245 of SEQ ID NO: 59 or amino acids 126-232 of SEQ ID NO: 61 or amino acids 135-245 of SEQ ID NO: 109, which are modified to include two or more cysteine residues in FR1 and/or a N-terminal threonine/serine residue. For example, the $V_L$ comprises a sequence set forth in:
(i) amino acids 121-234 of SEQ ID NO: 57;
(ii) amino acids 121-234 of SEQ ID NO: 63;
(iii) amino acids 121-234 of SEQ ID NO: 75;
(iv) amino acids 121-234 of SEQ ID NO: 77;
(v) amino acids 121-234 of SEQ ID NO: 99;
(vi) amino acids 135-245 of SEQ ID NO: 65;
(vii) amino acids 135-245 of SEQ ID NO: 87;
(viii) amino acids 135-245 of SEQ ID NO: 89;
(ix) amino acids 135-245 of SEQ ID NO: 91;
(x) amino acids 135-245 of SEQ ID NO: 93;
(xi) amino acids 135-245 of SEQ ID NO: 97;
(xii) amino acids 126-232 of SEQ ID NO: 79;
(xiii) amino acids 126-232 of SEQ ID NO: 81;
(xiv) amino acids 126-232 of SEQ ID NO: 83;
(xv) amino acids 126-232 of SEQ ID NO: 85; and/or
(xvi) amino acids 126-232 of SEQ ID NO: 95.

The $V_H$ and $V_L$ described in the foregoing paragraphs can be arranged in any order and linked by a suitable linker as described herein. For a diabody, the linker preferably comprises the sequence GGGS. For a triabody or tetrabody, preferably there is no linker or a single glycine residue.

In one example, a diabody binds to TAG72 and comprises at least one polypeptide chain comprising (and preferably two polypeptide chains each comprising) a sequence set forth in SEQ ID NO: 55 which are modified to include two or more cysteine residues in FR1 and/or a N-terminal threonine/serine residue. For example, a diabody comprises at least one polypeptide chain comprising (and preferably two polypeptide chains each comprising) a sequence set forth in one or more of SEQ ID NO: 57, 63, 75, 77 or 79.

In one example, a triabody binds to TAG72 and comprises at least one polypeptide chain comprising (and preferably two or three polypeptide chains each comprising) a sequence set forth in SEQ ID NO: 102.

In another example, a diabody binds to Her2 and comprises at least one polypeptide chain comprising (and preferably two polypeptide chains each comprising) a sequence set forth in SEQ ID NO: 109 which are modified to include two or more cysteine residues in FR1 and/or a N-terminal threonine/serine residue. For example, a diabody comprises at least one polypeptide chain comprising (and preferably two polypeptide chains each comprising) a sequence set forth in one or more of SEQ ID NO: 65, 87, 89, 91, 93 or 97.

In another example, a diabody binds to MUC1 and comprises at least one polypeptide chain comprising (and preferably two polypeptide chains each comprising) a sequence set forth in SEQ ID NO: 61 which are modified to include two or more cysteine residues in FR1 and/or a N-terminal threonine/serine residue. For example, a diabody comprises at least one polypeptide chain comprising (and preferably two polypeptide chains each comprising) a sequence set forth in one or more of SEQ ID NO: 79, 81, 83, 85 or 95.

Single Chain Fv (scFv) Fragments

The skilled artisan will be aware that scFvs comprise $V_H$ and $V_L$ regions in a single polypeptide chain. Preferably, the polypeptide chain further comprises a polypeptide linker between the $V_H$ and $V_L$ which enables the scFv to form the desired structure for antigen binding (i.e., for the $V_H$ and $V_L$ of the single polypeptide chain to associate with one another to form a Fv). This is distinct from a diabody or higher order multimer in which variable regions from different polypeptide chains associate or bind to one another. For example, the linker comprises in excess of 12 amino acid residues with $(Gly_4Ser)_3$ (i.e., GGGGSGGGGSGGGGS (SEQ ID NO: 53)) being one of the more favored linkers for a scFv.

Exemplary scFvs comprise a $V_H$ sequence set forth in amino acids 1-115 of SEQ ID NO: 55 or amino acids 1-129 of SEQ ID NO: 59 or amino acids 1-120 of SEQ ID NO: 61 or amino acids 1-129 of SEQ ID NO: 109, which are modified to include two or more cysteine residues in FR1 and/or a N-terminal threonine/serine residue. In one example the scFv binds to TAG72 and the $V_H$ comprises a sequence set forth in one of:
(i) amino acids 1-115 of SEQ ID NO: 57;
(ii) amino acids 1-115 of SEQ ID NO: 63;
(iii) amino acids 1-115 of SEQ ID NO: 75;
(iv) amino acids 1-115 of SEQ ID NO: 77; or
(v) amino acids 1-115 of SEQ ID NO: 99;
and the $V_L$ comprises a sequence set forth in one of:
(i) amino acids 121-234 of SEQ ID NO: 57;
(ii) amino acids 121-234 of SEQ ID NO: 63;

(iii) amino acids 121-234 of SEQ ID NO: 75;
(iv) amino acids 121-234 of SEQ ID NO: 77; or
(v) amino acids 121-234 of SEQ ID NO: 99.

In one example, a scFv binds to TAG72 and comprises a sequence set forth in SEQ ID NO: 101.

In another example, the scFv binds to Her2 and the $V_H$ comprises a sequence set forth in one of:
(i) amino acids 1-129 of SEQ ID NO: 65;
(ii) amino acids 1-129 of SEQ ID NO: 87;
(iii) amino acids 1-129 of SEQ ID NO: 89;
(iv) amino acids 1-129 of SEQ ID NO: 91;
(v) amino acids 1-129 of SEQ ID NO: 93; or
(vi) amino acids 1-129 of SEQ ID NO: 97.
and the $V_L$ comprises a sequence set forth in one of:
(i) amino acids 135-245 of SEQ ID NO: 65;
(ii) amino acids 135-245 of SEQ ID NO: 87;
(iii) amino acids 135-245 of SEQ ID NO: 89;
(iv) amino acids 135-245 of SEQ ID NO: 91;
(v) amino acids 135-245 of SEQ ID NO: 93; or
(vi) amino acids 135-245 of SEQ ID NO: 97.

In another example, a scFv binds to HER2 and comprises a sequence set forth in SEQ ID NO: 105.

In a further example, the scFv binds to MUC1 and the $V_H$ comprises a sequence set forth in one of:
(i) amino acids 1-120 of SEQ ID NO: 79;
(ii) amino acids 1-120 of SEQ ID NO: 81;
(iii) amino acids 1-120 of SEQ ID NO: 83;
(iv) amino acids 1-120 of SEQ ID NO: 85; or
(v) amino acids 1-120 of SEQ ID NO: 95.
and the $V_L$ comprises a sequence set forth in one of:
(i) amino acids 126-232 of SEQ ID NO: 79;
(ii) amino acids 126-232 of SEQ ID NO: 81;
(iii) amino acids 126-232 of SEQ ID NO: 83;
(iv) amino acids 126-232 of SEQ ID NO: 85; or
(v) amino acids 126-232 of SEQ ID NO: 95.

The present invention also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv (see, for example, Brinkmann et al., 1993).

Alternatively, or in addition, the present invention provides a dimeric scFv, i.e., a protein comprising two scFv molecules linked by a non-covalent or covalent linkage. Examples of such dimeric scFv include, for example, two scFvs linked to a leucine zipper domain (e.g., derived from Fos or Jun) whereby the leucine zipper domains associate to form the dimeric compound (see, for example, Kostelny 1992 or Kruif and Logtenberg, 1996). Alternatively, two scFvs are linked by a peptide linker of sufficient length to permit both scFvs to form and to bind to an antigen, e.g., as described in US20060263367. In a further example, each scFv is modified to include a cysteine residue, e.g., in the linker region or at a terminus, and the scFvs are linked by a disulfide bond, e.g., as described in Albrecht et al., (2004).

Modified forms of scFv are also contemplated by the present invention, e.g., scFv comprising a linker modified to permit glycosylation, e.g., as described in US623322.

The skilled artisan will be readily able to produce a scFv or modified form thereof comprising a suitable modified $V_H$ and/or $V_L$ according to the present invention based on the disclosure herein. Exemplary sequences of $V_H$ and/or $V_L$ are described herein and are to be taken to apply mutatis mutandis to this embodiment of the invention.

Additional description of scFv is to be found in, for example, U.S. Pat. No. 5,260,203.

Minibodies

The skilled artisan will be aware that a minibody comprises the $V_H$ and $V_L$ domains of an immunoglobulin fused to the $C_H2$ and/or $C_H3$ domain of an immunoglobulin. Optionally, the minibody comprises a hinge region between the $V_H$ and a $V_L$, sometimes this conformation is referred to as a Flex Minibody (Hu et al., 1996). A minibody does not comprise a $C_H1$ or a CL. Preferably, the $V_H$ and $V_L$ domains are fused to the hinge region and the $C_H3$ domain of an immunoglobulin. Each of the regions may be derived from the same immunoglobulin. Alternatively, the $V_H$ and $V_L$ domains can be derived from one immunoglobulin and the hinge and $C_H2/C_H3$ from another, or the hinge and $C_H2/C_H3$ can also be derived from different immunoglobulins. The present invention also contemplates a multispecific minibody comprising a $V_H$ and $V_L$ from one immunoglobulin and a $V_H$ and a $V_L$ from another immunoglobulin. At least one of the variable regions of said minibody comprises cysteine residues in FR1 as described herein.

The skilled artisan will be readily able to produce a minibody of the invention using methods known in the art together with the teaching provided herein.

Based on the foregoing, the skilled artisan will appreciate that minibodies are small versions of whole immunoglobulins encoded in a single protein chain which retain the antigen binding region, the $C_H3$ domain (or a $C_H2$ domain) to permit assembly into a bivalent molecule and the immunoglobulin hinge to accommodate dimerization by disulfide linkages.

Exemplary minibodies and methods for their production are described, for example, in WO94/09817.

Other Variable Region Containing Proteins

U.S. Pat. No. 5,731,168 describes molecules in which the interface between a pair of Fv is engineered to maximize the percentage of heterodimers which are recovered from recombinant cell culture to thereby produce bi-specific proteins. The preferred interface comprises at least a part of a $C_H3$ domain. In this method, one or more small amino acid side chains from the interface of the first protein are replaced with larger side chains {e.g., tyrosine or tryptophan). Compensatory "cavities" of identical or similar size to the large side chain(s) are created on the interface of the second protein by replacing large amino acid side chains with smaller ones (e.g., alanine or threonine).

Bispecific proteins comprising variable regions include cross-linked or "heteroconjugate" proteins. For example, one of the proteins in the heteroconjugate can be coupled to avidin, the other to biotin. Such proteins have, for example, been proposed to target immune system cells to unwanted cells (U.S. Pat. No. 4,676,980). Heteroconjugate proteins comprising variable regions may be made using any convenient cross-linking methods. Suitable cross-linking agents are known in the art, and are disclosed in U.S. Pat. No. 4,676,980, along with a number of cross-linking techniques.

Bispecific proteins comprising variable regions can also be prepared using chemical linkage. Brennan (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific protein.

Progress has facilitated the direct recovery of Fab'-SH fragments from E. coli, which can be chemically coupled to form bispecific proteins comprising variable regions. Shalaby (1992) describe the production of a fully humanized bispecific F(ab')$_2$ molecule. Each Fab' fragment was separately secreted from *E. coli* and subjected to directed chemical coupling in vitro to form the bispecific protein comprising variable regions. The bispecific protein thus formed was able to bind to cells expressing the relevant antigen and normal human T cells, as well as trigger the lytic activity of human cytotoxic lymphocytes against human breast tumour targets.

Additional variable region containing proteins include, for example, domain antibodies (dAbs) and fusions thereof (e.g., as described in U.S. Pat. No. 6,248,516), single chain Fab (e.g., Hust et al., 2007) or a Fab$_3$ (e.g., as described in EP19930302894).

Constant Domain Fusions

The present invention encompasses proteins comprising a variable region and a constant region (e.g., Fc) or a domain thereof, e.g., $C_H2$ and/or $C_H3$ domain. For example, the present invention provides a minibody (as discussed above) or a scFv-Fc fusion or a diabody-Fc fusion or a triabody-Fc fusion or a tetrabody-Fc fusion or a scFc-$C_H2$ fusion or a diabody-$C_H2$ fusion or a triabody-$C_H2$ fusion or a tetrabody-$C_H2$ fusion or a scFv-$C_H3$ fusion or a diabody-$C_H3$ fusion or a triabody-$C_H3$ fusion or a tetrabody-$C_H3$ fusion. Any of these proteins may comprise a linker, preferably an immunoglobulin hinge region, between the variable region and the constant region or constant domain.

As used herein, the term "hinge region" includes the portion of a heavy chain molecule that joins the $C_H1$ domain to the $C_H2$ domain. This hinge region comprises approximately 25 residues and is flexible, thus allowing the two N-terminal antigen binding regions to move independently. Hinge regions can be subdivided into three distinct domains: upper, middle, and lower hinge domains (Roux et al. 1998).

As used herein, the term "$C_H2$ domain" includes the portion of a heavy chain immunoglobulin molecule that extends, e.g., from between about positions 231-340 according to the Kabat EU numbering system. Two N-linked branched carbohydrate chains are generally interposed between the two CH$_2$ domains of an intact native IgG molecule. In one embodiment, a protein of the invention comprises a $C_H2$ domain derived from an IgG1 molecule (e.g. a human IgG1 molecule). In another embodiment, a protein of the invention comprises a $C_H2$ domain derived from an IgG4 molecule (e.g., a human IgG4 molecule).

As used herein, the term "$C_H3$ domain" includes the portion of a heavy chain immunoglobulin molecule that extends approximately 110 residues from N-terminus of the $C_H2$ domain, e.g., from about position 341-446b (Kabat EU numbering system). The $C_H3$ domain typically forms the C-terminal portion of the immunoglobulin. In some immunoglobulins, however, additional domains may extend from $C_H3$ domain to form the C-terminal portion of the molecule (e.g. the $C_H4$ domain in the μ chain of IgM and the e chain of IgE). In one embodiment, a protein of the invention comprises a $C_H3$ domain derived from an IgG1 molecule (e.g., a human IgG1 molecule). In another embodiment, a protein of the invention comprises a $C_H3$ domain derived from an IgG4 molecule (e.g., a human IgG4 molecule).

Constant domain sequences useful for producing the proteins of the present invention may be obtained from a number of different sources. In preferred embodiments, the constant region domain or portion thereof of the protein is derived from a human immunoglobulin. It is understood, however, that the constant region domain or portion thereof may be derived from an immunoglobulin of another mammalian species, including for example, a rodent (e.g. a mouse, rat, rabbit, guinea pig) or non-human primate (e.g. chimpanzee, macaque) species. Moreover, the constant region domain or portion thereof may be derived from any immunoglobulin class, including IgM, IgG, IgD, IgA and IgE, and any immunoglobulin isotype, including IgG1, IgG2, IgG3 and IgG4. In a preferred example, the human isotype IgG1 is used.

A variety of constant region gene sequences (e.g. human constant region gene sequences) are available in the form of publicly accessible deposits or the sequence thereof is available from publicly available databases. Constant region domains can be selected having a particular effector function (or lacking a particular effector function) or with a particular modification to reduce immunogenicity.

As used herein, the term "effector function" refers to the functional ability of the Fc region or portion thereof (e.g., $C_H2$ domain) to bind proteins and/or cells of the immune system and mediate various biological effects. Effector functions may be antigen-dependent or antigen-independent. "Antigen-dependent effector function" refers to an effector function which is normally induced following the binding of an immunoglobulin to a corresponding antigen. Typical antigen-dependent effector functions include the ability to bind a complement protein (e.g. C1q). For example, binding of the C1 component of complement to the Fc region can activate the classical complement system leading to the opsonisation and lysis of cell pathogens, a process referred to as complement-dependent cytotoxicity (CDCC). The activation of complement also stimulates the inflammatory response and may also be involved in autoimmune hypersensitivity. Other antigen-dependent effector functions are mediated by the binding of immunoglobulins, via their Fc region, to certain Fc receptors ("FcRs") on cells. There are a number of Fc receptors which are specific for different classes of immunoglobulin, including IgG (gamma receptors, or IgλRs), IgE (epsilon receptors, or IgεRs), IgA (alpha receptors, or IgαRs) and IgM (mu receptors, or IgμRs). Binding of immunoglobulin to Fc receptors on cell surfaces triggers a number of important and diverse biological responses including endocytosis of immune complexes, engulfment and destruction of immunoglobulin-coated particles or microorganisms (also called antibody-dependent phagocytosis, or ADCP), clearance of immune complexes, lysis of antibody-coated target cells by killer cells (called antibody-dependent cell-mediated cytotoxicity, or ADCC), release of inflammatory mediators, regulation of immune system cell activation, placental transfer and control of immunoglobulin production.

As used herein, the term "antigen-independent effector function" refers to an effector function which may be induced by an immunoglobulin, regardless of whether it has bound its corresponding antigen. Typical antigen-independent effector functions include cellular transport, circulating half-life and clearance rates of immunoglobulins, and facilitation of purification. A structurally unique Fc receptor, the "neonatal Fc receptor" or "FcRn", also known as the salvage receptor, plays a critical role in regulating half-life and cellular transport. Other Fc receptors purified from microbial cells (e.g. Staphylococcal Protein A or G) are capable of binding to the Fc region with high affinity and can be used to facilitate the purification of the Fc-containing protein.

Constant region domains can be cloned, e.g., using the polymerase chain reaction and primers which are selected to amplify the domain of interest. The cloning of immunoglobulin sequences is described in for example, in U.S. Pat. No. 5,658,570.

The protein of the invention may comprise any number of constant region domains of different types.

The constant region domains or portions thereof making up the constant region of a protein may be derived from different immunoglobulin molecules. For example, a protein may comprise a $C_H2$ domain or portion thereof derived from an IgG1 molecule and a $C_H3$ region or portion thereof derived from an IgG3 molecule.

In another example of the invention, the protein of the invention comprises at least a region of an Fc sufficient to confer FcRn binding. For example, the portion of the Fc region that binds to FcRn comprises from about amino acids 282-438 of IgG1, according to Kabat numbering.

In one example, a protein of the invention comprises an altered synthetic constant region wherein or more constant region domains therein are partially or entirely deleted ("domain-deleted constant regions"). The present invention also encompasses modified Fc regions or parts there having altered, e.g., improved or reduced effector function. Many such modified Fc regions are known in the art and described, for example, in U.S. Pat. No. 7,217,797; U.S. Pat. No. 7,217,798; or US20090041770 (having increased half-life) or US2005037000 (increased ADCC).

Mutations to Proteins

The present invention contemplates the use of mutant forms of a protein of the invention. For example, such a mutant polypeptide comprises one or more conservative amino acid substitutions compared to a sequence set forth herein. In some examples, the polypeptide comprises 10 or fewer, e.g., 9 or 8 or 7 or 6 or 5 or 4 or 3 or 2 conservative amino acid substitutions. A "conservative amino acid substitution" is one in which the amino acid residue is replaced with an amino acid residue having a similar side chain and/or hydropathicity and/or hydrophilicity.

In a preferred example, a mutant protein has only, or not more than, one or two or three or four conservative amino acid changes when compared to a naturally occurring protein. Details of conservative amino acid changes are provided below. As the skilled person would be aware, such minor changes can reasonably be predicted not to alter the activity of the polypeptide when expressed in a recombinant cell Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine).

The present invention also contemplates one or more insertions or deletions compared to a sequence set forth herein. In some examples, the polypeptide comprises 10 or fewer, e.g., 9 or 8 or 7 or 6 or 5 or 4 or 3 or 2 insertions and/or deletions.

Positioning of Cysteine Residues

The present invention contemplates positioning of cysteine residues in FR1 at any site as described herein in any embodiment or example.

In one example, the present invention provides an isolated protein comprising an immunoglobulin variable region comprising at least two cysteine residues positioned within framework region (FR)1, wherein the cysteine residues are positioned such that at least one of the residues is capable of being conjugated to a compound and wherein if at least one of the cysteine residues is not conjugated to a compound a disulphide bond is capable of forming between the cysteine residues.

In another example, the present invention provides an isolated protein comprising an immunoglobulin variable region comprising at least two cysteine residues positioned within framework region (FR)1, wherein the cysteine residues are positioned such that at least one of the residues is capable of being conjugated to a compound and wherein if at least two of the cysteine residues are not conjugated to a compound a disulphide bond is capable of forming between the cysteine residues.

In an alternative or additional example, the present invention provides an isolated protein comprising an immunoglobulin heavy chain variable region ($V_H$) and an immunoglobulin light chain variable region ($V_L$), wherein at least one of the variable regions comprises at least two cysteine residues positioned within framework region (FR)1, wherein the cysteine residues are positioned such that at least one of the residues is capable of being conjugated to a compound and wherein if at least one of the cysteine residues is not conjugated to another compound a disulphide bond is capable of forming between the cysteine residues.

In an alternative or additional example, the present invention provides an isolated protein comprising an immunoglobulin heavy chain variable region ($V_H$) and an immunoglobulin light chain variable region ($V_L$), wherein at least one of the variable regions comprises at least two cysteine residues positioned within framework region (FR)1, wherein the cysteine residues are positioned such that at least one of the residues is capable of being conjugated to a compound and wherein if at least two of the cysteine residues are not conjugated to another compound a disulphide bond is capable of forming between the cysteine residues.

In each of the above examples of the invention, it is preferable that at least two or the at least two cysteine residues are positioned such that they are capable of being conjugated to a compound.

In one example of the invention, the cysteine residues are positioned within a loop region of FR1 As used herein, the term "loop region of FR1" shall be taken to mean a sequence of amino acids within FR1 that is provides flexibility for two regions and/or two amino acids of FR1 to associate with or bind to one another (e.g., by virtue of a hydrogen bond), e.g., that provides sufficient flexibility for two amino acids in a beta sheet to associate with or bind to one another. A loop region of FR1 is not part of the CDR1.

In another example, the cysteine residues in a FR1 are positioned so as to permit formation of a disulfide bond between the residues.

By "positioned so as to permit formation of a disulphide bond" shall be understood to mean that two cysteine residues are positioned within a protein such that when the protein folds they are sufficiently close for a disulphide bond to be formed between the residues. For example, the distance between two carbon atoms in two cysteine residues may be within about 6-7 Å of one another or 2-9 Å of one another, such as about 3.5-6.8 Å of one another, e.g., about 4 Å of one another. Methods for predicting the proximity of residues in a protein and/or predicting the likelihood of disulphide bond formation will be apparent to the skilled artisan and/or described herein.

Thus, in one example, a protein of the invention comprises at least two cysteine residues positioned within framework region (FR)1, wherein the cysteine residues are within about 2-9 Å of one another, preferably, within about 6-7 Å of one another.

In another example, the cysteine residues are positioned at residues in a protein at which their side chains will be exposed to solvent. Methods for determining solvent exposure or solvent accessible surface area are known in the art and include, for example, the Shrake-Rupley algorithm or the LCPO method.

Thus in another example, a protein of the invention comprises at least two cysteine residues positioned within framework region (FR)1, wherein the cysteine residues are positioned such that their side chains (preferably their thiol groups) are exposed to solvent.

By "exposed to solvent" shall be understood to mean that the side chains of the cysteine residues are on the surface of a protein when folded such that they are capable of being in contact with a solvent in which the protein is present or suspended. Preferably, at least one (or one or both) of the side chains are sufficiently exposed to solvent such that a compound can be conjugated thereto.

Preferably, the protein of the invention comprises at least two cysteine residues positioned at one or more of, preferably two or more of, preferably all of:
(i) positioned such that their side chains are angled towards one another;
(ii) positioned such that their side chain atoms are exposed to solvent; and/or
(iii) positioned such that their C$\alpha$ carbon atoms are about 6-7 Å of one another.

The proteins of the present invention (as described herein according to any one or more example of the invention) thus provide at least two cysteine residues positioned within framework region 1 (FR1) that can form a disulphide bond within FR1 and which can alternatively be reduced for stoichiometric conjugation of compounds. These products of the invention have an advantage over other cysteine conjugation strategies that do not provide at least two cysteine residues positioned within framework region (FR) 1 that can form a disulphide bond within FR1. These prior and ineffective strategies include single cysteine residues (Kim et al., 2008), C-terminal cysteine residues (Sirk et al., 2008) and single cysteine residues in intact antibodies (Junutula et al., 2008) all of which result in poor expression yield, variable conjugation and complications for large scale processing. Furthermore, antibodies that are conjugated on cysteine residues by partial reduction of interchain-disulfide bonds have variable stoichiometry (zero to eight drugs per antibody) and potentially yield>100 species (Junutula et al., 2008).

Methods for predicting loops and/or the position of residues within a folded protein will be apparent to the skilled artisan and include in silico methods. For example, structural features of a protein are determined using appropriate software available on the website of the National Center for Biotechnology Information (NCBI) at the National Institutes of Health, 8600 Rockville Pike, Bethesda Md. 20894 such as, for example, through the NCBI Molecules Modelling Database (MMDB) including three-dimensional biomolecular structures determined using X-ray crystallography and/or NMR spectroscopy. The NCBI conserved domain database (CDD) includes domains from the known Smart and Pham collections, with links to a 3D-structure viewer (Cn3D). The NCBI Conserved Domain Architecture Retrieval Tool (CDART) uses precalculated domain assignments to neighbor proteins by their domain architecture.

Additional methods for predicting protein or peptide secondary structure are known in the art and/or described, for example, in Moult, 1996; Chou et al., 1974; Chou et al., 1974; Chou et al., 1978; Chou et al., 1978; or Chou et al., 1979.

Additionally, computer programs are currently available to assist with predicting secondary structure of a protein or peptide. One such method of predicting secondary structure is based upon homology modeling. For example, two proteins that have a sequence identity of greater than 30%, or similarity greater than 40%, often have similar structural topologies. The recent growth of the protein structural database (PDB) has provided enhanced predictability of secondary structure, including the potential number of folds within the structure of a protein (Holm et al., 1999). For example, methods for determining the structure of a protein are described, for example, in US20020150906, or using a computer program or algorithm, such as, for example, MODELLER, (Sali and Blundell, 1993). These techniques rely upon aligning the sequence of a protein with the sequences of proteins that have a characterized structure. Such alignment algorithms are known in the art and are accessed through software packages such as, for example BLAST at NCBI. Structural information, i.e., three-dimensional structure, of a query protein is then be predicted based upon structural information corresponding to the sequence or subsequences aligned in the proteins or peptides that have previously been characterized. In this way it is possible to generate a library of three-dimensional structures of proteins corresponding to a FR1 region of an immunoglobulin.

Additional methods of predicting secondary structure include, for example, "threading" (Jones, 1996), "profile analysis" (Bowie et al., 1991; Gribskov et al., 1990; Gribskov et al., 1989), and "evolutionary linkage". Conventional threading of protein sequence is used to predict the 3D structure scaffold of a protein. Typically, threading is a process of assigning the folding of the protein by threading (or comparing) its sequence to a library of potential structural templates (e.g., known structures of Fv or Fabs or FR1) by using a scoring function that incorporates the sequence as well as the local parameters such as secondary structure and solvent exposure (Rost et al. 1997; Xu and Xu 2000; and Panchenko et al. 2000). For example, the threading process starts from prediction of the secondary structure of the amino acid sequence and solvent accessibility for each residue of the query sequence. The resulting one-dimensional (1D) profile of the predicted structure is threaded into each member of a library of known 3D structures. The optimal threading for each sequence-structure pair is obtained using dynamic programming. The overall best sequence-structure pair constitutes the predicted 3D structure for the query sequence. Threading is made relatively simple in the present case because of the number of Fv and Fab fragments of immunoglobulins for which the secondary structure has been solved.

In the case of proteins comprising more than two cysteine residues, it is preferred that an even number of cysteine resides are included, e.g., 4 or 6 or 8 or 10 cysteine residues are included. For example, the cysteine residues are paired, i.e., combinations of two residues are arranged such that a disulphide bond can form between them.

Preferably, a protein of the invention does not comprise a free thiol in FR1 under non-reducing conditions and/or does not comprise a cysteine residue that is not linked to another cysteine residue or to a compound under non-reducing conditions.

Protein Production

Mutagenesis

DNA encoding a protein comprising a variable region is isolated using standard methods in the art. For example, primers are designed to anneal to conserved regions within a variable region that flank the region of interest, and those primers are then used to amplify the intervening nucleic acid, e.g., by PCR. Suitable methods and/or primers are known in the art and/or described, for example, in Borrebaeck (ed), 1995 and/or Froyen et al., 1995. Suitable sources of template DNA for such amplification methods is derived from, for example, hybridomas, transfectomas and/or cells expressing proteins comprising a variable region, e.g., as described herein.

Following isolation, the DNA is modified to include cysteine residues at the requisite locations by any of a variety of methods known in the art. These methods include, but are not limited to, preparation by site-directed (or oligonucleotide-mediated) mutagenesis, PCR mutagenesis, and cassette mutagenesis of an earlier prepared DNA encoding the protein. Variants of recombinant proteins may be constructed also by restriction fragment manipulation or by overlap extension PCR with synthetic oligonucleotides. Mutagenic primers encode the cysteine codon replacement(s), for example include residues that make up a codon encoding cysteine (i.e., TGT or TGC). Standard mutagenesis techniques can be employed to generate DNA encoding such mutant DNA. General guidance can be found in Sambrook et al 1989; and/or Ausubel et al 1993.

Site-directed mutagenesis is one method for preparing substitution variants, i.e. mutant proteins. This technique is known in the art (see for example, Carter et al 1985; Ho et al 1989; and Kunkel 1987). Briefly, in carrying out site-directed mutagenesis of DNA, the starting DNA is altered by first hybridizing an oligonucleotide encoding the desired mutation (e.g., insertion of one or more cysteine encoding codons) to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA. Site-directed mutagenesis may be carried out within the gene expressing the protein to be mutagenized in an expression plasmid and the resulting plasmid may be sequenced to confirm the introduction of the desired cysteine replacement mutations. Site-directed protocols and formats include commercially available kits, e.g. QuikChange® Multi Site-Directed Mutagenesis Kit (Stratagene, La Jolla, Calif.).

PCR mutagenesis is also suitable for making amino acid sequence variants of the starting protein. See Higuchi, 1990; Ito et al 1991; Bernhard et al 1994; and Vallette et al 1989. Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al, 1985. The starting material is the plasmid (or other vector) comprising the starting protein DNA to be mutated. The codon(s) in the starting DNA to be mutated are identified. There must be a unique restriction endonuclease site on each side of the identified mutation site(s). If no such restriction sites exist, they may be generated using the above described oligonucleotide-mediated mutagenesis method to introduce them at appropriate locations in the starting DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence. Mutant DNA containing the encoded cysteine replacements can be confirmed by DNA sequencing.

Single mutations are also generated by oligonucleotide directed mutagenesis using double stranded plasmid DNA as template by PCR based mutagenesis (Sambrook and Russel, 2001; Zoller et al 1983; Zoller and Smith, 1982).

Recombinant Expression

In the case of a recombinant protein, nucleic acid encoding same is preferably placed into expression vectors, which are then transfected into host cells, preferably cells that can produce a disulphide bridge or bond, such as $E.\ coli$ cells, yeast cells, insect cells, or mammalian cells, such as simian COS cells, Chinese Hamster Ovary (CHO) cells, or myeloma cells that do not otherwise produce immunoglobulin protein, to obtain the synthesis of proteins in the recombinant host cells. Review articles on recombinant expression in bacteria of DNA encoding the immunoglobulin include Skerra et al, (1993) and Plückthun, (1992). Molecular cloning techniques to achieve these ends are known in the art and described, for example in Ausubel or Sambrook. A wide variety of cloning and in vitro amplification methods are suitable for the construction of recombinant nucleic acids. Methods of producing recombinant immunoglobulins are also known in the art. See U.S. Pat. No. 4,816,567; U.S. Pat. No. 5,225,539, U.S. Pat. No. 6,054,297, U.S. Pat. No. 7,566,771 or U.S. Pat. No. 5,585,089.

Following isolation, the nucleic acid encoding a protein of the invention is preferably inserted into an expression construct or replicable vector for further cloning (amplification of the DNA) or for expression in a cell-free system or in cells. Preferably, the nucleic acid is operably linked to a promoter, As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Preferred promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Cell free expression systems are also contemplated by the present invention. For example, a nucleic acid encoding a protein of the invention is operably linked to a suitable promoter, e.g., a T7 promoter, and the resulting expression construct exposed to conditions sufficient for transcription and translation. Typical expression vectors for in vitro expression or cell-free expression have been described and include, but are not limited to the TNT T7 and TNT T3 systems (Promega), the pEXP1-DEST and pEXP2-DEST vectors (Invitrogen).

Many vectors for expression in cells are available. The vector components generally include, but are not limited to, one or more of the following: a signal sequence, a sequence encoding protein of the present invention (e.g., derived from the information provided herein), an enhancer element, a promoter, and a transcription termination sequence. The skilled artisan will be aware of suitable sequences for expression of a protein. For example, exemplary signal sequences include prokaryotic secretion signals (e.g., pelB, alkaline phosphatase, penicillinase, Ipp, or heat-stable enterotoxin II), yeast secretion signals (e.g., invertase leader, α factor leader, or acid phosphatase leader) or mammalian secretion signals (e.g., herpes simplex gD signal).

Exemplary promoters include those active in prokaryotes (e.g., phoA promoter, β-lactamase and lactose promoter systems, alkaline phosphatase, a tryptophan (trp) promoter system, and hybrid promoters such as the tac promoter). These promoter are useful for expression in prokaryotes including eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. Preferably, the host is *E. coli*. One preferred *E. coli* cloning host is *E. coli* 294 (ATCC 31,446), although other strains such as *E. coli* B, *E. coli* X 1776 (ATCC 31,537), and *E. coli* W3110 (ATCC 27,325), DH5α or DH10B are suitable.

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Typical promoters suitable for expression in insect cells include, but are not limited to, the OPEI2 promoter, the insect actin promoter isolated from *Bombyx muri*, the *Drosophila* sp. dsh promoter (Marsh et al 2000) and the inducible metallothionein promoter. Preferred insect cells for expression of recombinant proteins include an insect cell selected from the group comprising, BT1-TN-5B1-4 cells, and *Spodoptera frugiperda* cells (e.g., sf19 cells, sf21 cells). Suitable insects for the expression of the nucleic acid fragments include but are not limited to *Drosophila* sp. The use of *S. frugiperda* is also contemplated.

Means for introducing the isolated nucleic acid molecule or a gene construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., WI, USA) amongst others.

The host cells used to produce the protein of this invention may be cultured in a variety of media, depending on the cell type used. Commercially available media such as Ham's F10 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

Isolation of Proteins

A protein of the present invention is preferably isolated. By "isolated" is meant that the protein is substantially purified or is removed from its naturally-occurring environment, e.g., is in a heterologous environment. By "substantially purified" is meant the protein is substantially free of contaminating agents, e.g., at least about 70% or 75% or 80% or 85% or 90% or 95% or 96% or 97% or 98% or 99% free of contaminating agents.

Methods for purifying a protein of the invention are known in the art and/or described herein.

When using recombinant techniques, the protein of the invention can be produced intracellularly, in the periplasmic space, or directly secreted into the medium. If the protein is produced intracellularly, as a first step, the particulate debris, either host cells or lysed fragments, is removed, for example, by centrifugation or ultrafiltration. Carter et al. (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the protein is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein prepared from the cells can be purified using, for example, hydroxyl apatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the protein (if present at all). Protein A can be used to purify immunoglobulins that are based on human γ1, γ2, or γ4 heavy chains (Lindmark et al. 1983). Protein G is recommended for all mouse isotypes and for human γ3 (Guss et al. 1986). Otherwise affinity purification can be performed using the antigen or epitopic determinant to which a variable region in a protein of the invention binds or was raised. The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the protein to be recovered.

The skilled artisan will also be aware that a protein of the invention can be modified to include a tag to facilitate purification or detection, e.g., a poly-histidine tag, e.g., a hexahistidine tag, or a influenza virus hemagglutinin (HA) tag, or a Simian Virus 5 (V5) tag, or a FLAG tag, or a glutathione S-transferase (GST) tag. Preferably, the tag is a hexa-his tag. The resulting protein is then purified using methods known in the art, such as, affinity purification. For example, a protein comprising a hexa-his tag is purified by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in a addition a ligand or antibody that binds to a tag is used in an affinity purification method.

Following any preliminary purification step(s), the mixture comprising the protein of the invention and contaminants may be subjected to low pH hydrophobic interaction chromatography.

Protein Synthesis

A protein of the present invention is readily synthesized from its determined amino acid sequence using standard techniques, e.g., using BOC or FMOC chemistry. Synthetic peptides are prepared using known techniques of solid phase, liquid phase, or peptide condensation, or any combination thereof, and can include natural and/or unnatural amino acids. Amino acids used for peptide synthesis may be standard Boc (Nα-amino protected Nα-t-butyloxycarbonyl) amino acid resin with the deprotecting, neutralization, coupling and wash protocols of the original solid phase procedure of Merrifield, 1963, or the base-labile Nα-amino protected 9-fluorenylmethoxycarbonyl (Fmoc) amino acids described by Carpino and Han, 1972. Both Fmoc and Boc Nα-amino protected amino acids can be obtained from various commercial sources, such as, for example, Fluka, Bachem, Advanced Chemtech, Sigma, Cambridge Research Biochemical, Bachem, or Peninsula Labs.

Conjugates

The present invention also provides conjugates of proteins described herein according to any embodiment. Examples of compounds to which a protein can be conjugated are the compound is selected from the group consisting of a radioisotope, a detectable label, a therapeutic compound, a colloid, a toxin, a nucleic acid, a peptide, a protein, a compound that increases the half life of the protein in a subject and mixtures thereof. Exemplary therapeutic agents include, but are not limited to an anti-angiogenic agent, an anti-neovascularization and/or other vascularization agent, an anti-proliferative agent, a pro-apoptotic agent, a chemotherapeutic agent or a therapeutic nucleic acid.

A toxin includes any agent that is detrimental to (e.g., kills) cells. For a description of these classes of drugs which are known in the art, and their mechanisms of action, see Goodman et al., Goodman and Gilman's The Pharmacological Basis of Therapeutics, 8th Ed., Macmillan Publishing Co., 1990. Additional techniques relevant to the preparation of immunoglobulin-immunotoxin conjugates are provided in for instance Vitetta (1993) and U.S. Pat. No. 5,194,594. Exemplary toxins include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232.

Suitable chemotherapeutic agents for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-de-hydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)).

Examples of suitable angiogenesis inhibitors (anti-angiogenic agents) include, but are not limited to, urokinase inhibitors, matrix metalloprotease inhibitors (such as marimastat, neovastat, BAY 12-9566, AG 3340, BMS-275291 and similar agents), inhibitors of endothelial cell migration and proliferation (such as TNP-470, squalamine, 2-methoxyestradiol, combretastatins, endostatin, angiostatin, penicillamine, SCH66336 (Schering-Plough Corp, Madison, N.J.), R115777 (Janssen Pharmaceutica, Inc, Titusville, N.J.) and similar agents), antagonists of angiogenic growth factors (such as such as ZD6474, SU6668, antibodies against angiogenic agents and/or their receptors (such as VEGF, bFGF, and angiopoietin-1), thalidomide, thalidomide analogs (such as CC-5013), Sugen 5416, su5402, antiangiogenic ribozyme (such as angiozyme), interferon α (such as interferon α2a), suramin and similar agents), VEGF-R kinase inhibitors and other anti-angiogenic tyrosine kinase inhibitors (such as SU011248), inhibitors of endothelial-specific integrin/survival signaling (such as vitaxin and similar agents), copper antagonists/chelators (such as tetrathiomolybdate, captopril and similar agents), carboxyamido-triazole (CAI), ABT-627, CM101, interleukin-12 (IL-12), IM862, PNU145156E as well as nucleotide molecules inhibiting angiogenesis (such as antisense-VEGF-cDNA, cDNA coding for angiostatin, cDNA coding for p53 and cDNA coding for deficient VEGF receptor-2) and similar agents. Other examples of inhibitors of angiogenesis, neovascularization, and/or other vascularization are anti-angiogenic heparin derivatives and related molecules (e.g., heperinase III), temozolomide, NK4, macrophage migration inhibitory factor (MIF), cyclooxygenase-2 inhibitors, inhibitors of hypoxia-inducible factor 1, anti-angiogenic soy isoflavones, oltipraz, fumagillin and analogs thereof, somatostatin analogues, pentosan polysulfate, tecogalan sodium, dalteparin, tumstatin, thrombospondin, NM-3, combrestatin, canstatin, avastatin, antibodies against other relevant targets (such as anti-alpha-v/beta-3 integrin and anti-kininostatin mAbs) and similar agents.

In one example, a protein as described herein according to any embodiment is conjugated or linked to another protein, including another protein of the invention or a protein comprising an immunoglobulin variable region, such as an immunoglobulin or a protein derived therefrom, e.g., as described herein. Other proteins are not excluded. Additional proteins will be apparent to the skilled artisan and include, for example, an immunomodulator or a half-life extending protein or a peptide or other protein that binds to serum albumin amongst others.

Exemplary immunomodulators include cytokines and chemokines. The term "cytokine" is a generic term for proteins or peptides released by one cell population which act on another cell as intercellular mediators. Examples of cytokines include lymphokines, monokines, growth factors and traditional polypeptide hormones. Included among the cytokines are growth hormones such as human growth hormone, N-methionyl human growth hormone, and bovine growth hormone; parathyroid hormone, thyroxine, insulin, proinsulin, relaxin, prorelaxin, glycoprotein hormones such as follicle stimulating hormone (FSH), thyroid stimulating hormone (TSH) and luteinizing hormone (LH), hepatic growth factor; prostaglandin, fibroblast growth factor, prolactin, placental lactogen, OB protein, tumour necrosis factor-α and -β; mullerian-inhibiting substance, gonadotropin-associated peptide, inhibin, activin, vascular endothelial growth factor, integrin, thrombopoietin (TPO), nerve growth factors such as NGF-B, platelet-growth factor, transforming growth factors (TGFs) such as TGF-α and TGF-β, insulin-like growth factor-I or -II, erythropoietin (EPO), osteoinductive factors, interferons such as interferon-α, -β, or -γ; colony stimulating factors (CSFs) such as macrophage-CSF (M-CSF), granulocyte-macrophage-CSF (GM-CSF); and granulocyte-CSF (G-CSF), interleukins (ILs) such as IL-1, IL-1α, IL-2, IL-3, IL-4, IL-5, IL-6, IL-7, IL-8, IL-9, IL-IO5 IL-I1, IL-12; IL-13, IL-14, IL-15, IL-16, IL-17, IL-18, IL-21 and LIF.

Chemokines generally act as chemoattractants to recruit immune effector cells to the site of chemokine expression. Chemokines include, but are not limited to, RANTES, MCAF, M1P1-alpha or MIP1-Beta. The skilled artisan will recognize that certain cytokines are also known to have chemoattractant effects and could also be classified under the term chemokines.

Exemplary serum albumin binding peptides or protein are described in US20060228364 or US20080260757.

A variety of radionuclides are available for the production of radioconjugated proteins. Examples include, but are not limited to, low energy radioactive nuclei (e.g., suitable for diagnostic purposes), such as $^{13}C$, $^{15}N$, $^{2}H$, $^{125}I$, $^{123}I$, $^{99}Tc$, $^{43}K$, $^{52}Fe$, $^{67}Ga$, $^{68}Ga$, $^{111}In$ and the like. Preferably, the radionuclide is a gamma, photon, or positron-emitting radionuclide with a half-life suitable to permit activity or detection after the elapsed time between administration and localization to the imaging site. The present invention also encompasses high energy radioactive nuclei (e.g., for therapeutic purposes) such as $^{125}I$, $^{131}I$, $^{123}I$, $^{111}In$, $^{105}Rh$, $^{153}Sm$, $^{67}Cu$, $^{67}Ga$, $^{166}Ho$, $^{141}Lu$, $^{186}Re$ and $^{188}Re$. These isotopes typically produce high energy α- or β-particles which have a short path length. Such radionuclides kill cells to which they are in close proximity, for example neoplastic cells to which the conjugate has attached or has entered. They have little or no effect on non-localized cells and are essentially non-immunogenic. Alternatively, high-energy isotopes may be generated by thermal irradiation of an otherwise stable isotope, for example as in boron neutron-capture therapy (Guan et al., 1998).

In another embodiment, the protein is conjugated to a "receptor" (such as streptavidin) for utilization in cell pretargeting wherein the conjugate is administered to the patient, followed by removal of unbound conjugate from the circulation using a clearing agent and then administration of a "ligand" (e.g., avidin) that is conjugated to a therapeutic agent (e.g., a radionucleotide).

The proteins of the present invention can be modified to contain additional nonproteinaceous moieties that are known in the art and readily available. Preferably, the moieties suitable for derivatization of the protein are water soluble polymers. Non-limiting examples of water soluble polymers include, but are not limited to, polyethylene glycol (PEG), polyvinyl alcohol (PVA), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol (PPG) homopolymers, prolypropylene oxide/ethylene oxide co-polymers, polyoxyethylated polyols (e.g., glycerol; POG), polyvinyl alcohol, and mixtures thereof. Polyethylene glycol propionaldehyde may have advantages in manufacturing due to its stability in water.

The polymer molecules are typically characterized as having for example from about 2 to about 1000, or from about 2 to about 300 repeating units.

For example water-soluble polymers, including but not limited to PEG, poly(ethylene oxide) (PEO), polyoxyethylene (POE), polyvinyl alcohols, hydroxyethyl celluloses, or dextrans, are commonly conjugated to proteins to increase stability or size, etc., of the protein.

PEG, PEO or POE refers to an oligomer or polymer of ethylene oxide. In the case of PEG, these oligomers or polymers are produced by, e.g., anionic ring opening polymerization of ethylene oxide initiated by nucleophilic attack of a hydroxide ion on the epoxide ring. One of the more useful forms of PEG for protein modification is monomethoxy PEG (mPEG).

Preferred PEGs are monodisperse or polydisperse, preferably monodisperse. The skilled artisan will be aware that PEG can be polydisperse or monodisperse. Polydisperse PEG comprises a mixture of PEGs having different molecular weights. In the case of polydisperse PEGs, reference to a specific molecular weight will be understood to refer to the number average molecular weight of PEGs in the mixture. The size distribution is characterized statistically by its weight average molecular weight (MW) and its number average molecular weight (Mn), the ratio of which is called the polydispersity index (Mw/Mn). MW and Mn are measured, in certain aspects, by mass spectroscopy. Most of the PEG-protein conjugates, particularly those conjugated to PEG larger than 1 KD, exhibit a range of molecular weights due to a polydisperse nature of the parent PEG molecule. For example, in case of mPEG2K (Sunbright ME-020HS, NOF), actual molecular masses are distributed over a range of 1.5~3.0 KD with a polydispersity index of 1.036.

Based on the foregoing, the skilled artisan will be aware that monodisperse PEG comprises a mixture of PEGs comprising substantially the same molecular weight. Monodisperse PEGs are commercially available, e.g., from Polypure AS, Norway.

The average or preferred molecular weight of the PEG will range from about 500 Da to about 200 kDa. For example, the molecular weight of the PEG is from about 1 to about 100 kDa, from about 1.5 to about 50 kDa, from about 1.5 to about 10 kDa, from about 1.5 kDa to about 5 kDa, from about 1.5 kDa to about kDa, from about 1.5 to about 2 kDa.

Preferably, the PEG is monodisperse and has a molecular weight of about 500 Da. Preferably, the PEG has a molecular weight of about 1.5 kDa. Preferably, the PEG has a molecular weight of about 2 kDa.

Preferably, the PEG comprises a reactive group, such as a maleimide group. Preferably, the PEG is $PEG_{24}$-maleimide.

The physiologically acceptable polymer molecule is not limited to a particular structure and is, in various aspects, linear (e.g. alkoxy PEG or bifunctional PEG), branched or multi-armed (e.g. forked PEG or PEG attached to a polyol core), dentritic, or with degradable linkages. Moreover, the internal structure of the polymer molecule is organized in any number of different patterns and is selected from the group consisting of homopolymer, alternating copolymer, random copolymer, block copolymer, alternating tripolymer, random tripolymer, and block tripolymer.

The number of polymers attached to the protein may vary, and if more than one polymer is attached, they can be the same or different molecules. In general, the number and/or type of polymers used for derivatization can be determined based on considerations including, but not limited to, the particular properties or functions of the protein to be improved, whether the protein derivative will be used in a therapy under defined conditions, etc.

The skilled artisan will be aware that prior to conjugation to a protein a polymer (e.g., PEG) may need to be activated by preparing a derivative having a functional group at one or both termini.

Particularly preferred compounds for conjugation to the protein of the present invention are set out in Table 1.

TABLE 1

Preferred compounds for conjugation

| Group | Detail |
|---|---|
| Radioisotopes (either directly or indirectly) | $^{123}$I, $^{125}$I, $^{130}$I, $^{133}$I, $^{135}$I, $^{47}$Sc, $^{72}$As, $^{72}$Sc, $^{90}$Y, $^{88}$Y, $^{97}$Ru, $^{100}$Pd, $^{101m}$Rh, $^{101m}$Rh, $^{119}$Sb, $^{128}$Ba, $^{197}$Hg, $^{211}$At, $^{212}$Bi, $^{153}$Sm, $^{169}$Eu, $^{212}$Pb, $^{109}$Pd, $^{111}$In, $^{67}$Gu, $^{68}$Gu, $^{67}$Cu, $^{75}$Br, $^{76}$Br, $^{77}$Br, $^{99m}$Tc, $^{11}$C, $^{13}$N, $^{15}$O, $^{18}$I, $^{188}$Rc, $^{203}$Pb, $^{64}$Cu, $^{105}$Rh, $^{198}$Au, $^{199}$Ag or $^{177}$Lu |
| Half life extenders | Polyethylene glycol<br>Glycerol<br>Glucose |
| Fluorescent probes | Phycoerythrin (PE)<br>Allophycocyanin (APC)<br>Alexa Fluor 488<br>Cy5.5 |
| Biologics | Fluorescent proteins such as Renilla luciferase, GFP<br>Immune modulators<br>Toxins<br>An Immunoglobulin<br>Half life extenders such as albumin |
| Chemo-therapeutics | Taxol<br>5-FU<br>Doxorubicin<br>Idarubicin |

In one example of the invention, a spacer moiety is included between the compound and the protein to which it is conjugated. The spacer moieties of the invention may be cleavable or non-cleavable. For example, the cleavable spacer moiety is a redox-cleavable spacer moiety, such that the spacer moiety is cleavable in environments with a lower redox potential, such the cytoplasm and other regions with higher concentrations of molecules with free sulfhydryl groups. Examples of spacer moieties that may be cleaved due to a change in redox potential include those containing disulfides. The cleaving stimulus can be provided upon intracellular uptake of the conjugated protein where the lower redox potential of the cytoplasm facilitates cleavage of the spacer moiety.

In another example, a decrease in pH causes cleavage of the spacer to thereby release of the compound into a target cell. A decrease in pH is implicated in many physiological and pathological processes, such as endosome trafficking, tumour growth, inflammation, and myocardial ischemia. The pH drops from a physiological 7.4 to 5-6 in endosomes or 4-5 in lysosomes. Examples of acid sensitive spacer moieties which may be used to target lysosomes or endosomes of cancer cells, include those with acid-cleavable bonds such as those found in acetals, ketals, orthoesters, hydrazones, trityls, cis-aconityls, or thiocarbamoyls (see for example, U.S. Pat. Nos. 4,569,789, 4,631,190, 5,306,809, and 5,665,358). Other exemplary acid-sensitive spacer moieties comprise dipeptide sequences Phe-Lys and Val-Lys.

Cleavable spacer moieties may be sensitive to biologically supplied cleaving agents that are associated with a particular target cell, for example, lysosomal or tumour-associated enzymes. Examples of linking moieties that can be cleaved enzymatically include, but are not limited to, peptides and esters. Exemplary enzyme cleavable linking moieties include those that are sensitive to tumour-associated proteases such as Cathepsin B or plasmin. Cathepsin B cleavable sites include the dipeptide sequences valine-citrulline and phenylalanine-lysine.

Conjugation Methods
Conjugation to Cysteine (Thiol)

Various methods are known in the art for conjugating a compound to a cysteine residue are known in the art and will be apparent to the skilled artisan. Reagents for such conjugation typically bear reactive functionality which may react (i) directly with a cysteine thiol of a cysteine to form the labelled protein, (ii) with a linker reagent to form a linker-label intermediate, or (iii) with a linker protein to form the labelled protein. In the case of a linker several routes, employing organic chemistry reactions, conditions, and reagents are known to those skilled in the art, including: (1) reaction of a cysteine group of the protein of the invention with a linker reagent, to form a protein-linker intermediate, via a covalent bond, followed by reaction with an activated compound; and (2) reaction of a nucleophilic group of a compound with a linker reagent, to form compound-linker intermediate, via a covalent bond, followed by reaction with a cysteine group of a protein of the invention. As will be apparent to the skilled artisan from the foregoing, bifunctional linkers are useful in the present invention. For example, the bifunctional linker comprises a thiol modification group for covalent linkage to the cysteine residue(s) and at least one attachment moiety (e.g., a second thiol modification moiety) for covalent or non-covalent linkage to the compound.

A variety of proteins and compounds, (and linkers) can be used to prepare a conjugate of the invention. Cysteine thiol groups are nucleophilic and capable of reacting to form covalent bonds with electrophilic groups on linker reagents or compound-linker intermediates or drugs including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a compound or linker include, but are not limited to amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Preferred labelling reagents include maleimide, haloacetyl, iodoacetamide succinimidyl ester, isothiocyanate, sulfonyl chloride, 2,6-dichlorotriazinyl, pentafluorophenyl ester, and phosphoramidite, although other functional groups can also be used.

Maytansine may, for example, be converted to May-SSCH$_3$, which can be reduced to the free thiol, May-SH, and reacted with a protein of the invention (Chari et al, 1992) to generate a maytansinoid-immunoconjugate with a disulfide linker. Maytansinoid conjugates with disulfide linkers have been reported (WO 04/016801; U.S. Pat. No. 6,884,874; and WO 03/068144). The disulfide linker SPP is constructed with linker reagent N-succinimidyl 4-(2-pyridylthio)pentanoate.

Another exemplary reactive functional group is N-hydroxysuccinimidyl ester (NHS) of a carboxyl group substituent of a compound, e.g. biotin or a fluorescent dye or a toxin or a protein. The NHS ester of the compound may be preformed, isolated, purified, and/or characterized, or it may be formed in situ and reacted with a nucleophilic group of the protein. Typically, the carboxyl form of the compound is activated by reacting with some combination of a carbodiimide reagent, e.g. dicyclohexylcarbodiimide, diisopropylcarbodiimide, or a uronium reagent, e.g. TSTU (O—(N-Succinimidyl)-N,N, N',N'-tetramethyluronium tetrafluoroborate, HBTU (O-benzotriazol-1-yl)-N,N,N',N'-tetramethyluronium hexafluorophosphate), or HATU (O-(7-azabenzotriazol-1-yl)-N,N,N', N'-tetramethyluronium hexafluorophosphate), an activator, such as 1-hydroxy benzotriazole (HOBt), and N-hydroxysuccinimide to give the NHS ester of the compound. In some cases, the compound and the protein, may be coupled by in situ activation of the compound and reaction with the protein to form the conjugate in one step. Other activating and coupling reagents include TBTU (2-(1H-benzotriazo-1-yl)-1-1, 3,3-tetramethyluronium hexafluorophosphate), TFFH(N,N', N',N'-tetramethyluronium 2-fluoro-hexafluorophosphate), PyBOP (benzotriazole-1-yl-oxy-tris-pyrrolidino-phosphonium hexafluorophosphate, EEDQ (2-ethoxy-1-ethoxycarbonyl-1,2-dihydro-quinoline), DCC (dicyclohexylcarbodiimide); DIPCDI (diisopropylcarbodiimide), MSNT (1-(mesitylene-2-sulfonyl)-3-nitro-1H-1,2,4-triazole, and aryl sulfonyl halides, e.g. triisopropylbenzenesulfonyl chloride.

Additional conjugation methods include, for example, the use of maleimides, iodoacetimides or haloacetyl/alkyl halides, aziridne, acryloyl derivatives to react with the thiol of a cysteine to produce a thioeter that is reactive with a compound (e.g., Schelte et al., 2000 (use of maleimides); Reddy et al., 1988 (use of maleimide derivatives); Ramseier and Chang, 1994 (use of iodacetamide); Eisen et al., 1953 (use of 2,4-dinitrobenzeneulfonic acid); Grossman et al., 1981 (use of aziridine); or Yem et al., 1992 (use of acryloyl derivatives). Disulphide exchange of a free thiol with an activated piridyldisulphide is also useful for producing a conjugate (King et al., 1978 and references cited therein, e.g., use of 5-thio-2-nitrobenzoic (TNB) acid). Preferably, a maleimide is used.

With respect to the use of radiolabelled conjugates, proteins of the invention may be directly labelled (such as through iodination) or may be labelled indirectly through the use of a chelating agent. As used herein, the phrases "indirect labelling" and "indirect labelling approach" both mean that a chelating agent is covalently attached to a protein and at least one radionuclide is associated with the chelating agent. Such chelating agents are typically referred to as bifunctional chelating agents as they bind both the protein and the radio-isotope. Exemplary chelating agents comprise 1-isothiocycmatobenzyl-3-methyldiothelene triaminepentaacetic acid ("MX-DTPA") and cyclohexyl diethylenetriamine pentaacetic acid ("CHX-DTPA") derivatives, or DOTA. Linker reagents such as DOTA-maleimide (4-maleimidobutyramidobenzyl-DOTA) can be prepared by the reaction of aminobenzyl-DOTA with A-maleimidobutyric acid (Fluka) activated with isopropylchloroformate (Aldrich), following the procedure of Axworthy et al, (2000). DOTA-maleimide reagents react with free cysteine amino acids of the proteins of the invention and provide a metal complexing ligand thereon (Lewis et al, 1998). Chelating linker labelling reagents such as DOTA-NHS (1,4,7,10-tetraazacyclododecane-1,4,7,10-tetraacetic acid mono (N-hydroxysuccinimide ester) are commercially available (Macrocyclics, Dallas, Tex.).

Prior to linkage it is preferred that the protein of the invention is made reactive for conjugation with linker reagents by treatment with a reducing agent such as DTT (Cleland's reagent, dithiothreitol) or TCEP (tris(2-carboxyethyl)phosphine hydrochloride; Getz et al, 1999; Soltec Ventures, Beverly, Mass.). Disulfide bonds can be re-established between cysteine residues that are not required for linkage with dilute (200 nM) aqueous copper sulfate ($CuSO_4$) at room temperature. Other oxidants, i.e. oxidizing agents, and oxidizing conditions, which are known in the art may be used. Ambient air oxidation is also effective. This mild, partial reoxidation step forms intrachain disulfides efficiently with high fidelity.

Conjugation to Threonine/Serine

Methods are also known in the art for conjugating a compound to a threonine or serine residue. For example, Zhang and Tam (1996) described a method in which carbonyl precursors are derived from the 1,2-aminoalcohols of serine or threonine, which can be selectively and rapidly converted to aldehyde form by periodate oxidation. Reaction of the aldehyde with a 1,2-aminothiol of cysteine in a compound to be attached to a protein of the invention forms a stable thiazolidine product. This method is particularly useful for labelling proteins at N-terminal serine or threonine residues.

PEGylation Methods

Various methods are known in the art for conjugating compounds, e.g., PEG, to a protein. In the case of PEG, the molecule can be activated to facilitate its binding to amines or imidazoles, a carboxylic group, a hydroxyl group or a sulfhydryl group.

For example, Abuchowski et al (1977) activated PEG using cyanuric chloride to produce a PEG dichlorotriazine derivative. This derivative can react with multiple functional nucleophilic functional groups, such as lysine, serine, tyrosine, cysteine and histidine. A modified form of this protocol produced PEG-chlorotriazine, which has lower reactivity and conjugates more selectively with lysine or cysteine residues (Mutsushima et al., 1980).

Two widely used forms of PEG used to conjugate to proteins are succinimidyl carbonate PEG (SC-PEG; Zalipsky et al., 1992) and benzotriazole carbonate PEG (BTC-PEG; U.S. Pat. No. 5,560,234). Both of these compounds react preferentially with lysine residues to form carbamate linkages, however are also known to react with hystidine and tyrosine. SC-PEG is slightly more resistant to hydrolysis than BTC-PEG.

Another PEG useful for conjugating to proteins is PEG-propionaldehyde (U.S. Pat. No. 5,252,714). An advantage of this chemistry is that under acidic conditions (about pH5) it is largely selective for N-terminal α-amine thus avoiding potential problems with non-specific conjugation. A acetal derivative of PEG-propionaldehyde, i.e., PEG-acetalaldehyde provides an additional benefit in so far as it provides for longer storage than PEG-propionaldehyde (U.S. Pat. No. 5,990,237).

Active esters of PEG carboxylic acids are probably one of the most used acylating agents for protein conjugation. Active esters react with primary amines near physiological conditions to form stable amides. Activation of PEG-carboxylic acids to succinimidyl active esters is accomplished by reacting the PEG-carboxylic acid with N-hydroxysuccinimide (NHS or HOSu) and a carbodiimide. Exemplary carboxylic acid derivatives of PEG include carboxymethylated PEG (CM-PEG; Zalipsky et al., 1990), butanoic acid derivatives and propionic acid derivatives (U.S. Pat. No. 5,672,662). Changing the distance between the active ester and the PEG backbone by the addition of methylene units can dramatically influence reactivity towards water and amines (e.g., by reducing hydrolysis). Alternatively or in addition, hydrolysis can be reduced by introducing an α-branching moiety to the carboxylic acid.

PEGylation of free cysteine residues in a protein is useful for site-specific conjugation (e.g., using a protein modified to include cysteine residues as described herein). Exemplary PEG derivatives for cysteine conjugation include PEG-maleimide, PEG-vinylsulfone, PEG-iodoacetamide and PEG-orthopyridyl disulfide. Exemplary methods for conjugating PEG to cysteine residues are described in Goodson and Katre (1990) and/or above. Exemplary methods for conjugation using PEG-vinylsulfone are described, for example, in Li et al. (2006).

U.S. Pat. No. 5,985,263 describes methods for conjugating PEG to the secondary amine group of histidine, which has a lower pKa than the primary amine. An advantage of this approach is that the acyl-histidne bond is not stable meaning that the protein is slowly released (i.e., the conjugate behaves as a slow release formulation or a pro-drug).

Another approach for PEGylation is to take advantage of a N-terminal serine or threonine, which can be converted to periodate as discussed above. Using this approach, PEG has been conjugated to bioactive proteins (e.g., Gaertner and Offord, 1996).

PEG can also be conjugated to carbohydrate groups.

The present invention also encompasses the use of reversible PEGylation strategies.

Uses

The proteins of the present invention are useful in a variety of applications, including research, diagnostic and therapeutic applications. Depending on the antigen to which the protein binds it may be useful for delivering a compound to a cell, e.g., to kill the cell or prevent growth and/or for imaging and/or for in vitro assays. In one example, the protein is useful for both imaging and delivering a cytotoxic agent to a cell, i.e., it is conjugated to a detectable label and a cytotoxic agent or a composition comprises a mixture of proteins some of which are conjugated to a cytotoxic agent and some of which are conjugated to a detectable label.

The proteins described herein can also act as inhibitors to inhibit (which can be reducing or preventing) (a) binding (e.g., of a ligand, an inhibitor) to a receptor, (b) a receptor signaling function, and/or (c) a stimulatory function. Proteins which act as inhibitors of receptor function can block ligand binding directly or indirectly (e.g., by causing a conformational change).

Antigens

The present invention contemplates a protein comprising at least one variable region comprising at least two cysteine residues in FR1 capable of specifically binding to any antigen(s), i.e., an example of the invention is generic as opposed to requiring a specific antigen.

Examples of the present invention contemplate a protein that specifically binds to an antigen associated with a disease or disorder (i.e., a condition) e.g., associated with or expressed by a cancer or cancerous/transformed cell and/or associated with an autoimmune disease and/or associated with an inflammatory disease or condition and/or associated with a neurodegenerative disease and/or associated with an immune-deficiency disorder.

Exemplary antigens against which a protein of the invention can be produced include BMPR1B (bone morphogenetic protein receptor-type IB, Dijke. et al 1994, WO2004063362); E16 (LAT1, SLC7A5, WO2004048938); STEAP1 (six transmembrane epithelial antigen of prostate; WO2004065577); CA125 (MUC16, WO2004045553); MPF (MSLN, SMR, megakaryocyte potentiating factor, mesothelin, WO2003101283); Napi3b (NAPI-3B, NPTIIb, SLC34A2, solute carrier family 34; WO2004022778); Sema 5b (F1110372, KIAA1445, SEMA5B, SEMAG, Semaphorin 5b, sema domain, seven thrombospondin repeats (type 1 and type Hike), transmembrane domain (TM) and short cytoplasmic domain, (semaphorin) 5B, WO2004000997); PSCA (US2003129192); ETBR (Endothelin type B receptor, WO2004045516); MSG783 (RNF124, WO2003104275); STEAP2 (HGNC_8639, IPCA-I, PCANAP1, STAMP1, STEAP2, STMP, prostate cancer associated gene 1, prostate cancer associated protein 1, six transmembrane epithelial antigen of prostate 2, six transmembrane prostate protein, WO2003087306); TrpM4 (BR22450, FLJ20041, TRPM4, TRPM4B, transient receptor potential cation channel, subfamily M, member 4, US2003143557); CRIPTO (CR, CR1, CRGF, CRIPTO, TDGF1, teratocarcinoma-derived growth factor, US2003224411); CD21 (CR2 (Complement receptor T) or C3DR (C3d/Epstein Barr virus receptor) WO2004045520); CD79b (CD79B, CD79β, IGb (immunoglobulin-associated beta), B29, WO2004016225); FcRH2 (DFGP4, IRTA4, SPAP1A (SH2 domain containing phosphatase anchor protein Ia), SPAP1B, SPAP1C, WO2004016225); HER2 (ErbB2, WO2004048938); NCA (CEACAM6, WO2004063709); MDP (DPEP1, WO2003016475); IL20Rα (IL20Ra, ZCYTOR7, EP1394274); Brevican (BCAN, BEHAB, US2003186372); EphB2R (DRT, ERK, Hek5, EPHT3, Tyro5, WO2003042661); ASLG659 (B7h, US20040101899); PSCA (Prostate stem cell antigen precursor, WO2004022709); GEDA (lipoma HMGIC fusion-partner-like protein WO2003054152); BAFF-R (B cell-activating factor receptor, BLyS receptor 3, BR3, WO2004058309); CD22 (B-cell receptor CD22-B isoform, BL-CAM, Lyb-8, Lyb8, SIGLEC-2, FLJ22814, WO2003072036); CD79a (CD79A, CD79a, immunoglobulin-associated alpha, a B cell-specific protein that covalently interacts with Ig beta (CD79B) and forms a complex on the surface with Ig M molecules, transduces a signal involved in B-cell differentiation; WO2003088808); CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia WO2004040000); HLA-DOB (Beta subunit of MHC class II molecule (Ia antigen) that binds peptides and presents them to CD4+ T lymphocytes; WO9958658); P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability; WO2004047749); CD72 (B-cell differentiation antigen CD72, Lyb-2; WO2004042346); LY64 (Lymphocyte antigen 64 (RP 105), type I membrane protein of the leucine rich repeat (LRR) family, regulates B-cell activation and apoptosis, loss of function is associated with increased disease activity in patients with systemic lupus erythematosus; US2002193567); FcRH1 (Fc receptor-like protein 1, a putative receptor for the immunoglobulin Fc domain that contains C2 type Ig-like and ITAM domains, may have a role in B-lymphocyte differentiation WO2003077836); IRTA2 (Immunoglobulin superfamily receptor translocation associated 2, a putative immunoreceptor with possible roles in B cell development and lymphomagenesis; deregulation of the gene by translocation occurs in some B cell malignancies; WO2003077836); TENB2 (TMEFF2, tomoregulin, TPEF, HPP1, TR, putative transmembrane proteoglycan, related to the EGF/heregulin family of growth factors and follistatin;

WO2004074320); CD20 (WO94/11026); VEGF-A (Presta et al., 1997); p53; EGFR; progesterone receptor; cathepsin D; Bcl-2; E cadherin; CEA; Lewis X; Ki67; PCNA; CD3; CD4; CD5; CD7; CD11c; CD11d; c-Myc; tau; PrPSC; or Aβ.

Preferably, the protein of the invention specifically binds to Her2 (e.g., comprising a sequence set forth in SEQ ID NO: 70), MUC1 (e.g., comprising a sequence set forth in SEQ ID NO: 72 or 73), TAG72 (a high molecular weight mucin like protein e.g., as described in Johnson et al., 1986) or PSMA (e.g., comprising a sequence set forth in SEQ ID NO: 71). For example, the protein of the invention specifically binds to Her2. For example, the protein of the invention specifically binds to MUC1. For example, the protein of the invention specifically binds to TAG72. For example, the protein of the invention specifically binds to PSMA.

Other exemplary antibodies from which a protein of the invention can be derived will be apparent to the skilled artisan and include, for example, Rituximab (C2B8; WO94/11026); or bevacizumab (humanized A.4.6.1; Presta et al., 1997)).

Exemplary bispecific proteins may bind to two different epitopes of the antigen of interest. Other such proteins may combine one antigen binding site with a binding site for another protein. Alternatively, an anti-antigen of interest region may be combined with a region which binds to a triggering molecule on a leukocyte such as a T-cell receptor molecule (e.g., CD3), or Fc receptors for IgG (FcγR), such as FcγRI (CD64), FcγRII (CD32) and/or FcγRIII (CD16), so as to focus and localize cellular defense mechanisms to the cells expressing the antigen of interest. Bispecific proteins may also be used to localize cytotoxic agents to cells which express the antigen of interest. These proteins possess a region that binds the antigen of interest and a region which binds the cytotoxic agent (e.g., saporin, anti-interferon-α, vinca alkaloid, ricin A chain, methotrexate or radioactive isotope hapten). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Pharmaceutical Compositions and Methods of Treatment

The proteins of the present invention (syn. active ingredients) are useful for parenteral, topical, oral, or local administration, aerosol administration, or transdermal administration for prophylactic or for therapeutic treatment. The pharmaceutical compositions can be administered in a variety of unit dosage forms depending upon the method of administration. For example, unit dosage forms suitable for oral administration include powder, tablets, pills, capsules and lozenges or by parenteral administration. It is recognized that the pharmaceutical compositions of this invention, when administered orally, should be protected from digestion. This is typically accomplished either by complexing the proteins with a composition to render it resistant to acidic and enzymatic hydrolysis or by packaging the compound in an appropriately resistant carrier such as a liposome. Means of protecting proteins from digestion are known in the art.

Typically, a therapeutically effective amount of the protein will be formulated into a composition for administration to a subject. The phrase "a therapeutically effective amount" refers to an amount sufficient to promote, induce, and/or enhance treatment or other therapeutic effect in a subject. As will be apparent, the concentration of proteins of the present invention in these formulations can vary widely, and will be selected primarily based on fluid volumes, viscosities, body weight and the like in accordance with the particular mode of administration selected and the patient's needs. Depending on the type and severity of the disease, a therapeutically effective amount may be about 1 μg/kg to 15 mg/kg (e.g. 0.1-20 mg/kg) of molecule, whether, for example, by one or more separate administrations, or by continuous infusion. A typical daily dosage might range from about 1 μg/kg to 100 mg/kg or more. An exemplary dosage of the protein to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises administering an initial loading dose of about 4 mg/kg, followed by a weekly maintenance dose of about 2 mg/kg of the protein. Other dosage regimens may be useful. The progress of this therapy is easily monitored by conventional techniques and assays.

Alternatively, the protein of the invention is formulated at a concentrated does that is diluted to a therapeutically effective dose prior to administration to a subject.

The pharmaceutical compositions of this invention are particularly useful for parenteral administration, e.g., formulated for injection via the intravenous, intramuscular, sub-cutaneous, transdermal, or other such routes, including peristaltic administration and direct instillation into a tumour or disease site (intracavity administration). The compositions for administration will commonly comprise a solution of the proteins of the present invention dissolved in a pharmaceutically acceptable carrier, preferably an aqueous carrier. A variety of aqueous carriers can be used, e.g., buffered saline and the like. Other exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

Techniques for preparing pharmaceutical compositions are generally known in the art as exemplified by Remington's Pharmaceutical Sciences, 16th Ed. Mack Publishing Company, 1980.

WO2002/080967 describes compositions and methods for administering aerosolized compositions comprising proteins for the treatment of, e.g., asthma, which are also suitable for administration of protein of the present invention.

Suitable dosages of compounds of the present invention will vary depending on the specific protein, the condition to be diagnosed/treated/prevented and/or the subject being treated. It is within the ability of a skilled physician to determine a suitable dosage, e.g., by commencing with a sub-optimal dosage and incrementally modifying the dosage to determine an optimal or useful dosage. Alternatively, to determine an appropriate dosage for treatment/prophylaxis, data from cell culture assays or animal studies are used, wherein a suitable dose is within a range of circulating concentrations that include the ED50 of the active compound with little or no toxicity. The dosage may vary within this range depending upon the dosage form employed and the route of administration utilized. A therapeutically/prophylactically effective dose can be estimated initially from cell culture assays. A dose may be formulated in animal models to achieve a circulating plasma concentration range that includes the IC50 (i.e., the concentration of the compound which achieves a halfmaximal inhibition of symptoms) as determined in cell culture. Such information can be used to more accurately determine useful doses in humans. Levels in plasma maybe measured, for example, by high performance liquid chromatography.

A protein of the invention may be combined in a pharmaceutical combination formulation, or dosing regimen as combination therapy, with a second compound. The second compound of the pharmaceutical combination formulation or dosing regimen preferably has complementary activities to the protein of the combination such that they do not adversely affect each other.

The second compound may be a chemotherapeutic agent, cytotoxic agent, cytokine, growth inhibitory agent, anti-hormonal agent, and/or cardioprotectant. Such molecules are suitably present in combination in amounts that are effective for the purpose intended. A pharmaceutical composition containing a protein of the invention may also have a therapeutically effective amount of a chemotherapeutic agent such as a tubulin-forming inhibitor, a topoisomerase inhibitor, or a DNA binder. Pharmaceutical "slow release" capsules or compositions may also be used. Slow release formulations are generally designed to give a constant drug level over an extended period and may be used to deliver compounds of the present invention.

The present invention also provides a method of treating or preventing a condition in a subject, the method comprising administering a therapeutically effective amount of a protein of the invention to a subject in need thereof.

As used herein, the terms "preventing", "prevent" or "prevention" in the context of preventing a condition include administering an amount of a protein described herein sufficient to stop or hinder the development of at least one symptom of a specified disease or condition.

As used herein, the terms "treating", "treat" or "treatment" include administering a therapeutically effective amount of an inhibitor(s) and/or agent(s) described herein sufficient to reduce or eliminate at least one symptom of a specified disease or condition.

As used herein, the term "subject" shall be taken to mean any animal including humans, preferably a mammal. Exemplary subjects include but are not limited to humans, primates, livestock (e.g. sheep, cows, horses, donkeys, pigs), companion animals (e.g. dogs, cats), laboratory test animals (e.g. mice, rabbits, rats, guinea pigs, hamsters), captive wild animals (e.g. fox, deer). Preferably the mammal is a human or primate. More preferably the mammal is a human.

As used herein, a "condition" is a disruption of or interference with normal function, and is not to be limited to any specific condition, and will include diseases or disorders. In an example, the condition is a cancer or an immunopathological disorder.

Exemplary cancers include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. Preferably a cancer is breast cancer or ovarian cancer or prostate cancer.

In one example of the invention, the cancer expresses Her2. Exemplary cancers include breast cancer, ovarian cancer, stomach cancer or uterine cancer, preferably breast cancer. Such a cancer can be treated, for example, with a protein of the invention that binds to Her2.

In another example of the invention, the cancer expresses PSMA. Exemplary cancers include prostate cancer. Such a cancer can be treated, for example, with a protein of the invention that binds to PSMA.

In a further example of the invention, the cancer expresses Tag72. Exemplary cancers include carcinomas, such as colorectal cancer, gastric cancer, pancreatic cancer, ovarian cancer, endometrial cancer, breast cancer, non-small cell lung cancer, and prostate cancer. Such a cancer can be treated, for example, with a protein of the invention that binds to Tag72.

In a further example of the invention, the cancer expresses MUC1, preferably a glycoform of MUC1 associated with cancer. Exemplary cancers include carcinomas, such as colorectal cancer, gastric cancer, pancreatic cancer, breast cancer, lung cancer, and bladder cancer. Such a cancer can be treated, for example, with a protein of the invention that binds to MUC1.

Immunopathology is the study of disease having an immunological cause and immunologic disease is any condition caused by the reactions of immunoglobulins to antigens. Thus, an "immunopathological disorder" can be defined as a disorder arising from reaction of a subject's immune system to antigens. Immunopathological disorders include autoimmune diseases and hypersensitivity responses (e.g. Type I: anaphylaxis, hives, food allergies, asthma; Type II: autoimmune haemolytic anemia, blood transfusion reactions; Type III: serum sickness, necrotizing vasculitis, glomerulonephritis, rheumatoid arthritis, lupus; Type IV: contact dermatitis, graft rejection). Autoimmune diseases include rheumatologic disorders (such as, for example, rheumatoid arthritis, Sjogren's syndrome, scleroderma, lupus such as SLE and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjogren's syndrome, Graves' disease, IDDM, pernicious anemia, thyroiditis, and glomerulonephritis.

In another embodiment, the disorder is an inflammatory disease. Inflammation is a protective response of body tissues to irritation or injury- and can be acute or chronic. Thus, inflammatory disorders include diseases involving neutrophils, monocytes, mast cells, basophils, eosinophils, macrophages where cytokine release, histamine release, oxidative burst, phagocytosis, release of other granule enzymes and chemotaxis occur. Hypersensitivity responses (defined above under immunopathological disorders) can also be regarded as inflammatory diseases (acute or chronic) since they often involve complement activation and recruitment/infiltration of various leukocytes such as neutrophils, mast cells, basophils, etc.

The compositions of the present invention will be administered in a manner compatible with the dosage formulation and in such amount as is therapeutically/prophylactically effective. Formulations are easily administered in a variety of manners, e.g., by ingestion or injection or inhalation.

Other therapeutic regimens may be combined with the administration of a protein of the invention. The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Prior to therapeutic use, a protein of the invention is preferably tested in vitro and/or in vivo, e.g., as described below.
In Vitro Testing In one example, a protein of the invention binds to an antigen, even if conjugated to a compound. The protein may bind to the antigen at least as well as the protein from which it is derived. Alternatively, the protein or conjugate comprising same binds to the antigen with at least about 10% or 20% or 30% or 40% or 50% or 60% or 70% or 80% or 90% of the affinity or avidity of the protein from which it is derived or a form of the protein lacking the cysteine residues and/or not conjugated to the compound.

Exemplary methods for determining binding affinity of a protein include a simple immunoassay showing the ability of the protein to block the binding of the unmodified protein or unconjugated protein to a target antigen, e.g., a competitive binding assay. Competitive binding is determined in an assay in which the protein under test inhibits specific binding of a reference protein to a common antigen. Numerous types of competitive binding assays are known, for example, solid phase direct or indirect radioimmunoassay (RIA), solid phase direct or indirect enzyme immunoassay (EIA), sandwich competition assay; solid phase direct biotin-avidin EIA; solid phase direct labelled assay, solid phase direct labelled sandwich assay; solid phase direct label RIA using $^{125}$I label; solid phase direct biotin-avidin EIA; or direct labelled RIA (see, for example, Harlow and Lane, 1988). Typically, such an assay involves the use of purified antigen bound to a solid surface or cells bearing either of these, an unlabelled test protein and a labelled reference protein. Competitive inhibition is measured by determining the amount of label bound to the solid surface or cells in the presence of the test protein The present invention also encompasses methods for testing the activity of a protein of the invention. Various assays are available to assess the activity of a protein of the present invention in vitro. For example, a protein of the present invention is administered to a cell or population thereof to determine whether or not it can bind to said cell and/or be internalized by said cell. Such an assay is facilitated by labelling the protein of the present invention with a detectable label (i.e., producing a conjugate), however this is not essential since the protein of the present invention can also be detected with a labelled protein. Such an assay is useful for assessing the ability of a protein of the present invention to deliver a compound (i.e., a payload) to a cell and/or its utility in imaging. Preferably the cell expresses an antigen to which the protein of the present invention binds and more preferably is a cell line or primary cell culture of a cell type that it desired to be detected or treated.

Generally, the cytotoxic or cytostatic activity of a protein of the present invention, e.g. conjugated to a cytotoxic molecule is measured by: exposing cells expressing an antigen to which the protein of the present invention binds to the protein of the present invention; culturing the cells for a suitable period for the protein to exert a biological effect, e.g., from about 6 hours to about 5 days; and measuring cell viability, cytotoxicity and/or cell death. Cell-based in vitro assays useful for measure viability (proliferation), cytotoxicity, and cell death are known in the art.

For example, the CellTiter-Glo® Luminescent Cell Viability Assay is a commercially available (Promega Corp., Madison, Wis.), homogeneous assay method based on the recombinant expression of Coleoptera luciferase (U.S. Pat. Nos. 5,583,024; 5,674,713 and 5,700,670). This cell proliferation assay determines the number of viable cells in culture based on quantitation of the ATP present in a cell, an indicator of metabolically active cells (U.S. Pat. No. 6,602,677). Alternatively, cell viability is assayed using non-fluorescent resazurin, which is added to cells cultured in the presence of a protein of the present invention. Viable cells reduce resazurin to red-fluorescent resorufin, easily detectable, using, for example microscopy or a fluorescent plate reader. Kits for analysis of cell viability are available, for example, from Molecular Probes, Eugene, Oreg., USA. Other assays for cell viability include determining incorporation of $^3$H-thymidine or $^{14}$C-thymidine into DNA as it is synthesized is an assay for DNA synthesis associated with cell division. In such an assay, a cell is incubated in the presence of labelled thymidine for a time sufficient for cell division to occur. Following washing to remove any unincorporated thymidine, the label (e.g. the radioactive label) is detected, e.g., using a scintiation counter. Alternative assays for determining cellular proliferation, include, for example, measurement of DNA synthesis by BrdU incorporation (by ELISA or immunohistochemistry, kits available from Amersham Pharmacia Biotech). Exemplary assays for detecting cell death include APOPTEST (available from Immunotech) stains cells early in apoptosis, and does not require fixation of the cell sample. This method utilizes an annexin V antibody to detect cell membrane re-configuration that is characteristic of cells undergoing apoptosis. Apoptotic cells stained in this manner can then be sorted either by fluorescence activated cell sorting (FACS), ELISA or by adhesion and panning using immobilized annexin V antibodies. Alternatively, a terminal deoxynucleotidyl transferase-mediated biotinylated UTP nick end-labelling (TUNEL) assay is used to determine the level of cell death. The TUNEL assay uses the enzyme terminal deoxynucleotidyl transferase to label 3'-OH DNA ends, generated during apoptosis, with biotinylated nucleotides. The biotinylated nucleotides are then detected by using streptavidin conjugated to a detectable marker. Kits for TUNEL staining are available from, for example, Intergen Company, Purchase, N.Y..

Stability of a protein of the present invention can also be assessed by exposing a protein of the present invention to serum and/or cells and subsequently isolating the protein of the present invention using, for example, immunoaffinity purification. A reduced amount of recovered protein of the present invention indicates that the protein of the present invention is degraded in serum or when exposed to cells.

In another example, the ability of the protein of the present invention to block binding of a ligand to a receptor is assessed using a standard radio-immunoassay or fluorescent-immunoassay.

In Vivo Testing

A protein of the present invention can also be tested for its stability and/or efficacy in vivo. For example, the protein of the present invention is administered to a subject and the serum levels of the protein is detected over time, e.g., using an ELISA or by detecting a detectable label conjugated to the protein. This permits determination of the in vivo stability of the protein of the present invention.

A protein of the present invention can also be administered to an animal model of a human disease. The skilled artisan will be readily able to determine a suitable model based on the antigen to which the protein of the present invention binds. Exemplary models of, for example, human cancer are known in the art. For example, mouse models of breast cancer include mice overexpressing fibroblast growth factor 3 (Muller et al., 1990); TGF-alpha (Matsui et al, 1990); erbB2 (Guy, et al., 1992); RET-1 (Iwamoto et al., 1990) or transplantation of human breast cancer cells into SCID mice. Models of ovarian cancer include transplantation of ovarian cancer cells into mice (e.g., as described in Roby et al., 2000); transgenic mice chronically secreting luteinising hormone (Risma et al., 1995); or Wx/Wv mice. Mouse models of prostate cancer are also known in the art and include, for example, models resulting from enforced expression of SV40 early genes (e.g., the TRAMP model that utilizes the minimal rat probasin promoter to express the SV40 early genes or transgenic mice using the long probasin promoter to express large T antigen, collectively termed the 'LADY' model or mice expressing c-myc or Bcl-2 or Fgf8b or expressing dominant negative TGFβ (see, Matusik et al., 2001, for a review of transgenic models of prostate cancer).

A protein of the present invention can also be administered to an animal model of a disease other than cancer, e.g., NOD mice to test their ability to suppress, prevent, treat or delay diabetes (e.g., as described in Tang et al. (2004)) and/or to a mouse model of GVHD (e.g., as described in Trenado (2002)) and/or to a mouse model of psoriasis (e.g., Wang et al. 2008) and/or to a model of rheumatoid arthritis e.g., a SKG strain of mouse (Sakaguchi et al.), rat type II collagen arthritis model, mouse type II collagen arthritis model or antigen induced arthritis models in several species (Bendele, 2001)) and/or a model of multiple sclerosis (for example, experimental autoimmune encephalomyelitis (EAE; Bradl and Linington, 1996)) and/or inflammatory airway disease (for example, OVA challenge or cockroach antigen challenge (Chen et al. 2007; Lukacs et al. 2001) and/or models of inflammatory bowel disease (e.g., dextran sodium sulphate (DSS)-induced colitis or Muc2 deficient mouse model of colitis (Van der Sluis et al. 2006).

Diagnostic/Prognostic Methods

In one example, the present invention provides methods for diagnosing or prognosing a condition.

As used herein, the term "diagnosis", and variants thereof such as, but not limited to, "diagnose", "diagnosed" or "diagnosing" includes any primary diagnosis of a clinical state or diagnosis of recurrent disease.

"Prognosis", "prognosing" and variants thereof as used herein refer to the likely outcome or course of a disease, including the chance of recovery or recurrence.

In one example, the method comprises determining the amount of an antigen in a sample. Thus, the proteins of the invention have utility in applications such as cell sorting (e.g., flow cytometry, fluorescence activated cell sorting), for diagnostic or research purposes. For example, a sample is contacted with a protein of the invention for a time and under conditions sufficient for it to bind to an antigen and form a complex and the complex is then detected or the level of complex is determined. For these purposes, the proteins can be labelled or unlabelled. The proteins can be directly labelled, e.g., using a method described herein. When unlabelled, the proteins can be detected using suitable means, as in agglutination assays, for example. Unlabelled antibodies or fragments can also be used in combination with another (i.e., one or more) suitable reagent which can be used to detect a protein, such as a labelled antibody (e.g., a second antibody) reactive with the protein or other suitable reagent (e.g., labelled protein A).

Preferably, a protein of the invention is used in an immunoassay. Preferably, using an assay selected from the group consisting of, immunohistochemistry, immunofluorescence, enzyme linked immunosorbent assay (ELISA), fluorescence linked immunosorbent assay (FLISA) Western blotting, RIA, a biosensor assay, a protein chip assay and an immunostaining assay (e.g. immunofluorescence).

Standard solid-phase ELISA or FLISA formats are particularly useful in determining the concentration of a protein from a variety of samples.

In one form such an assay involves immobilizing a biological sample onto a solid matrix, such as, for example a polystyrene or polycarbonate microwell or dipstick, a membrane, or a glass support (e.g. a glass slide). A protein of the invention that specifically binds to an antigen of interest is brought into direct contact with the immobilized sample, and forms a direct bond with any of its target antigen present in said sample. This protein of the invention is generally labelled with a detectable reporter molecule, such as for example, a fluorescent label (e.g. FITC or Texas Red) or a fluorescent semiconductor nanocrystal (as described in U.S. Pat. No. 6,306,610) in the case of a FLISA or an enzyme (e.g. horseradish peroxidase (HRP), alkaline phosphatase (AP) or β-galactosidase) in the case of an ELISA, or alternatively a labelled antibody can be used that binds to the protein of the invention. Following washing to remove any unbound protein the label is detected either directly, in the case of a fluorescent label, or through the addition of a substrate, such as for example hydrogen peroxide, TMB, or toluidine, or 5-bromo-4-chloro-3-indol-beta-D-galaotopyranoside (x-gal) in the case of an enzymatic label. Such ELISA or FLISA based systems are particularly suitable for quantification of the amount of a protein in a sample, by calibrating the detection system against known amounts of a protein standard to which the protein binds, such as for example, an isolated and/or recombinant protein or immunogenic fragment thereof or epitope thereof.

In another form, an ELISA or FLISA comprises of immobilizing a protein of the invention or an antibody that binds to an antigen of interest on a solid matrix, such as, for example, a membrane, a polystyrene or polycarbonate microwell, a polystyrene or polycarbonate dipstick or a glass support. A sample is then brought into physical relation with said protein of the invention, and the protein to which said compound binds is bound or 'captured'. The bound protein is then detected using a labelled protein of the invention that binds to a different protein or a different site in the same protein. Alternatively, a third labelled antibody can be used that binds the second (detecting) antibody.

Imaging Methods

As will be apparent to the skilled artisan from the foregoing, the present invention also contemplates imaging methods using a protein of the invention. For imaging, protein of the invention is conjugated to a detectable label, which can be any molecule or agent that can emit a signal that is detectable by imaging. For example, the detectable label may be a protein, a radioisotope, a fluorophore, a visible light emitting fluorophore, infrared light emitting fluorophore, a metal, a ferromagnetic substance, an electromagnetic emitting substance a substance with a specific MR spectroscopic signature, an X-ray absorbing or reflecting substance, or a sound altering substance.

The protein of the present invention can be administered either systemically or locally to the tumour, organ, or tissue to be imaged, prior to the imaging procedure. Generally, the protein is administered in doses effective to achieve the desired optical image of a tumour, tissue, or organ. Such doses may vary widely, depending upon the particular protein employed, the tumour, tissue, or organ subjected to the imaging procedure, the imaging equipment being used, and the like.

In some embodiments of the invention, the protein of the invention is used as in vivo optical imaging agents of tissues and organs in various biomedical applications including, but not limited to, imaging of tumours, tomographic imaging of organs, monitoring of organ functions, coronary angiography, fluorescence endoscopy, laser guided surgery, photoacoustic and sonofluorescence methods, and the like. Exemplary diseases, e.g., cancers, in which a protein of the invention is useful for imaging are described herein and shall be taken to apply *mutatis mutandis* to the present embodiment of the invention. In one example, the protein conjugates of the invention are useful for the detection of the presence of tumours and other abnormalities by monitoring where a particular protein of the invention is concentrated in a subject. In another embodiment, the protein of the invention is useful for laser-assisted guided surgery for the detection of micro-metastases of tumours upon laparoscopy. In yet another embodiment, the protein of the invention is useful in the diagnosis of atherosclerotic plaques and blood clots.

Examples of imaging methods include magnetic resonance imaging (MRI), MR spectroscopy, radiography, CT, ultrasound, planar gamma camera imaging, single-photon emission computed tomography (SPECT), positron emission tomography (PET), other nuclear medicine-based imaging, optical imaging using visible light, optical imaging using luciferase, optical imaging using a fluorophore, other optical imaging, imaging using near infrared light, or imaging using infrared light.

Certain examples of the methods of the present invention further include imaging a tissue during a surgical procedure on a subject.

A variety of techniques for imaging are known to those of ordinary skill in the art. Any of these techniques can be applied in the context of the imaging methods of the present invention to measure a signal from the detectable label. For example, optical imaging is one imaging modality that has gained widespread acceptance in particular areas of medicine. Examples include optical labelling of cellular components, and angiography such as fluorescein angiography and indocyanine green angiography. Examples of optical imaging agents include, for example, fluorescein, a fluorescein derivative, indocyanine green, Oregon green, a derivative of Oregon green derivative, rhodamine green, a derivative of rhodamine green, an eosin, an erytlirosin, Texas red, a derivative of Texas red, malachite green, nanogold sulfosuccinimidyl ester, cascade blue, a coumarin derivative, a naphthalene, a pyridyloxazole derivative, cascade yellow dye, dapoxyl dye.

Gamma camera imaging is contemplated as a method of imaging that can be utilized for measuring a signal derived from the detectable label. One of ordinary skill in the art would be familiar with techniques for application of gamma camera imaging. In one embodiment, measuring a signal can involve use of gamma-camera imaging of an $^{111}$In or $^{99m}$Tc conjugate, in particular $^{111}$In-octreotide or $^{99m}$Tc-somatostatin analogue.

Computerized tomography (CT) is contemplated as an imaging modality in the context of the present invention. By taking a series of X-rays from various angles and then combining them with a computer, CT made it possible to build up a three-dimensional image of any part of the body. A computer is programmed to display two-dimensional slices from any angle and at any depth. The slices may be combined to build three-dimensional representations.

In CT, intravenous injection of a radiopaque contrast agent conjugated to a protein of the invention, which binds to an antigen of interest can assist in the identification and delineation of soft tissue masses when initial CT scans are not diagnostic. Similarly, contrast agents aid in assessing the vascularity of a soft tissue lesion. For example, the use of contrast agents may aid the delineation of the relationship of a tumour and adjacent vascular structures.

CT contrast agents include, for example, iodinated contrast media. Examples of these agents include iothalamate, iohexyl, diatrizoate, iopamidol, ethiodol, and iopanoate. Gadolinium agents have also been reported to be of use as a CT contrast agent, for example, gadopentate.

Magnetic resonance imaging (MRI) is an imaging modality that uses a high-strength magnet and radio-frequency signals to produce images. In MRI, the sample to be imaged is placed in a strong static magnetic field and excited with a pulse of radio frequency (RF) radiation to produce a net magnetization in the sample. Various magnetic field gradients and other RF pulses then act to code spatial information into the recorded signals. By collecting and analyzing these signals, it is possible to compute a three-dimensional image which, like a CT image, is normally displayed in two-dimensional slices. The slices may be combined to build three-dimensional representations.

Contrast agents used in MRI or MR spectroscopy imaging differ from those used in other imaging techniques. Examples of MRI contrast agents include gadolinium chelates, manganese chelates, chromium chelates, and iron particles. For example, a protein of the invention is conjugated to a compound comprising a chelate of a paramagnetic metal selected from the group consisting of scandium, titanium, vanadium, chromium, manganese, iron, cobalt, nickel, copper, molybdenum, ruthenium, cerium, indium, praseodymium, neodymium, promethium, samarium, europium, gadolinium, terbium, dysprosium, holmium, erbium, thulium, and ytterbium. A further example of imaging agents useful for the present invention is halocarbon-based nanoparticle such as PFOB or other fluorine-based MRI agents. Both CT and MRI provide anatomical information that aid in distinguishing tissue boundaries and vascular structure.

Imaging modalities that provide information pertaining to information at the cellular level, such as cellular viability, include positron emission tomography (PET) and single-photon emission computed tomography (SPECT). In PET, a patient ingests or is injected with a radioactive substance that emits positrons, which can be monitored as the substance moves through the body.

Closely related to PET is single-photon emission computed tomography, or SPECT. The major difference between the two is that instead of a positron-emitting substance, SPECT uses a radioactive tracer that emits high-energy photons. SPECT is valuable for diagnosing multiple illnesses including coronary artery disease, and already some 2.5 million SPECT heart studies are done in the United States each year.

For PET, a protein of the invention is commonly labelled with positron-emitters such as $^{11}$C, 13N, $^{15}$O, $^{18}$F, $^{82}$Rb, $^{62}$Cu, and $^{68}$Ga. Proteins of the invention are labelled with positron emitters such as $^{99}$mTc, $^{201}$Tl, and $^{67}$Ga, $^{111}$In for SPECT.

Non-invasive fluorescence imaging of animals and humans can also provide in vivo diagnostic information and be used in a wide variety of clinical specialties. For instance, techniques have been developed over the years including simple observations following UV excitation of fluorophores up to sophisticated spectroscopic imaging using advanced equipment (see, e.g., Andersson-Engels et al, 1997). Specific devices or methods known in the art for the in vivo detection of fluorescence, e.g., from fluorophores or fluorescent proteins, include, but are not limited to, in vivo near-infrared fluorescence (see, e.g., Frangioni, 2003), the Maestro™ in vivo fluorescence imaging system (Cambridge Research & Instrumentation, Inc.; Woburn, Mass.), in vivo fluorescence imaging using a flying-spot scanner (see, e.g., Ramanujam et al, 2001), and the like.

Other methods or devices for detecting an optical response include, without limitation, visual inspection, CCD cameras, video cameras, photographic film, laser-scanning devices, fluorometers, photodiodes, quantum counters, epifluorescence microscopes, scanning microscopes, flow cytometers, fluorescence microplate readers, or signal amplification using photomultiplier tubes.

In some examples, an imaging agent is tested using an in vitro or in vivo assay prior to use in humans, e.g., using a model described herein.

Articles of Manufacture

The present invention also provides an article of manufacture, or "kit", containing a protein of the invention. The article of manufacture optionally, comprises a container and a label or package insert on or associated with the container, e.g., providing instructions to use the protein of the invention in a method described herein according to any embodiment. Suitable containers include, for example, bottles, vials, syringes, blister pack, etc. The containers may be formed from a variety of materials such as glass or plastic. The container holds a protein of the invention composition and may have a sterile access port (for example the container may be an intravenous solution bag or a vial having a stopper pierceable by a hypodermic injection needle). Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The present invention is described further in the following non-limiting examples.

Example 1

Molecular Modelling 1.1 Generation of Molecular Models for Avibodies

Avibodies are recombinant proteins comprising variable domains of antibodies. Avibodies utilize the variable domains of monoclonal antibodies by fusing them into a single polypeptide chain interspersed by a short linker region in either $V_H$-to-$V_L$ or $V_L$-to-$V_H$ orientation. Depending on the linker length, these Avibodies are designed to form stable, biologically active monobodies (scFv), diabodies, triabodies or tetrabodies containing one, two, three or four functional binding sites respectively.

The $V_H$ and $V_L$ domain sequences of the Avibodies modeled were used to search the RCSB PDB Data bank (www-.pdb.org) using both BLAST and/or FASTA searches. The structure hits with the highest sequence identity, resolution and completeness were selected for use as templates for the Fv domains of the modeled Avibodies. If the asymmetric unit in a pdb file contained more than one template model all templates were used and treated identically.

For Avibody diabodies and triabodies, quaternary templates were used to set the arrangement of the template Fvs in space and allow modeling of these Avibodies. For the diabodies 1LMK (Perisic et. al., 1994) or 1MOE (Carmichael et. al., 2003) were variously used and for the triabodies 1NQB (Pei et. al., 1997) was used to arrange the templates in quaternary space for modeling.

For quaternary arrangement, copies of the core coordinate set generated by Israel Gelfand for the Fv domain (Gelfand et. al., 1998a) were least squares aligned to the quaternary template to form a "core" homo-dimer or homo-trimer. The selected Fv templates for each Avibody were then least squares aligned to each Fv in this "core" homo-dimer or homo-trimer to form template homo-dimers or homo-trimers. These files were subsequently edited to reflect the connectivity required for modeling the various Avibodies.

In all cases, the "core" quaternary models were not used for the Fv domain modeling in the final modeling runs and the linking residues were modeled "ab initio" as loops.

Molecular models of Avibodies were generated using Discovery Studio (DS) Software (v2.5, Accelrys, Calif., USA) using the MODELLER algorithm (Sali and Blundell, 1993) embedded in the software and evaluated using the scoring functions contained in the software. The best model was selected on the basis of the presence of a high ranking score in each of the MODELLER generated Probability Density Function (PDF) for total and physical energy and the Discrete Optimized Protein Energy (DOPE) score, (Shen et. al., 2006). The selected model was written out to a pdb file for further analysis. Images of the resulting models were also generated using DS.

Further analysis of each selected model included visual inspection on a graphics workstation and calculation of the solvent accessible surface area (ASA) of relevant residues. The ASA is used here as an assessment of the modeled disulphide mutant's ability to be available for conjugation. The standard deviation from the mean ASA (calculated in Excel) was then used as an indication as to whether both or one of the Cysteine residues in a disulphide or other group of residues (i.e., CDRs) were similarly exposed. For example, a large standard deviation indicates that one of the residues in the disulphide may be less exposed for reduction and/or conjugation. An average per residue average ASA is also included for the CDRs to facilitate comparison of the disulphides to a group of generally exposed residues. The intra-sheet conserved disulphide average ASA was used to facilitate comparison of the disulphides to a group of generally buried or inaccessible residues.

For the work presented here, no significant differences were apparent in the accessibility of the disulphide mutants modeled with respect to the ASA as an indication of conjugation probability whether they were in monomer, dimer or trimer configuration or whether the respective scFvs were in $V_H$ to $V_L$ orientation or $V_L$ to $V_H$ orientation.

1.2 Generation of a $V_H$ to $V_L$ Linked Molecular Model for the AVP04-07 Diabody The AVP04-07 Avibody (SEQ ID NO. 55) is a recombinant diabody with a theoretical pI/Mw: 8.0/51 KDa, a $V_L\kappa$ light chain and a subgroup I $V_H$ chain. AVP04-07 recognizes the tumour associated antigen TAG72.

This Avibody utilizes the variable regions of the murine monoclonal antibody CC49, fusing them in sequence to form a stable, biologically active diabody containing two functional binding sites. The variable domains of CC49 have been modified (Roberge, et al, 2006) in amino acid sequence in order to achieve a high-expressing and highly stable recombinant molecule with exceptional in vitro and in vivo properties.

Searching the PDB with the $V_H$ and $V_L$ domain sequences of the AVP04-07 highlighted one antibody in the PDB, 1ZA6 (Larson et al., 2005), which had an 82% identity match with AVP04-07 in both $V_H$ and $V_L$ domains in an un-gapped alignment.

The 1ZA6 template encodes the structure of an antitumour CH2-domain-deleted humanized antibody. This recombinant humanized antibody also recognizes the TAG72 antigen.

Figure 1:
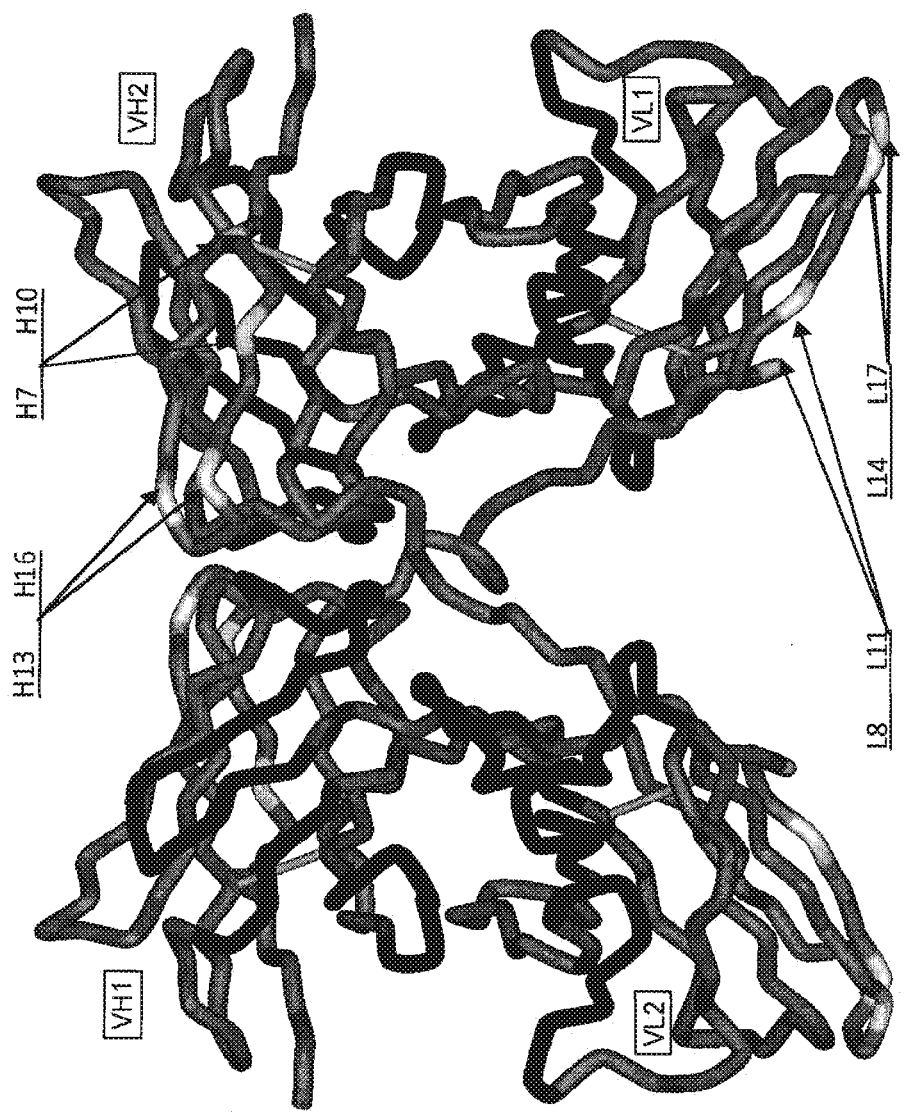
FIG. 1 is a diagrammatic representation showing the in silico homology modeled, un-mutated AVP04-07 diabody (comprising a polypeptide comprising a sequence set forth in SEQ ID NO: 57). Framework residues are shown in grey, CDR residues shown in black, potential disulphide insertion residues identified for mutation are shown in white. Arrows identify residues in one of the Fvs with Kabat numbering.

The Fv structure in the 1ZA6 pdb file was used to model the Fv domains of the AVP04-07 diabody. The 1 LMK described above was used for the quaternary spatial alignment of the templates to form an AVP04-07 diabody in the method described above. The selected highest scoring model of the AVP04-07 diabody is shown in FIG. 1 and represents the "un-mutated" configuration of this Avibody dimer.

1.3 Generation of a $V_H$ to $V_L$ Linked Molecular Model for the AVP07-17 Diabody The AVP07-17 Avibody (SEQ ID NO: 59) is a recombinant diabody with a theoretical pI/Mw: 6.4/55 KDa, an exceptionally long CDRH3 loop a $V_L\lambda$ light chain and a subgroup I $V_H$ chain. AVP07-17 recognizes the tumour associated antigen HER2.

AVP07-17 has lower identity with the structures available in the RCSB pdb when using standard Fasta and Blast searches compared to the AVP04-07. No Fv pair of VL and VH showed as high an identity with AVP07-17 when compared with the results obtained for AVP04-07.

Alternative methods of searching the PDB were tested to improve template selection for entire Fv domains. The MATRAS server (Kawabata 2003, Kawabata, et. al. 2000) uses a standard sequence homology search against the current PDB using the BLAST program with a graphical representation of the aligned regions to assist in template selection. This method revealed two good templates, both with greater than 64% sequence identity in both the $V_L$ and $V_H$ domains.

The selected Fv templates were contained in the pdb files of a) 2B1H (Stanfield et. al., 2006) which had 80.6% identity to AVP07-17 excluding the linker residues and CDRH3 and b) 3G04 (Sanders et. al., 2007) which had 73.5% identity to AVP07-17 excluding the linker residues and CDRH3.

The 1LMK diabody described above was used for the quaternary spatial alignment of the template Fvs to form an AVP07-17 ("un-mutated") diabody in the method described above. The long CDRH3 loop length of AVP07-17 was also problematic for modeling as no homologous structures could be found for use as templates. These were modeled as loops with no template constraints (essentially ab initio) and assessed for structural violations after modeling. In all cases presented here, the CDR3 loops are modeled with low confidence levels and are not included in some analyses as they were not considered to affect the overall structure or framework regions of the Avibodies.

Figure 2:
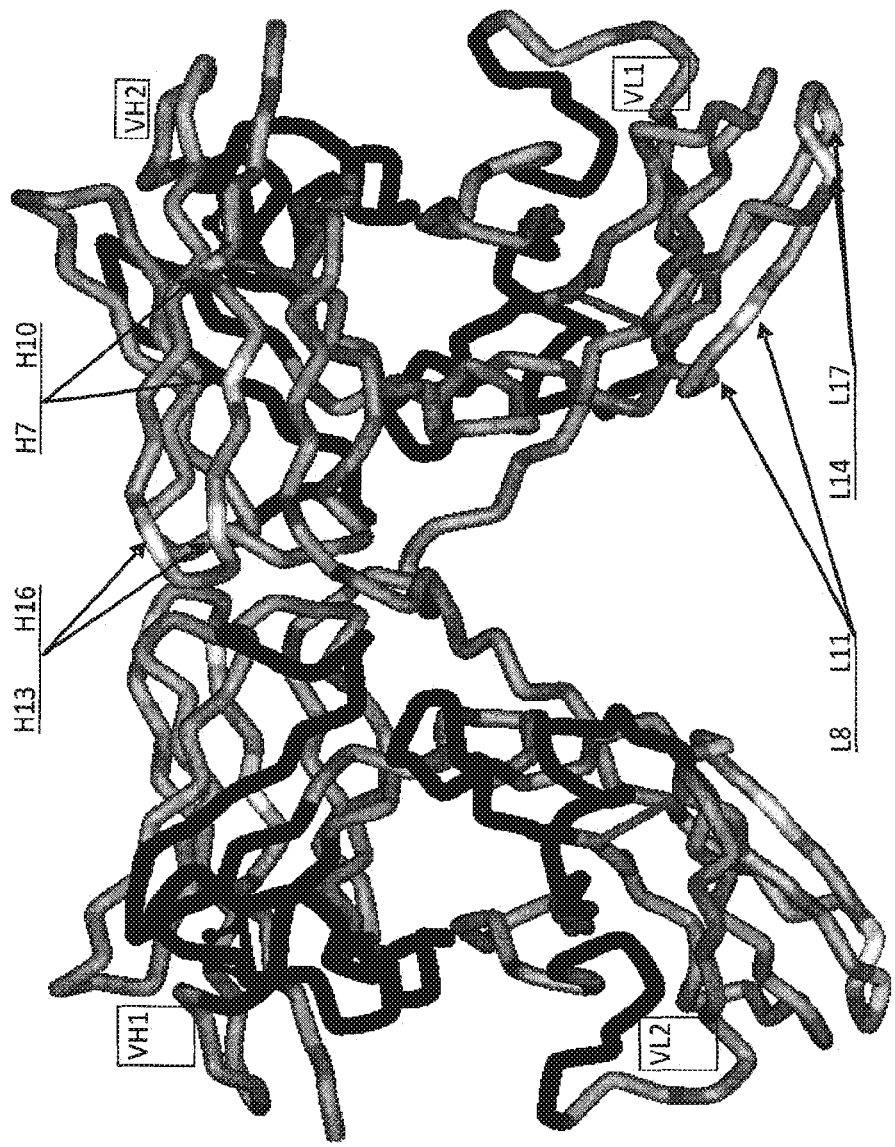
FIG. 2 is a diagrammatic representation showing the in silico homology modeled, un-mutated AVP07-17 diabody (comprising a polypeptide comprising a sequence set forth in SEQ ID NO: 59). Framework residues are shown in grey, CDR residues shown in black, potential disulphide insertion residues identified for mutation are shown in white. Arrows identify residues in one of the Fvs with Kabat numbering.

The selected highest scoring model of the AVP07-17 diabody is shown in FIG. 2 and represents the "un-mutated" configuration for this Avibody dimer.

1.4 Generation of a Molecular Model for the AVP02-60 Diabody

The AVP02-60 Avibody (SEQ ID NO: 61) is a recombinant diabody with a theoretical pI/Mw: 8.47/50.1 kDa, a $V_L$ chain kappa and a subgroup III $V_H$ chain. It is based on the primary mouse monoclonal C595 antibody that recognizes a breast cancer associated mucin encoded by the MUC1 gene, CD227 (Gendler et. al., 1990). It recognizes the epitope RPAP within the protein core of the mucin, a motif repeated some 40 times in the sequence.

Blast and Fasta searching with the $V_L$ or $V_H$ revealed several templates with high identity scores that contained both the $V_L$ and $V_H$ domains. However, only one template had a $V_H$ with sufficient identity in sequence and length to model the CDRH3. Hence two templates were selected for $V_H$ and $V_L$ modeling while one extra template was selected for $V_H$ only modeling. The templates selected were: a) 1MHP $V_H$ and $V_L$ (86.9% identity, 89.6% homology; Karpusas, et. al., 2003), b) 2B2X $V_H$ and $V_L$ (85.7% identity, 88.3% homology; Clark, et. al., 2006) and c) 2ADG $V_H$: (86.8% identity, 96.5% homology; Zhou et. al., 2005) which was the only template with an un-gapped alignment for CDRH3, the $V_L$ domain of this Fv was not used in the modeling.

Over all the templates the AVP02-60 has 88.4% and identity and 91.1% homology. The 1 LMK diabody described above was used for the quaternary spatial alignment of the template Fvs to form an AVP02-60 ("un-mutated") diabody in the method described above.

Figure 3:
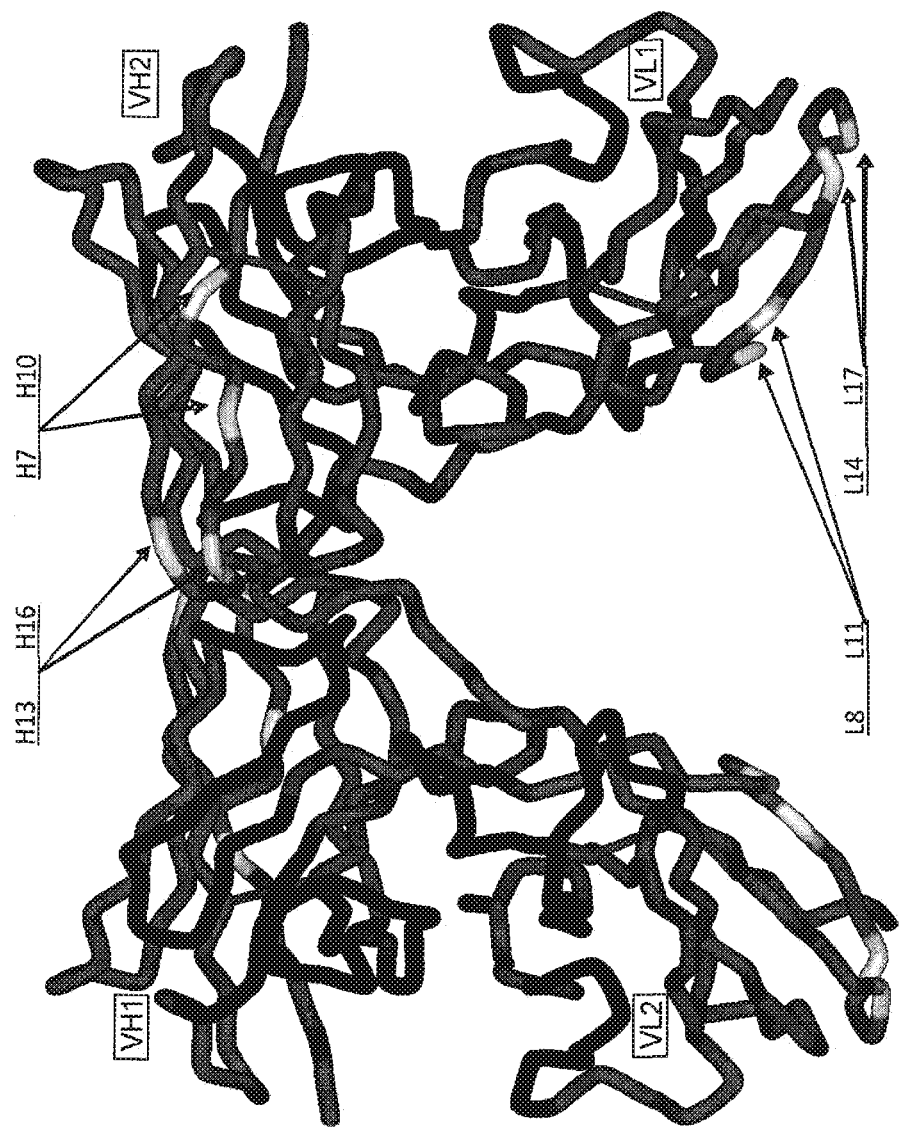
FIG. 3 is a diagrammatic representation showing the in silico homology modeled, un-mutated AVP02-60 diabody (comprising a polypeptide comprising a sequence set forth in SEQ ID NO: 61). Framework residues are shown in grey, CDR residues shown in black, potential disulphide insertion residues identified for mutation are shown in white. Arrows identify residues in one of the Fvs with Kabat numbering.

The selected highest scoring model of the AVP02-60 diabody is shown in FIG. 3 and represents the "un-mutated" configuration of this Avibody dimer.

1.5 Identification of Framework 1 Cysteine Insertion Positions for Engineering Replacement Cysteine Mutations and Molecular Modelling of the Same.

Framework 1 (FR1) in the architecture of an immunoglobulin V domain is a good candidate for engineering cysteine replacements because it is located on the edge of one of the two β-sheets and so is generally well exposed to solvent except for residues adjacent to the conserved inter-domain disulphide bond. This region should thus allow free access for conjugation chemistry to disulphide containing constructs.

Avibodies which contain engineered intra-framework 1 cysteine replacements are herein referred to as a "Thiolated Avibody".

The $V_L$ and $V_H$ domains of antibodies are firstly members of the Immunoglobulin superfamily classically containing 7-10 β strands in two sheets with a typical topology and connectivity. These domains are secondly members of the V-type immunoglobulins showing symmetry of the B-sheets within the domain axis (Halaby, et. al., 1999). The antibody V-type or V-set domains are divided $V_H$ (type 1-4), $V_L\kappa$, $V_L\lambda$ domains in online databases such as SCOP (http://scop.mrc-lmb.cam.ac.uk/scop/data/scop.b.c.b.b.b.html, Murzin, et. al., 1995), InterPro (http://www.ebi.ac.uk/interpro/IEntry?ac=IPR013106, Hunter et. al., 2009) and Pfam (http://pfam.sbc.su.se/family/PF07686, Bateman, et. al., 2004).

Given these well defined similarities, it is reasonable to assume that all potential intra-framework 1 cysteine pair replacement mutations identified in the AVP04-07 $V_L\kappa$ domain should be structurally transferable to both $V_H$ (type 1-4) domains and $V_L\lambda$ domains.

The $V_L$ domain of the model generated for AVP04-07 was inspected on a graphics workstation for pairs of residues that could be mutated to Cysteine and be able to form an intra-framework 1 disulphide bridges as well as be available for reduction and subsequent conjugation to payloads. Pairs of residues in FR1 which have side chains generally angled towards each other, which have side chains atoms generally exposed to solvent and which have Cα carbon atoms were ~6-7 Å apart were considered as good candidates for intra-framework 1 cysteine insertions capable of forming a disulphide bond.

For transfer to $V_H$ domains, a structural alignment of the $V_H$ and $V_L$ domains of the Gelfand core co-ordinates (Gelfand et. al., 1998a; Gelfand et. al., 1998b) was generated. These aligned $V_L$ and $V_H$ cores were subsequently used to align the $V_H$ and $V_L$ domains from each un-mutated Fv domain model. This structural alignment was used for mapping the identified Cysteine mutant pairs from the $V_L$ to the $V_H$ sequences that were then used for modeling the $V_H$ domain cysteine insertion mutants. In each case, a single modeling run was used to generate a double cysteine insertion mutant model containing single analogous cysteine mutant pairs in each of the $V_L$ and $V_H$ domains.

1.6 Framework 1 Cysteine Insertion Positions Identified for Engineering Cysteine Replacement Mutations and Molecular Modelling in AVP04 Avibody Diabodies.

The un-mutated AVP04-07 model was the starting point for the mapping of intra-framework 1 cysteine insertion mutants as described above. This mapping showed that the identified $V_L$ cysteine insertion positions could indeed be structurally mapped to the $V_H$ domain with ease and that these residues were likely to form a disulphide bond.

In Framework 1 $V_L$ (Kabat residues 1 to 23 inclusive) and Framework 1 $V_H$ (Kabat residues 1 to 30 inclusive) of AVP04-07, the preferred positions for intra-framework 1 cysteine insertions were identified as:

Light chain framework 1 Kabat residues L8 and L11 (AVP04-50, SEQ ID NO: 57)
Heavy chain framework 1 Kabat residues H7-H10 (AVP04-84, SEQ ID NO: 63)
Light chain framework 1 Kabat residues L14 and L17 (AVP04-78, SEQ ID NO: 77)
Heavy chain framework 1 Kabat residues H13-H16 (AVP04-85, SEQ ID NO: 75)

Modelling was repeated using the method outlined for the AVP04-07 model (Example 1.2) using the same input parameters except for the sequence input which reflected the desired mutations above. Model assessment was also carried out as for the AVP04-07 models.

Figure 4A:
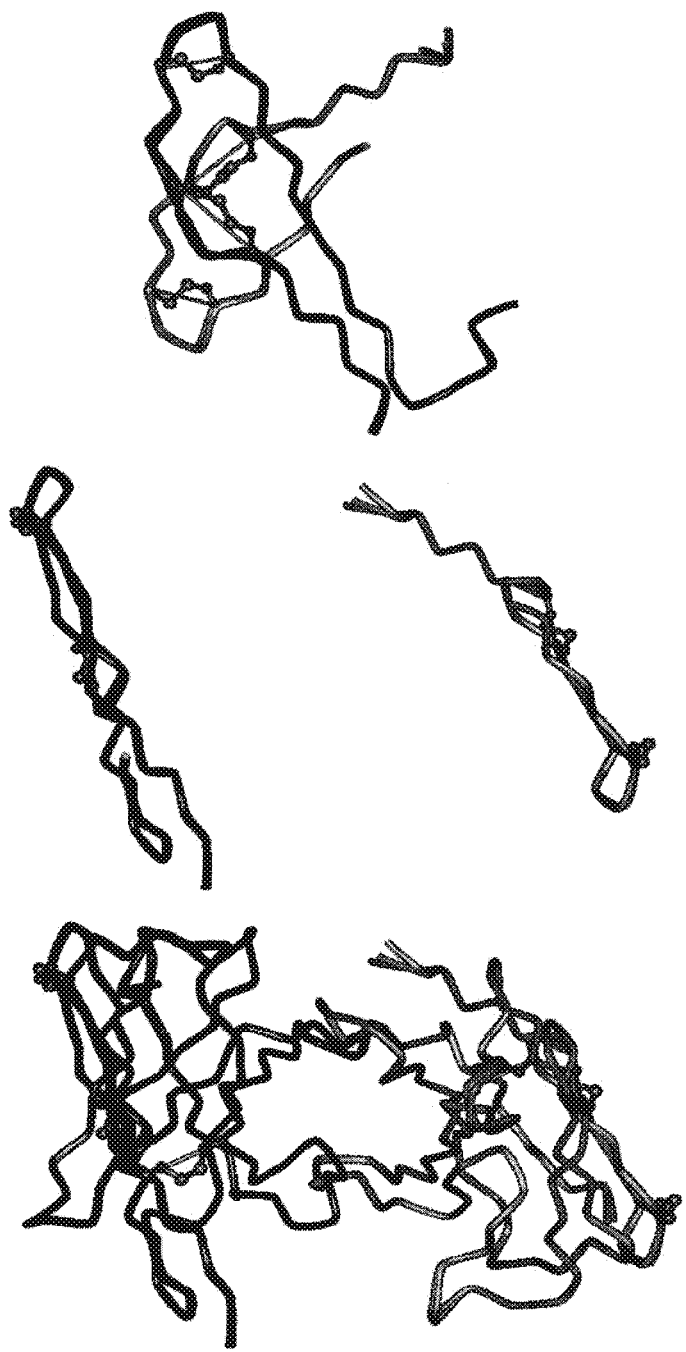
FIG. 4A is a diagrammatic representation showing the in silico homology modeled intra-Framework 1 disulphide insertion mutations in the $V_L$ and $V_H$ of the AVP04-07 diabody (comprising a polypeptide comprising a sequence set forth in SEQ ID NO: 57). Heavy chain is shown in black, light chain shown in grey, in silico mutated disulphide insertion mutant side chains shown as ball and stick. Left hand side: aligned Fvs from un-mutated and two disulphide insertion mutant diabody models. Middle: as for left hand side but only showing FR1. Right hand side as for middle but rotated on the horizontal axis by 100°.
Figure 4B:
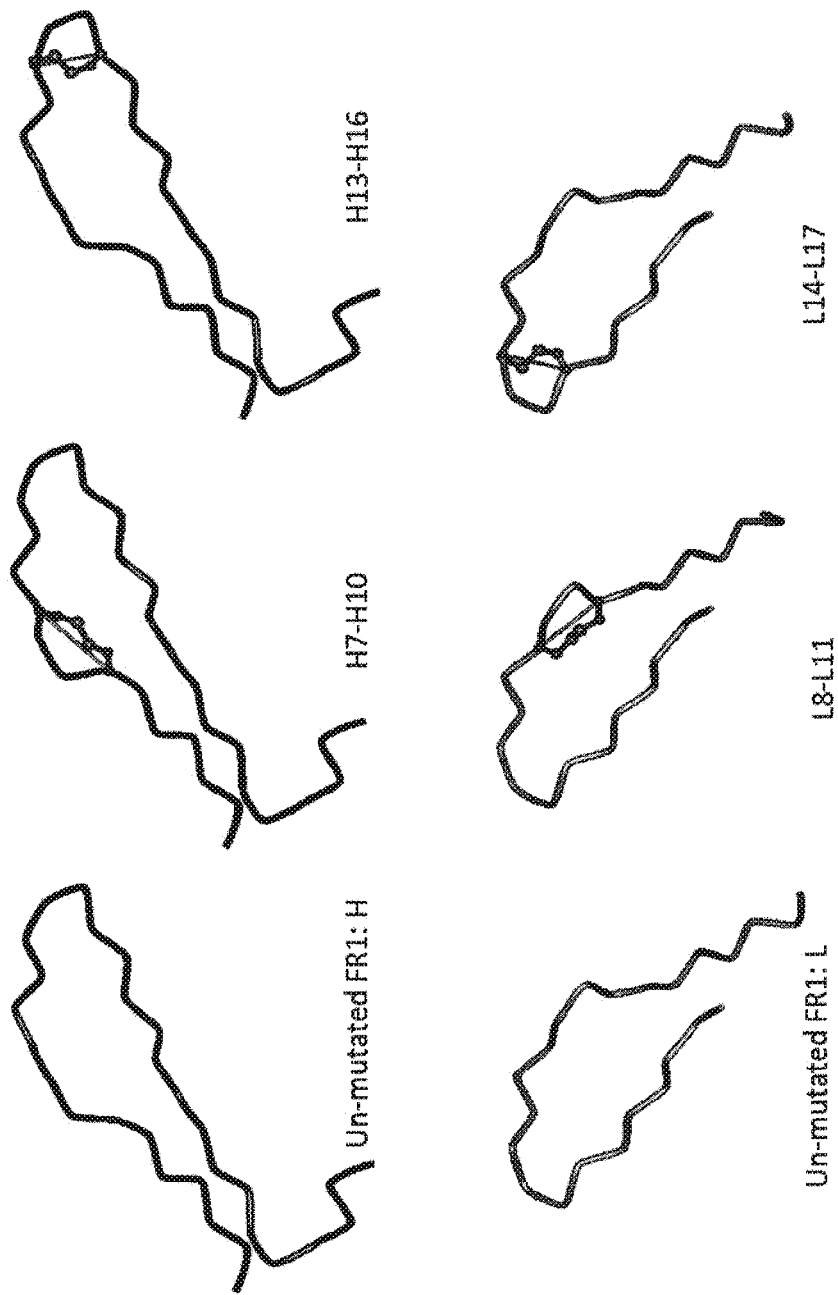
FIG. 4B is a diagrammatic representation showing the in silico homology modeled intra-Framework 1 disulphide insertion mutations in the $V_L$ and $V_H$ of the AVP04-07 diabody (comprising a polypeptide comprising a sequence set forth in SEQ ID NO: 57). Depicted are models of FR1 comprising various mutations as indicated. H=heavy chain. L=light chain. Numbers indicate positions of cysteine residues (if present). Un-mutated FR1 H/Un-mutated FR1 L=AVP04-07, H7-H10=AVP04-84, L8-L11=AVP04-50, H13-H16=AVP04-85, L14-L17=AVP04-78.

Each cysteine insertion was subjected to modeling with one $V_L$ cysteine pair mutant and its analogous $V_H$ cysteine pair mutant included in each modeling run. The results of the cysteine insertion modeling onto the AVP04-07 FR1 structure are shown in FIGS. 4A and B. FIG. 4B shows that there was little structural change in the vicinity of the engineered intra-framework 1 cysteine mutations even when a disulphide bond is formed.

Figure 5:
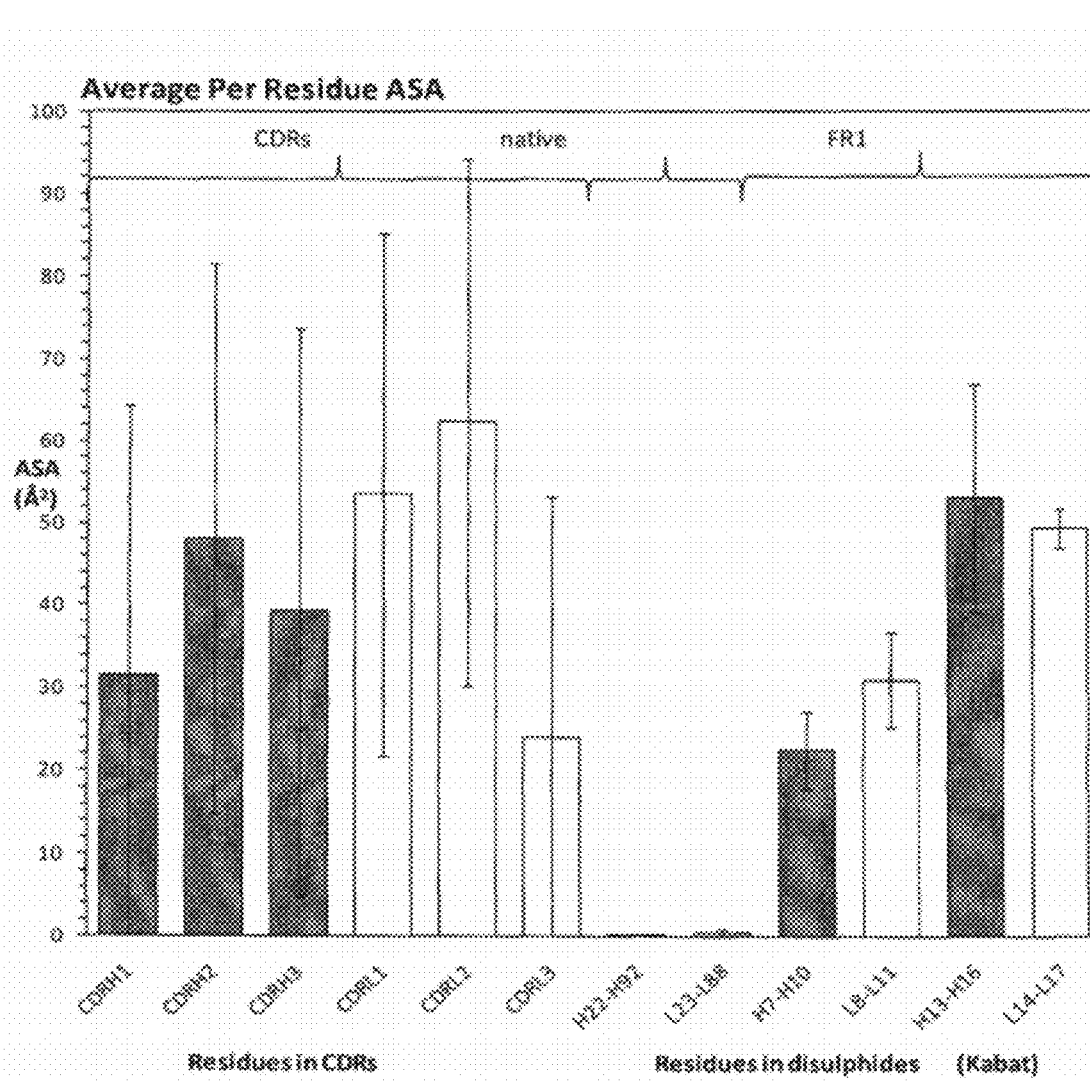
FIG. 5 is a graph of the average per residue solvent accessible surface areas (ASA) for the CDR groups and disulphides of the AVP04-xx Avibodies, $V_H$ derived columns are shown in grey, $V_L$ derived columns are shown in white. Shown as average per residue ASA for residues in CDR groups, conserved inter sheet disulphide residues (H22-H92 and L23-L88) and disulphide insertion mutation residues, error bars show standard deviation. H=heavy chain. L=light chain. Numbers indicate positions of cysteine residues (if present), H7-H10=AVP04-84, L8-L11=AVP04-50, H13-H16=AVP04-85, L14-L17=AVP04-78.

As expected, with the aim of defining mutatable residue pairs that would be available for reduction and subsequent conjugation to payloads, the solvent accessible surface area (ASA) values for each cysteine mutant pair was shown to be significantly higher than the highly conserved, and structurally buried, cysteine pairs H22-H92 and L23-L88 and similar to the structurally exposed CDR residues (FIG. 5).

1.7 Framework 1 Cysteine Insertion Positions Identified for Engineering Cysteine Replacement Mutations and Molecular Modelling in AVP07-xx and AVP02-xx Avibody Diabodies.

As outlined above, structural similarity between the VH (type 1-4), $V_L\kappa$, $V_L\lambda$ domains across the antibody families is known and accepted. Due to this structural similarity, the cysteine insertion positions identified from the model of AVP04-07, were structurally transferred to the AVP02-xx and AVP07-xx cysteine insertion Avibody models.

In the case of AVP02-60, the preferred Kabat positions for cysteine insertion were identical to that of AVP04-07, namely:

Light chain framework 1 Kabat residues L8 and L11 (AVP02-101, SEQ ID NO: 79)
Heavy chain framework 1 Kabat residues H7-H10 (AVP02-104, SEQ ID NO: 81)
Light chain framework 1 Kabat residues L14 and L17 (AVP02-102, SEQ ID NO: 83)
Heavy chain framework 1 Kabat residues H13-H16 (AVP02-105, SEQ ID NO: 85)

Figure 6A:
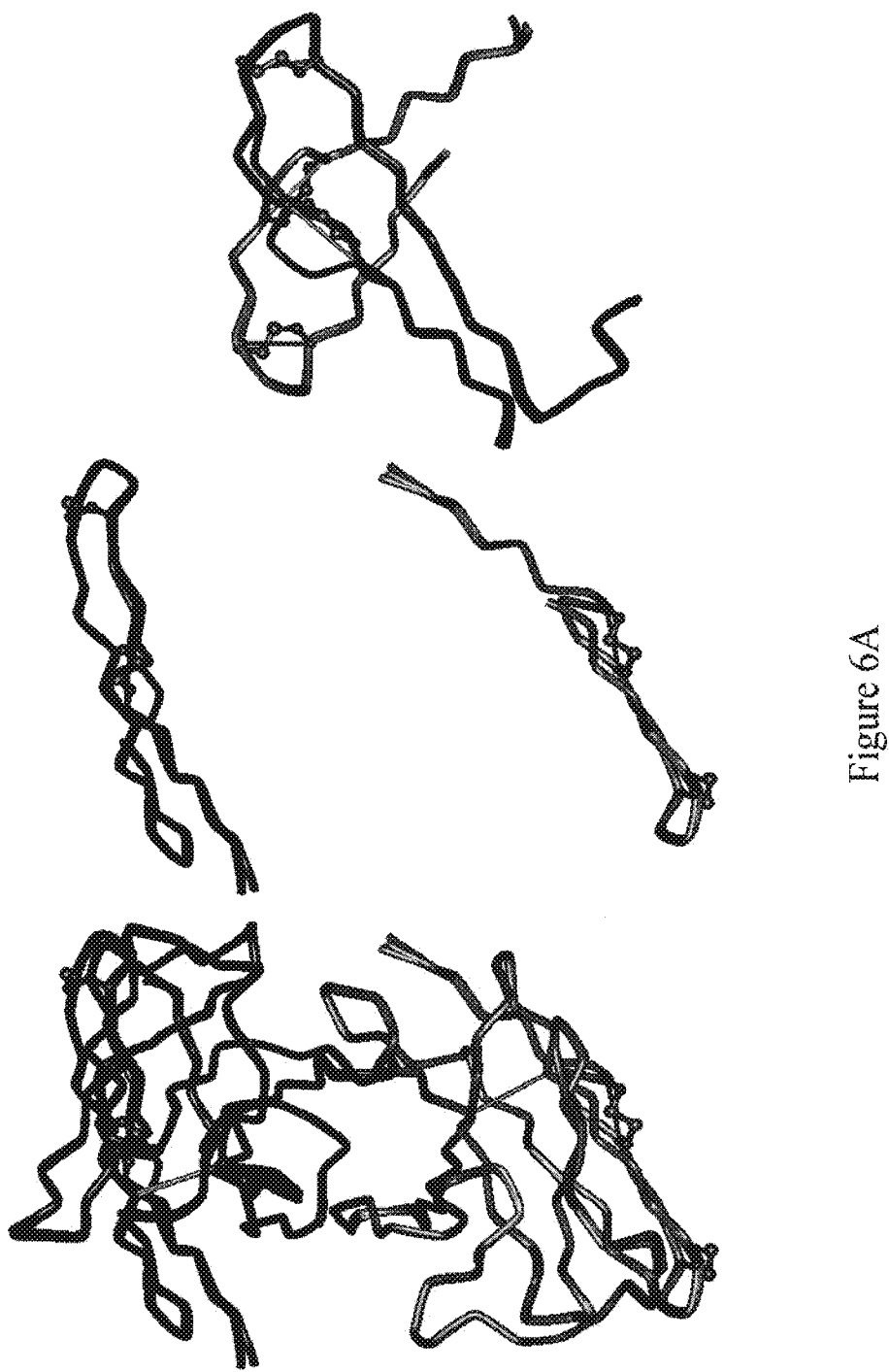
FIG. 6A is a diagrammatic representation showing the in silico homology modeled intra-Framework 1 disulphide insertion mutations in the $V_L$ and $V_H$ of the AVP02-60 diabody (comprising a polypeptide comprising a sequence set forth in SEQ ID NO: 61). Heavy chain shown in black, light chain shown in grey, in silico mutated disulphide insertion mutant side chains shown as ball and stick. Left hand side: aligned Fvs from un-mutated and two disulphide insertion mutant diabody models. Middle: as for left hand side but only showing FR1. Right hand side as for middle but rotated on the horizontal axis by 100°.

The AVP02-60 model has a $V_H$ type III domain that is structurally a little different, in the region of Kabat H7-H10, to the $V_H$ type I domain of AVP04-07 and AVP07-17. However the structural transfer of the AVP04-07 cysteine insertion could still be achieved because a) the Cα positions of H7 and H10 were very similar and b) although the intervening H8 and H9 residue positions differed, both of these residues were Gly, a small and more flexible residue with respect to other amino acids. Based on the V-gene germline sequences provided by the online Immunogenetics Database; IMGT (http://imgt.cines.fr), 98% of human sequences have a Gly at H8 and 48% have Gly at H9. This flexibility allowed the structural transfer of the H7-H10 disulphide from AVP04-84 to AVP02-104. The results of the intra-framework 1 cysteine insertion/disulphide bond formation modeling onto the AVP02-60 FR1 structure is shown in FIGS. 6A and B.

In the case of AVP07-xx Avibodies, as this construct contains a $V_L\lambda$ chain, the cysteine insertion at Kabat position L8-L11, found in both $V_L\kappa$ containing AVP04-50 and AVP02-101 Avibodies, translates structurally to L7-L11. In AVP07, the preferred intra-framework 1 cysteine insertion positions were thus identified as:

Light chain framework 1 Kabat residues L7 and L11 (AVP07-88, SEQ ID NO: 87)
Heavy chain framework 1 Kabat residues H7-H10 (AVP07-90, SEQ ID NO: 89)
Light chain framework 1 Kabat residues L14 and L17 (AVP07-89, SEQ ID NO: 91)
Heavy chain framework 1 Kabat residues H13-H16 (AVP07-91, SEQ ID NO: 93)

Figure 7A:
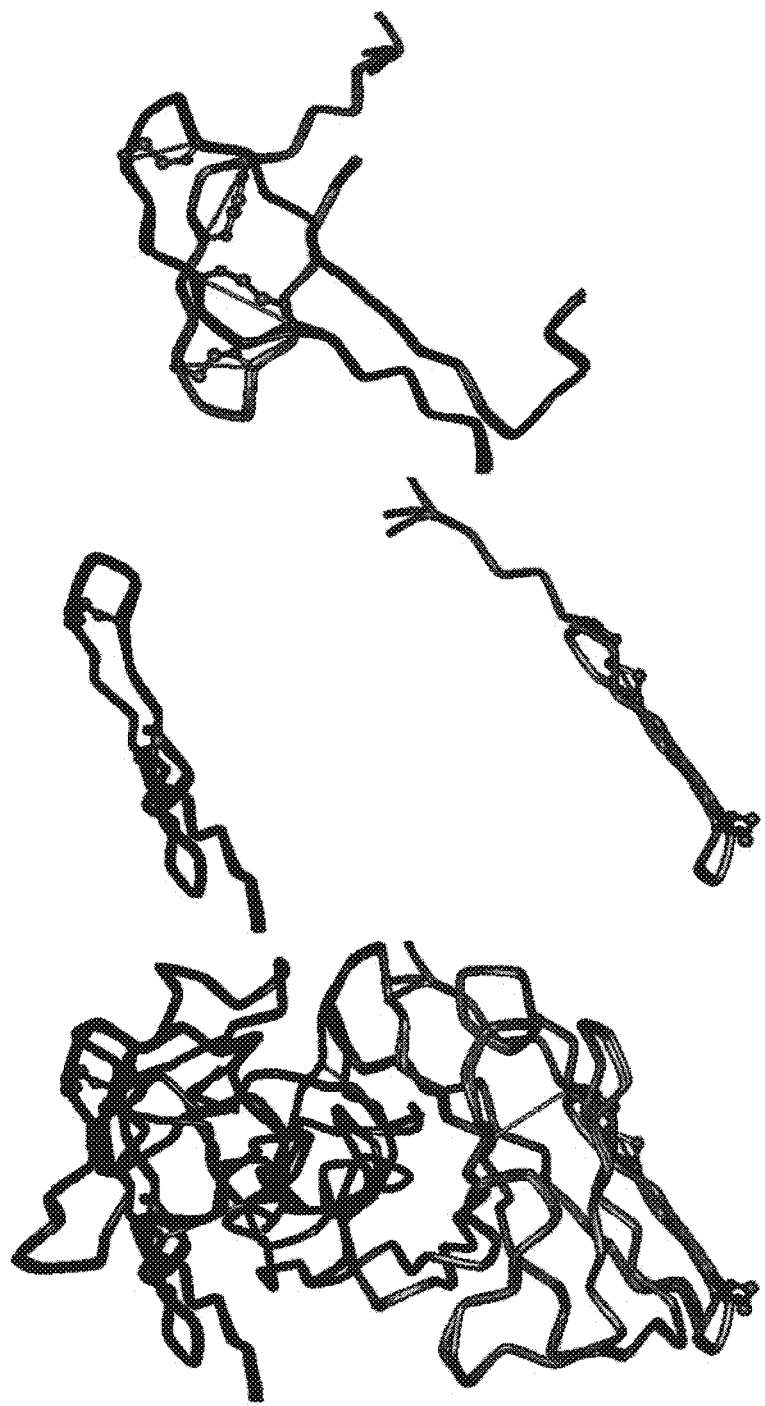
FIG. 7A is a diagrammatic representation showing the in silico homology modeled intra-Framework 1 disulphide insertion mutations in the $V_L$ and $V_H$ of the AVP07-17 diabody (comprising a polypeptide comprising a sequence set forth in SEQ ID NO: 59). Heavy chain shown in black, light chain shown in grey, in silico mutated disulphide insertion mutant side chains shown as ball and stick. Left hand side: aligned Fvs from un-mutated and two disulphide insertion mutant diabody models. Middle: as for left hand side but only showing FR1. Right hand side as for middle but rotated on the horizontal axis by 100°.
Figure 7B:
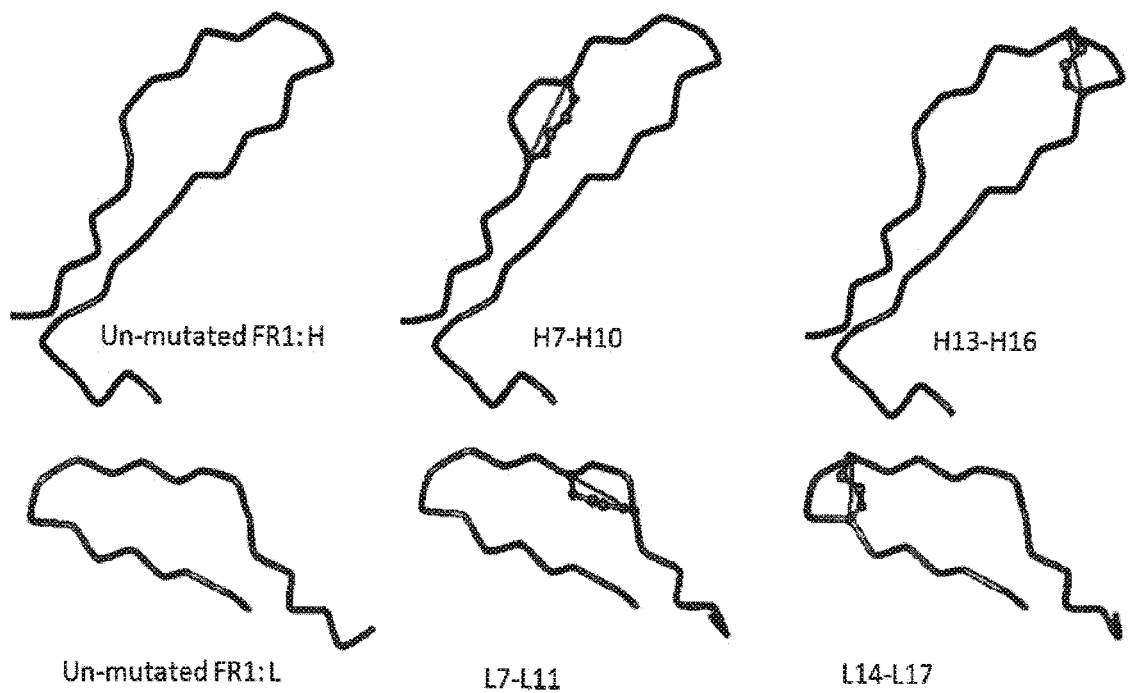
FIG. 7B is a diagrammatic representation showing the in silico homology modeled intra-Framework 1 disulphide insertion mutations in the $V_L$ and $V_H$ of the AVP07-17 diabody (comprising a polypeptide comprising a sequence set forth in SEQ ID NO: 59). Depicted are models of FR1 comprising various mutations as indicated. H=heavy chain. L=light chain. Numbers indicate positions of cysteine residues (if present). Un-mutated FR1 H/Un-mutated FR1 L=AVP07-17, H7-H10=AVP07-90, L7-L11=AVP07-88, H13-H16=AVP07-91, L14-L17=AVP07-89.

The $V_L\lambda$, in the Kabat numbering system is missing the L10 sequence position (Johnson and Wu, 2000), which necessitated the renumbering mentioned above. Structurally however, in the context of the current invention, $V_L\kappa$ L8-L11 is equivalent to $V_L\lambda$ L7-L11 with no residues missing. This can clearly be seen when comparing the models for the AVP04-07 $V_L$ FR1 and AVP07-17 $V_L$ FR1 in FIG. 4 and FIG. 7 respectively where in these specific cases the residue deletion in the sequence is N-terminal the cysteine insertion.

Figure 8:
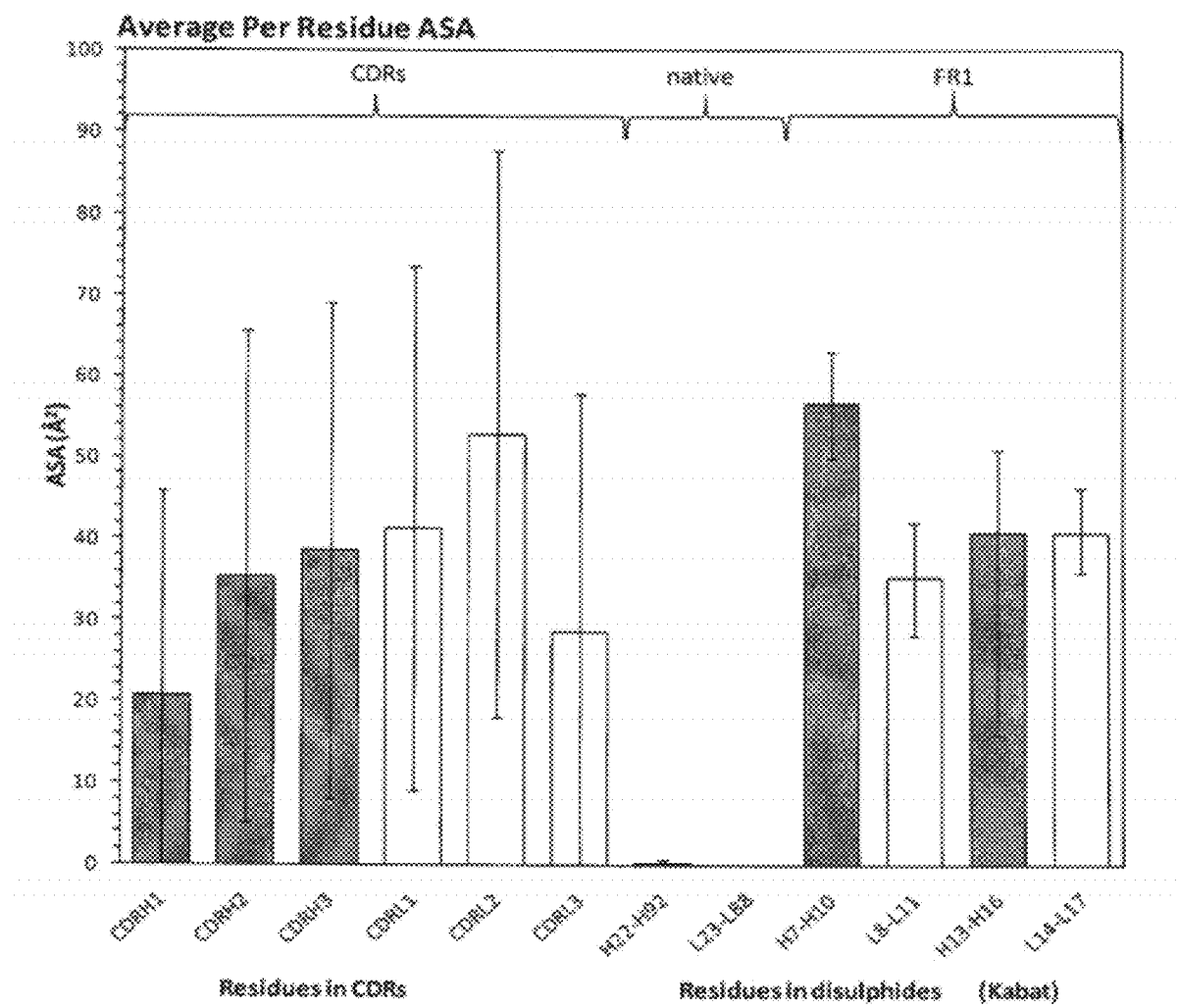
FIG. 8 is a graph of the average per residue solvent ASAs for the CDR groups and disulphides of the AVP02-xx Avibodies, $V_H$ derived columns are shown in grey, $V_L$ derived columns are shown in white. Shown as average per residue ASA for residues in CDR groups, conserved inter-sheet disulphide residues and disulphide insertion mutation residues, error bars show standard deviation. H=heavy chain. L=light chain. Numbers indicate positions of cysteine residues (if present), H7-H10=AVP02-104, L8-L11=AVP02-101, H13-H16=AVP02-105, L14-L17=AVP02-102.
Figure 9:
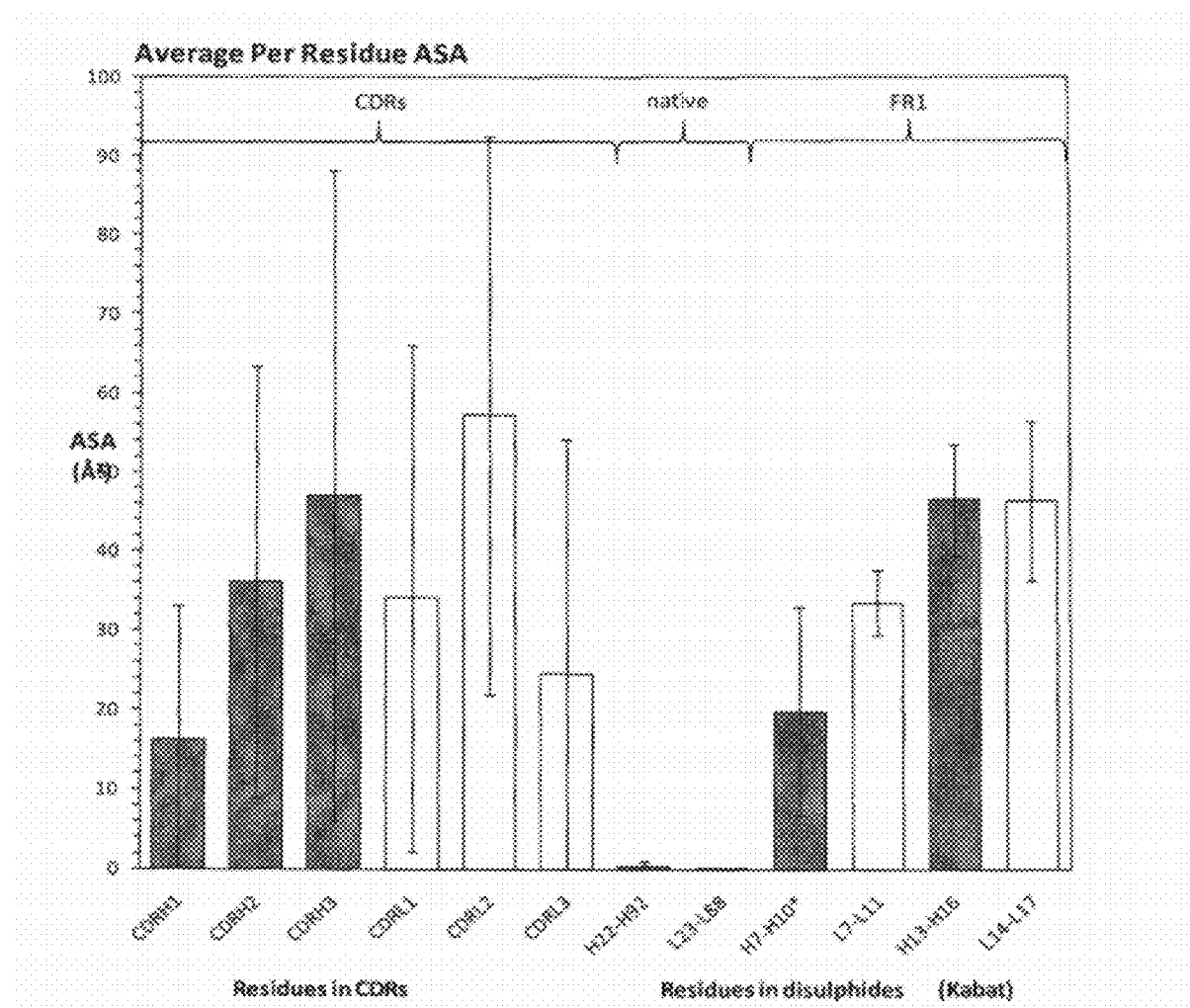
FIG. 9 is a graph of the average per residue solvent ASAs for the CDR groups and disulphides of the AVP07-xx Avibodies, $V_H$ derived columns are shown in grey, $V_L$ derived columns are shown in white. Shown as average per residue ASA for residues in CDR groups, conserved inter-sheet disulphide residues and disulphide insertion mutation residues, error bars show standard deviation. H=heavy chain. L=light chain. Numbers indicate positions of cysteine residues (if present), H7-H10=AVP07-90, L7-L11=AVP07-88, H13-H16=AVP07-91, L14-L17=AVP07-89.

Following the trend observed with the cysteine insertion positions outlined for AVP04-07, the accessible surface area (ASA) values for each preferred cysteine insertion, in AVP02 (FIG. 8) and AVP07 (FIG. 9) Avibodies, were shown to be significantly higher than the highly conserved, and structurally buried/inaccessible, cysteine pairs H22-H92 and L23-L88 and similar to the structurally exposed CDR residues.

The V domains of antibodies ($V_H$ and $V_L$) have long been subdivided into sequential and structural subtypes, for example the $V_H$ types I-IV and the $V_L\kappa$ and Wk. These subtypes are largely based on differences in the FR1 sequence and structure of these domains (Lefranc, 2001a; LeFranc, 2001b; Pallarès, 1999). The current work shows that despite this subdivision the preferred disulphide insertion positions are readily transferable in models of a variety of these subtypes without significant distortion of the non-mutated model frameworks.

However, the inventors noted that during visual inspection of un-mutated structural models, some $V_L/V_H$ subtypes contained additional (alternate) positions where intra-framework 1 cysteine insertions could be placed, generally by shifting the preferred disulphide insertion positions outlined above by 1-2 residues towards the N-terminus (for example AVP02-103, with FR1 H6-H9 mutation, SEQ ID NO: 95) or 1-2 residues towards the C-terminus of the polypeptide chain (for example corresponding clones AVP07-63 (SEQ ID NO: 65) and AVP07-68 (SEQ ID NO: 97), with FR1 L8-L12).

In all cases discussed above however, the preferred and/or alternate positions identified as being compatible with intra-framework 1 disulphide insertions all met the key modeling constraints outlined in Example 1.5

2 Synthesis of Avibody Constructs
2.1 Synthesis of "Un-mutated" Avibodies Without Engineered Intra-Framework 1 Disulphide Insertions.

DNA constructs encoding the $V_H$ and $V_L$ regions of a mouse mAb specific for TAG72 (SEQ ID NO: 54), a human mAb specific for HER2 (SEQ ID NO: 58) and a murine mAb specific for MUC1 (SEQ ID NO: 60) were synthesized with the appropriate restriction sites and cloned into pUC57 by GenScript (Piscataway, N.J., USA). Although Avibodies have been isolated in either orientation of V region i.e. $V_H$-Linker-$V_L$ and $V_L$-Linker-$V_H$ (Carmichael et al., 2003), all constructs described herein were arranged as $V_H$-Linker-$V_L$.

All DNA manipulations were carried out according to standard protocols with reagents purchased from New England Biolabs (Ipswich, Mass., USA). Diabody encoding DNA constructs were excised from pUC57 with the appropriate restriction enzymes, resolved on a 1% (w/v) agarose gel and purified from the gel using the Qiaquick gel extraction kit (Qiagen). Constructs were ligated into similarly prepared pET22b expression vectors and the ligation mixtures transformed by the electroporation method into E. coli XL1-Blue cells. Miniprep DNA was extracted from transformants using the Qiagen miniprep spin kit and recombinant clones identified by sequencing with T7 promoter and terminator primers using Dye Terminator Cycle Sequencing kits with AmpliTaq. The clone containing the V regions of the anti-TAG72 mAb in the $V_H$-Gly$_4$Ser-$V_L$ orientation was designated AVP04-07 (SEQ ID NO: 54). The clone containing the V regions of the anti-HER2 mAb in the $V_H$-Gly$_4$Ser-$V_L$ orientation was designated AVP07-17 (SEQ ID NO: 58). The clone containing the V regions of the anti-MUC1 mAb in the $V_H$-Gly$_4$Ser-$V_L$ orientation was designated AVP02-60 (SEQ ID NO: 60). These three clones formed the base parental sequences from which all other Thiolated Avibodies were derived.

This method of cloning allowed for the insertion of an amino-terminal pelB leader sequence for periplasmic expression of the target protein and either a carboxy-terminal (His)$_6$ tag or a carboxy-terminal Myc+(His)$_6$ tag. The addition of an affinity tag, such as (His)$_6$ was routinely used to streamline downstream purification processes and is known to be neutral in biological activity.

In some cases, an identical $V_H/V_L$ Avibody sequence was constructed in both carboxy-terminal (His)$_6$ tag and carboxy-terminal Myc+(His)$_6$ versions. One example of this is AVP07-63 (SEQ ID NO: 64) containing the Myc+(His)$_6$ tag, and AVP07-68 (SEQ ID NO: 96) containing only the (His)$_6$ tag. Although these two Avibodies had different carboxy-terminal tags, the $V_H$ and $V_L$ sequences were completely identical and thus these two constructs were used interchangeably.

2.2 Introduction of Intra-Framework 1 Engineered Cysteines and N-terminal Serine Substitution by Site-Directed Mutagenesis.

Based on modeling data generated, the intra-framework 1 engineered cysteine insertion mutations were introduced into the un-mutated Avibody sequences of AVP04-07, AVP07-17 and AVP02-60 to form the following thiolated Avibodies:

AVP04-xx Family Template Sequences (TAG72-Specific):

As discussed herein the use of the symbols "xx" in the context of an Avibody name indicates that numerous Avibodies of the same series exist and that the description relates to all Avibodies in that series. Replacement of the "xx" with a specific number indicates that the description refers to the Avibody having that number (based on the nomenclature used herein).

AVP04-50 Diabody nucleic acid sequence (SEQ ID NO: 56), forming the Avibody mutated in Kabat residues L8 and L11, (SEQ ID NO: 57).
AVP04-51 Diabody nucleic acid sequence (SEQ ID NO: 98), forming the Avibody mutated in Kabat residues L13 and L19 (SEQ ID NO: 99).
AVP04-78 Diabody nucleic acid sequence (SEQ ID NO: 76), forming the Avibody mutated in Kabat residues L14 and L17 (SEQ ID NO: 77).
AVP04-84 Diabody nucleic acid sequence (SEQ ID NO: 62), forming the Avibody mutated in Kabat residues H7 and H10 (SEQ ID NO: 63).
AVP04-85 Diabody nucleic acid sequence (SEQ ID NO: 74), forming the Avibody mutated in Kabat residues H13 and H16 (SEQ ID NO: 75).
AVP04-70 scFv nucleic acid sequence (SEQ ID NO: 100), forming the Avibody mutated in Kabat residues L8 and L11 (SEQ ID NO: 101).
AVP04-74 Triabody nucleic acid sequence (SEQ ID NO: 102), forming the Avibody mutated in Kabat residues L8 and L11 (SEQ ID NO: 103).

AVP07-xx Family Template Sequences (HER2-Specific):
AVP07-88 Diabody nucleic acid sequence (SEQ ID NO:86), forming the Avibody mutated in Kabat residues L7 and L11 (SEQ ID NO:87).
AVP07-71 scFv nucleic acid sequence (SEQ ID NO: 104), forming the Avibody mutated in Kabat residues L8 and L12 (SEQ ID NO: 105).
AVP07-63 Diabody nucleic acid sequence (SEQ ID NO: 64), forming the Avibody mutated in Kabat residues L8 and L12 (SEQ ID NO: 65).
AVP07-68 Diabody, identical to AVP07-63 but containing a carboxy-terminal (His)$_6$ tag and not a carboxy-terminal Myc+(His)$_6$ tag, nucleic acid sequence (SEQ ID NO: 96), forming the Avibody mutated in Kabat residues L8 and L12 (SEQ ID NO: 97).

AVP02-xx Family Template Sequences (MUC1-Specific):
AVP02-101 Diabody nucleic acid sequence (SEQ ID NO: 78), forming the Avibody mutated in Kabat residues L8 and L11 (SEQ ID NO: 79).

These thiolated Avibodies were exemplified herein to demonstrate that the preferred intra-framework 1 engineered cysteine insertion mutations were a) functionally transferable between $V_L$ and $V_H$ domains and different subtypes thereof, b) compatible with proteins (e.g., Avibodies) containing a single (scFv) or multiple (diabody/triabody) Fv domains and c) robust enough to allow for movement (e.g., +/−1-2 residues) either side of the preferred intra-framework 1 disulphide position without abrogating functionality, as suggested as feasible by modeling (refer to Example 1.7).

In all cases, cysteine residues were introduced by altering the nucleotide sequences encoding for the specific amino acid of interest using a QuikChange® site-directed mutagenesis method (Stratagene) as per instructions. Using the AVP04-07 Avibody as an illustration, the Proline residue at Kabat position L8 (FR1 VL region) is encoded by the sequence CCG and the Leucine residue at Kabat position L11 (FR1 VL region) is encoded by the sequence CTG. The QuikChange® site-directed mutagenesis technique was used to alter both of these nucleotide sequences to TGC, which encodes Cysteine.

The QuikChange® site-directed mutagenesis PCR-based method uses two complementary synthetic oligonucleotides that contain the desired mutations as primers and plasmid DNA as the template to synthesize the double-stranded mutant PCR product. Using the example above, to introduce cysteine residues at Kabat positions L8 and L11 of the FR1 region of the VL chain in AVP04-07, the following sequence 5'—GAT ATC GTG ATG ACC CAG AGC TGC AGC AGC TGC CCG GTG AGC GTG GGC GAA AAA G—3' (SEQ ID NO: 106) was used as the forward primer and 5'—C TTT TTC GCC CAC GCT CAC CGG GCA GCT GCT GCA GCT CTG GGT CAT CAC GAT ATC—3' (SEQ ID NO: 107) was used as the reverse primer. Amplification was performed using the following conditions in sequence: 95° C. for 30 sec; 18 cycles consisting of 95° C. for 30 sec, 55° C. for 30 sec and 68° C. for 13 min; a final extension of 68° C. for 7 min. The template was digested with DpnI at 37° C. for 1 hour. Transformants were obtained following the manufacturer's instructions and identified by DNA sequencing as described above.

Similar mutagenesis approaches were utilized to generate all thiolated Avibodies or were employed to replace the native N-terminal residue of the protein with a Serine residue. N-terminal Serine substitution was carried out either before or after introduction of the intra-framework 1 disulphide mutations. An example nucleotide sequence used for substituting the N-terminal Gln of AVP04-07 with a Ser residue in is presented in SEQ ID NO: 66 and SEQ ID NO: 67.

2.3 Sequence Modification of Avibody Constructs

Standard molecular biology techniques known to those skilled in the art were employed for all other modifications to DNA sequences described. Where an Avibody sequence contained 'native' Cysteine residues in hypervariable CDR regions, positions that were likely to be surface exposed as suggested by modeling data (refer to FIG. 5, FIG. 8 and FIG. 9), these residues were mutated to alternative, non-thiol-containing amino acids by site-directed mutagenesis essentially as described above. As an example, the parental clone for the AVP07 family; AVP07-17, contained two such Cysteine residues; Cys104 (Kabat numbering H100) and Cys109 (H100E) within the $V_H$ CDR3 region. These residues were substituted to Alanine using standard Quikchange® site-directed mutagenesis using mutagenic primers SEQ ID NO: 68 and SEQ ID NO: 69, forming AVP07-86 (SEQ ID NO: 109). All AVP07-xx Thiolated Avibodies contain this extra modification of $V_H$ CDR3, rendering the AVP07-xx family compatible with the intra-framework 1 disulphide mutation strategy.

Thiolated Avibodies were also generated with modified linker lengths in order to generate thiolated versions of scFv or Triabodies. It is well known from published literature in the antibody field that modification of linker composition and length can affect formation of Avibody multimers (Kortt et al. 1997). Promotion of scFv formation was engineered by modifying the linker length of the diabody parent from five residues, typically GGGGS (SEQ ID NO: 135) to fifteen, GGGGSGGGGSGGGGS (SEQ ID NO: 53) using a mutagenic primer encoding the extra residues.

Similarly, triabody formation was encouraged by removal of the linker residues and, in some cases, even removal of up to two residues of the preceding variable domain. For example, the nucleic acid encoding the AVP04-74 Avibody (SEQ ID NO: 102), encodes a triabody with the residues 'VTVSS-DIVM' instead of the linker region. This clone was engineered from the parent AVP04-50 by deletion mutagenesis using mutagenic primers encoding the desired sequence above.

3. Expression and Purification of "Un-Mutated" and Thiolated Avibodies Using Bacterial Expression The DNA of individual Avibody constructs was transformed into chemically competent E. coli BL21 cells using the manufacturer's standard protocol (Stratagene). The E. coli BL21 expression strain served as the major expression strain for all Avibodies exemplified. Expression was by means of two interchangeable approaches depending on expected yield requirements; either bacterial shake-flask expression or bacterial fed-batch fermentation. Quality assessment on protein Avibody from either method clearly indicated that the two methods were interchangeable and protein quality and properties were comparable.

3.1 Bacterial Shake-Flask Expression

A single transformant colony was inoculated into 500 ml 2×YT containing 1% D-glucose and 100 µg/ml ampicillin and incubated at 37° C. overnight, shaking at 220 rpm. 18 L of the same media was seeded with the overnight culture to a final $OD_{600}$ of 0.1 and incubated at 30° C. until the $OD_{600}$ was between about 0.6-0.8. The cultures were transferred to 12° C. and shaking continued until the induction temperature was reached. Protein expression was induced with the addition of 0.2 mM IPTG and the cultures incubated at 12° C. for 15 hours. Bacterial pellets were prepared by centrifugation at 10,000×g, harvested, weighed and stored at −20° C.

Bacterial pellets containing expressed protein from this expression system averaged approximately 6 g/L of culture media.

3.2 Bacterial Fed-Batch Fermentation

Seed cultures were grown in 2 L baffled Erlenmeyer flasks containing 500 mL of a complex medium and incubated at 37° C. shaking at 200 rpm for 16 h; the complex medium contained (per L): Tryptone, 16 g; Yeast Extract, 5 g; NaCl, 5 g; ampicillin, 200 mg. Defined medium was used for protein expression and contained (per L): $KH_2PO_4$, 10.64 g; $(NH_4)_2HPO_4$, 4.0 g; and citric acid monohydrate, 1.7 g; glucose 25 g; $MgSO_4.7H_2O$, 1.25 g; PTM4 trace salts, 5 mL; ampicillin, 200 mg; thiamine-HCl, 4.4 mg. PTM4 trace salts contained (per L): $CuSO_4.5H_2O$, 2.0 g; NaI, 0.08 g; $MnSO_4.H_2O$, 3.0 g; $NaMoO_4.2H_2O$, 0.2 g; $H_3BO_3$, 0.02 g; $CoCl_2.6H_2O$, 0.5 g; $ZnCl_2$, 7.0 g; $FeSO_4.7H_2O$, 22.0 g; $CaSO_4.2H_2O$, 0.5 g; $H_2SO_4$, 1 mL. All media and additives were sterilized by autoclaving at 121° C. for 30 minutes except PTM4 trace salts, thiamine hydrochloride and ampicillin which were filter sterilised.

Protein expression was completed in 2 L glass Biostat B bioreactors (Sartorius Stedim Biotech, Germany) containing 1.6 L of defined medium. The dissolved oxygen concentration was maintained at 20% by automatically varying the agitation rate between 500 and 1,200 rpm and the aeration rate (air supplemented with 5% oxygen) between 0.3 and 1.5 L $min^{-1}$. Oxygen supplementation of the air flow was manually increased as required. The pH of the culture was controlled at 7.0 via automatic addition of 10% (v/v) $H_3PO_4$ or 10% (v/v) $NH_3$ solution and foam was controlled by the automatic addition of antifoaming agent [10% (v/v) polypropylene 2025)]. Unless specified otherwise, the vessel temperature was maintained at 37° C. Bioreactors were inoculated with seed culture to attain a starting optical density (measured at 600 nm) of 0.25.

After complete utilization of the glucose added to the medium, nutrient solution (feed) containing (per L): glucose, 600 g; and $MgSO_4.7H_2O$ 22.4 g, was pumped into the bioreactor at a flow rate of 40 mL $h^{-1}$. Two hours after initiation of the feed the vessel temperature was slowly reduced to 20° C. over a 2.5 hour period (6.8° C. $h^{-1}$) after which protein expression was induced by the addition of 0.2 mM IPTG and the feed rate was decreased to 6 mL $h^{-1}$. Cultures were harvested 12 hours after induction and typically optical densities (measured at 600 nm) reached 110 and approximately 330 g of wet cell paste was recovered from each 2 L culture.

3.3 Purification of Avibodies Expressed in *E. coli*

Irrespective of the expression approach that was implemented, all Avibody proteins were purified essentially as outlined below.

Bacterial pellets harvested from expression culture (approximately 50-400 g depending on expression method) were lysed, protein extracted and subsequently purified by standard chromatographic techniques. 5 mL of His-Tag affinity chromatography lysis buffer (20 mM phosphate, 500 mM NaCl, 20 mM Imidazole, 0.25 mg/ml Lysozyme, 1 mM PMSF, 50 ug/ml DNAseI, pH 7.4) for every gram of bacterial pellet was used to resuspend the cell pellet prior to lysis by mechanical homogenisation then either sonicated (6×30 second pulses on ice) or by three passages through an Emulsiflex-C5 cell disruptor (AVESTIN Inc., Canada). The bacterial lysate was subsequently incubated at room temperature for 1 hour prior to centrifugation (16,000×g, 30 min) and filtration (0.45 μm filter membrane).

Figure 10A:
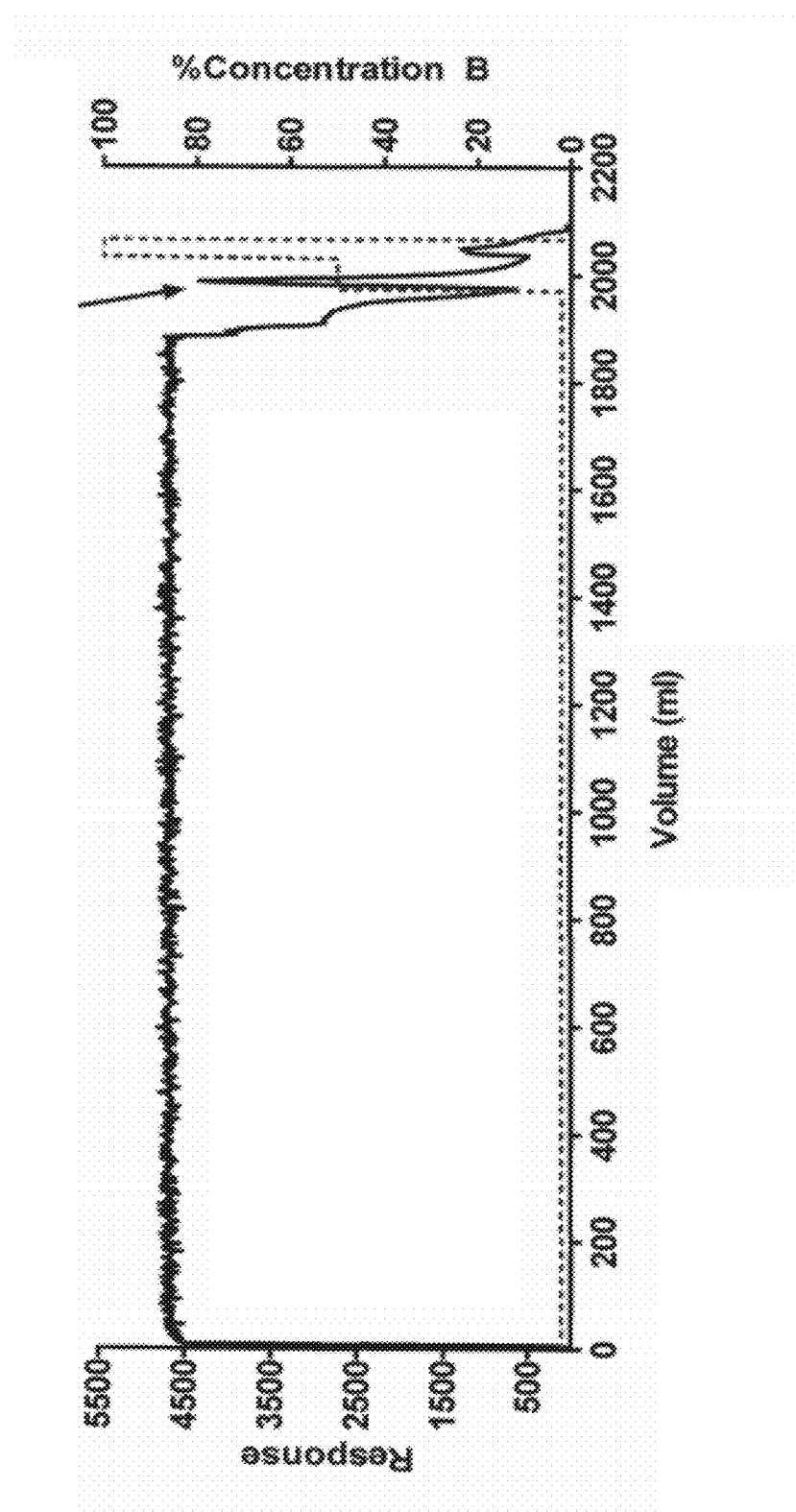
FIG. 10A is a graphical representation showing the 280 nm chromatograph of AVP04-50 (comprising polypeptide comprising a sequence set forth in SEQ ID NO: 57) His-Tag affinity chromatography purification. Arrow indicates elution peak of interest. Dotted line indicates proportion of elution buffer.

His-Tag affinity chromatography purification using the AKTA Purifier 10 (GE LifeSciences) was then used to purify diabodies from filtered bacterial lysate. Between one and four 5 mL HisTrap™ (GE LifeSciences) crude FF columns were employed in series for purification depending on the scale of purification. Lysate was passed through the HisTrap™ column via an external P960 pump. HisTrap™ columns were washed with 10 column volumes of His-Tag affinity chromatography extraction buffer (20 mM sodium phosphate, 500 mM NaCl, 20 mM Imidazole, pH7.4). Purified protein was eluted in 50% His-Tag affinity chromatography elution buffer (20 mM sodium phosphate, 500 mM NaCl, 500 mM Imidazole, pH7.4) and 50% His-Tag affinity chromatography extraction buffer (a final concentration of 260 mM Imidazole). Fractions containing eluted proteins (as determined by 280 mM absorbance on AKTA Unicorn software) were collected, pooled, protein concentration determined and dialysed in the appropriate ion exchange buffer. A typical His-Tag affinity chromatography elution profile, using the TAG72-specific AVP04-50 (SEQ ID NO: 57) diabody is shown in FIG. 10A. All Avibodies described herein showed similar elution profiles.

Partially purified Avibodies were subsequently dialysed in a buffer 1.0-1.5 pH units lower than the calculated pI of the protein (for cation exchange) or 1.0-1.5 pH units higher than the pI of the protein (for anion exchange). Typically, Avibodies with a pI of 7.0-8.0 were dialysed in MES buffer (50 mM MES, pH 6.0 for cation exchange), those with a pI of 8.0-9.0 were dialysed in phosphate buffer (50 mM phosphate, pH 7.0 for cation exchange) and those with a pI of 5.0-6.5 were dialysed in Tris buffer (20 mM Tris-HCl, pH 8 for anion exchange). All Avibody pI values fell within these ranges. Avibodies were dialysed into more than 200× volume of buffer with three buffer exchanges no less than 2 hours apart. Dialysis was performed using Spectrapor 6-8000 Da MW cut-off dialysis tubing at 4° C.

Following dialysis, the protein sample was centrifuged at 3220×g for 10 minutes to pellet denatured insoluble material prior to ion exchange. Ion exchange was performed using the AKTA purifier 10, employing up to two 5 mL HiTrap™ SP HP columns in series, passing the cleared dialysed material through the column via a P960 external pump. Following this step, the column was washed with 10 column volumes of ion-exchange buffer prior to commencement of a linear buffer gradient (salt gradient) for elution of the protein from the column. In this process, the ion exchange buffer was replaced over a linear gradient with the identical buffer with the addition of NaCl to 1M final concentration. The elution gradient was performed over 300 mL with a final concentration of 600 mM NaCl.

Figure 10B:
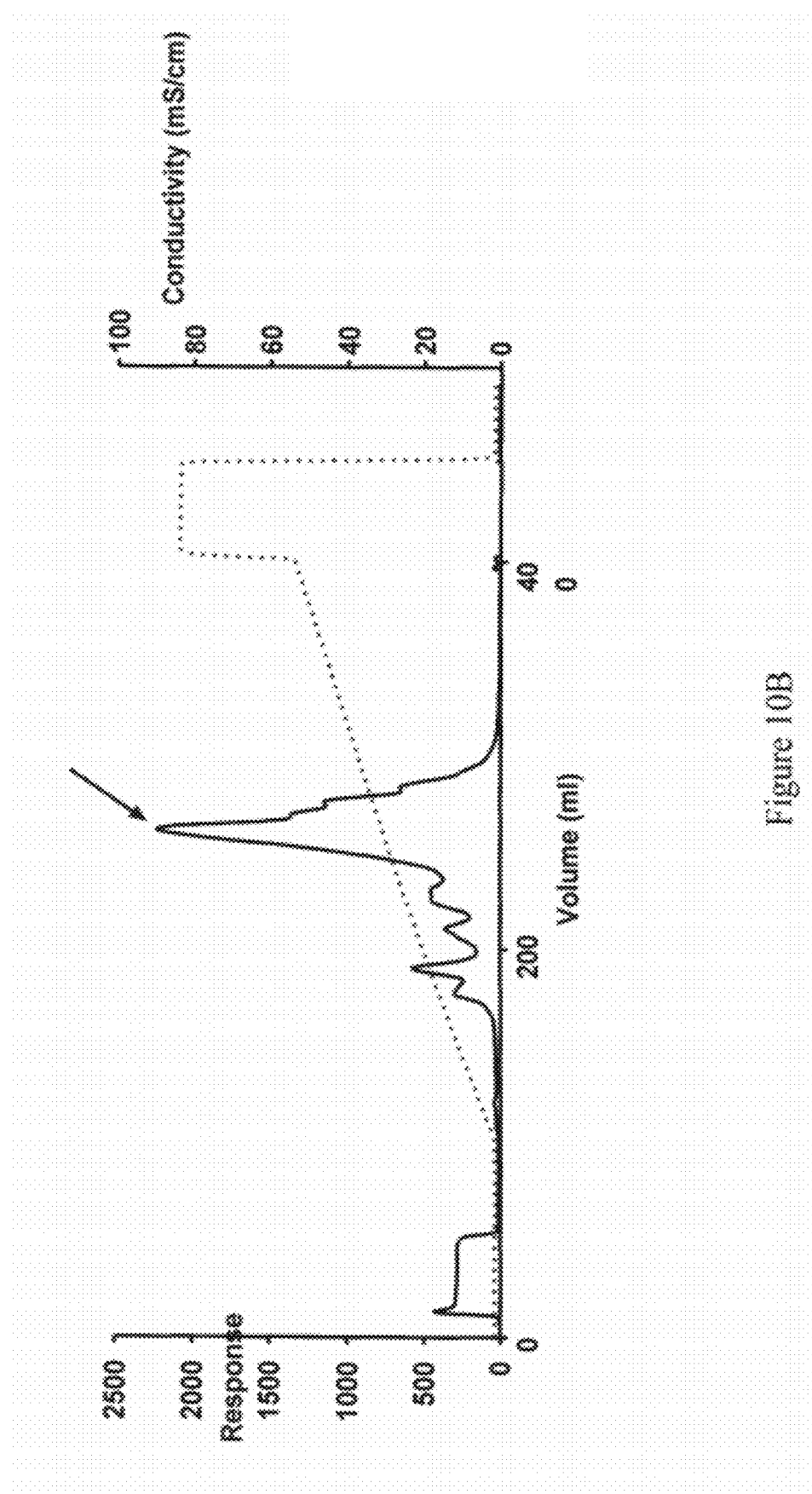
FIG. 10B is a graphical representation showing results of cation purification of AVP04-50 (comprising polypeptide comprising a sequence set forth in SEQ ID NO: 57). Arrow indicates elution peak of interest. Dotted line indicates proportion of elution buffer.

Fractions corresponding to the eluted diabody (as determined by the 280 nm absorbance profile on Unicorn software) were pooled and quantified. A typical ion exchange elution profile for AVP04-50 is presented in FIG. 10B. The AVP04-50 diabody routinely eluted at a salt concentration of approximately 37 mS/cm or 32% B in which the major dimeric isoform (arrow) of AVP04-50 could be easily separated from other charge and size variants. The diabody clones, even those from different families, routinely eluted at similar point in the salt gradient. In some cases, analytical size exclusion using a calibrated Superdex 200 10/300 column (GE LifeSciences) in 1×PBS buffer (137 mM NaCl, 2.7 mM KCl, 8.1 mM $Na_2HPO_4$, 1.47 mM $KH_2PO_4$, pH7.4) was carried out to confirm peak identity of the desired species or composition of specific fractions before pooling. The elution fractions containing the major isoform of interest were pooled for downstream purification.

Figure 10C:
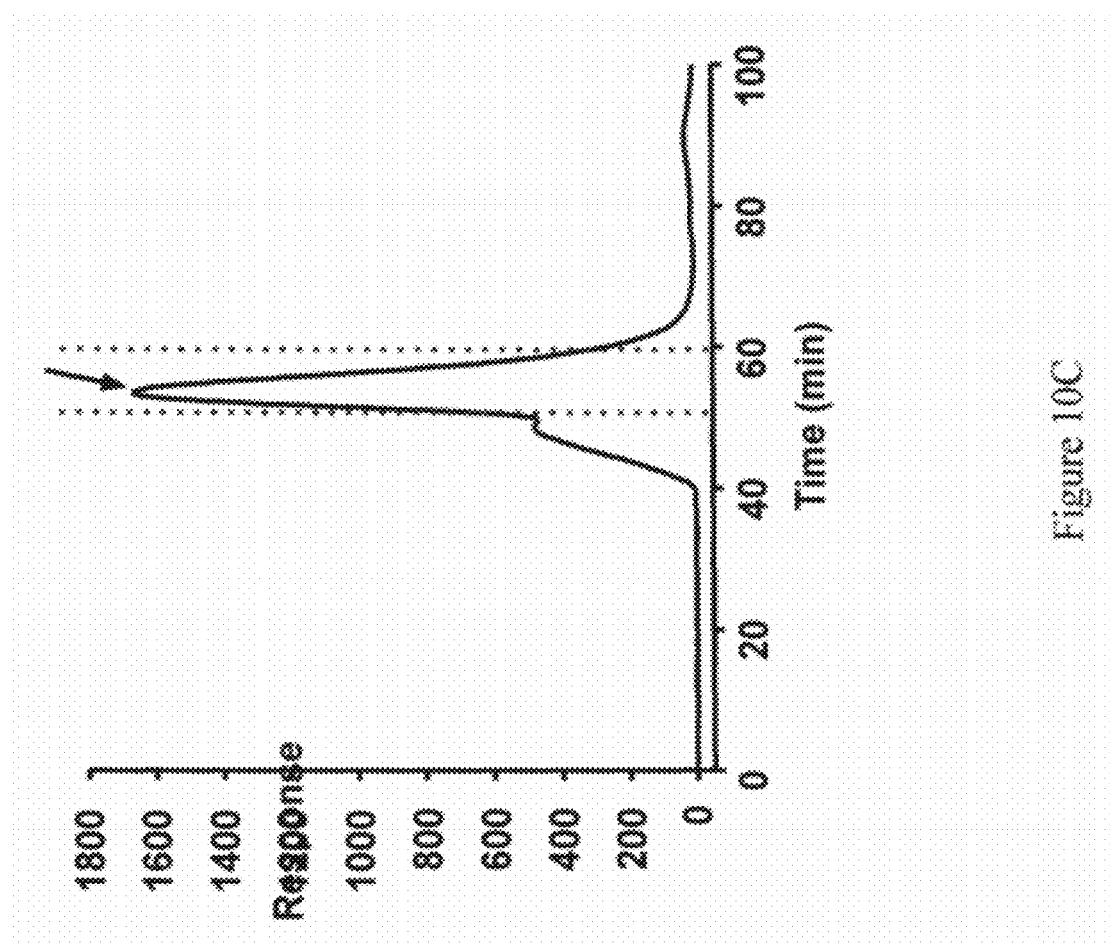
FIG. 10C is a graphical representation showing results of size exclusion chromatography of AVP04-50 (comprising polypeptide comprising a sequence set forth in SEQ ID NO: 57). Arrow indicates elution peak of interest. Dotted lines outline fractions of interest.

Following ion exchange, eluted protein material was concentrated to approximately 3 mg/mL at 4° C. prior to gel filtration. Gel filtration was performed using the Pharmacia Amersham (GE LifeSciences) Superdex® 75 26/60 prep-grade column in PBS on the AKTA Purifier 10. Using the AVP04-50 diabody as an example, the diabody eluted at approximately 140 ml (or 53.5 minutes) post injection (FIG. 10C). Diabody variants, both within the AVP04 family and others, routinely eluted at similar elution volumes as expected of any globular protein with a molecular weight of approximately 54 kDa. Fractions within the margins outlined in FIG. 10C, corresponding to the eluted AVP04-50 dimer, were pooled and concentrated to between 0.5-3 mg/ml using Amicon Ultrafree spin concentrators with a 10K MWCO (Millipore, USA) at 3200×g, 4° C.

Figure 10E:
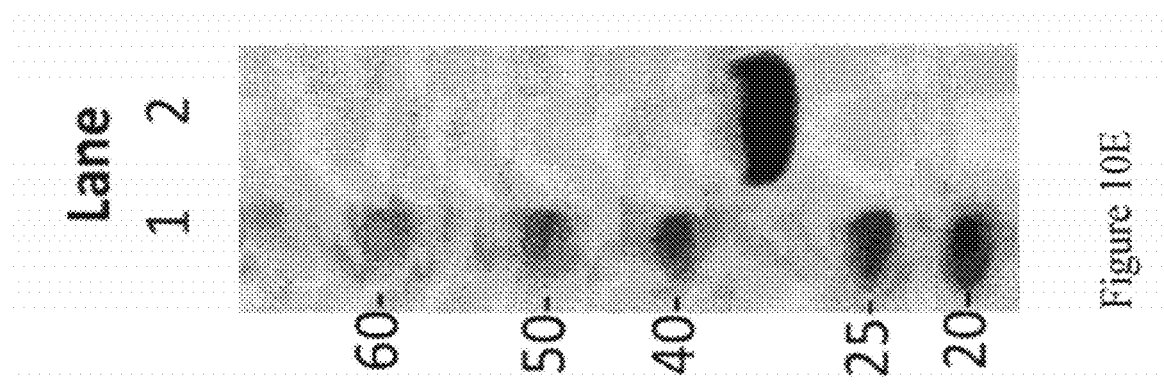
FIG. 10E is a copy of a photographic representation showing results of a reducing SDS-PAGE gel showing the purity of AVP04-50 (comprising polypeptide comprising a sequence set forth in SEQ ID NO: 57) post purification. Lane 1: Invitrogen Benchmark Pre-stained molecular weight marker, Lane 2: AVP04-50 protein band.

The final purity of the purified product was routinely assessed by gel filtration chromatography on a Superdex® 200 10/300 column and SDS-PAGE electrophoresis. As example, the purification method of AVP04-50 routinely returned protein with purities resulting in a single clean elution peak on gel filtration (FIG. 10D) and a single defined species on SDS-PAGE electrophoresis (FIG. 10E).

Figure 11A:
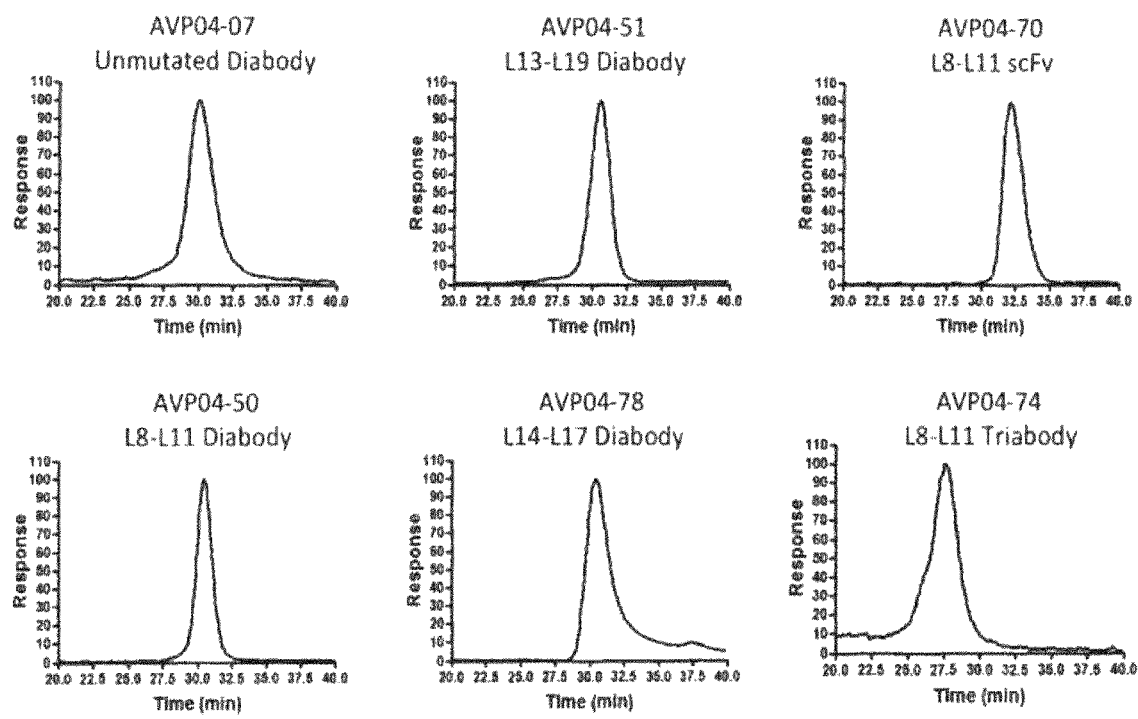
FIGS. 11A-C include graphical representations of the purified Avibodies mentioned herein (as indicated, nomenclature corresponds to that used throughout the text and in the sequence listing) following size exclusion chromatography.
Figure 11B:
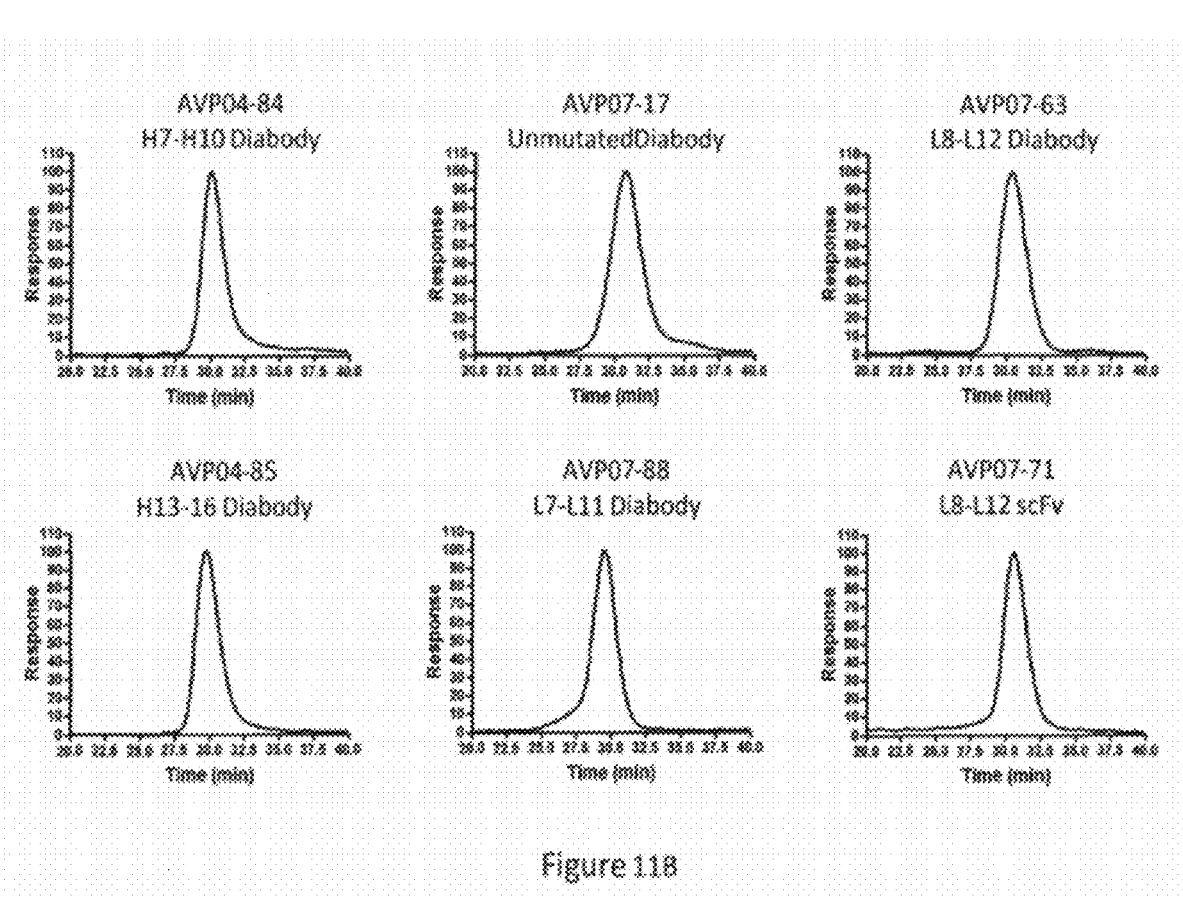
Figure 11C:
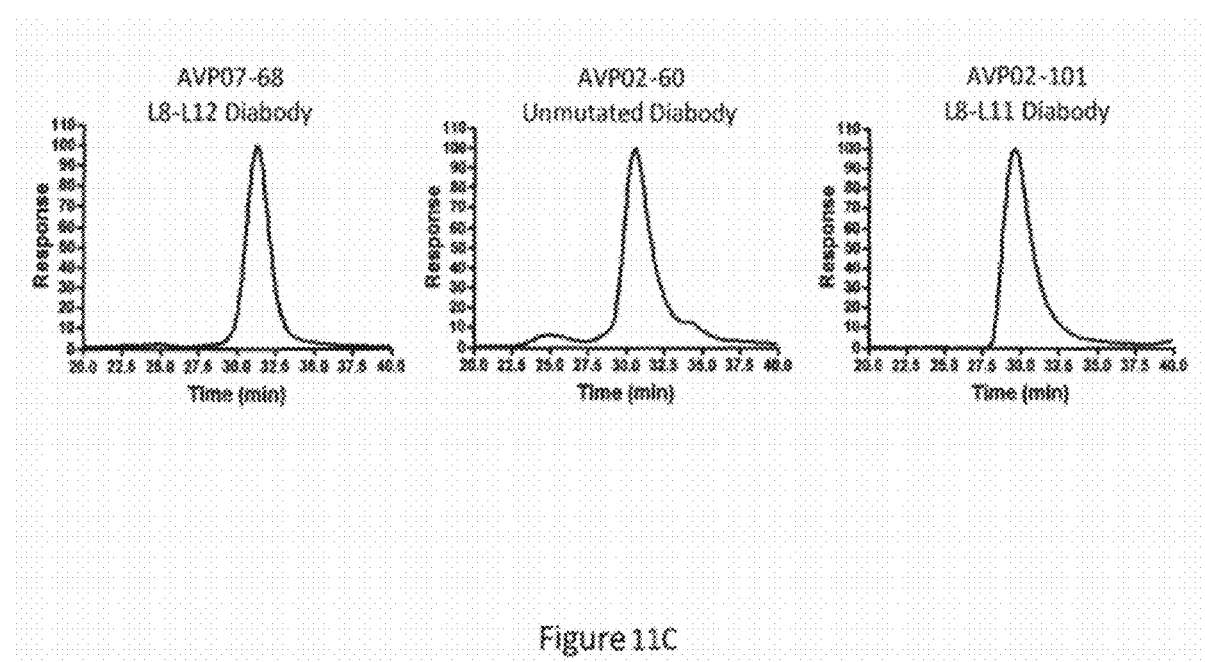

The purification strategy and resultant purity profiles did not differ significantly between any of the Avibodies tested. FIGS. 11A-C highlight the final size exclusion chromatography profiles of Avibodies described herein and as indicated in the Figures. As expected, aside from a small degree of variance both within and between different Avibody families, the elution times of the Avibodies corresponded well to the expected molecular size; triabodies eluted earlier than diabodies which eluted later than scFvs. All Avibodies described herein could be functionally expressed and purified to substantial homogeneity. The presence of intra-Framework 1 cysteine replacement mutations did not have any effect on the ability to functionally express and purify the Avibody to substantial uniformity, partially confirming modeling data suggesting the placement of engineered cysteines within Framework 1 of Thiolated Avibodies did not cause detrimental structural conformational changes leading to Avibody destabilization.

Example 4

In Vitro Immunoreactive Assessment of Diabodies

Binding activity to soluble antigen was established by a column shift assay using size exclusion chromatography. The antigen for the AVP04-xx Avibodies is TAG72, available in soluble form from bovine submaxillary mucin (BSM) (Sigma). For the AVP07-xx Avibodies, the soluble antigen is recombinant HER2 ectodomain. For the AVP02-xx Avibodies, the soluble antigen is recombinant full length MUC1. Irrespective of Avibody or antigen, the column shift assay was performed essentially as described below.

At least two times molar excess of soluble antigen to diabody was incubated for 1 hr in PBS buffer at ambient temperature. Binding activity was determined by comparing the resulting Avibody-antigen complex peak to the free diabody peak. A positive binding result was regarded as the depletion of the peak corresponding to free Avibody and/or increased size of the peak corresponding to an Avibody-antigen complex following incubation. The elution profiles of the Avibody or Avibody-antigen complex was monitored though absorbance at 280 nm. In all cases, Avibody alone eluted between 28-33 minutes, and Avibody-Antigen complexes eluted at 10-25 minutes.

Figure 12A:
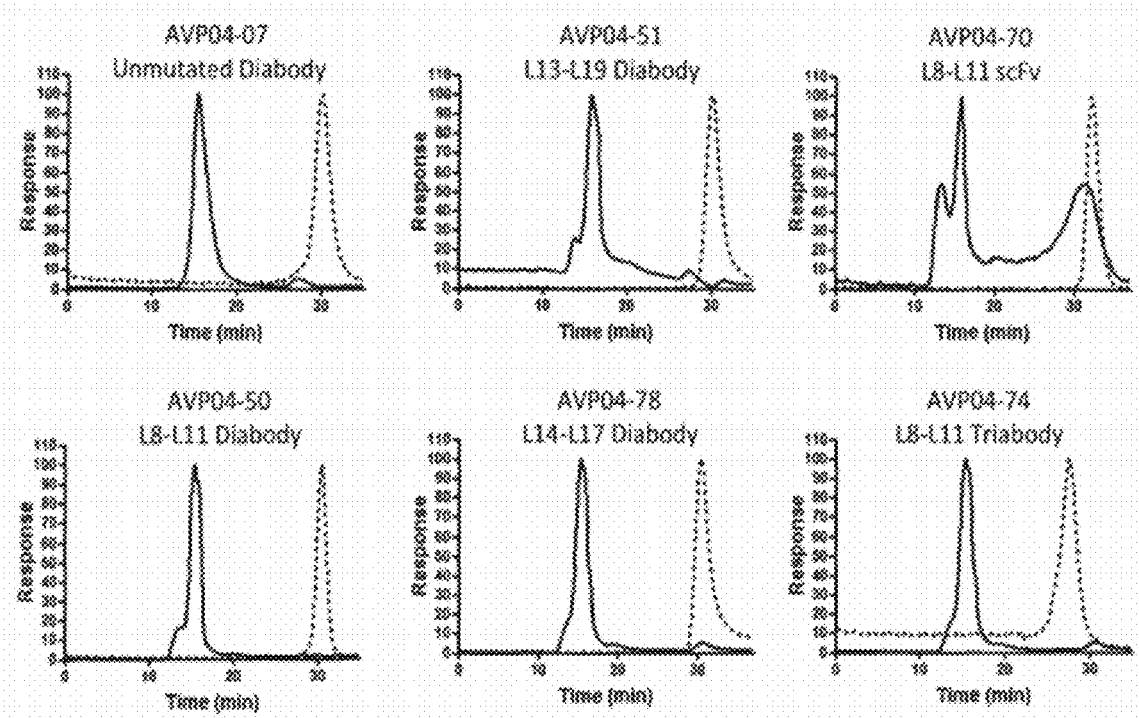
FIGS. 12A-C include graphical representations of a column shift assay used to determine immunoreactivity of Avibodies mentioned herein (as indicated, nomenclature corresponds to that used throughout the text and in the sequence listing). Each graph comprises two overlaid size exclusion chromatography profiles; of the Avibody incubated either in the presence (solid line) or absence (dotted line) of antigen.
Figure 12B:
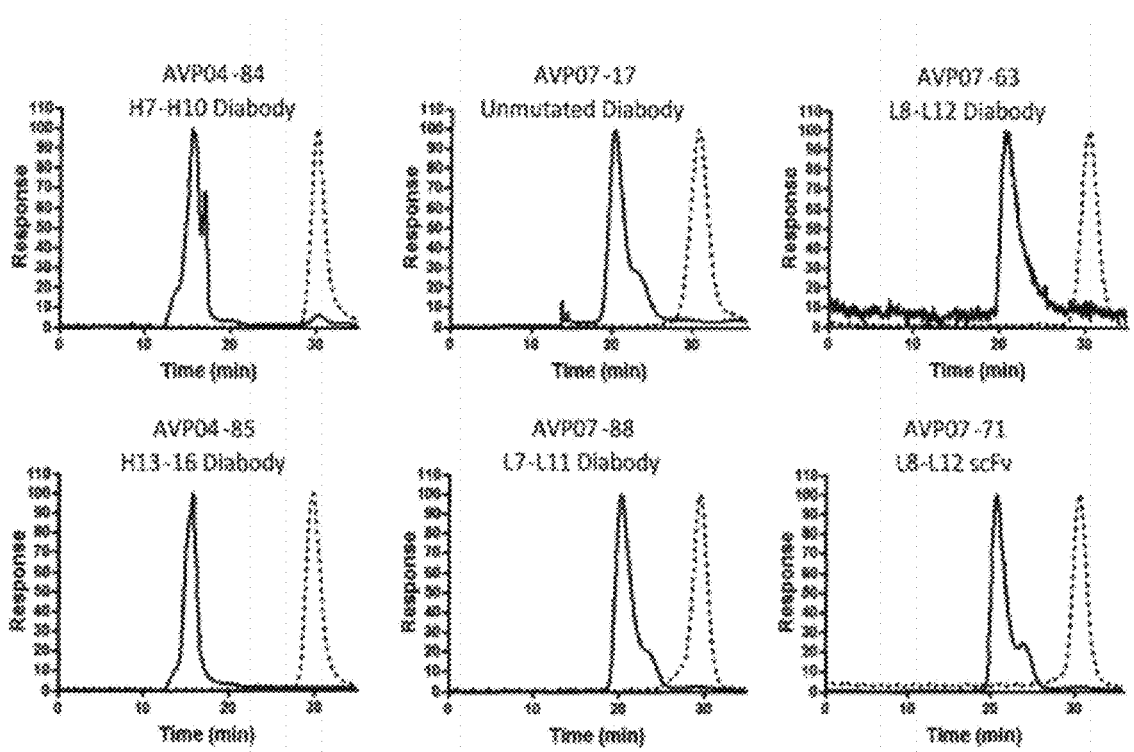
Figure 12C:
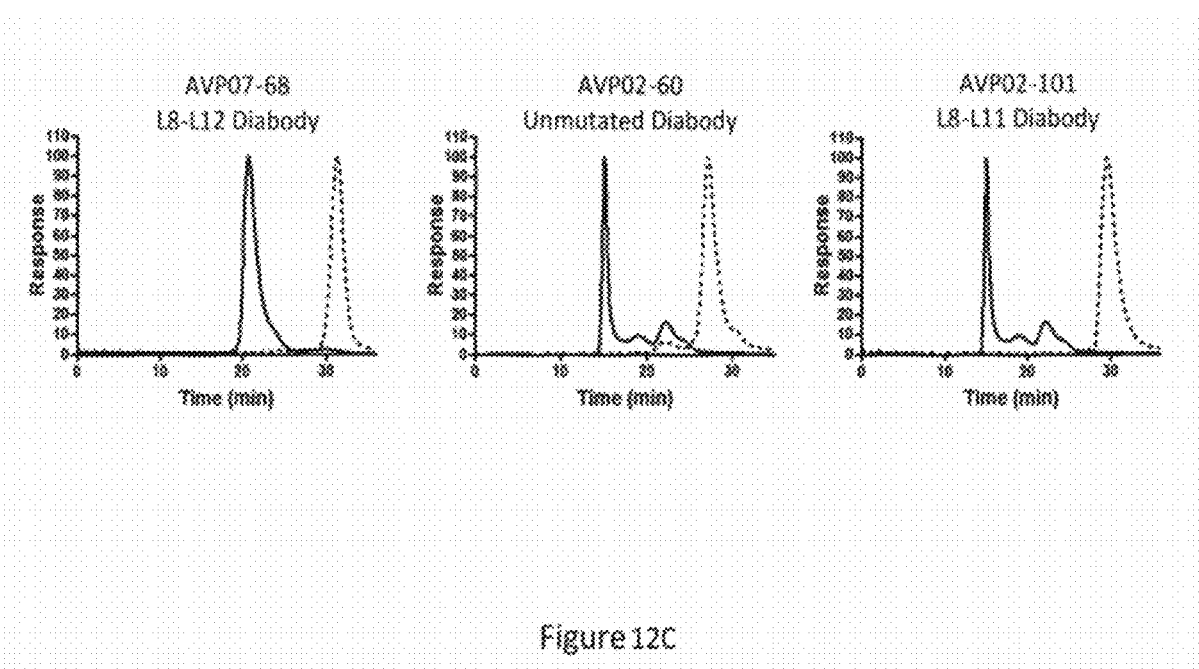

The immunoreactivity of all Avibodies described herein was assessed using the protocol described above and the results depicted in FIGS. 12A-C. In all cases, the formation of an Avibody-antigen complex, evidenced by a significant shortening of elution times in gel filtration, and/or reduced amount of unbound Avibody was observed; indicating Avibodies are immunoreactive. scFv Avibodies have just one binding site on each molecule so are expected to display weaker binding properties than diabodies and triabodies that have multiple binding sites and as such, display avid binding. As expected, AVP04-70 scFv forms a less stable Avibody: Antigen complex than the diabody or triabody clones, as evidenced by a different SEC profile. However, depletion of the 'unbound' AVP04-70 peak and formation of an Avibody: Antigen complex peak is evident in the profile, indicating it is immunoreactive.

Complex formation was not observed when Avibodies were incubated with an irrelevant antigen indicating a specific binding interaction occurred.

The presence or absence of intra-Framework 1 cysteine replacement mutations in thiolated Avibodies did not abrogate binding, further indicating that the intra-Framework 1 cysteine replacement mutations sites were engineered in positions which had little or no effect on the functional properties of the Avibody.

Example 5

Quantification of Free Sulphydryls in Thiolated Avibodies

Thiolated Avibodies could be routinely expressed and purified to substantial homogeneity and were shown to be functionally active. The presence of engineered intra-Framework 1 disulphide bridges in thiolated Avibodies, and their availability to reduction, was assessed by a colorimetric assay.

Thiolated Avibodies were incubated with 3.8 mM of TCEP (Tris(2-carboxyethyl)phosphine hydrochloride) (Pierce, Rockford, Ill., USA) in PBS for 25 min at RT. Following reduction, TCEP was removed with a PD10 desalting column pre-equilibrated with 100 mM phosphate buffer+1 mM EDTA pH 6.5, collecting 0.5 mL fractions. Peak protein fractions were identified by UV spectroscopy and pooled.

To test reactive thiols, 50-75 µg of reduced protein was diluted in 100 mM sodium phosphate buffer, 1 mM EDTA, pH 8.0 with 5 µl of 4 mg/mL Ellman's reagent (5,5'-Dithiobis(2-nitrobenzoic acid); DTNB) (Pierce, Rockford, Ill.). The reaction was allowed to proceed at ambient temperature for 15 min. Reactive sulphydryl concentration was quantified by spectroscopy, assuming the molar extinction coefficient of TNB in this buffer system at 412 nm, is 14,150 $M^{-1}$ $cm^{-1}$. Estimation of reactive sulphydryl groups per diabody was obtained by dividing the molar concentration of sulphydryls by the molar concentration of diabody. Intact IgG and a non-Thiolated Avibody not containing intra-Framework 1 cysteine replacement mutations (interchangeably either AVP04-07 or AVP02-60) were used as standardizing controls.

Under these reducing conditions, the conserved disulphide bond between invariant Kabat positions L23 and L88 and invariant Kabat positions H22 and H92 are not reactive and are not available for conjugation as expected.

Using the reducing conditions outlined above, an intact IgG control indicated on average, 8 reactive thiols following reduction, as expected from sequence analysis (data not shown). In contrast, control Avibody such as AVP04-07 and AVP02-60 consistently showed no free or reactive thiols.

Table 2 shows a subset of AVP04-xx, AVP02-xx and AVP07-xx Thiolated Avibodies with intra-framework 1 cysteine replacement mutations in $V_L$ L8-L11 (or L7-L11 in the case of the $V_L\lambda$ containing AVP07-xx family). In all cases, unreduced Avibodies containing intra-Framework 1 cysteine replacement mutations appeared to have less than 0.5 reactive thiols on the surface, clearly indicating that the intra-Framework 1 cysteine replacement mutations, in the unreduced state, did indeed form a disulphide bridge.

This disulphide bridge could be readily reduced as described, making them available for conjugation. In the reduced state, all Avibodies containing intra-Framework 1 cysteine replacement mutations displayed an average of 4 reactive thiols.

TABLE 2

Quantification of reactive thiols by molar absorptivity.

| Sample | Protein Conc. (mol/L) | Conc. S—H (mol/L) | Average Number of reactive Thiols |
|---|---|---|---|
| AVP04-50 native | 1.838E−05 | 7.915E−06 | 0.4 |
| AVP04-50 reduced | 1.268E−05 | 5.853E−05 | 4.6 |
| AVP2-101 native | 1.179E−05 | 5.497E−06 | 0.5 |
| AVP2-101 reduced | 6.369E−05 | 2.869E−04 | 4.5 |
| AVP07-88 native | 8.758E−06 | 1.187E−05 | 1.4 |
| AVP07-88 reduced | 7.532E−06 | 3.769E−05 | 5.0 |

Example 6

Payload Conjugation to Reduced Engineered Disulphides in Thiolated Avibodies

The availability of engineered intra-Framework 1 disulphide bridges in thiolated Avibodies to reduction indicated that any of a number of thiol-reactive payloads could be conjugated to the exposed and reduced cysteines.

To demonstrate this ability, a maleimide-PEG$_{24}$-methoxy payload was conjugated to the reduced engineered intra-framework 1 cysteines essentially as described herein.

Following the reduction of Thiolated Avibodies and removal of reducing agent, an excess of maleimide-PEG$_{24}$-methoxy (mal-PEG$_{24}$-OMe) (Quanta Biodesign, OH, USA) was added at 20 equivalents per Avibody and allowed to react overnight at 4° C. Following PEGylation, unreacted PEG was removed by extensive dialysis and success of PEG loading was determined by SDS-PAGE and mass spectroscopy.

Figure 13A:
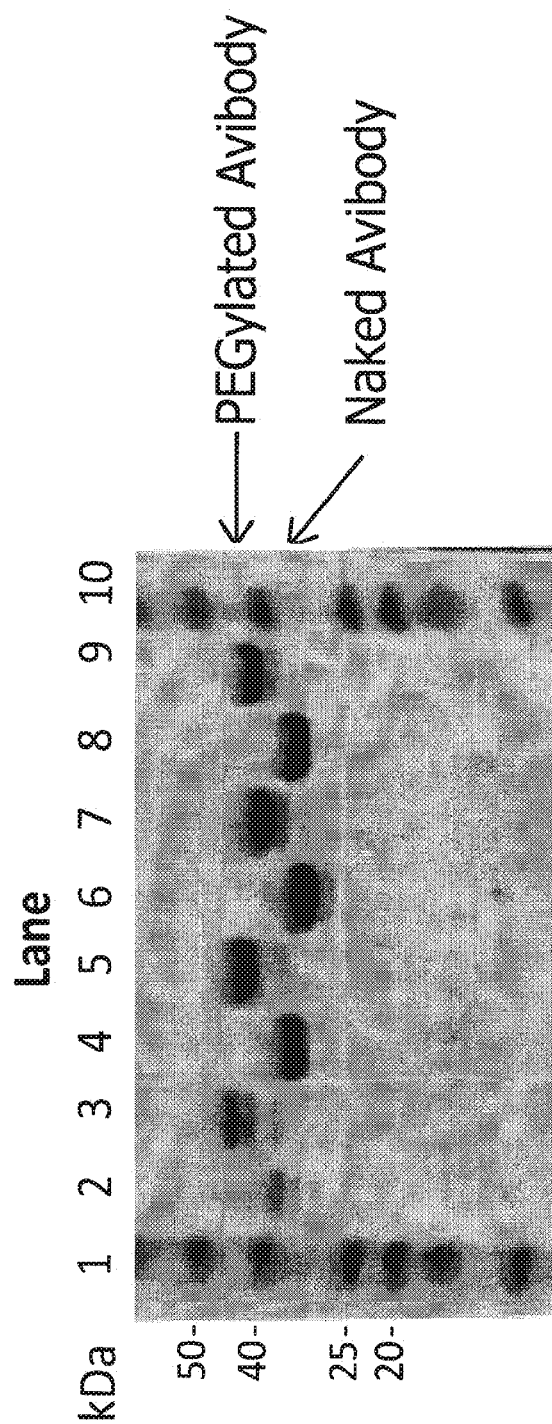
FIG. 13A includes a copy of a photographic representation showing results of Avibody conjugation with mal-PEG$_{24}$-MeOH indicating an increase in molecular weight with respect to unpegylated control ("naked") Avibody by SDS-PAGE. Lane 1 and 10: Benchmark pre-stained molecular weight standard, Lane 2 and 3: Naked AVP07-71 and AVP07-71-PEG$_{24}$ respectively. Lane 4 and 5: Naked AVP07-88 and AVP07-88-PEG$_{24}$ respectively. Lane 6 and 7: Naked AVP02-101 and AVP02-101-PEG$_{24}$ respectively. Lane 8 and 9: Naked AVP04-50 and AVP04-50-PEG$_{24}$ respectively.
Figure 13B:
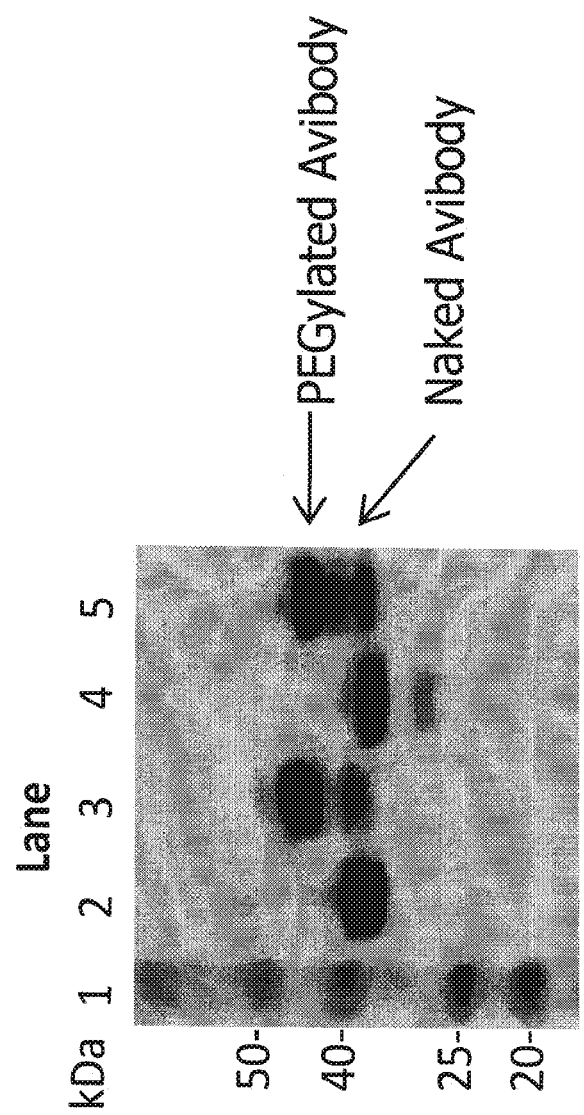
FIG. 13B includes a copy of a photographic representation showing results of Avibody conjugation with mal-PEG$_{24}$-MeOH indicating an increase in molecular weight with respect to unpegylated control ("naked") Avibody by SDS-PAGE. Lane 1: Benchmark pre-stained molecular weight standard, Lane 2 and 3: Naked AVP04-70 and AVP04-70-PEG$_{24}$ respectively. Lane 4 and 5: Naked AVP04-84 and AVP04-84-PEG$_{24}$ respectively.
Figure 13C:
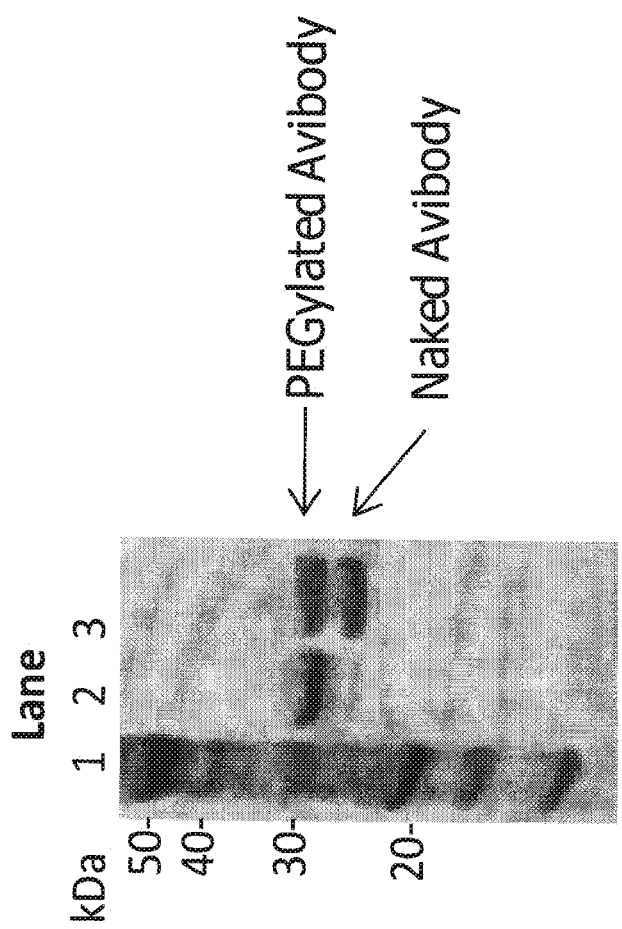
FIG. 13C includes a copy of a photographic representation showing results of Avibody conjugation with mal-PEG$_{24}$-

For SDS-PAGE analysis, 2 μg of total protein was loaded per well and resolved using NuPAGE 4-12% bis-tris gel in MES-SDS buffer (Invitrogen). The resulting protein bands were visualized using Coomassie Blue stain. Successful PEGylation reproducibly exhibited an approximate mass increase of 5 kDa per monomeric-chain (FIG. 13A-C).

For mass spectroscopy analysis, an Agilent esiTOF mass spectrometer with a MassPREP on-line desalting cartridge (Waters Corporation, USA) was used to record mass spectra of PEGylated Avibodies. The system was equilibrated for 1 min with 5% CH$_3$CN, followed by an elution gradient from 5-95% acetonitrile over 9 min. PEGylated Avibodies typically eluted at 7 min. MassHunter software was used to determine average mass of the sample by deconvolution of the relevant m/z charge peaks produced. Data is reported in Table 3 summarizes the average monomeric-chain Avibody mass obtained following deconvolution of mass spectra. The formula mass of PEG$_{24}$ is reported as 1239.44 g/mol, therefore an increase of at least 2478.88 mass units indicates full conjugation to engineered cysteines. Examples of typical mass spectrum for AVP07-71, AVP04-50, AVP07-88 and AVP02-101 are shown in FIGS. 14A-D respectively.

TABLE 3

PEG loading on thiolated Avibodies as determined by mass spectroscopy.

| Construct | Observed Mass (Da.) | PEGylated Mass (Da.) | Mass Increase (Da.) | PEG loaded |
|---|---|---|---|---|
| AVP04-50 | 25685.99 | 28166.84 | 2480.85 | 2 |
| AVP04-70 | 27453.01 | 29933.96 | 2480.95 | 2 |
| AVP04-74 | 26506.93 | 28987.58 | 2480.65 | 2 |
| AVP04-78 | 26816.32 | 29296.94 | 2480.62 | 2 |
| AVP04-84 | 26816.32 | 29297.16 | 2480.84 | 2 |
| AVP07-68 | 54564.88 | 57046.4 | 2481.52 | 2 |
| AVP07-71 | 27597.92 | 30078.36 | 2480.44 | 2 |
| AVP07-88 | 26780.09 | 29196.72 | 2416.63 | 2 |
| AVP07-89 | 26343.95 | 28824.74 | 2480.79 | 2 |
| AVP02-101 | 23509.78 | 24749.05 | 1239.27 | 1 |

Example 7

In Vitro Immunoreactive Assessment of Payload-Conjugated Thiolated Avibodies

Thiolated Avibodies could be expressed, purified, and were shown to be immunoreactive in their native (un-conjugated) state. Data reported above clearly indicated that stoichiometrically defined conjugation to engineered cysteines was occurring with high efficiency. The following data show that immunoreactivity was not abrogated when the intra-framework 1 cysteine replacement mutations were selectively reduced and small, thiol-reactive payloads were conjugated.

To this end, Thiolated Avibodies payloaded with maleimide-PEG$_{24}$-methoxy (Example 6) were assessed for immunoreactivity essentially as described in Example 4.

In all cases, Avibody-antigen complex formation, evidenced by a significant shortening of elution times in gel filtration, was observed (FIGS. 15A-C). In all cases, Avibody alone eluted between 28-33 minutes, and Avibody-Antigen complexes eluted at 10-25 minutes. As expected, complex formation was not observed when Avibodies were incubated with an irrelevant antigen. This result indicated that conjugation of relatively small payloads to reduced intra-Framework 1 cysteine replacement mutations in thiolated Avibodies did not abrogate binding.

Payloading to engineered intra-framework 1 cysteine replacement mutations is however not limited to PEG or PEG-like molecules.

To show that thiolated Avibodies could be conjugated with payloads very different from the above exemplified PEG-conjugates, again without abrogating binding, AVP04-50 was payloaded with detectable Label Europium.

The Eu$^{3+}$ chelate of 1-(p-iodoacetamidobenzyl)diethylen-etriamine-N$^1$—N$^1$,N$^2$,N$^3$,N$^3$-pentacetic acid (DTPA) (PerkinElmer, Turku, Finland) was used to conjugate to reduced intra-Framework 1 cysteine replacement mutations in AVP04-50 according to manufacturer's instructions. Briefly, protein was concentrated to 3 mg/ml in 50-100 mM sodium hydrogen carbonate buffer+4 mM EDTA, pH 8.5. Eu-DTPA was added at 30 times (Eu-DTPA: protein) molar excess to reduced AVP04-50. The reaction was completed following 3-16 hrs at 4° C. Unreacted Eu-DTPA was separated from the protein by gel filtration on a Superdex® 200 10/300 column, pre-equilibrated with Tris-buffered saline, pH 7.4. Each resulting fraction was diluted in Enhancement Solution (PerkinElmer, Turku, Finland) and assayed for Europium counts using a Victor time resolved fluorometer. Peak Europium counts corresponding with peak protein fractions were pooled and stabilized with 0.1% of highly pure BSA, and stored at 4° C., protected from light. Concentration of incorporated Eu-DTPA was determined by calculating Eu counts of the sample relative to a 100 nM Eu standard supplied with the kit.

Eu3+-DTPA-conjugated AVP04-50 was shown to be immunoreactive by methods essentially as described in Example 4. Eu3+-DTPA-conjugated AVP04-50 showed specificity to BSM as indicated by the formation of an Antigen:Avibody complex. This complex formation was evidenced by a shortening of protein elution times in gel filtration chromatography on a Superdex® 200 10/300 column (FIG. 16).

Immunoreactivity of Eu3+-DTPA-conjugated AVP04-50 was determined by cell binding assay. The labelled Avibody was incubated with TAG72 positive (LS174T) and negative (SK-OV-3) cell lines. Following the incubation period (1 hr, ambient temperature), cells were washed extensively and assayed for europium activity. Europium labelled AVP04-50 showed intact immunoreactivity and antigen specificity as indicated by a significant increase in fluorescent intensity on LS174T (TAG72 positive) compared with SK-OV3 (TAG72 negative) cells line (FIG. 17).

Taken together, these data suggest that it is possible to site-specifically conjugate payloads to engineered intra-framework 1 cysteine replacement mutations in Thiolated Avibodies without abrogating binding to antigen.

Example 8

In Vivo Performance of Radiolabelled AVP04-xx Avibodies

The Thiolated Avibody AVP04-50, was used in vivo in a mouse xenograft model to show that Intra-Framework 1

Engineered Cysteines mutations in Thiolated Avibodies did not affect in vivo stability or performance. Biodistribution using ($^{125}$I or $^{111}$In) of AVP04-50 was compared to that of the "un-mutated" parental AVP04-07.

8.1 Radiolabelling of Avibodies with $^{125}$I

Radioiodination of the AVP04-07 and AVP-04-50 Avibodies with $^{125}$I (Perkin Elmer) was performed using the standard Iodogen method (Yazaki et al., 2001). The required volume (5-10 µL) of Na $^{125}$I (26 mBq) was added to 200 µg of Avibody in a tube pre-coated with 20 µg Iodogen (Pierce). After incubation at RT for 3 min, the labelled material was purified by FPLC using a Superdex-75 or 200 column as described above. The column eluate was fractionated and counted, after which peak fractions were pooled and used for in vitro and in vivo studies. Radiolabelling yields were typically 80-100%.

8.2 Conjugation of NHS-DOTA to Avibodies and Radiolabelling with $^{111}$In

AVP04-07 was conjugated to NHS-DOTA [1,4,7,10-Tetraazacyclododecane-1,4,7,10-tetraacetic acid mono (N-hydroxysuccinimide ester)]. AVP04-07 and AVP04-50 were concentrated to 3-6 mg/mL using an Amicon Centricon YM-10 (10 kDa MWCO) centrifugal filter device (Millipore Corp, Bedford, Mass., USA) by centrifugation at 4,000 rpm at 4° C. (Allegra X15R, SX4750 rotor, Beckman Coulter). To remove metal contaminants, the protein (0.4 mL) was dialyzed against 14 volumes conjugation buffer (0.1M sodium bicarbonate, 5 mM 9 diethylenetriamene pentaacetate (DTPA), pH 8.5) for 2 hours, using a modified ultrafiltration cell with a Biomax ultrafiltration membrane (Millipore, PBQK02510). 19 uL of NHS-DOTA (B-280; Macrocyclics, Dallas, Tex., USA) at 10 mg/mL (0.19 mg, 250 nmole) in plasmagrade water (Fisher Scientific, Waltham, Mass., USA) was added to the Avibodies (2.5 mg, 48 nmole) at a 5-fold molar excess in the ultrafiltration cell and stirred for 1 h at RT. The protein was subsequently dialyzed against 14 volumes of 250 mM sodium acetate, pH 7.2 and stored at 4° C.

Radiometal labelling of DOTA-conjugated Avibody (AVP04-07-DOTA and AVP04-50-DOTA) was performed using $^{111}$InCl2 (Trace Life 11 Sciences, Denton, Tex., USA). In a typical experiment, 19 mBq of $^{111}$InCl2 was diluted with additional 0.1 M HCl and added to 125 µg DOTA-conjugated AVP04-07 in 0.25 M ammonium acetate pH 7.0 (final pH adjusted to 5.5). After incubation at 43° C. for 45 min, the solution was adjusted to 0.1 mM DTPA to bind any residual $^{111}$In and incubated at RT for an additional 10 min. Radiolabelling yields were typically 70-90%. The labelled material was then purified by HPLC using a Superdex-75 or 200 column, and the column eluate was fractionated and counted.

8.3 In vivo Biodistribution Using LS-174T Xenografts

For the mouse xenograft model, female, athymic nu/nu mice (Charles River Laboratories), 6-8 weeks old, were injected with LS-174T cells (ATCC) ($10^6$) subcutaneously in the flank, and tumours were allowed to grow for about 10 days prior to study. Mice bearing LS-174T xenografts were injected intravenously with a mixture (200 µl) of 370 kBq of $^{125}$I- and 150 kBq of $^{111}$In-labelled AVP04-07 or AVP04-50 (2-6 µg of total protein) for biodistribution studies. Mice (4-6 mice/group) were euthanized at various time points and the tumour, blood and major organs were collected, weighed and counted. The counts were corrected for crossover of $^{111}$In counts in the $^{125}$I channel. Percentages of the injected dose per gram of tissue (% ID/g) were calculated for each radionuclide.

8.4 In Vivo bBiodistribution of Avibodies

The biodistribution of $^{125}$I- and $^{111}$In-DOTA labelled Avibodies was measured in athymic mice bearing LS-174T xenografts.

The performance of AVP04-07 and AVP04-50 Avibodies in vivo were absolutely comparable, suggesting the introduction of a modeling-defined intra-Framework 1 disulphide bridge did not destabilize or negatively impact Avibody performance (FIGS. 18A and B).

The two radiotracers ($^{125}$I- and $^{111}$In) were cleared from the blood in a similar manner with only a marginal difference observed between clearance of AVP04-50 and AVP04-07. Approximately 50% cleared by 1 h post-injection and about 6-12% still in circulation at 4 h. As expected for proteins of this size, there was considerable kidney uptake (>100% ID/g at 24 h) for the $^{111}$In-labelled, but not for the $^{125}$I-labelled Avibody, demonstrating that the kidney was the major route of clearance.

For $^{111}$In-AVP04-07, there was significant uptake in the tumour, with over 25% ID/g observed as early as 4 h post injection and more than 20% ID/g still in the tumour at 48 h. The tumour uptake of $^{111}$In-AVP04-50 matched that of $^{111}$In-AVP04-07 in the 0-4 hour time period post injection, but then surpassed that of $^{111}$In-AVP04-07 to reach a maximum tumour uptake of greater than 30% ID/g at 24 hours. Tumour uptake was for both $^{111}$In-AVP04-07 and $^{111}$In-AVP04-50 remained comparable at 48 hrs post injection. Tumour to blood ratio for $^{111}$In-AVP04-07 was >50:1 at 24 h. In the case of $^{111}$In-AVP04-50, tumour to blood ratio was increased to >60:1 at 24 h. Iodine-125 labelled Avibodies exhibited somewhat lower tumour to blood ratios and tumour uptake (about 17% and 10% ID/g at 4 and 48 h respectively for AVP04-07 and 19% and 10% ID/g at 4 and 48 h respectively for AVP04-50). As expected, some $^{111}$In was retained in the spleen, liver and carcass, while $^{125}$I-labelled Avibody was not retained in these tissues.

In addition to the biodistribution of AVP04-07 and AVP04-50, a thiolated HER2-specific Avibody, AVP07-63 (SEQ ID NO: 65), was also shown to be as efficient in vivo as its non-thiolated parental AVP07-17.

In these in vivo experiments, AVP07-17 and AVP07-63 were radiolabelled with $^{125}$I using the chloramine T method ($^{125}$I: protein ratio, 1:10), essentially as described (Adams et al. 1993). The quality and immunoreactivity of the radiopharmaceuticals were evaluated by SDS-PAGE and in a live cell-binding assay as described (Adams et al. 1993). CB.17 Icr scid mice, 6-8 weeks of age, were implanted subcutaneously on the abdomen with SKOV3 cells ($2.5 \times 10^6$). When the tumours had achieved a size of 50-200 mg (approximately 8 weeks), Lugol's solution was placed in their drinking water to block thyroid accumulation of radioiodine, and biodistribution studies were initiated. Twenty micrograms (100 ml) of radioiodinated AVP07-17 or AVP07-63 was administered by intravenous tail vein injection to each mouse. Cohorts of five mice that received the $^{125}$I-Avibody were sacrificed at 24 hr after injection. The mean and SEM of retention of each radiopharmaceutical in tissue (% ID/g) and blood (% ID/ml) were determined from decay-corrected counts, as described (Adams et al. 1993).

The 24 hr biodistribution results indicated that tumour uptake of AVP04-17 and AVP07-63 was very similar, ranging between 3.0-3.6% ID/g (FIG. 19). Although the tumour uptake between thiolated and non-thiolated Avibody was very similar, in all other tissues, AVP07-63 uptake at 24 hr was favorably less than that of the parental, non-thiolated AVP07-17.

These results clearly indicate the robustness of the Framework 1 region in accepting intra-framework 1 disulphide insertions without negatively affecting in vivo performance, stability or functionality. Furthermore, the addition of preferred intra-framework 1 disulphide insertions (such as in AVP04-50) can be shifted slightly by 1-2 residues (such as in AVP07-63), as long as core modeling constraints are still met, without affecting Avibody performance or disulphide formation.

Example 9

In Vivo Performance of Payload-Conjugated Thiol Avibodies is Superior to Non "Un-Mutated" Avibodies Disulphide insertional mutations were designed to allow for site-specific and stoichiometrically defined payload-conjugations to Fv containing proteins. The insertion of an engineered intra-framework 1 disulphide bridge was shown not to affect Thiolated Avibody performance, both in vitro and in vivo.

To show that site-specifically and stoichiometrically defined payload conjugation to engineered intra-framework 1 disulphide insertion mutations on the surface of Avibodies provided in vivo advantages over random conjugation of payloads to other Avibody surface residues such as lysines, a size monodispersed Polyethylene glycol of 48-PEG repeats (dPEG$_{48}$, Quanta Biodesign Ltd, OH, USA) was conjugated to AVP04-50 through the engineered intra-framework 1 sites. The biodistribution of this reagent (PEG$_{48}$-AVP04-50) was compared to the in vivo biodistribution result obtained for the PEG-conjugate of AVP04-07 in which PEG was conjugated to surface Lysines (PEG3400-AVP04-07).

9.1 Generating the DOTA-Cys-VS-PEG3400 Conjugate of the AVP04-07 Avibody.

NHS-PEG3400-VS was conjugated to AVP04-07 diabody at a molar ratio of 15:1 and pH 6.0 as previously described (Li et al. 2008). Briefly, NHSPEG3400-VS (3.1 mg, 800 nmole) was mixed with 2.75 mg (50 nmole) of diabody (based on the dimeric molecular weight of 52,500 daltons) in 1 mL of pH 7.5 PBS, the pH was adjusted to 6.0 with 0.1 M NaOH, and the mixture was allowed to react for 2 h at RT. When the reaction was monitored by SDS gels, it appeared to be >70% complete by 2 h. After 2 h the entire reaction mixture was applied to a Superdex 75 column and the conjugate, which eluted at 16.3 min, was collected. The conjugate (8 mL) was concentrated to 0.35 ml in a 10,000 kDa cut-off Vivaspin (Sartorius Stedim Biotech, Germany), mixed with 1.4 mg (2.76 µmole) Cysteineamido-DOTA (Lewis et al. 1998), the pH was adjusted to 8.5 and the mixture was reacted on a sample rotator for 17 h at RT. The sample was dialyzed vs. 0.25 M ammonium acetate, concentrated to 1-3 mg/L on a 10,000 kDa cut-off Vivaspin and sterile filtered. The resulting conjugate was radiolabelled with 111In essential as described in Example 8.2.

9.2 Generating the DOTA-PEG$_{48}$ Conjugate of the AVP04-50 Avibody.

N-FMOC-amido-PEG$_{48}$-acid (0.1 mmole) was activated with DCC/HOBt in N-methylpyrrolidine/dichloromethane for 90 min at RT, DCU removed by filtration, and the activated N-FMOC-PEG$_{48}$ acid was coupled to Cys-polystyrene Wang resin (0.3 mmole cys/g resin) for 3 min at 75° C. The FMOC group removed with 0.5 M piperazine in ethanol/DMF (13:200, v/v) for 3 min at 65° C., washed with DMF, ethanol, and DCM, and then coupled to the active ester of tri-t-butyl-DOTA (0.5 mmole) as above. The resin was treated with 5 mL of TFA (5% water, 5% tri-isopropyl silane, 5% ethane dithiol) for 60 min at 40° C. The crude product was extracted with DCM/hexane (5 mL, 2:5 v/v, 5×), precipitated with 10 mL of t-butylmethyl ether at −20° C. and chromatographed on a PRP-1 column (Hamilton, Reno, Nev., 10×250 mm) using a gradient of 100% A (0.1 TFA, 94.9 water, 5 MeCN) to 100% B (0.1 TFA, 29.9 water, 70 MeCN) over 15 min at a flow of 8 mL/min. DOTA-PEG$_{48}$-Cys in DMF was added vinyl sulfone and triethylamine, and the reaction mixture was stirred for 23 h at RT under argon. After solvent evaporation, the residue was re-dissolved in water, purified by reversed phase HPLC on a Gemini C18 column (Phenomenex, Calif.), and lyophilized. DOTA-PEG$_{48}$-Cys-VS was conjugated to diabody at a molar ratio of between 20:1 and 50:1. Briefly, AVP04-50 was added to the DOTA-PEG$_{48}$-Cys-VS at the ratios described and the pH was adjusted to 9.0 with 0.1 NaOH. The mixture was reacted for 18 h at RT on a rotator. The sample was dialyzed vs. 0.25 M ammonium acetate, concentrated to 1~4 mg/mL in a 10,000 kDa cut off Vivaspin (Sartorius Stedim Biotech, Germany) and sterile filtered. Aliquots were removed to confirm conjugation by SDS and IEF gel electrophoresis and mass spectrometry.

9.3 Comparative Biodistribution of AVP04-07-PEG3400 and AVP04-50-PEG$_{48}$

The biodistribution using PEG3400 significantly reduced kidney uptake compared to non-PEGylated AVP04-07. PEG3400-AVP04-07 displayed a kidney uptake of approximately 8.4% ID/g at 24 h (FIG. 20 Panel A). The large reduction of kidney uptake with PEGylation was accompanied by an increase in tumour uptake (with respect to non-PEGylated AVP04-07, as shown in FIG. 18) from 22 to 46% ID/g at 24 h. The increase in tumour retention is evidently due to the prolonged blood clearance of PEGylated diabody (t½b, 36 h) versus non-PEGylated diabody (t½b, 18 h).

The biodistribution of PEG$_{48}$-AVP04-50 (PEGylated to engineered intra-framework 1 cysteine replacement mutations) displayed a further general improvement in tumour uptake, faster blood clearance and higher tumour-to-blood ratios with respect to PEG3400-AVP04-07 (FIG. 20 Panel B). PEG$_{48}$-AVP04-50 tumour uptake was further increased to 70% ID/g, with a tumour to blood ratio of 11:1 at 24 h, which rose to as high as 19:1 at 48 h.

The improved tumour-to-blood ratio, higher tumour uptake and acceptable non-specific kidney uptake observed for PEG$_{48}$-AVP04-50 with respect to lysine-directed conjugates such as PEG3400-AVP04-07, clearly indicated that the conjugation of payloads to engineered intra-framework 1 cysteine replacement mutations did not affect in vivo performance or functionality.

9.4 Comparative PET Imaging of AVP04-07-PEG3400 and AVP04-50-PEG$_{48}$

Comparative PET imaging was performed essentially as described elsewhere (Li et al. 2008). In summary, tumour-bearing mice were injected intravenously with $^{64}$Cu labelled AVP04-07 or AVP04-07 diabody-PEG conjugate (conjugated to Lysines) or AVP04-50 diabody-PEG conjugate (conjugated to engineered intra-framework 1 cysteine replacement mutations) and imaged at 1, 4, 21-22, and 45-46 h with a small-animal PET scanner (microPET model R4; Siemens/CTIMI). Mice anesthetized with isoflurane were scanned for 20 min at the 1- and 4-h time points; 45 min at 21-22 h, and 60 min at 45-46 h. Data were sorted into 2-dimensional sinograms using the Fourier rebinning method and corrected for intrascan radiodecay, detector nonuniformity, and random coincidence noise. Images were reconstructed by the iterative ordered-subsets expectation maximization method (4 iterations, 16 subsets).

PET images obtained from un-modified and unconjugated AVP04-07 showed significant kidney uptake (FIG. 21A), as expected for proteins of this size. This parallels the $^{111}$In biodistributions of AVP04-07 reported above in FIG. 18. The addition of a size-monodispersed PEG of 27-residues (size optimized to provide the best in vivo biodistribution possible) to random surface AVP04-07 lysines dramatically improved overall biodistribution by increasing tumour uptake and significantly reducing kidney uptake (FIG. 21A).

Figure 21B:
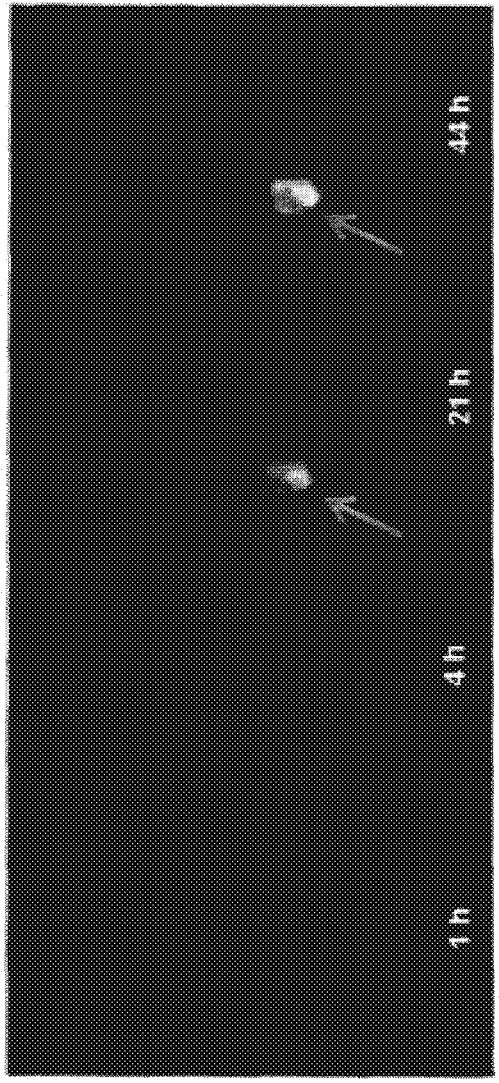

The site specific and stoichiometrically defined addition of size-monodispersed PEG to engineered intra-framework 1 cysteine replacement mutations of AVP04-50 also improved biodistribution with respect to non-PEGylated AVP04-07 (FIG. 21B), demonstrating a significant reduction in unwanted kidney uptake and a general increase in tumour-specific uptake. Although the PET image generated for AVP04-07 PEGylated to lysines and AVP04-50 PEGylated to engineered thiols was very similar, the reproducibility, site- and stoichiometrically-defined conjugation to engineered intra-framework 1 cysteine replacement mutations provides a robust clinical advantage without negatively impacting in vivo performance.

Example 10

Anti-TAG72 Diabody Conjugates and Their Use for Imaging 10.1 Experimental Procedures
Materials, Radiolabels, Mass Spectrometry LS-174T cells were obtained from ATCC and maintained in sterile growth media consisting of Eagle's Minimal Essential Media 1× (EMEM) (Cellgro, Herndon, Va., USA) supplemented with 10% heat inactivated fetal bovine serum (FBS) (Omega Scientific, Tarzana, Calif., USA), 1% L-glutamine, 10 mM sodium pyruvate and 0.1 mM non-essential amino acids. 1,4,7,10-Tetraazacyclododecane-1,4,7-tris(t-butyl acetate)-10-acetic acid was obtained from Macrocyclics, Inc., Dallas, Tex. NHS-PEG3400-VS (Cat No 4M5B0F02) was purchased from Nektar (San Carlos, Calif.). N-FMOC-amido-dPEG-27 acid was obtained from Novabiochem (EMD Biosciences, San Diego, Calif.) and N-FMOC-amido-dPEG-12 acid was purchased from Quanta Biodesign Ltd (Powell, Ohio). Chelate conjugated antibodies were radiolabelled with $^{111}$In chloride (Amersham, 2-9 mCi/mg of protein) or $^{64}$Cu (Washington University School of Medicine, 10 mCi/mg of antibody) substantially as previously described (Lewis et al., 1994), or with $^{125}$I (Perkin Elmer, 3-9 mCi/mg of antibody) by the iodogen method (substantially as described in Yazaki et al., 2001). Percent labelling was determined by ITLC or by size exclusion chromatography (SEC) on a Superdex 75 or 200 column (1×30 cm, GE Healthcare). Radiolabelled antibody was purified by SEC on the same column (in saline, flow rate 0.5 mL/min, fraction size was 0.5 mL). Mass spectra were recorded on an Agilent 6520 quadrupole time-of-flight liquid chromatography mass spectrometry device.

Construction, Cloning, Expression, and Purification of Anti-TAG72 Diabody

A sequence encoding an anti-TAG72 diabody was derived from the sequence encoding the CC49 monoclonal antibody and codon optimized for E. coli expression. A DNA construct was designed, with the orientation of the V domains ($V_H$—$V_L$) preserved and linked by a 5-residue linker ($G_4S$). The DNA sequence was synthesized with the appropriate restriction sites (NcoI and NotI) and cloned into pUC57 by GenScript Corp (Piscataway, N.J., USA). The sequence was excised from pUC57 with NcoI and NotI (New England Biolabs, Ipswich, Mass., USA), purified and cloned into the pET22b (+) expression vector (Novagen, Madison, Wis., USA) and electroporated into E. coli XL1-Blue (recA1 endA1 gyrA96 thi-I hsdR17 supE44 relA1 lac [F' proAB lacI$^q$ZΔM15 Tn10 (Tet$^r$)]) (Stratagene, La Jolla, Calif., USA). A positive clone was identified by sequencing and designated AVP04-07 (sequence encoding the diabody is set forth in SEQ ID NO: 54).

Bacterial Production and Purification of AVP04-07

AVP04-07 was subcloned into E. coli BL21 (DE3)(F$^−$ ompT hsdS$_B$($r_B^-$ $m_B^-$) gal dcm (DE3)) (Novagen) using standard protocols. A single colony was used to inoculate 500 mL 2×YT containing 1% (v/v) D-glucose and 100 mg/mL ampicillin and incubated with shaking at 37° C. overnight. Eighteen liters of the same media (glucose reduced to 0.1%) was seeded with the overnight culture to a final $A_{600nm}$ of 0.1 and incubated at 30° C. until the $OD_{600}$ was 0.6-0.8 at which cultures were transferred to 12° C. AVP04-expression was induced with the addition of 0.2 mM isopropyl-b-D-thiogalactopyranoside (IPTG) (Promega, Madison, Wis., USA) and the cultures incubated at 12° C. overnight. Bacterial pellets were harvested by centrifugation, weighed and stored at −20° C. until purification.

On commencement of purification, the expressed bacterial pellets were thawed and resuspended in HisTrap extraction buffer (20 mM phosphate, 500 mM NaCl, 20 mM Imidazole, pH 7.4) containing 0.25 mg/mL lysozyme (Sigma Aldrich, St Louis, Mo., USA), 1 mM PMSF (Sigma) and 25 U Benzonase (Merck, Darmstadt, Germany), and lysed at 4° C. by sonication using a Misonix S-4000 sonicator (Misonix, Farmingdale, N.Y., USA). The bacterial lysate was incubated at 37° C. for 30 min, prior to clearing by centrifugation (16,000× g, 30 min) and filtration at 0.45 μm. Cleared lysate containing expressed AVP04-07 was purified according to a three-step purification strategy, using the AKTA Purifier 10 (GE Healthcare, Uppsala, Sweden).

The cleared lysate containing AVP04-07 was loaded onto pre-equilibrated HisTrap Crude FF columns (2×5 mL) (GE Healthcare). Unbound proteins were washed off with HisTrap extraction buffer prior to eluting AVP04-07 from the column in HisTrap elution buffer (20 mM phosphate, 500 mM NaCl, 260 mM imidazole). Eluted AVP04-07 was dialysed against 50 mM MES, pH 6.0 at 4° C. and cleared of any precipitates by centrifugation. Dialysed AVP04-07 was loaded onto HiTrap SP HP columns (2×5 mL) (GE Healthcare) pre-equilibrated in 50 mM MES, pH 6.0. Unbound protein was removed by washing the columns in 50 mM MES, pH 6.0 prior to eluting bound AVP04-07 in 50 mM MES, pH 6.0 under a linear increasing NaCl gradient (0-600 mM NaCl). Fractions containing the eluted AVP04-07 diabody were pooled, quantified, and concentrated prior to being subjected to size exclusion chromatography using a Superdex 75 (26/60 prep-grade) column (GE Healthcare) in PBS pH7.2. Fractions corresponding to a single peak at 280 nm were pooled, quantified, concentrated to ~3 mg/mL, dialysed against PBS and stored at 4° C.

AVP04-07 Isoform Confirmation by Analytical Ultracentrifugation

Purified AVP04-07 was confirmed to be dimeric by analytical ultracentrifugation. Sedimentation velocity experiments were conducted using a Beckman model XL-I analytical ultracentrifuge (Fullerton, Calif., USA) at 20° C. Purified AVP04-07 was dialysed against 20 mM Tris, 150 mM NaCl, pH 7.4, loaded into a double sector quartz cell and mounted in a Beckman 4-hole An-60 Ti rotor. AVP04-07 and the reference solution were centrifuged at a rotor speed of 40,000 rpm and data was collected at $A_{290nm}$ in continuous mode, using a time interval of 300 sec and a step-size of 0.003 cm, without averaging. Estimates of the solvent density (1.00499 g/mL at 20° C.), solvent viscosity (1.0214 cp), as well as an estimate of the partial specific volume for AVP04-07 were computed using the program SEDNTERP. Sedimentation velocity data at multiple time points were fitted to a continuous size-distribution model using the program SEDFIT.

In Vitro Assessment of Immunoreactivity

The ability of AVP04-07 to bind soluble antigen TAG72, present in Bovine Submaxillary Mucin (BSM, Aldrich-Sigma (St. Louis, Mo.)) was assessed by column shift assay. A two molar excess of BSM was heated to 55° C. for 5 min and cleared by centrifugation prior to the addition of the AVP04-07 diabody and incubated for 1 hr at room temperature. The sample was immediately resolved by gel filtration on a Superdex 200 column. Diabody-antigen complex formation was determined by comparing the elution profile to relevant controls.

Conjugation of AVP04-07 to NHS-DOTA

AVP04-07 was conjugated to NHS-DOTA [1, 4, 7, 10-Tetraazacyclododecane –1, 4, 7, 10-tetraacetic acid mono (N-hydroxysuccinimide ester)]. AVP04-07 was concentrated to 5.8 mg/mL using an Amicon Centricon YM-10 (10 kDa MWCO) centrifugal filter device (Millipore Corp, Bedford, Mass., USA) by centrifugation at 4,000 rpm at 4° C. (Allegra X15R, SX4750 rotor, Beckman Coulter). To remove metal contaminants, the protein (0.5 mL) was dialysed against 14 volumes conjugation buffer (0.1M sodium bicarbonate, 5 mM diethylenetriamene pentaacetate (DTPA), pH 8.5) for 2 hours, using a modified ultrafiltration cell with a Biomax ultrafiltration membrane (Millipore, PBQK02510). NHS-DOTA (B-280; Macrocyclics, Dallas, Tex., USA) at 10 mg/mL in plasma-grade water (Fisher Scientific, Waltham, Mass., USA) was added to AVP04-07 at a 15-fold molar excess in the ultrafiltration cell and stirred for 1 hr at room temperature. The protein was subsequently dialyzed against 14 volumes 250 mM Sodium Acetate, pH 7.2, removed from the cassette and stored at 4° C.

Conjugation of AVP04-07 to DOTA-PEG

DOTA-Cys-VS-PEG3400-diabody. NHS-PEG3400-VS was conjugated to AVP04-07 diabody at a molar ratio of 30:1 and pH 6.0 as previously described (Li et al., 2008). Briefly, NHS-PEG3400-VS (3.1 mg, 800 nmole) was mixed with 2.75 mg (50 nmole) of diabody in 1 mL of pH 7.5 PBS, the pH was adjusted to 6.0 with 0.1 M NaOH, and the mixture was allowed to react for 2 hr at RT. When the reaction was monitored by SDS gels, it appeared to be >70% complete at the end of 2 hrs. At the end of 2 hr the entire reaction mixture was applied to a Superdex 75 column (1×30 cm, 0.5 ml/min, Pharmacia), and the conjugate, which eluted at 16.3 min, was collected. The conjugate (8 mL) was concentrated to 0.35 ml in a 10,000 kDa cut-off Vivaspin (Sartorius Stedim Biotech, Germany), mixed with 1.4 mg (2.76 µmole) cysteineamido-DOTA, the pH was adjusted to 8.5 and the mixture was reacted on a sample rotator for 17 hr at RT. The sample was dialyzed vs 0.25 M ammonium acetate, concentrated to 1-3 mg/L on a 10,000 kDa cut-off Vivaspin and sterile filtered. The conjugate was characterized by SDS and IEF gel electrophoresis.

DOTA-$PEG_{27}$-Cys-VS-diabody. N-FMOC-amido-$PEG_{27}$-acid (0.1 mmole) was activated with DCC/HOBt in N-methylpyrrolidine/dichloromethane for 90 min at RT, DCU removed by filtration, and the activated N-FMOC-PEG acid was coupled to Cys-polystyrene Wang resin (0.3 mmole cys/g resin) for 3 min at 75° C. The FMOC group removed with 0.5 M piperazine in ethanol/DMF (13:200, v/v) for 3 min at 65° C., washed with DMF, ethanol, and DCM, and then coupled to the active ester of tri-t-butyl-DOTA (0.5 mmole) as above. The resin was treated with 5 mL of TFA (5% water, 5% tri-isopropyl silane, 5% ethane dithiol) for 60 min at 40° C. The crude product was extracted with DCM/hexane (5 mL, 2:5 v/v, 5×), precipitated with 10 mL of t-butylmethyl ether at –20° C. and chromatographed on a PRP-1 column (10×250 mm) using a gradient of 100% A (0.1 TFA, 94.9 water, 5 MeCN) to 100% B (0.1 TFA, 29.9 water, 70 MeCN) over 15 min at a flow of 8 mL/min. To 200 µL of DOTA-$PEG_{27}$-Cys (30 mg, 16.6 µmol) in DMF was added vinyl sulfone (12 µl, 116 µmol) and triethylamine (6 µl, 43 µmol), and the reaction mixture was stirred for 23 h at RT under argon. After solvent evaporation, the residue was re-dissolved in 300 µl of water, purified by reversed phase HPLC on a Gemini C18 column (Phenomenex, Calif.), and lyophilized (yield 55%). DOTA-$PEG_{27}$-Cys-VS was conjugated to diabody at a molar ratio of 50:1. Briefly, 2 mg (38 nmole) of diabody (2.75 mg/mL in PBS) was added to 22 µL of DOTA-$PEG_{27}$-Cys-VS (0.175 mg/mL in water, 2 mmoles), the pH was adjusted to 9.0 with 0.1 NaOH, and the mixture was reacted for 18 h at RT on a rotator. The sample was dialyzed vs 0.25 M ammonium acetate, concentrated to 1-4 mg/mL in a 10,000 kDa cut off Vivaspin (Sartorius stedim biotech, Germany) and sterile filtered. Aliquots were removed to confirm conjugation by SDS and IEF gel electrophoresis and mass spectrometry.

Diabody-VSC-$PEG_{12}$-DOTA. The synthesis and conjugation of DOTA-$PEG_{12}$-Cys-VS to diabody at molar ratios of 20:1 and 50:1 was performed as described above.

Isoelectric Focusing of AVP04-07 Conjugates

Isoelectric focusing gel electrophoresis was run either on an IEF Precast gel (pH 3-10) (Novex) or on a Pharmacia PhastGel as per the manufacturer's instructions.

Radiolabelling of AVP04-07 and its Conjugates

Radioiodination of AVP04-07 and its conjugates with $^{125}I$ (Perkin Elmer) was performed using the standard Iodogen method (Yazaki et al., 2001). The required volume (5-10 µL) of Na 125I (26 mBq) was added to 200 µg of AVP04-07 in a tube pre-coated with 20 µg Iodogen (Pierce). After incubation at RT for 3 min, the labelled material was purified by HPLC using a Superdex-75 or 200 10/300 GL FPLC column (GE Healthcare). The column eluate was fractionated and counted, after which peak fractions were pooled and used for in vitro and in vivo studies. Radiolabelling yields were typically 80-100%.

Radiometal labelling of DOTA-AVP04-07 was performed using $^{111}InCl_2$ (Trace Life Sciences, Denton, Tex., USA) or $^{64}CuCl2$ (Washington University, St. Louis, Mo.). In a typical experiment, 19 mBq of $^{111}InCl2$ was diluted with additional 0.1 M HCl and added to 125 µg DOTA-conjugated AVP04-07 in 0.25 M ammonium actetate pH 7.0 (final pH adjusted to 5.5). After incubation at 43° for 45 min, the solution was adjusted to 0.1 mM DTPA to bind any residual $^{111}In$ and incubated at RT for an additional 10 min. $^{64}Cu$ labellings were performed in the same manner. Radiolabelling yields were typically 70-90%. The labelled material was then purified by HPLC using a Superdex-75 or 200 10/300 GL FPLC column, and the column eluate was fractionated and counted.

Radiolabelled products were analyzed for purity by HPLC-SEC using a Superose-6 10/300 GL column (GE Healthcare). Radiolabelled protein (4 kBq) was diluted in 1% HSA/PBS and injected onto the column at 0.5 ml/min. Radioactivity and UV absorbance was detected using flow-thru detectors.

LS-174T Xenograft Model

Female, athymic nu/nu mice (Charles River Laboratories), 6-8 weeks old, were injected with LS-174T cells (ATCC) ($10^6$) subcutaneously in the flank, and tumours were allowed to grow for about 10 days prior to study. Mice bearing LS-174T xenografts were injected intravenously with a mixture (200 μl) of 370 kBq of $^{125}$I- and 150 kBq of $^{111}$In-labelled AVP04-07 (2-6 μg of total protein) for biodistribution studies. Mice were sacrificed at various time points and the tumour, blood and major organs were collected, weighed and counted. The counts were corrected for background and inclusion of $^{111}$In counts in the $^{125}$I channel. Percentages of the injected dose per gram of tissue (% ID/g) were calculated for each radionuclide.

PET Imaging

Tumour-bearing mice (21-25 g) were injected intravenously with $^{64}$Cu-labelled diabody or diabody-PEG conjugates and imaged beginning at 1.0 h, 4 h, 21-22 h and 45-46 h with a small-animal PET scanner (microPET Model R4; Siemens/CTIMI, Knoxville, Tenn.). Injected activity and protein load ranged from 63 to 169 kBq/g and 0.4 to 0.7 μg/g, respectively. Shortly before scanning, mice were anesthetized with isoflurane, secured in a prone position and centered in the instrument's field of view. Scan duration was 20 min for the 1 and 4 hr time points, 45 min for the 21-22 h time point and 60 min for the 45-46 hr time point. The microPET's laser alignment tool was used to position the base of the tail approximately 4.0 cm from the axial center of the 8.0 cm-long field of view in each scan.

Immediately after completion of the final scan, a blood sample (0.2 cc) was obtained by cardiac puncture, the mouse was sacrificed, and the tumour and various major organs were excised, weighed, and counted. Measured activities were corrected for radiodecay after injection, and % ID/g was calculated for each specimen. Tumour weights at time of sacrifice ranged from 107 to 275 mg.

Image processing was performed with the standard microPET software. Scan data were sorted into two-dimensional sinograms using the Fourier rebinning method and corrected for intrascan radiodecay, detector non-uniformity and random coincidence noise. Images were reconstructed by the iterative ordered subsets expectation maximization (OSEM) method (4 iterations, 16 subsets).

10.2 Results

Construction, Expression and Characterization of AVP04-07 Diabody

AVP04-07 was produced as a soluble protein in *E. coli* BL21 (DE3) and purified by a three-step purification strategy. The purified product eluted as a single species from a Superdex 200 gel filtration column. Continuous mass c(M)-distribution analyses yielded an excellent fit as represented by the random distribution of residuals and statistical parameters resulting for the best-fits (i.e. all rmsd values <0.0054 and Runs test Z values <14.4). The c(M) distribution analysis of AVP04-07 suggested that it existed as a monodispersed dimer (i.e: diabody), with an apparent molecular mass of 52.5 kDa.

Purified AVP04-07 was shown to bind soluble antigen in vitro by a column shift assay on a Superdex 200 column. When allowed to complex with its antigen in the context of BSM, the elution profile of AVP04-07 changed significantly from that of AVP04-07 alone. The major protein peak eluted from the column at approximately 16 min, in comparison to the expected 31 minute elution time of purified AVP04-07 alone. Similar reductions to elution times, indicating diabody-antigen complex formation, were not observed with a non correlated diabody or non correlated antigen.

Biodistribution and Imaging of $^{111}$In-DOTA- and $^{125}$I-AVP04-07 in a Nude Mouse LS174T Xenograft Model Biodistributions were measured in athymic mice bearing LS174T xenografts injected with $^{125}$I- or $^{111}$In-DOTA-AVP04-07. The two radiotracers were cleared from the blood in a similar manner, with about 50% cleared by 1 hr post-injection and about 10% still in circulation at 4 hr (FIGS. 22A and B). As expected for proteins of this size, there was considerable kidney uptake (100% ID/g at 24 hrs) for the $^{111}$In-labelled, but not for the $^{125}$I-labelled diabody, demonstrating that the kidney was the major route of clearance For $^{111}$In-AVP04-07, there was significant uptake in the tumour, with over 25% ID/g observed as early as 4 hr post injection and more than 20% ID/g still in the tumour at 48 hr. Tumour to blood ratio for $^{111}$In-AVP04-07 was >50:1 at 24 hr. Iodine-125 labelled AVP04-07 exhibited somewhat lower tumour to blood ratios and tumour uptake (about 17% and 10% ID/g at 4 and 48 hr respectively). As expected, some 111In was retained in the spleen, liver and carcass, while $^{125}$I-AVP04-07 was not retained in these tissues.

Generation of DOTA-Cys-VS-PEG3400-AVP04-07 and Biodistribution Studies

AVP04-07 was conjugated to DOTA-Cys-VS-PEG3400-NHS essentially as previously described (Li et al., 2006). VS-PEG3400-NHS is a heterobifunctional PEGylation agent that can be first conjugated to surface lysines of proteins (via the active ester), followed by reaction with reagents possessing a reactive thiol (via the vinyl sulfone). A thiol version of DOTA, namely DOTA-Cys (Lewis et al., 1998) was conjugated to VS-PEG3400-AVP04-07 and the conjugate analyzed by IEF and SDS gel electrophoresis (FIG. 23). The results indicate a shift to lower pI due to the addition of acidic DOTA (IEF gel, FIG. 23A) and a shift to higher apparent molecular size due to the addition of PEG3400 (SDS gel, FIG. 23B). The conjugate was radiolabelled with $^{111}$In, chromatographed on Superdex 75 and compared to unconjugated AVP04-07 (FIGS. 23A-B). The apparent molecular size of the PEG3400 derivative was 80 kDa compared to 50 kda for the unconjugated diabody. The increase in apparent molecular size can be attributed to the effect of PEGylation on the Stoke's radius of a protein.

The results of a biodistribution study for $^{111}$In radiolabelled AVP04-07 are shown in FIG. 22C. Kidney uptake was 98% ID/g at 24 h for the unmodified diabody (FIG. 7A) and 8.4% ID/g at 24 h for the PEGylated diabody (FIG. 22C). This large reduction of kidney uptake was accompanied by an increase in tumour uptake from 23% to 47% ID/g at 24 hr and a reduction in tumour/blood ratio (>46:1 to 2:1 at 24 h). The increase in tumour retention is evidently due to the prolonged blood clearance of PEGylated diabody (t½=36 h) vs the unconjugated diabody (t½=18 h). Surprisingly, the reduction in kidney uptake was much greater than previously observed with $^{111}$In-DOTA-Cys-VS-PEG3400 anti-CEA-diabody (Li et al., 2006).

Generation of a Monodisperse PEG$_{27}$ AVP04-07 Conjugate and Biodistribution Studies Although conjugation of AVP04-07 to a PEG3400 moiety achieved the desired kidney uptake reduction, PEG3400 may have drawbacks as a clinical product, due to its inherent polydispersity and the consequent inability to manufacture products that are easy to characterize chemically. In this respect, several monodispersed PEG building blocks are commercially available that can be converted into heterobifunctional reagents using peptide synthesis methodology. A heterobifunctional monodisperse PEGylation agent was produced using the commercially available monodispersed PEG FMOC-NH-PEG$_{27}$-acid, one of the largest PEGs available in this category. The active ester of this PEG derivative was coupled first to Cys-Polystyrene Wang resin via a standard peptide synthesis protocol, the FMOC removed, and coupled to DOTA using the commercially available tri-t-butyl protected mono-acid derivative. DOTA-PEG$_{27}$-Cys was cleaved from the resin with TFA, purified, reacted with excess vinyl sulfone, and re-purified using reversed phase HPLC. The synthesis of the product is shown in FIG. 10. Since DOTA-PEG$_{27}$-Cys-VS has an expected molecular weight of 1928.6, approximately half that of PEG3400, it was not clear if the additional molecular size would be sufficient to effect a reduction in kidney clearance. Nonetheless, it was conjugated to the surface lysines of the diabody at pH 9.5 and a molar ratio of 50:1. When the conjugate was characterized by IEF and SDS gel electrophoresis (FIG. 8), the expected shift in pI and molecular size was observed. The dual $^{111}$In and $^{125}$I radiolabelled product was chromatographed on Superdex 75 (FIG. 24), the major peak collected and biodistribution studies performed. Inspection of the chromatogram and comparison to un-conjugated diabody reveals a shift in apparent molecular size equivalent to the PEG3400-diabody derivative.

The results of the biodistribution study are shown in FIGS. 26A-B. In spite of the lower molecular size of the PEG$_{27}$ derivative compared to the PEG3400 derivative, nearly equivalent results were obtained. At 24 h, kidney uptake for the $^{111}$In-labelled conjugate was 8.3% ID/g, tumour uptake a 49% ID/g, and the tumour to blood ratio 4.2:1. Given the surprisingly good results for the PEG$_{27}$ derivative, a PEG$_{12}$ derivative was produced.

Generation of Monodisperse PEG$_{12}$ AVP04-07 and Biodistribution Studies

FMOC-NH-PEG$_{12}$-Carboxyl was converted to DOTA-PEG$_{12}$-Cys-VS by the same chemistry as above (FIG. 25) and conjugated to AVP04-07 at pH 9.0 using molar ratios of 20:1 and 50:1. The unmodified and two conjugates were analyzed by high resolution nanospray mass spectrometry to determine their degree of substitution. The unmodified diabody gives a series of m/z species that when deconvoluted give a calculated mass of 26,869, a mass in good agreement with that predicted from the amino acid sequence. When conjugated to DOTA-PEG$_{12}$-Cys-VS at a molar ratio of 20:1, a series of deconvoluted peaks are obtained that all differ by 1225 mass units, the expected mass of DOTA-PEG$_{12}$-Cys-VS. Similarly the mass difference is the same for the 50:1 molar ratio conjugation, but shifted to a higher degree of substitution. Since the expected Gaussian distribution is obtained for reactions of this type, it is reasonable to assume that the peak heights correspond to the actual amount of each species present. Using peak heights as an estimate, an average of 1.7 PEGs per diabody for the 20:1 conjugate was estimated, and an average of 3.0 PEGs per conjugate for the 50:1 conjugate. When each conjugate was test labelled with $^{111}$In (178 mBq/mg), the 20:1 conjugate gave 8.3% incorporation and the 50:1 92% incorporation of radiolabel. These results indicate that the higher molar ratio with the resultant higher level of substitution gives superior results for radiolabelling.

Biodistribution studies were performed with dual $^{111}$In- and $^{125}$I-labelled DOTA-PEG$_{12}$-Cys-VS-AVP04-07. Overall, the tumour and kidney uptakes, blood clearance, and tumour to blood ratios were equivalent to the PEG3400 and PEG$_{27}$ derivatives (FIG. 26B). Notably, kidney uptake was initially higher (13.4% ID/g) in the PEG$_{12}$ vs the PEG$_{27}$ conjugate, but fell to lower levels (6.1% ID/g) by 96 h. However, tumour uptake levels and blood clearance curves are nearly identical between the two conjugates.

$^{64}$Cu PET Imaging of DOTA-PEG Conjugates AVP04-07

$^{64}$Cu, a positron emitter with a half-life of 13 h is well matched to the blood clearance kinetics ($t_{1/2\beta}$=18 h) of PEGylated AVP04-07. The PET imaging characteristics of AVP04-07 vs the DOTA-PEG conjugates were evaluated using the LS174T xenograft model. The results for non-PEGylated diabody shown in FIG. 27A demonstrate relatively modest tumour uptake and very high kidney uptake throughout the 2-day time course of the imaging experiment. In contrast, the PEG$_{12}$ and 27 conjugates showed relatively little kidney uptake throughout and high tumour uptake as early as 21-22 h. The PEG$_{27}$ conjugate measured tumour uptake was 45.1% ID/g for tumour at 46 h with a tumour to blood ratio of 7.9:1 (FIG. 27B) The measured tumour uptake for PEG$_{12}$ was 49±3% ID/g for tumour at 46 h with a tumour to blood ratio of (9±4):1 (Values are mean±SD, n=2) (FIG. 27C). These results closely match the biodistribution results for the $^{111}$In-labelled conjugate and suggest that choice of radiometal has little effect on the biodistribution 10.3 Discussion The search for an ideal radiolabelled antibody based imaging agent has focused on antibody fragments because their rapid blood clearance leads to improved tumour to blood ratios at earlier times than intact IgGs. However, the usual mechanism for increased blood clearance is excretion via the kidneys, and in the case of radiometal labelled fragments, the net accumulation in the kidneys, offsets their chief advantage. Furthermore, a too rapid course of blood clearance does not allow adequate time for tumour targeting, thus requiring administration of high doses of radiolabel to achieve adequate images. PEGylation is an attractive method for reducing kidney accumulation. Yazaki et. al. (2001) has shown that by conjugating a relatively large, polydisperse PEG3400 to an anti-CEA diabody, kidney uptake could be reduced from 200% ID/g to 50% ID/g at 24 h. This reduction, although significant, still results in unacceptable kidney uptake. Here it is demonstrated for the first time that PEGylating a diabody with smaller, monodisperse PEG is able to reduce kidney uptake to levels below 12% ID/g at 24-48 h. The results demonstrate that all of the PEGylated conjugates are superior to unmodified diabody. From the in vivo results obtained, the following order of in vivo improvement can be concluded: intact<<PEG3400<PEG$_{27}$<PEG$_{12}$.

REFERENCES

Abuchowski et al., *J. Biol. Chem.*, 252: 3582-3586, 1977;
Adams et al., *Cancer Res* 53:4026-4034, 1993;
Al-Lazikani et al., *J Mol Biol* 273, 927-948, 1997;
Albrecht et al., *Bioconjug Chem.* 15:16-26, 2004;
Andersson-Engels et al, *Phys. Med. Biol,* 42:815-824, 1997;
F. M. Ausubel et al. (editors), Current Protocols in Molecular Biology, Greene Pub. Associates and Wiley-Interscience (1988, including all updates until present);
Axworthy et al *Proc. Natl. Acad. Sci. USA* 97(4): 1802-1807, 2000;
Bateman et al., *Nucleic Acids Res.* 32: D138-41, 2004;
Bendele *J Musculoskel Neuron Interact;* 1(4):377-385, 2001;
Bernhard et al *Bioconjugate Chem.* 5:126-132, 1994;
Bork et al., *J Mol. Biol.* 242, 309-320, 1994;
Borrebaeck (ed), Antibody Engineering, Oxford University Press, 1995 (ISBN0195091507);
Bowie et al., *Science,* 253:164-70, 1991;
Bradl and Linington *Brain Pathol.,* 6:303-311, 1996
Bradley, et al. *Proc. Natl. Acad. Sci. USA* 98:14819-14824, 2001;
Brennan et al, *Science,* 229: 81-83, 1985;
Brinkmann et al., *Proc. Natl. Acad. Sci. USA,* 90: 7538-7542, 1993;
Carmichael et al. *J. Mol. Biol.* 326: 341-351, 2003;
Carpino and Han, *J. Org. Chem.,* 37:3403-3409, 1972;
Carter et al *Nucleic Acids Res.* 13:4431-4443, 1985;
Carter et al. *Bio/Technology* 10: 163-167, 1992;

Chari et al *Cancer Research* 52:127-131, 1992;
Chen et al. *Nature,* 446:203-207, 2007;
Chothia and Lesk *J. Mol. Biol.* 196:901-917, 1987;
Chothia et al. *Nature* 342, 877-883, 1989;
Chou et al., *Biochemistry* 13:222-45, 1974;
Chou et al., *Biochemistry* 13:211-22, 1974;
Chou et al., *Adv. Enzymol. Relat. Areas Mol. Biol.* 47:45-48, 1978;
Chou et al., *Ann. Rev. Biochem.* 47:251-276, 1978;
Chou et al., *Biophys. J.* 26:367-84, 1979;
Clark, et al *Genome Res.* 13, 2265-2270, 2003;
Clark et al., *Protein Sci.* 15: 949-960, 2006;
Coussens et al *Science* 230(4730): 1132-1139, 1985;
Eisen et al., *J. Am. Chem. Soc.,* 75: 4583-4585, 1953;
Feild et al *Biochem. Biophys. Res. Commun.* 258 (3):578-582, 1999;
Frangioni, *Curr. Opin. Chem. Biol,* 7:626-634, 2003;
Froyen et al., *Mol. Immunol.,* 37: 515-521, 1995;
Gaertner and Offord, *Bioconj. Chem.,* 7: 38-44, 1996;
Garman, Non-Radioactive Labelling: A Practical Approach, Academic Press, London, 1997;
Gaugitsch et al. *J. Biol. Chem.* 267 (16):1 1267-1273, 1992;
Gelfand et al. *Protein Eng.* 11: 1015-1025, 1998a;
Gelfand et al., *Journal of computational biology* 5: 467-477, 1998b;
Gendler et al., *J. Biol. Chem.* 265: 15286-15293, 1990;
Getz et al *Anal. Biochem.* 273:73-80, 1999;
Gillies et al, *J. Immunol. Methods* 125:191-202, 1989;
Goding, Monoclonal Antibodies: Principles and Practice, Academic Press, (1986) pp. 59-103;
Goodson and Katre, *Biotechnology,* 8: 227-231, 1990;
Gribskov et al., *Methods Enzymol.* 183:146-59, 1990;
Gribskov et al., *Proc. Nat. Acad. Sci. U.S.A.* 84:4355-58, 1989;
Grossman et al., *Biochemistry,* 21: 6122-6128, 1981;
Guan et al., *Proc. Natl. Acad. Sci. USA,* 95: 13206-10, 1998;
Guss et al. *EMBO J.* 5: 1567-1575, 1986;
Guy et al., *Mol Cell Biol.* 12(3):954-61, 1992;
Halaby et al., *Protein Engineering* 12: 563-571, 1999;
Harlow and Lane, Antibodies: A Laboratory Manual, Cold Spring Harbor Press, 1988;
Higuchi, in *PCR Protocols, pp.* 177-183, Academic Press, 1990;
Ito et al *Gene* 102:67-70, 1991;
Ho et al *Gene (Amst.)* 77:51-59, 1989;
Holliger et al *Proc. Natl. Acad. Sci. USA* 90: 6444-6448, 1993;
Hollinger and Hudson *Nature Biotechnology,* 23: 1126-1136, 2005;
Holm et al., *Nucleic Acids Res.* 27:244-47, 1999;
Hu et al., *Cancer Res.,* 56: 3055-3061, 1996;
Hubert, et al *Proc. Natl. Acad. Sci. U.S.A.* 96: 14523-14528, 1999;
Hudson and Kortt *J. Immunol. Methods,* 231: 177-189, 1999;
Hunter et al., *Nucleic Acids Research* 37: D211-D215, 2009;
Hust et al., *BMC Biotechnology* 7:14, 2007;
Iwamoto et al., *Oncogene.* 5(4):535-42, 1990;
Johnson and Wu, *Nucleic acids research* 28: 214-218, 2000;
Jakobovits et al. *Nature Biotechnology* 25, 1134-1143, 2007
Jones et al. *Nature,* 321:522-525, 1989;
Jones, *Curr. Opin. Struct. Biol.* 7:377-87, 1997;
Jones, *Curr. Opin. Struct. Biol.* 7:377-87, 1997;
Junutula et al., *Nature Biotechnology* 26: 925-932, 2008;
Kabat *Sequences of Proteins of Immunological Interest,* National Institutes of Health, Bethesda, Md., 1987 and 1991;
Karpusas et al., *J Mol. Biol.* 327:1031-1041, 2003;
Kim et al., *Proc. Natl. Acad. Sci. USA* 102: 11600-11605, 2005;
Kawabata et al., *Proteins* 41: 108-122, 2000;
Kawabata, *Nucleic Acids Res.* 31: 3367-3369, 2003;
Kim. et al., *Mol Cancer Ther.* 7: 2486-2497, 2008;
King et al., *Biochemistry,* 17: 1499-1506, 1978;
Kohler and Milstein *Nature,* 256:495-497, 1975;
Kortt et al *Protein Eng,* 10: 423-433, 1997;
Kortt et al., *Biomol. Eng.,* 18: 95-108, 2001;
Kostelny et al, *J. Immunol.,* 148(5):1547-1553, 1992;
Kruif and Logtenberg *J. Biol. Chem.,* 271: 7630-7634, 1996;
Kunkel et al *Proc. Natl. Acad. Sci. USA* 82:488, 1987;
Lambert *Curr. Opinion in Pharmacology* 5:543-549, 2005;
Largaespada et al, *Curr. Top. Microbiol. Immunol,* 166, 91-96, 1990;
Larson et al., *J. Mol. Biol.* 348: 1177-1190, 2005;
Laue et al., Analytical Ultracentrifugation in Biochemistry and Polymer Science 1992:90-125, 1992;
Le Gall et al *FEBS Lett,* 453: 164-168, 1999;
Lefranc, *Exp Clin Immunogenet* 18: 242-254, 2001a;
Lefranc, *Exp Clin Immunogenet* 18: 161-174, 2001b;
Lewis et al *Bioconj. Chem.* 9:72-86, 1998;
Li et al., *Bioconjug Chem* 17: 68-76, 2006;
Li et al., *Bioconjug Chem.* 19: 89-96, 2008;
Lindmark et al. *J Immunol Meth.* 62: 1-13, 1983;
Lonberg, N. "Transgenic Approaches to Human Monoclonal Antibodies." *Handbook of Experimental Pharmacology* 113: 49-101, 1994;
Lukacs et al. *J. Exp. Med.,* 194: 551-555, 2001;
Marsh et al *Hum. Mol. Genet.* 9, 13-25, 2000;
Matsui et al., *Cell.* 61(6):1147-55, 1990;
Matusik et al., Transgenic mouse models of prostate cancer. In: Transgenics in Endocrinology, ed. by M M Matzuk, C W Brown, and T R Kumar. The Humana Press Inc (Totowa, N.J.) Chapter 19, pp 401-425, 2001
Merrifield, *J. Am. Chem. Soc.,* 85:2149-2154, 1963;
Morrison et al. *Proc. Natl. Acad. Sci. USA* 81:6851-6855, 1984;
Morrison, *Science* 229:1202, 1985;
Moult, *Curr. Opin. Biotechnol.* 7:422-27, 1996;
Muller et al *Eur. J. Immunol.* 22 (6): 1621-1625, 1992;
Muller et al *EMBO J.* 9(3):907-13, 1990;
Murzin et al., *J. Mol. Biol.* 247: 536-540, 1995;
Mutsushima et al., *Chem. Lett.,* 773-776, 1980;
Nakayama et al *Biochem. Biophys. Res. Commun.* 277(1): 124-127, 2000;
Oi et al, *BioTechniques* 4:214, 1986;
Pallares et al., *Exp Clin Immunogenet* 16: 36-60, 1999;
Panchenko et al. *J. Mol. Biol.* 296: 1319-1331, 2000;
Pei et al. *Proc Natl Acad Sci USA.* 94: 9637-9642, 1997;
Perisic et al. *Structure* 2: 1217-1226, (1994);
Plückthun, *Immunol. Revs.,* 130:151-188, 1992;
Presta *Curr Op Struct Biol,* 2:593-59, 1992;
Presta et al., *Cancer Res.,* 57: 4593-4599, 1997
Ramseier and Chang *Analyt. Biochem.,* 221: 231-233, 1994;
Ramanujam et al, *IEEE Transactions on Biomedical Engineering,* 48:1034-1041, 2001;
Reddy et al., *Synthesis Stutgart:* 999-1002, 1988;
Reiter et al *Proc. Natl. Acad. Sci. U.S.A.* 95, 1735-1740, 1998;
Riechmann et al. *Nature,* 332:323-329, 1988;
Risma et al., *Proc Natl Acad Sci USA.;* 92(5):1322-6, 1995;
Roberge et al., *Protein Eng. Des. Sel.* 19: 141-145, 2006;
Roby et al., *Carcinogenesis.* 21(4):585-91, 2000;
Rodwell et al, *Proc. Natl. Acad. Sci. USA* 83: 2632-2636, 1986;
Rost et al. 270: 471-480, 1997;

Roux et al. *J. Immunol.* 161:4083, 1998;
Saha et al., BcePred: Prediction of Continuous B-Cell Epitopes in Antigenic Sequences Using Physico-chemical Properties. In Nicosia, Cutello, Bentley and Timis (Eds.) ICARIS 2004, LNCS 3239, 197-204, Springer, 2004;
Sakaguchi et al. *Nature,* 426: 454-460;
Sali and Blundell, *J. Mol. Biol.* 234, 779-815, 1993;
Sambrook et al. Molecular Cloning: A Laboratory Manual, Cold Spring Harbour Laboratory Press, 1989;
Sanders et al., *Thyroid* 17: 395-410, 2007;
Schelte et al., *Bioconj. Chem.* 11: 118-123, 2000;
Schuck *Biophys J;* 78:1606-19, 2000;
Shalaby et al, *J. Exp. Med.,* 175: 217-225, 1992;
Shen et al., *Protein Sci.* 15: 2507-2524, 2006;
Sippl et al., *Structure* 4:15-19, 1996;
Sirk et al., *Bioconjug Chem.* 19: 2527-2534, 2008;
Skerra et al, *Curr. Opinion in Immunol.,* 5:256-262, 1993;
Solovyev and Salamov *Computer Applications in the Biosciences,* 10,661-669, 1994;
Stanfield et al., *J. Virol.* 80:6093-6105, 2006;
Tang et al. *J. Exp. Med.,* 199: 1455-1465, 2004;
Todorovska et al., *J. Immunol. Methods,* 248: 47-66, 2001;
Trenado et al. *J. Clin. Invest.,* 112: 1688-1696, 2002;
Vallette et al *Nuc. Acids Res.* 17:723-733, 1989;
Van der Sluis et al. *Gastroenterology* 131: 117-129, 2006;
Verhoeyen et al. *Science,* 239:1534-1536, 1988;
Wang et al. *J Clin Invest.* 118(7): 2629-2639, 2008;
Weissinger et al. *Proc. Natl. Acad. Sci. USA,* 88, 8735-8739, 1991;
Wells et al *Gene* 34:315-323, 1985;
Xu and Xu *Proteins: Structure, Function, and Genetics* 40: 343-354, 2000;
Yazaki et al., *Bioconjug Chem* 12: 220-228, 2001;
Yem et al., *J. Biol. Chem.,* 267: 3122-3128, 1992;
Zalipsky et al., *J. Bioact. Compat. Polym.,* 5: 227-231, 1990
Zalipsky et al., *Biotechnol. Appl. Biochem.,* 15: 100-114, 1992;
Zhang and Tam, *Anal. Biochem.* 233: 87-93, 1996;
Zhou et al., *Proc Natl Acad Sci USA.* 102: 14575-14580, 2005;
Zoller et al *Methods Enzymol.* 100:468-500, 1983; and
Zoller and Smith. *Nucl. Acids Res.* 10:6487-6500, 1982.

What is claimed is:

1. An isolated protein comprising an immunoglobulin heavy chain variable region ($V_H$) and an immunoglobulin light chain variable region ($V_L$), wherein at least one of the variable regions comprises at least two cysteine residues substituted at positions exposed to solvent within a framework region 1 (FR1), wherein: (i) the at least two cysteine residues consist of 2, 4, or 6 cysteine residues, (ii) if at least two of the cysteine residues are not conjugated to a compound then a disulphide bond is capable of forming within the FR1 between the cysteine residues; and (iii) if the $V_L$ comprises the at least two cysteine residues, they are substituted at any of Kabat positions L7 to L19, and if the $V_H$ comprises the at least two cysteine residues, they are substituted at any of Kabat positions H7 to H20.

2. The isolated protein of according to claim 1 comprising a compound conjugated to at least one of the cysteine residues, wherein the conjugated compound does not reduce binding of the isolated protein to an antigen.

3. The isolated protein according to claim 1, wherein at least one of the variable regions comprises an N-terminal threonine residue or an N-terminal serine residue.

4. The isolated protein according to claim 3 additionally comprising a compound conjugated to the threonine or serine residue.

5. The isolated protein according to claim 1, comprising a plurality of polypeptides each comprising an immunoglobulin heavy chain variable region ($V_H$) and an immunoglobulin light chain variable region ($V_L$), wherein:
(i) at least one of the polypeptides comprises a $V_H$ comprising a sequence set forth in SEQ ID NO: 111; and
(ii) at least another of the polypeptides comprises a $V_L$ comprising a sequence set forth in SEQ ID NO: 113, wherein the $V_H$ of the polypeptide at (i) and the $V_L$ of the polypeptide at (ii) associate to form a Fv capable of specifically binding to tumour antigen TAG-72, and wherein at least one of the immunoglobulin variable regions comprises the at least two cysteine residue substitutions.

6. The isolated protein of claim 5, wherein the isolated protein is a diabody, triabody, or tetrabody.

7. The isolated protein according to claim 1, wherein the isolated protein comprises an N-terminal serine or threonine residue.

8. The isolated protein according to claim 1, comprising a disulphide bond between the at least two cysteine residues.

9. The isolated protein according to claim 1, wherein the at least two cysteine residues consist of 2 or 4 cysteine residues.

10. The isolated protein according to claim 9, wherein the at least two cysteine residues consist of 2 cysteine residues.

11. The isolated protein according to claim 1, wherein $V_L$ Kabat positions are selected from the group consisting of: (i) L7 and L11; (ii) L8 and L11; (iii) L8 and L12; (iv) L14 and L17; and (v) L13 and L19.

12. The isolated protein according to claim 1, wherein the $V_H$ Kabat positions are selected from the group consisting of: (i) H7 and H10; (ii) H13 and H16; or (iii) H12 and H18.

13. The isolated protein according to claim 1, wherein both the immunoglobulin heavy chain variable region ($V_H$) and the immunoglobulin light chain variable region ($V_L$) comprise the at least two cysteine residue substitutions.

14. The isolated protein according to claim 1, wherein the isolated protein is an avibody.

15. A composition comprising the isolated protein according to claim 1 and a pharmaceutically acceptable carrier.

16. A composition comprising the isolated protein according to claim 5 and a pharmaceutically acceptable carrier.

17. A method for producing a protein comprising a compound conjugated to at least one of the at least two cysteine residues, the method comprising:
    (i) obtaining the protein of claim 1; and
    (ii) conjugating a compound to at least one of the cysteine residues in FR1 of the polypeptide(s) to thereby produce the protein.

18. A method for producing a protein comprising a compound conjugated to a N-terminal serine or threonine residue, the method comprising conjugating a compound to at least one serine or threonine residue at the N-terminus of a polypeptide of the protein according to claim 7 to thereby produce the protein.

19. A method for localizing or detecting an antigen in a subject, said method comprising:
    (i) administering to a subject the protein according claim 2 for a time and under conditions sufficient for the protein to bind to an antigen, wherein the conjugated compound is a detectable label; and
    (ii) detecting or localizing the detectable label in vivo.

20. A method for detecting an antigen in a biological sample, the method comprising contacting the biological sample with the protein according to claim 1 for a time and under conditions sufficient for the protein to bind to the antigen and form a complex, and detecting the complex.

* * * * *

```
                        SEQUENCE LISTING

<160> NUMBER OF SEQ ID NOS: 135

<210> SEQ ID NO 1
<211> LENGTH: 30
<212> TYPE: PRT
<213> ORGANISM: artificial sequence
<220> FEATURE:
<223> OTHER INFORMATION: amino acid sequence within FR1 of a human
      antibody heavy chain

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 2
<211> LENGTH: 30
<212> TYPE: PRT
<213> ORGANISM: artificial sequence
<220> FEATURE:
<223> OTHER INFORMATION: amino acid sequence within FR1 of a human
      antibody heavy chain

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr
            20                  25                  30

<210> SEQ ID NO 3
<211> LENGTH: 30
<212> TYPE: PRT
<213> ORGANISM: artificial sequence
<220> FEATURE:
<223> OTHER INFORMATION: amino acid sequence within FR1 of a human
      antibody heavy chain

<400> SEQUENCE: 3

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr
            20                  25                  30
```

```
<210> SEQ ID NO 4
<211> LENGTH: 30
<212> TYPE: PRT
<213> ORGANISM: artificial sequence
<220> FEATURE:
<223> OTHER INFORMATION: amino acid sequence within FR1 of a human
      antibody heavy chain

<400> SEQUENCE: 4

Gln Met Gln Leu Val Gln Ser Gly Pro Glu Val Lys Lys Pro Gly Thr
1               5                   10                  15
Ser Val Lys Val Ser Cys Lys Ala Ser Gly Phe Thr Phe Thr
            20                  25                  30

<210> SEQ ID NO 5
<211> LENGTH: 30
<212> TYPE: PRT
<213> ORGANISM: artificial sequence
<220> FEATURE:
<223> OTHER INFORMATION: amino acid sequence within FR1 of a human
      antibody heavy chain

<400> SEQUENCE: 5

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser
            20                  25                  30

<210> SEQ ID NO 6
<211> LENGTH: 30
<212> TYPE: PRT
<213> ORGANISM: artificial sequence
<220> FEATURE:
<223> OTHER INFORMATION: amino acid sequence within FR1 of a human
      antibody heavy chain

<400> SEQUENCE: 6

Gln Val Thr Leu Lys Glu Ser Gly Pro Val Leu Val Lys Pro Thr Glu
1               5                   10                  15
Thr Leu Thr Leu Thr Cys Thr Val Ser Gly Phe Ser Leu Ser
            20                  25                  30

<210> SEQ ID NO 7
<211> LENGTH: 30
<212> TYPE: PRT
<213> ORGANISM: artificial sequence
<220> FEATURE:
<223> OTHER INFORMATION: amino acid sequence within FR1 of a human
      antibody heavy chain

<400> SEQUENCE: 7

Gln Ile Thr Leu Lys Glu Ser Gly Pro Thr Leu Val Lys Pro Thr Gln
1               5                   10                  15
Thr Leu Thr Leu Thr Cys Thr Phe Ser Gly Phe Ser Leu Ser
            20                  25                  30

<210> SEQ ID NO 8
<211> LENGTH: 30
<212> TYPE: PRT
<213> ORGANISM: artificial sequence
<220> FEATURE:
<223> OTHER INFORMATION: amino acid sequence within FR1 of a human
      antibody heavy chain

<400> SEQUENCE: 8
```

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser
            20                  25                  30

<210> SEQ ID NO 9
<211> LENGTH: 30
<212> TYPE: PRT
<213> ORGANISM: artificial sequence
<220> FEATURE:
<223> OTHER INFORMATION: amino acid sequence within FR1 of a human
      antibody heavy chain

<400> SEQUENCE: 9

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 10
<211> LENGTH: 30
<212> TYPE: PRT
<213> ORGANISM: artificial sequence
<220> FEATURE:
<223> OTHER INFORMATION: amino acid sequence within FR1 of a human
      antibody heavy chain

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 11
<211> LENGTH: 30
<212> TYPE: PRT
<213> ORGANISM: artificial sequence
<220> FEATURE:
<223> OTHER INFORMATION: amino acid sequence within FR1 of a human
      antibody heavy chain

<400> SEQUENCE: 11

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 12
<211> LENGTH: 30
<212> TYPE: PRT
<213> ORGANISM: artificial sequence
<220> FEATURE:
<223> OTHER INFORMATION: amino acid sequence within FR1 of a human
      antibody heavy chain

<400> SEQUENCE: 12

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp
            20                  25                  30

<210> SEQ ID NO 13
<211> LENGTH: 30
<212> TYPE: PRT
```

```
<213> ORGANISM: artificial sequence
<220> FEATURE:
<223> OTHER INFORMATION: amino acid sequence within FR1 of a human
      antibody heavy chain

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 14
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 15
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 15

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 16
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 16

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 17
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 17

Glu Ile Val Leu Thr Gln Ser Pro Ala Thr Leu Ser Leu Ser Pro Gly
1               5                   10                  15

Glu Arg Ala Thr Leu Ser Cys
```

```
                    20

<210> SEQ ID NO 18
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 19
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 19

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 20
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 20

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 21
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 21

Asp Ile Val Met Thr Gln Ser Pro Ser Ser Leu Ser Ala Ser Val Gly
1               5                   10                  15

Asp Arg Val Thr Ile Thr Cys
            20

<210> SEQ ID NO 22
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain
```

```
<400> SEQUENCE: 22

Glu Ile Val Met Thr Gln Ser Pro Ala Thr Leu Ser Leu Ser Pro Gly
1               5                   10                  15

Glu Arg Ala Thr Leu Ser Cys
            20

<210> SEQ ID NO 23
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 23

Asp Ile Gln Met Thr Gln Ser Pro Asp Phe Leu Ala Val Ser Leu Gly
1               5                   10                  15

Glu Arg Ala Thr Ile Asn Cys
            20

<210> SEQ ID NO 24
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 24

Glu Ile Val Leu Thr Gln Ser Pro Ser Ser Leu Ser Ala Ser Val Gly
1               5                   10                  15

Asp Arg Val Thr Ile Thr Cys
            20

<210> SEQ ID NO 25
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 25

Asp Ile Val Met Thr Gln Thr Pro Leu Ser Leu Pro Val Thr Pro Gly
1               5                   10                  15

Glu Pro Ala Ser Ile Ser Cys
            20

<210> SEQ ID NO 26
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 26

Asp Ile Val Met Thr Gln Thr Pro Leu Ser Leu Ser Val Thr Pro Gly
1               5                   10                  15

Gln Pro Ala Ser Ile Ser Cys
            20

<210> SEQ ID NO 27
<211> LENGTH: 23
```

```
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 27

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 28
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 28

Glu Thr Thr Leu Thr Gln Ser Pro Ala Phe Met Ser Ala Thr Pro Gly
1               5                   10                  15

Asp Lys Val Asn Ile Ser Cys
            20

<210> SEQ ID NO 29
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 29

Ala Ile Arg Met Thr Gln Ser Pro Phe Ser Leu Ser Ala Ser Val Gly
1               5                   10                  15

Asp Arg Val Thr Ile Thr Cys
            20

<210> SEQ ID NO 30
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 30

Ala Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 31
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 31

Asn Ile Gln Met Thr Gln Ser Pro Ser Ala Met Ser Ala Ser Val Gly
1               5                   10                  15
```

```
Asp Arg Val Thr Ile Thr Cys
            20

<210> SEQ ID NO 32
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 32

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 33
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 33

Asp Ile Val Met Thr Gln Thr Pro Leu Ser Ser Pro Val Thr Leu Gly
1               5                   10                  15

Gln Pro Ala Ser Ile Ser Cys
            20

<210> SEQ ID NO 34
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 34

Asp Val Val Met Thr Gln Ser Pro Ala Phe Leu Ser Val Thr Pro Gly
1               5                   10                  15

Glu Lys Val Thr Ile Thr Cys
            20

<210> SEQ ID NO 35
<211> LENGTH: 23
<212> TYPE: PRT
<213> ORGANISM: artificial sequence
<220> FEATURE:
<223> OTHER INFORMATION: amino acid sequence within FR1 of a human
      antibody kappa light chain

<400> SEQUENCE: 35

Val Ile Trp Met Thr Gln Ser Pro Ser Leu Leu Ser Ala Ser Thr Gly
1               5                   10                  15

Asp Arg Val Thr Ile Ser Cys
            20

<210> SEQ ID NO 36
<211> LENGTH: 23
<212> TYPE: PRT
<213> ORGANISM: artificial sequence
<220> FEATURE:
<223> OTHER INFORMATION: amino acid sequence within FR1 of a human ant
      ibody kappa light chain
```

<400> SEQUENCE: 36

Ala Ile Arg Met Thr Gln Ser Pro Ser Ser Phe Ser Ala Ser Thr Gly
1               5                   10                  15

Asp Arg Val Thr Ile Thr Cys
            20

<210> SEQ ID NO 37
<211> LENGTH: 22
<212> TYPE: PRT
<213> ORGANISM: artificial sequence
<220> FEATURE:
<223> OTHER INFORMATION: amino acid sequence within FR1 of a human
      antibody lambda light chain

<400> SEQUENCE: 37

Gln Ser Val Leu Thr Gln Pro Pro Ser Val Ser Ala Ala Pro Gly Gln
1               5                   10                  15

Lys Val Thr Ile Ser Cys
            20

<210> SEQ ID NO 38
<211> LENGTH: 22
<212> TYPE: PRT
<213> ORGANISM: artificial sequence
<220> FEATURE:
<223> OTHER INFORMATION: amino acid sequence within FR1 of a human
      antibody lambda light chain

<400> SEQUENCE: 38

Gln Ser Val Leu Thr Gln Pro Pro Ser Ala Ser Gly Thr Pro Gly Gln
1               5                   10                  15

Arg Val Thr Ile Ser Cys
            20

<210> SEQ ID NO 39
<211> LENGTH: 22
<212> TYPE: PRT
<213> ORGANISM: artificial sequence
<220> FEATURE:
<223> OTHER INFORMATION: amino acid sequence within FR1 of a human
      antibody lambda light chain

<400> SEQUENCE: 39

Gln Ser Ala Leu Thr Gln Pro Ala Ser Val Ser Gly Ser Pro Gly Gln
1               5                   10                  15

Ser Ile Thr Ile Ser Cys
            20

<210> SEQ ID NO 40
<211> LENGTH: 22
<212> TYPE: PRT
<213> ORGANISM: artificial sequence
<220> FEATURE:
<223> OTHER INFORMATION: amino acid sequence within FR1 of a human
      antibody lambda light chain

<400> SEQUENCE: 40

Gln Ser Ala Leu Thr Gln Pro Arg Ser Val Ser Gly Ser Pro Gly Gln
1               5                   10                  15

Ser Val Thr Ile Ser Cys
            20

<210> SEQ ID NO 41

```
<211> LENGTH: 22
<212> TYPE: PRT
<213> ORGANISM: artificial sequence
<220> FEATURE:
<223> OTHER INFORMATION: amino acid sequence within FR1 of a human
      antibody lambda light chain

<400> SEQUENCE: 41

Ser Tyr Val Leu Thr Gln Pro Pro Ser Val Ser Val Ala Pro Gly Lys
1               5                   10                  15

Thr Ala Arg Ile Thr Cys
            20

<210> SEQ ID NO 42
<211> LENGTH: 22
<212> TYPE: PRT
<213> ORGANISM: artificial sequence
<220> FEATURE:
<223> OTHER INFORMATION: amino acid sequence within FR1 of a human
      antibody lambda light chain

<400> SEQUENCE: 42

Ser Tyr Glu Leu Thr Gln Pro Pro Ser Val Ser Val Ser Pro Gly Gln
1               5                   10                  15

Thr Ala Ser Ile Thr Cys
            20

<210> SEQ ID NO 43
<211> LENGTH: 22
<212> TYPE: PRT
<213> ORGANISM: artificial sequence
<220> FEATURE:
<223> OTHER INFORMATION: amino acid sequence within FR1 of a human
      antibody lambda light chain

<400> SEQUENCE: 43

Gln Leu Val Leu Thr Gln Ser Pro Ser Ala Ser Ala Ser Leu Gly Ala
1               5                   10                  15

Ser Val Lys Leu Thr Cys
            20

<210> SEQ ID NO 44
<211> LENGTH: 22
<212> TYPE: PRT
<213> ORGANISM: artificial sequence
<220> FEATURE:
<223> OTHER INFORMATION: amino acid sequence of FR1 of a camelid
      immunoglobulin

<400> SEQUENCE: 44

Gly Gly Ser Val Gln Thr Gly Gly Ser Leu Arg Leu Ser Cys Glu Ile
1               5                   10                  15

Ser Gly Leu Thr Phe Asp
            20

<210> SEQ ID NO 45
<211> LENGTH: 22
<212> TYPE: PRT
<213> ORGANISM: artificial sequence
<220> FEATURE:
<223> OTHER INFORMATION: amino acid sequence of FR1 of a camelid
      immunoglobulin

<400> SEQUENCE: 45

Gly Gly Ser Val Gln Thr Gly Gly Ser Leu Arg Leu Ser Cys Ala Val
1               5                   10                  15
```

```
Ser Gly Phe Ser Phe Ser
            20

<210> SEQ ID NO 46
<211> LENGTH: 22
<212> TYPE: PRT
<213> ORGANISM: artificial sequence
<220> FEATURE:
<223> OTHER INFORMATION: amino acid sequence of FR1 of a camelid
      immunoglobulin

<400> SEQUENCE: 46

Gly Gly Ser Glu Gln Gly Gly Ser Leu Arg Leu Ser Cys Ala Ile
1               5                   10                  15

Ser Gly Tyr Thr Tyr Gly
            20

<210> SEQ ID NO 47
<211> LENGTH: 22
<212> TYPE: PRT
<213> ORGANISM: artificial sequence
<220> FEATURE:
<223> OTHER INFORMATION: amino acid sequence of FR1 of a camelid
      immunoglobulin

<400> SEQUENCE: 47

Gly Gly Ser Val Gln Pro Gly Gly Ser Leu Thr Leu Ser Cys Thr Val
1               5                   10                  15

Ser Gly Ala Thr Tyr Ser
            20

<210> SEQ ID NO 48
<211> LENGTH: 22
<212> TYPE: PRT
<213> ORGANISM: artificial sequence
<220> FEATURE:
<223> OTHER INFORMATION: amino acid sequence of FR1 of a camelid
      immunoglobulin

<400> SEQUENCE: 48

Gly Gly Ser Val Gln Ala Gly Gly Ser Leu Arg Leu Ser Cys Thr Gly
1               5                   10                  15

Ser Gly Phe Pro Tyr Ser
            20

<210> SEQ ID NO 49
<211> LENGTH: 21
<212> TYPE: PRT
<213> ORGANISM: artificial sequence
<220> FEATURE:
<223> OTHER INFORMATION: amino acid sequence of FR1 of a camelid
      immunoglobulin

<400> SEQUENCE: 49

Gly Gly Ser Val Gln Ala Gly Gly Ser Leu Arg Leu Ser Cys Val Ala
1               5                   10                  15

Gly Phe Gly Thr Ser
            20

<210> SEQ ID NO 50
<211> LENGTH: 21
<212> TYPE: PRT
<213> ORGANISM: artificial sequence
<220> FEATURE:
<223> OTHER INFORMATION: amino acid sequence of FR1 of a camelid
``` immunoglobulin

<400> SEQUENCE: 50

Gly Gly Ser Val Gln Ala Gly Gly Ser Leu Arg Leu Ser Cys Val Ser
1               5                   10                  15

Phe Ser Pro Ser Ser
            20

<210> SEQ ID NO 51
<211> LENGTH: 24
<212> TYPE: PRT
<213> ORGANISM: artificial sequence
<220> FEATURE:
<223> OTHER INFORMATION: amino acid sequence of FR1 of a spiny dogfish
      shark IgNAR

<400> SEQUENCE: 51

Ala Trp Val Glu Gln Thr Pro Arg Thr Ala Lys Glu Thr Gly Glu Ser
1               5                   10                  15

Leu Thr Ile Asn Cys Val Leu Thr
            20

<210> SEQ ID NO 52
<211> LENGTH: 25
<212> TYPE: PRT
<213> ORGANISM: artificial sequence
<220> FEATURE:
<223> OTHER INFORMATION: amino acid sequence of FR1 of a nurse shark
      IgNAR

<400> SEQUENCE: 52

Ala Arg Val Asp Gln Thr Pro Lys Thr Ile Thr Lys Glu Thr Gly Glu
1               5                   10                  15

Ser Leu Thr Ile Asn Cys Val Leu Ser
            20                  25

<210> SEQ ID NO 53
<211> LENGTH: 15
<212> TYPE: PRT
<213> ORGANISM: artificial sequence
<220> FEATURE:
<223> OTHER INFORMATION: amino acid sequence of a linker

<400> SEQUENCE: 53

Gly Gly Gly Gly Ser Gly Gly Gly Gly Ser Gly Gly Gly Gly Ser
1               5                   10                  15

<210> SEQ ID NO 54
<211> LENGTH: 702
<212> TYPE: DNA
<213> ORGANISM: artificial
<220> FEATURE:
<223> OTHER INFORMATION: nucleotide sequence encoding AVP04-07
      anti-TAG72 diabody

<400> SEQUENCE: 54
caggtgcagc tgcagcagag cgatgcggaa ctggtgaaac cgggcgcgag cgtgaaaatt      60
agctgcaaag cgagcggcta cctttacc gatcatgcga ttcattgggt gaaacagaat       120
ccggaacagg gcctggaatg gattggctat tttagcccgg gcaacgatga ttttaaatat    180
aacgaacgtt ttaaaggcaa agcgaccctg accgcggata aaagcagcag caccgcgtat    240
ctgcagctga acagcctgac cagcgaagat agcgcggtgt atttttgcac ccgtagcctg    300
aatatggcgt attggggtca gggcaccctcg gtcaccgtga gcagcggtgg cggcggcagc    360

```
gatatcgtga tgacccagag cccgagcagc ctgccggtga gcgtgggcga aaaagtgacc    420
ctgagctgca aaagcagcca gagcctgctg tatagcggca atcagaaaaa ctatctggcg    480
tggtatcagc agaaaccggg tcagagcccg aaactgctga tttattgggc gagcacccgt    540
gaaagcggcg tgccggatcg ttttaccggc agcggtagcg gcaccgattt tacccctgagc   600 attagcagcg tggaaaccga agatctggcg gtgtattatt gccagcagta ttatagctat    660 ccgctgaccct tggtgcgggg caccaaactg gtgctgaaac gt                      702
```

<210> SEQ ID NO 55
<211> LENGTH: 234
<212> TYPE: PRT
<213> ORGANISM: artificial
<220> FEATURE:
<223> OTHER INFORMATION: amino acid sequence of AVP04-07 anti-TAG72 diabody

<400> SEQUENCE: 55

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Asp Ile Val Met Thr Gln Ser Pro
        115                 120                 125

Ser Ser Leu Pro Val Ser Val Gly Glu Lys Val Thr Leu Ser Cys Lys
130                 135                 140

Ser Ser Gln Ser Leu Leu Tyr Ser Gly Asn Gln Lys Asn Tyr Leu Ala
145                 150                 155                 160

Trp Tyr Gln Gln Lys Pro Gly Gln Ser Pro Lys Leu Leu Ile Tyr Trp
                165                 170                 175

Ala Ser Thr Arg Glu Ser Gly Val Pro Asp Arg Phe Thr Gly Ser Gly
            180                 185                 190

Ser Gly Thr Asp Phe Thr Leu Ser Ile Ser Ser Val Glu Thr Glu Asp
        195                 200                 205

Leu Ala Val Tyr Tyr Cys Gln Gln Tyr Tyr Ser Tyr Pro Leu Thr Phe
    210                 215                 220

Gly Ala Gly Thr Lys Leu Val Leu Lys Arg
225                 230
```

<210> SEQ ID NO 56
<211> LENGTH: 702
<212> TYPE: DNA
<213> ORGANISM: artificial
<220> FEATURE:
<223> OTHER INFORMATION: nucleotide sequence encoding modified AVP04-07 anti-TAG72 diabody designated AVP04-50 comprising cysteine residues in FR1 and a N-terminal serine

<400> SEQUENCE: 56

```
agcgtgcagc tgcagcagag cgatgcggaa ctggtgaaac cgggcgcgag cgtgaaaatt      60
agctgcaaag cgagcggcta cctttacc gatcatgcga ttcattgggt gaaacagaat      120
ccggaacagg gcctggaatg gattggctat tttagcccgg caacgatga ttttaaatat     180
aacgaacgtt ttaaaggcaa agcgaccctg accgcggata aaagcagcag caccgcgtat    240
ctgcagctga acagcctgac cagcgaagat agcgcggtgt attttgcac ccgtagcctg     300
aatatggcgt attggggtca gggcacctcg gtcaccgtga gcagcggtgg cggcggcagc    360
gatatcgtga tgacccagag ctgcagcagc tgcccggtga gcgtgggcga aaaagtgacc    420
ctgagctgca aaagcagcca gagcctgctg tatagcggca atcagaaaaa ctatctggcg    480
tggtatcagc agaaaccggg tcagagcccg aaactgctga tttattgggc gagcacccgt    540
gaaagcggcg tgccggatcg ttttaccggc agcggtagcg gcaccgatt tacccctgagc   600
attagcagcg tggaaaccga agatctggcg gtgtattatt gccagcagta ttatagctat    660
ccgctgacct tggtgcggg caccaaactg gtgctgaaac gt                        702
```

<210> SEQ ID NO 57
<211> LENGTH: 234
<212> TYPE: PRT
<213> ORGANISM: artificial
<220> FEATURE:
<223> OTHER INFORMATION: amino acid sequence of modified AVP04-07 anti-TAG72 diabody designated AVP04-50 comprising cysteine residues in FR1 and a N-terminal serine

<400> SEQUENCE: 57

```
Ser Val Gln Leu Gln Gln Ser Asp Ala Glu Leu Val Lys Pro Gly Ala
1               5                   10                  15
Ser Val Lys Ile Ser Cys Lys Ala Ser Gly Tyr Thr Phe Thr Asp His
            20                  25                  30
Ala Ile His Trp Val Lys Gln Asn Pro Glu Gln Gly Leu Glu Trp Ile
        35                  40                  45
Gly Tyr Phe Ser Pro Gly Asn Asp Asp Phe Lys Tyr Asn Glu Arg Phe
    50                  55                  60
Lys Gly Lys Ala Thr Leu Thr Ala Asp Lys Ser Ser Ser Thr Ala Tyr
65                  70                  75                  80
Leu Gln Leu Asn Ser Leu Thr Ser Glu Asp Ser Ala Val Tyr Phe Cys
                85                  90                  95
Thr Arg Ser Leu Asn Met Ala Tyr Trp Gly Gln Gly Thr Ser Val Thr
            100                 105                 110
Val Ser Ser Gly Gly Gly Gly Ser Asp Ile Val Met Thr Gln Ser Cys
        115                 120                 125
Ser Ser Cys Pro Val Ser Val Gly Glu Lys Val Thr Leu Ser Cys Lys
    130                 135                 140
Ser Ser Gln Ser Leu Leu Tyr Ser Gly Asn Gln Lys Asn Tyr Leu Ala
145                 150                 155                 160
Trp Tyr Gln Gln Lys Pro Gly Gln Ser Pro Lys Leu Leu Ile Tyr Trp
                165                 170                 175
Ala Ser Thr Arg Glu Ser Gly Val Pro Asp Arg Phe Thr Gly Ser Gly
            180                 185                 190
Ser Gly Thr Asp Phe Thr Leu Ser Ile Ser Ser Val Glu Thr Glu Asp
        195                 200                 205
Leu Ala Val Tyr Tyr Cys Gln Gln Tyr Tyr Ser Tyr Pro Leu Thr Phe
    210                 215                 220
```

```
Gly Ala Gly Thr Lys Leu Val Leu Lys Arg
225                 230
```

<210> SEQ ID NO 58
<211> LENGTH: 735
<212> TYPE: DNA
<213> ORGANISM: artificial
<220> FEATURE:
<223> OTHER INFORMATION: nucleotide sequence encoding AVP07-17 anti-Her2
      diabody

<400> SEQUENCE: 58

```
caggtgcagc tggtgcagtc tggggcagag gtgaaaaagc ccggggagtc tctgaagatc    60
tcctgtaagg gttctggata cagctttacc agctactgga tcgcctgggt gcgccagatg   120
cccgggaaag cctggagta catggggctc atctatcctg gtgactctga caccaaatac   180
agcccgtcct tccaaggcca ggtcaccatc tcagtcgaca gtccgtcag cactgcctac    240
ttgcaatgga gcagtctgaa gccctcggac agcgccgtgt attttgtgc gagacatgac   300
gtgggatatt gcagtagttc caactgcgca agtggcctg aatacttcca gcattggggc   360
cagggcaccc tggtcaccgt ttcctcaggt ggaggcggtt cacagtctgt gttgacgcag   420
ccgcccctcag tgtctgcggc cccaggacag aaggtcacca tctcctgctc tggaagcagc   480
tccaacattg ggaataatta tgtatcctgg taccagcagc tcccaggaac agtccccaaa   540
ctcctcatct atggtcacac caatcggccc gcaggggtcc ctgaccgatt ctctggctcc   600
aagtctggca cctcagcctc cctggccatc agtgggttcc ggtccgagga tgaggctgat   660
tattactgtg cagcatggga tgacagcctg agtggttggg tgttcggcgg agggaccaag   720
ctgaccgtcc taggt                                                    735
```

<210> SEQ ID NO 59
<211> LENGTH: 245
<212> TYPE: PRT
<213> ORGANISM: artificial
<220> FEATURE:
<223> OTHER INFORMATION: amino acid sequence of AVP07-17 anti-Her2
      diabody

<400> SEQUENCE: 59

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Ser Ser Ser Asn Cys Ala Lys Trp
            100                 105                 110

Pro Glu Tyr Phe Gln His Trp Gly Gln Gly Thr Leu Val Thr Val Ser
        115                 120                 125

Ser Gly Gly Gly Gly Ser Gln Ser Val Leu Thr Gln Pro Pro Ser Val
    130                 135                 140
```

```
Ser Ala Ala Pro Gly Gln Lys Val Thr Ile Ser Cys Ser Gly Ser Ser
145                 150                 155                 160

Ser Asn Ile Gly Asn Asn Tyr Val Ser Trp Tyr Gln Gln Leu Pro Gly
                165                 170                 175

Thr Val Pro Lys Leu Leu Ile Tyr Gly His Thr Asn Arg Pro Ala Gly
            180                 185                 190

Val Pro Asp Arg Phe Ser Gly Ser Lys Ser Gly Thr Ser Ala Ser Leu
            195                 200                 205

Ala Ile Ser Gly Phe Arg Ser Glu Asp Glu Ala Asp Tyr Tyr Cys Ala
        210                 215                 220

Ala Trp Asp Asp Ser Leu Ser Gly Trp Val Phe Gly Gly Gly Thr Lys
225                 230                 235                 240

Leu Thr Val Leu Gly
                245

<210> SEQ ID NO 60
<211> LENGTH: 696
<212> TYPE: DNA
<213> ORGANISM: artificial
<220> FEATURE:
<223> OTHER INFORMATION: nucleotide sequence encoding AVP02-60 anti-MUC1
      diabody

<400> SEQUENCE: 60
gaagtgcagc tggttgaaag cggtggcgga gtggtgcagc caggtggaag cctgcgtctg      60
agctgcgcag caagcggttt taccttagc agctatggca tgagctgggt gcgtcaggcg     120
ccggataaag gcctggaact ggtggcgacc attaacagca cggtggaag cacctattat     180 ccggatagcg tgaaaggccg ttttaccatt agccgtgata cagcaaaaa caccctgtat     240 ctgcagatga acagcctgcg taccgaagat accgcggtgt attattgcgc gcgtgatcgt     300
gatggctatg atgaaggctt tgattattgg ggccagggca ccctggtgac cgtgagcagc     360 ggtggggggcg gaagccagat tcagctgacc cagagcccga gcagcctgag cgcaagcgtg     420
ggtgatcgtg tgaccattac ctgcagcgcg agcagcagcg tgagctatat gcattggtat     480
cagcagaaac cgggcaaagc gccgaaacgt tggatttatg ataccagcaa actggcgagc     540
ggcgtgccga gccgttttag cggcagcggc agcggcaccg attatacctt taccattagc     600
agcctgcagc cggaagatat tgcgacctat tattgccagc agtggagcag caacccgccg     660
acctttggcc agggcaccaa actgcagatt aaacgt                                696

<210> SEQ ID NO 61
<211> LENGTH: 232
<212> TYPE: PRT
<213> ORGANISM: artificial
<220> FEATURE:
<223> OTHER INFORMATION: amino acid sequence of AVP02-60 anti-MUC1
      diabody

<400> SEQUENCE: 61

Glu Val Gln Leu Val Glu Ser Gly Gly Gly Val Val Gln Pro Gly Gly
1               5                  10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Asp Lys Gly Leu Glu Leu Val
        35                  40                  45

Ala Thr Ile Asn Ser Asn Gly Gly Ser Thr Tyr Tyr Pro Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Thr Glu Asp Thr Ala Val Tyr Tyr Cys
                 85                  90                  95

Ala Arg Asp Arg Asp Gly Tyr Asp Glu Gly Phe Asp Tyr Trp Gly Gln
            100                 105                 110

Gly Thr Leu Val Thr Val Ser Gly Gly Gly Gly Ser Gln Ile Gln
        115                 120                 125

Leu Thr Gln Ser Pro Ser Ser Leu Ser Ala Ser Val Gly Asp Arg Val
130                 135                 140

Thr Ile Thr Cys Ser Ala Ser Ser Val Ser Tyr Met His Trp Tyr
145                 150                 155                 160

Gln Gln Lys Pro Gly Lys Ala Pro Lys Arg Trp Ile Tyr Asp Thr Ser
                165                 170                 175

Lys Leu Ala Ser Gly Val Pro Ser Arg Phe Ser Gly Ser Gly Ser Gly
                180                 185                 190

Thr Asp Tyr Thr Phe Thr Ile Ser Ser Leu Gln Pro Glu Asp Ile Ala
            195                 200                 205

Thr Tyr Tyr Cys Gln Gln Trp Ser Ser Asn Pro Pro Thr Phe Gly Gln
210                 215                 220

Gly Thr Lys Leu Gln Ile Lys Arg
225                 230
```

<210> SEQ ID NO 62
<211> LENGTH: 702
<212> TYPE: DNA
<213> ORGANISM: artificial
<220> FEATURE:
<223> OTHER INFORMATION: nucleotide sequence encoding modified AVP04-07
  anti-TAG72 diabody designated AVP04-84 comprising cysteine
  residues in FR1 and a N-terminal serine

<400> SEQUENCE: 62

```
agcgtgcagc tgcagcagtg cgatgcgtgc ctggtgaaac cgggcgcgag cgtgaaaatt      60
agctgcaaag cgagcggcta cctttacc gatcatgcga ttcattgggt gaaacagaat     120
ccggaacagg gcctggaatg gattggctat tttagcccgg caacgatga ttttaaatat     180
aacgaacgtt ttaaaggcaa agcgacccctg accgcggata aaagcagcag caccgcgtat     240
ctgcagctga cagcctgac cagcgaagat agcgcggtgt attttttgcac ccgtagcctg     300
aatatggcgt attggggtca gggcacctcg gtcaccgtga gcagcggtgg cggcggcagc     360
gatatcgtga tgacccagag cccgagcagc ctgccggtga gcgtgggcga aaaagtgacc     420
ctgagctgca aaagcagcca gagcctgctg tatagcggca tcagaaaaa ctatctggcg     480
tggtatcagc agaaaccggg tcagagcccg aaactgctga tttattgggc gagcaccgt     540
gaaagcggcg tgccggatcg ttttaccggc agcggtagcg gcaccgattt taccctgagc     600
attagcagcg tggaaaccga agatctggcg gtgtattatt gccagcagta ttatagctat     660
ccgctgacct ttggtgcggg caccaaactg gtgctgaaac gt                       702
```

<210> SEQ ID NO 63
<211> LENGTH: 234
<212> TYPE: PRT
<213> ORGANISM: artificial
<220> FEATURE:
<223> OTHER INFORMATION: amino acid sequence of modified AVP04-07
  anti-TAG72 diabody designated AVP04-84 comprising cysteine
  residues in FR1 and a N-terminal serine

<400> SEQUENCE: 63

Ser Val Gln Leu Gln Gln Cys Asp Ala Cys Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Asp Ile Val Met Thr Gln Ser Pro
        115                 120                 125

Ser Ser Leu Pro Val Ser Val Gly Glu Lys Val Thr Leu Ser Cys Lys
    130                 135                 140

Ser Ser Gln Ser Leu Leu Tyr Ser Gly Asn Gln Lys Asn Tyr Leu Ala
145                 150                 155                 160

Trp Tyr Gln Gln Lys Pro Gly Gln Ser Pro Lys Leu Leu Ile Tyr Trp
                165                 170                 175

Ala Ser Thr Arg Glu Ser Gly Val Pro Asp Arg Phe Thr Gly Ser Gly
            180                 185                 190

Ser Gly Thr Asp Phe Thr Leu Ser Ile Ser Ser Val Glu Thr Glu Asp
        195                 200                 205

Leu Ala Val Tyr Tyr Cys Gln Gln Tyr Tyr Ser Tyr Pro Leu Thr Phe
    210                 215                 220

Gly Ala Gly Thr Lys Leu Val Leu Lys Arg
225                 230

<210> SEQ ID NO 64
<211> LENGTH: 735
<212> TYPE: DNA
<213> ORGANISM: artificial
<220> FEATURE:
<223> OTHER INFORMATION: nucleotide sequence encoding modified AVP07-17
    anti-Her2 diabody designated AVP07-63 comprising cysteine residues
    in FR1, removal of cysteine residues in CDR3H and a N-terminal
    serine

<400> SEQUENCE: 64

```
agcgtgcagc tggtgcagtc tggggcagag gtgaaaaagc ccggggagtc tctgaagatc      60
tcctgtaagg gttctggata cagctttacc agctactgga tcgcctgggt gcgccagatg     120
cccgggaaag cctggagta catggggctc atctatcctg gtgactctga caccaaatac     180
agcccgtcct tccaaggcca ggtcaccatc tcagtcgaca gtccgtcag cactgcctac     240
ttgcaatgga gcagtctgaa gccctcggac agcgccgtgt attttgtgc gagacatgac     300
gtgggatatg cgagtagttc caacgcggca aagtggcctg aatacttcca gcattggggc     360
cagggcaccc tggtcaccgt tcctcaggt ggaggcggtt cacagtctgt gttgacgcag     420
ccgtgcagca gctgcgcggc cccaggacag aaggtcacca tctcctgctc tggaagcagc     480
tccaacattg gaataatta tgtatcctgg taccagcagc tcccaggaac agtccccaaa     540
ctcctcatct atggtcacac caatcggccc gcaggggtcc ctgaccgatt ctctggctcc     600
```

```
aagtctggca cctcagcctc cctggccatc agtgggttcc ggtccgagga tgaggctgat      660
tattactgtg cagcatggga tgacagcctg agtggttggg tgttcggcgg agggaccaag      720
ctgaccgtcc taggt                                                       735
```

<210> SEQ ID NO 65
<211> LENGTH: 245
<212> TYPE: PRT
<213> ORGANISM: artificial
<220> FEATURE:
<223> OTHER INFORMATION: amino acid sequence of modified AVP07-17
       anti-Her2 diabody designated AVP07-63 comprising cysteine residues
       in FR1, removal of cysteine residues in CDR3H and a N-terminal
       serine

<400> SEQUENCE: 65

```
Ser Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Ala Ser Ser Asn Ala Ala Lys Trp
            100                 105                 110

Pro Glu Tyr Phe Gln His Trp Gly Gln Gly Thr Leu Val Thr Val Ser
        115                 120                 125

Ser Gly Gly Gly Gly Ser Gln Ser Val Leu Thr Gln Pro Cys Ser Ser
    130                 135                 140

Cys Ala Ala Pro Gly Gln Lys Val Thr Ile Ser Cys Ser Gly Ser Ser
145                 150                 155                 160

Ser Asn Ile Gly Asn Asn Tyr Val Ser Trp Tyr Gln Gln Leu Pro Gly
                165                 170                 175

Thr Val Pro Lys Leu Leu Ile Tyr Gly His Thr Asn Arg Pro Ala Gly
            180                 185                 190

Val Pro Asp Arg Phe Ser Gly Ser Lys Ser Gly Thr Ser Ala Ser Leu
        195                 200                 205

Ala Ile Ser Gly Phe Arg Ser Glu Asp Glu Ala Asp Tyr Tyr Cys Ala
    210                 215                 220

Ala Trp Asp Asp Ser Leu Ser Gly Trp Val Phe Gly Gly Gly Thr Lys
225                 230                 235                 240

Leu Thr Val Leu Gly
                245
```

<210> SEQ ID NO 66
<211> LENGTH: 39
<212> TYPE: DNA
<213> ORGANISM: artificial sequence
<220> FEATURE:
<223> OTHER INFORMATION: nucleotide sequence of mutagenic primer for
       substituting the N-terminal Gln residue with a Ser residue in
       AVP04-07

<400> SEQUENCE: 66

-continued

```
cccagccggc catggcgagc gtgcagctgc agcagagcg                                  39
```

<210> SEQ ID NO 67
<211> LENGTH: 38
<212> TYPE: DNA
<213> ORGANISM: artificial
<220> FEATURE:
<223> OTHER INFORMATION: nucleotide sequence of mutagenic primer for
      substituting the N-terminal Gln residue with a Ser residue in
      AVP04-07

<400> SEQUENCE: 67

```
cgctctgctg cagctgcacg ctcgccatgg ccggctgg                                   38
```

<210> SEQ ID NO 68
<211> LENGTH: 57
<212> TYPE: DNA
<213> ORGANISM: artificial
<220> FEATURE:
<223> OTHER INFORMATION: nucleotide sequence of mutagenic primer for
      replacing cysteine for alanines residues into AVP07-17

<400> SEQUENCE: 68

```
gcgagacatg acgtgggata tgcgagtagt tccaacgcgg caaagtggcc tgaatac            57
```

<210> SEQ ID NO 69
<211> LENGTH: 57
<212> TYPE: DNA
<213> ORGANISM: artificial
<220> FEATURE:
<223> OTHER INFORMATION: nucleotide sequence of mutagenic primer for
      replacing cysteine for alanines residues into AVP07-17

<400> SEQUENCE: 69

```
gtattcaggc cactttgccg cgttggaact actcgcatat cccacgtcat gtctcgc             57
```

<210> SEQ ID NO 70
<211> LENGTH: 1255
<212> TYPE: PRT
<213> ORGANISM: Homo sapiens

<400> SEQUENCE: 70

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
```

```
                145                 150                 155                 160
Leu Cys Tyr Gln Asp Thr Ile Leu Trp Lys Asp Ile Phe His Lys Asn
                165                 170                 175
Asn Gln Leu Ala Leu Thr Leu Ile Asp Thr Asn Arg Ser Arg Ala Cys
                180                 185                 190
His Pro Cys Ser Pro Met Cys Lys Gly Ser Arg Cys Trp Gly Glu Ser
                195                 200                 205
Ser Glu Asp Cys Gln Ser Leu Thr Arg Thr Val Cys Ala Gly Gly Cys
                210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
                260                 265                 270
Thr Tyr Asn Thr Asp Thr Phe Glu Ser Met Pro Asn Pro Glu Gly Arg
                275                 280                 285
Tyr Thr Phe Gly Ala Ser Cys Val Thr Ala Cys Pro Tyr Asn Tyr Leu
                290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
                340                 345                 350
Val Arg Ala Val Thr Ser Ala Asn Ile Gln Glu Phe Ala Gly Cys Lys
                355                 360                 365
Lys Ile Phe Gly Ser Leu Ala Phe Leu Pro Glu Ser Phe Asp Gly Asp
                370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
                420                 425                 430
Gly Arg Ile Leu His Asn Gly Ala Tyr Ser Leu Thr Leu Gln Gly Leu
                435                 440                 445
Gly Ile Ser Trp Leu Gly Leu Arg Ser Leu Arg Glu Leu Gly Ser Gly
                450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
                500                 505                 510
Gln Leu Cys Ala Arg Gly His Cys Trp Gly Pro Gly Pro Thr Gln Cys
                515                 520                 525
Val Asn Cys Ser Gln Phe Leu Arg Gly Gln Glu Cys Val Glu Glu Cys
                530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
```

```
Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Val Ser
                645                 650                 655

Ala Val Val Gly Ile Leu Leu Val Val Leu Gly Val Val Phe Gly
                660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
        690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990
```

Asp Leu Gly Pro Ala Ser Pro Leu Asp Ser Thr Phe Tyr Arg Ser Leu
                995                 1000                1005

Leu Glu Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Ala Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 71
<211> LENGTH: 750
<212> TYPE: PRT
<213> ORGANISM: Homo sapiens

<400> SEQUENCE: 71

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
                20                  25                  30

Phe Leu Leu Gly Phe Leu Phe Gly Trp Phe Ile Lys Ser Ser Asn Glu
            35                  40                  45

Ala Thr Asn Ile Thr Pro Lys His Asn Met Lys Ala Phe Leu Asp Glu
        50                  55                  60

Leu Lys Ala Glu Asn Ile Lys Lys Phe Leu His Asn Phe Thr Gln Ile
65                  70                  75                  80

Pro His Leu Ala Gly Thr Glu Gln Asn Phe Gln Leu Ala Lys Gln Ile
                85                  90                  95

```
Gln Ser Gln Trp Lys Glu Phe Gly Leu Asp Ser Val Glu Leu Ala His
                100                 105                 110

Tyr Asp Val Leu Leu Ser Tyr Pro Asn Lys Thr His Pro Asn Tyr Ile
            115                 120                 125

Ser Ile Ile Asn Glu Asp Gly Asn Glu Ile Phe Asn Thr Ser Leu Phe
        130                 135                 140

Glu Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510
```

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
        530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
    690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750

<210> SEQ ID NO 72
<211> LENGTH: 475
<212> TYPE: PRT
<213> ORGANISM: Homo sapiens

<400> SEQUENCE: 72

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

```
Arg Pro Ala Pro Gly Ser Thr Ala Pro Ala His Gly Val Thr Ser
145                 150                 155                 160

Ala Pro Asp Asn Arg Pro Ala Leu Gly Ser Thr Ala Pro Pro Val His
                165                 170                 175

Asn Val Thr Ser Ala Ser Gly Ser Ala Ser Gly Ser Ala Ser Thr Leu
            180                 185                 190

Val His Asn Gly Thr Ser Ala Arg Ala Thr Thr Thr Pro Ala Ser Lys
        195                 200                 205

Ser Thr Pro Phe Ser Ile Pro Ser His His Ser Asp Thr Pro Thr Thr
    210                 215                 220

Leu Ala Ser His Ser Thr Lys Thr Asp Ala Ser Ser Thr His His Ser
225                 230                 235                 240

Thr Val Pro Pro Leu Thr Ser Ser Asn His Ser Thr Ser Pro Gln Leu
                245                 250                 255

Ser Thr Gly Val Ser Phe Phe Phe Leu Ser Phe His Ile Ser Asn Leu
            260                 265                 270

Gln Phe Asn Ser Ser Leu Glu Asp Pro Ser Thr Asp Tyr Tyr Gln Glu
        275                 280                 285

Leu Gln Arg Asp Ile Ser Glu Met Phe Leu Gln Ile Tyr Lys Gln Gly
290                 295                 300

Gly Phe Leu Gly Leu Ser Asn Ile Lys Phe Arg Pro Gly Ser Val Val
305                 310                 315                 320

Val Gln Leu Thr Leu Ala Phe Arg Glu Gly Thr Ile Asn Val His Asp
                325                 330                 335

Val Glu Thr Gln Phe Asn Gln Tyr Lys Thr Glu Ala Ala Ser Arg Tyr
            340                 345                 350

Asn Leu Thr Ile Ser Asp Val Ser Val Ser Asp Val Pro Phe Pro Phe
        355                 360                 365

Ser Ala Gln Ser Gly Ala Gly Val Pro Gly Trp Gly Ile Ala Leu Leu
    370                 375                 380

Val Leu Val Cys Val Leu Val Ala Leu Ala Ile Val Tyr Leu Ile Ala
385                 390                 395                 400

Leu Ala Val Cys Gln Cys Arg Arg Lys Asn Tyr Gly Gln Leu Asp Ile
                405                 410                 415

Phe Pro Ala Arg Asp Thr Tyr His Pro Met Ser Glu Tyr Pro Thr Tyr
            420                 425                 430

His Thr His Gly Arg Tyr Val Pro Pro Ser Ser Thr Asp Arg Ser Pro
        435                 440                 445

Tyr Glu Lys Val Ser Ala Gly Asn Gly Gly Ser Ser Leu Ser Tyr Thr
    450                 455                 460

Asn Pro Ala Val Ala Ala Thr Ser Ala Asn Leu
465                 470                 475

<210> SEQ ID NO 73
<211> LENGTH: 307
<212> TYPE: PRT
<213> ORGANISM: Homo sapiens

<400> SEQUENCE: 73

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
```

```
            35                  40                  45
Thr Glu Lys Asn Ala Val Ser Met Thr Ser Ser Val Leu Ser Ser His
 50                  55                  60

Ser Pro Gly Ser Gly Ser Thr Gln Gly Gln Asp Val Thr Leu
 65                  70                  75                  80

Ala Pro Ala Thr Glu Pro Ala Ser Gly Ser Ala Ala Thr Trp Gly Gln
                 85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Ala Gln Gly Val Thr Ser Ala Pro Glu Thr
130                 135                 140

Arg Pro Pro Pro Gly Ser Thr Ala Pro Ala His Gly Val Thr Ser
145                 150                 155                 160

Ala Pro Asp Asn Arg Pro Ala Leu Ala Ser Thr Ala Pro Val His
                165                 170                 175

Asn Val Thr Ser Ala Ser Gly Ser Ala Ser Gly Ser Ala Ser Thr Leu
            180                 185                 190

Val His Asn Gly Thr Ser Ala Arg Ala Thr Thr Thr Pro Ala Ser Lys
        195                 200                 205

Ser Thr Pro Phe Ser Ile Pro Ser His His Ser Asp Thr Pro Thr Thr
210                 215                 220

Leu Ala Ser His Ser Thr Lys Thr Asp Ala Ser Ser Thr His His Ser
225                 230                 235                 240

Thr Val Pro Pro Leu Thr Ser Ser Asn His Ser Thr Ser Pro Gln Leu
                245                 250                 255

Ser Thr Gly Val Ser Phe Phe Phe Leu Ser Phe His Ile Ser Asn Leu
            260                 265                 270

Gln Phe Asn Ser Ser Leu Glu Asp Pro Ser Thr Asp Tyr Tyr Gln Glu
        275                 280                 285

Leu Gln Arg Asp Ile Ser Glu Met Val Ser Ile Gly Leu Ser Phe Pro
290                 295                 300

Met Leu Pro
305

<210> SEQ ID NO 74
<211> LENGTH: 702
<212> TYPE: DNA
<213> ORGANISM: artificial
<220> FEATURE:
<223> OTHER INFORMATION: nucleotide sequence encoding modified AVP04-07
      anti-TAG72 diabody designated AVP04-85 comprising cysteine
      residues in FR1 and a N-terminal serine

<400> SEQUENCE: 74
agcgtgcagc tgcagcagag cgatgcggaa ctggtgtgcc cgggctgcag cgtgaaaatt       60
agctgcaaag cgagcggcta ccctttacc gatcatgcga ttcattgggt gaaacagaat      120
ccggaacagg gcctggaatg gattggctat tttagcccgg caacgatga ttttaaatat      180 aacgaacgtt ttaaaggcaa agcgaccctg accgcgata aaagcagcag caccgcgtat      240
ctgcagctga acagcctgac cagcgaagat agcgcggtgt attttttgcac ccgtagcctg      300 aatatggcgt attggggtca gggcaccctcg gtcaccgtga gcagcggtgg cggcggcagc      360
gatatcgtga tgacccagag cccgagcagc ctgccggtga gcgtgggcga aaaagtgacc      420
```

| ctgagctgca aaagcagcca gagcctgctg tatagcggca atcagaaaaa ctatctggcg | 480 |
| tggtatcagc agaaaccggg tcagagcccg aaactgctga tttattgggc gagcacccgt | 540 |
| gaaagcggcg tgccggatcg ttttaccggc agcggtagcg gcaccgattt taccctgagc | 600 |
| attagcagcg tggaaaccga agatctggcg gtgtattatt gccagcagta ttatagctat | 660 |
| ccgctgacct ttggtgcggg caccaaactg gtgctgaaac gt | 702 |

<210> SEQ ID NO 75
<211> LENGTH: 234
<212> TYPE: PRT
<213> ORGANISM: artificial
<220> FEATURE:
<223> OTHER INFORMATION: amino acid sequence of modified AVP04-07
    anti-TAG72 diabody designated AVP04-85 comprising cysteine
    residues in FR1 and a N-terminal serine

<400> SEQUENCE: 75

Ser Val Gln Leu Gln Gln Ser Asp Ala Glu Leu Val Cys Pro Gly Cys
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Asp Ile Val Met Thr Gln Ser Pro
        115                 120                 125

Ser Ser Leu Pro Val Ser Val Gly Glu Lys Val Thr Leu Ser Cys Lys
    130                 135                 140

Ser Ser Gln Ser Leu Leu Tyr Ser Gly Asn Gln Lys Asn Tyr Leu Ala
145                 150                 155                 160

Trp Tyr Gln Gln Lys Pro Gly Gln Ser Pro Lys Leu Leu Ile Tyr Trp
                165                 170                 175

Ala Ser Thr Arg Glu Ser Gly Val Pro Asp Arg Phe Thr Gly Ser Gly
            180                 185                 190

Ser Gly Thr Asp Phe Thr Leu Ser Ile Ser Ser Val Glu Thr Glu Asp
        195                 200                 205

Leu Ala Val Tyr Tyr Cys Gln Gln Tyr Tyr Ser Tyr Pro Leu Thr Phe
    210                 215                 220

Gly Ala Gly Thr Lys Leu Val Leu Lys Arg
225                 230

<210> SEQ ID NO 76
<211> LENGTH: 702
<212> TYPE: DNA
<213> ORGANISM: artificial
<220> FEATURE:
<223> OTHER INFORMATION: nucleotide sequence encoding modified AVP04-07
    anti-TAG72 diabody designated AVP04-78 comprising cysteine
    residues in FR1 and a N-terminal serine

<400> SEQUENCE: 76

```
agcgtgcagc tgcagcagag cgatgcggaa ctggtgaaac cgggcgcgag cgtgaaaatt      60
agctgcaaag cgagcggcta ccctttaccc gatcatgcga ttcattgggt gaaacagaat     120
ccggaacagg gcctggaatg gattggctat tttagcccgg caacgatga ttttaaatat     180
aacgaacgtt ttaaaggcaa agcgaccctg accgcggata aaagcagcag caccgcgtat    240
ctgcagctga acagcctgac cagcgaagat agcgcggtgt attttttgcac ccgtagcctg    300
aatatggcgt attggggtca gggcacctcg gtcaccgtga gcagcggtgg cggcggcagc    360
gatatcgtga tgacccagag cccgagcagc ctgccggtgt gcgtgggctg caaagtgacc    420
ctgagctgca aaagcagcca gagcctgctg tatagcggca atcagaaaaa ctatctggcg    480
tggtatcagc agaaaccggg tcagagcccg aaactgctga tttattgggc gagcacccgt    540
gaaagcggcg tgccggatcg ttttaccggc agcggtagcg gcaccgatt taccctgagc    600
attagcagcg tggaaaccga agatctggcg gtgtattatt gccagcagta ttatagctat    660
ccgctgacct tggtgcgggg caccaaactg gtgctgaaac gt                        702
```

<210> SEQ ID NO 77
<211> LENGTH: 234
<212> TYPE: PRT
<213> ORGANISM: artificial
<220> FEATURE:
<223> OTHER INFORMATION: amino acid sequence of modified AVP04-07 anti-TAG72 diabody designated AVP04-78 comprising cysteine residues in FR1 and a N-terminal serine

<400> SEQUENCE: 77

```
Ser Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Asp Ile Val Met Thr Gln Ser Pro
        115                 120                 125

Ser Ser Leu Pro Val Cys Val Gly Cys Lys Val Thr Leu Ser Cys Lys
130                 135                 140

Ser Ser Gln Ser Leu Leu Tyr Ser Gly Asn Gln Lys Asn Tyr Leu Ala
145                 150                 155                 160

Trp Tyr Gln Gln Lys Pro Gly Gln Ser Pro Lys Leu Leu Ile Tyr Trp
                165                 170                 175

Ala Ser Thr Arg Glu Ser Gly Val Pro Asp Arg Phe Thr Gly Ser Gly
            180                 185                 190

Ser Gly Thr Asp Phe Thr Leu Ser Ile Ser Ser Val Glu Thr Glu Asp
        195                 200                 205

Leu Ala Val Tyr Tyr Cys Gln Gln Tyr Tyr Ser Tyr Pro Leu Thr Phe
    210                 215                 220

Gly Ala Gly Thr Lys Leu Val Leu Lys Arg
225                 230
```

<210> SEQ ID NO 78
<211> LENGTH: 696
<212> TYPE: DNA
<213> ORGANISM: artificial
<220> FEATURE:
<223> OTHER INFORMATION: nucleotide sequence encoding modified AVP02-60 anti-MUC1 diabody designated AVP02-101 comprising cysteine residues in FR1 and a N-terminal serine

<400> SEQUENCE: 78

```
agcgtgcagc tggttgaaag cggtggcgga gtggtgcagc caggtggaag cctgcgtctg      60
agctgcgcag caagcggttt tacctttagc agctatggca tgagctgggt gcgtcaggcg     120
ccggataaag gcctggaact ggtggcgacc attaacagca acggtggaag cacctattat     180
ccggatagcg tgaaaggccg ttttaccatt agccgtgata cagcaaaaa caccctgtat     240
ctgcagatga acagcctgcg taccgaagat accgcggtgt attattgcgc gcgtgatcgt     300
gatggctatg atgaaggctt tgattattgg ggccagggca ccctggtgac cgtgagcagc     360
ggtgggggcg gaagccagat tcagctgacc cagagctgca gcagctgcag cgcaagcgtg     420
ggtgatcgtg tgaccattac ctgcagcgcg agcagcagcg tgagctatat gcattggtat     480
cagcagaaac cgggcaaagc gccgaaacgt tggatttatg ataccagcaa actggcgagc     540
ggcgtgccga ccgttttag cggcagcggc agcggcaccg attatacctt taccattagc     600
agcctgcagc cggaagatat tgcgacctat tattgccagc agtggagcag caacccgccg     660
acctttggcc agggcaccaa actgcagatt aaacgt                               696
```

<210> SEQ ID NO 79
<211> LENGTH: 232
<212> TYPE: PRT
<213> ORGANISM: artificial
<220> FEATURE:
<223> OTHER INFORMATION: amino acid sequence of modified AVP02-60 anti-MUC1 diabody designated AVP02-101 comprising cysteine residues in FR1 and a N-terminal serine

<400> SEQUENCE: 79

```
Ser Val Gln Leu Val Glu Ser Gly Gly Gly Val Val Gln Pro Gly Gly
1               5                   10                  15
Ser Leu Arg Leu Ser Cys Ala Ala Ser Gly Phe Thr Phe Ser Ser Tyr
            20                  25                  30
Gly Met Ser Trp Val Arg Gln Ala Pro Asp Lys Gly Leu Glu Leu Val
        35                  40                  45
Ala Thr Ile Asn Ser Asn Gly Gly Ser Thr Tyr Tyr Pro Asp Ser Val
    50                  55                  60
Lys Gly Arg Phe Thr Ile Ser Arg Asp Asn Lys Asn Thr Leu Tyr
65                  70                  75                  80
Leu Gln Met Asn Ser Leu Arg Thr Glu Asp Thr Ala Val Tyr Tyr Cys
                85                  90                  95
Ala Arg Asp Arg Asp Gly Tyr Asp Glu Gly Phe Asp Tyr Trp Gly Gln
            100                 105                 110
Gly Thr Leu Val Thr Val Ser Ser Gly Gly Gly Gly Ser Gln Ile Gln
        115                 120                 125
Leu Thr Gln Ser Cys Ser Ser Cys Ser Ala Ser Val Gly Asp Arg Val
    130                 135                 140
Thr Ile Thr Cys Ser Ala Ser Ser Val Ser Tyr Met His Trp Tyr
145                 150                 155                 160
```

```
Gln Gln Lys Pro Gly Lys Ala Pro Lys Arg Trp Ile Tyr Asp Thr Ser
            165                 170                 175

Lys Leu Ala Ser Gly Val Pro Ser Arg Phe Ser Gly Ser Gly Ser Gly
            180                 185                 190

Thr Asp Tyr Thr Phe Thr Ile Ser Ser Leu Gln Pro Glu Asp Ile Ala
            195                 200                 205

Thr Tyr Tyr Cys Gln Gln Trp Ser Ser Asn Pro Pro Thr Phe Gly Gln
            210                 215                 220

Gly Thr Lys Leu Gln Ile Lys Arg
225                 230

<210> SEQ ID NO 80
<211> LENGTH: 696
<212> TYPE: PRT
<213> ORGANISM: artificial
<220> FEATURE:
<223> OTHER INFORMATION: nucleotide sequence encoding modified AVP02-60
      anti-MUC1 diabody designated AVP02-104 comprising cysteine
      residues in FR1 and a N-terminal serine

<400> SEQUENCE: 80

Ala Gly Cys Gly Thr Gly Cys Ala Gly Cys Thr Gly Gly Thr Thr Gly
1               5                   10                  15

Ala Ala Thr Gly Cys Gly Gly Thr Gly Gly Cys Thr Gly Cys Gly Thr
            20                  25                  30

Gly Gly Thr Gly Cys Ala Gly Cys Cys Ala Gly Gly Thr Gly Gly Ala
            35                  40                  45

Ala Gly Cys Cys Thr Gly Cys Gly Thr Cys Thr Gly Ala Gly Cys Thr
50                  55                  60

Gly Cys Gly Cys Ala Gly Cys Ala Ala Gly Cys Gly Gly Thr Thr Thr
65                  70                  75                  80

Thr Ala Cys Cys Thr Thr Thr Ala Gly Cys Ala Gly Cys Thr Ala Thr
            85                  90                  95

Gly Gly Cys Ala Thr Gly Ala Gly Cys Thr Gly Gly Gly Thr Gly Cys
            100                 105                 110

Gly Thr Cys Ala Gly Gly Cys Gly Cys Cys Gly Gly Ala Thr Ala Ala
            115                 120                 125

Ala Gly Gly Cys Cys Thr Gly Gly Ala Ala Cys Thr Gly Gly Thr Gly
130                 135                 140

Gly Cys Gly Ala Cys Cys Ala Thr Thr Ala Cys Ala Gly Cys Gly Ala
145                 150                 155                 160

Ala Cys Gly Gly Thr Gly Gly Ala Ala Gly Cys Ala Cys Cys Thr Ala
            165                 170                 175

Thr Thr Ala Thr Cys Cys Gly Gly Ala Thr Ala Gly Cys Gly Thr Gly
            180                 185                 190

Ala Ala Ala Gly Gly Cys Cys Thr Thr Thr Ala Cys Cys Ala
            195                 200                 205

Thr Thr Ala Gly Cys Cys Gly Thr Gly Ala Thr Ala Ala Cys Ala Gly
            210                 215                 220

Cys Ala Ala Ala Ala Cys Ala Cys Cys Cys Thr Gly Thr Ala Thr
225                 230                 235                 240

Cys Thr Gly Cys Ala Gly Ala Thr Gly Ala Ala Cys Ala Gly Cys Cys
            245                 250                 255

Thr Gly Cys Gly Thr Ala Cys Cys Gly Ala Ala Gly Ala Thr Ala Cys
            260                 265                 270
```

```
Cys Gly Cys Gly Gly Thr Gly Thr Ala Thr Ala Thr Gly Cys
            275                 280                 285

Gly Cys Gly Cys Gly Thr Gly Ala Thr Cys Gly Thr Gly Ala Thr Gly
290                 295                 300

Gly Cys Thr Ala Thr Gly Ala Thr Gly Ala Ala Gly Gly Cys Thr Thr
305                 310                 315                 320

Thr Gly Ala Thr Thr Ala Thr Gly Gly Gly Cys Cys Ala Gly
                325                 330                 335

Gly Gly Cys Ala Cys Cys Thr Gly Gly Thr Gly Ala Cys Gly
                340                 345                 350

Thr Gly Ala Gly Cys Ala Gly Cys Gly Gly Thr Gly Gly Gly
                355                 360                 365

Cys Gly Gly Ala Ala Gly Cys Cys Ala Gly Ala Thr Thr Cys Ala Gly
370                 375                 380

Cys Thr Gly Ala Cys Cys Cys Ala Gly Ala Gly Cys Cys Cys Gly Ala
385                 390                 395                 400

Gly Cys Ala Gly Cys Cys Thr Gly Ala Gly Cys Gly Cys Ala Ala Gly
                405                 410                 415

Cys Gly Thr Gly Gly Gly Thr Gly Ala Thr Cys Gly Thr Gly Thr Gly
                420                 425                 430

Ala Cys Cys Ala Thr Thr Ala Cys Cys Thr Gly Cys Ala Gly Cys Gly
435                 440                 445

Cys Gly Ala Gly Cys Ala Gly Cys Ala Gly Cys Gly Thr Gly Ala Gly
450                 455                 460

Cys Thr Ala Thr Ala Thr Gly Cys Ala Thr Thr Gly Gly Thr Ala Thr
465                 470                 475                 480

Cys Ala Gly Cys Ala Gly Ala Ala Cys Cys Gly Gly Gly Cys Ala
                485                 490                 495

Ala Ala Gly Cys Gly Cys Cys Gly Ala Ala Ala Cys Gly Thr Thr Gly
                500                 505                 510

Gly Ala Thr Thr Thr Ala Thr Gly Ala Thr Ala Cys Cys Ala Gly Cys
                515                 520                 525

Ala Ala Ala Cys Thr Gly Gly Cys Gly Ala Gly Cys Gly Gly Cys Gly
530                 535                 540

Thr Gly Cys Cys Gly Ala Gly Cys Cys Gly Thr Thr Thr Ala Gly Cys
545                 550                 555                 560

Cys Gly Gly Cys Ala Gly Cys Gly Gly Cys Ala Gly Cys Gly Gly Cys
                565                 570                 575

Ala Cys Cys Gly Ala Thr Thr Ala Thr Ala Cys Cys Thr Thr Thr Ala
                580                 585                 590

Cys Cys Ala Thr Thr Ala Gly Cys Ala Gly Cys Cys Thr Gly Cys Ala
                595                 600                 605

Gly Cys Cys Gly Gly Ala Ala Gly Ala Thr Thr Thr Thr Gly Cys Gly
                610                 615                 620

Ala Cys Cys Thr Ala Thr Thr Ala Thr Thr Gly Cys Cys Ala Gly Cys
625                 630                 635                 640

Ala Gly Thr Gly Gly Ala Gly Cys Ala Gly Cys Ala Ala Cys Cys Cys
                645                 650                 655

Gly Cys Cys Gly Ala Cys Cys Thr Thr Thr Gly Gly Cys Cys Ala Gly
                660                 665                 670

Gly Gly Cys Ala Cys Cys Ala Ala Ala Cys Thr Gly Cys Ala Gly Ala
                675                 680                 685

Thr Thr Ala Ala Ala Cys Gly Thr
```

<210> SEQ ID NO 81
<211> LENGTH: 232
<212> TYPE: PRT
<213> ORGANISM: artificial
<220> FEATURE:
<223> OTHER INFORMATION: amino acid sequence of modified AVP02-60 anti-MUC1 diabody designated AVP02-104 comprising cysteine residues in FR1 and a N-terminal serine

<400> SEQUENCE: 81

Ser Val Gln Leu Val Glu Cys Gly Gly Cys Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Asp Lys Gly Leu Glu Leu Val
        35                  40                  45

Ala Thr Ile Asn Ser Asn Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Arg Asp Gly Tyr Asp Glu Gly Phe Asp Tyr Trp Gly Gln
            100                 105                 110

Gly Thr Leu Val Thr Val Ser Ser Gly Gly Gly Gly Ser Gln Ile Gln
        115                 120                 125

Leu Thr Gln Ser Pro Ser Ser Leu Ser Ala Ser Val Gly Asp Arg Val
    130                 135                 140

Thr Ile Thr Cys Ser Ala Ser Ser Ser Val Ser Tyr Met His Trp Tyr
145                 150                 155                 160

Gln Gln Lys Pro Gly Lys Ala Pro Lys Arg Trp Ile Tyr Asp Thr Ser
                165                 170                 175

Lys Leu Ala Ser Gly Val Pro Ser Arg Phe Ser Gly Ser Gly Ser Gly
            180                 185                 190

Thr Asp Tyr Thr Phe Thr Ile Ser Ser Leu Gln Pro Glu Asp Ile Ala
        195                 200                 205

Thr Tyr Tyr Cys Gln Gln Trp Ser Ser Asn Pro Pro Thr Phe Gly Gln
    210                 215                 220

Gly Thr Lys Leu Gln Ile Lys Arg
225                 230

<210> SEQ ID NO 82
<211> LENGTH: 696
<212> TYPE: DNA
<213> ORGANISM: artificial
<220> FEATURE:
<223> OTHER INFORMATION: nucleotide sequence encoding modified AVP02-60 anti-MUC1 diabody designated AVP02-102 comprising cysteine residues in FR1 and a N-terminal serine

<400> SEQUENCE: 82
agcgtgcagc tggttgaaag cggtggcgga gtggtgcagc caggtggaag cctgcgtctg      60
agctgcgcag caagcggttt tacctttagc agctatggca tgagctgggt gcgtcaggcg     120
ccggataaag gcctggaact ggtggcgacc attaacagca acggtggaag cacctattat     180
ccggatagcg tgaaaggccg ttttaccatt agccgtgata acagcaaaaa caccctgtat     240

```
ctgcagatga acagcctgcg taccgaagat accgcggtgt attattgcgc gcgtgatcgt    300
gatggctatg atgaaggctt tgattattgg ggccagggca ccctggtgac cgtgagcagc    360 ggtggggggcg aagccagat tcagctgacc cagagcccga gcagcctgag cgcatgcgtg    420
ggttgccgtg tgaccattac ctgcagcgcg agcagcagcg tgagctatat gcattggtat    480
cagcagaaac cgggcaaagc gccgaaacgt tggatttatg ataccagcaa actggcgagc    540
ggcgtgccga ccgttttag cggcagcggc agcggcaccg attatacctt taccattagc    600
agcctgcagc cggaagatat tgcgacctat tattgccagc agtggagcag caacccgccg    660
acctttggcc agggcaccaa actgcagatt aaacgt                              696
```

<210> SEQ ID NO 83
<211> LENGTH: 232
<212> TYPE: PRT
<213> ORGANISM: artificial
<220> FEATURE:
<223> OTHER INFORMATION: amino acid sequence of modified AVP02-60
      anti-MUC1 diabody designated AVP02-102 comprising cysteine
      residues in FR1 and a N-terminal serine

<400> SEQUENCE: 83

```
Ser Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Asp Lys Gly Leu Glu Leu Val
        35                  40                  45

Ala Thr Ile Asn Ser Asn Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Arg Asp Gly Tyr Asp Glu Gly Phe Asp Tyr Trp Gly Gln
            100                 105                 110

Gly Thr Leu Val Thr Val Ser Ser Gly Gly Gly Gly Ser Gln Ile Gln
        115                 120                 125

Leu Thr Gln Ser Pro Ser Ser Leu Ser Ala Cys Val Gly Cys Arg Val
    130                 135                 140

Thr Ile Thr Cys Ser Ala Ser Ser Ser Val Ser Tyr Met His Trp Tyr
145                 150                 155                 160

Gln Gln Lys Pro Gly Lys Ala Pro Lys Arg Trp Ile Tyr Asp Thr Ser
                165                 170                 175

Lys Leu Ala Ser Gly Val Pro Ser Arg Phe Ser Gly Ser Gly Ser Gly
            180                 185                 190

Thr Asp Tyr Thr Phe Thr Ile Ser Ser Leu Gln Pro Glu Asp Ile Ala
        195                 200                 205

Thr Tyr Tyr Cys Gln Gln Trp Ser Ser Asn Pro Pro Thr Phe Gly Gln
    210                 215                 220

Gly Thr Lys Leu Gln Ile Lys Arg
225                 230
```

<210> SEQ ID NO 84
<211> LENGTH: 696
<212> TYPE: DNA
<213> ORGANISM: artificial
<220> FEATURE:

<223> OTHER INFORMATION: nucleotide sequence encoding modified AVP02-60
anti-MUC1 diabody designated AVP02-105 comprising cysteine
residues in FR1 and a N-terminal serine

<400> SEQUENCE: 84

```
agcgtgcagc tggttgaaag cggtggcgga gtggtgtgcc caggttgcag cctgcgtctg      60
agctgcgcag caagcggttt tacctttagc agctatggca tgagctgggt gcgtcaggcg     120
ccggataaag gcctggaact ggtggcgacc attaacagca acggtggaag cacctattat     180
ccggatagcg tgaaaggccg ttttaccatt agccgtgata acagcaaaaa cacccgtat     240
ctgcagatga acagcctgcg taccgaagat accgcggtgt attattgcgc gcgtgatcgt     300
gatggctatg atgaaggctt tgattattgg ggccagggca ccctggtgac cgtgagcagc     360
ggtggggggcg aagccagat tcagctgacc cagagcccga gcagcctgag cgcaagcgtg     420
ggtgatcgtg tgaccattac ctgcagcgcg agcagcagcg tgagctatat gcattggtat     480
cagcagaaac cggcaaagc gccgaaacgt tggatttatg ataccagcaa actggcgagc     540
ggcgtgccga gccgttttag cggcagcggc agcggcaccg attatacctt taccattagc     600
agcctgcagc cggaagatat tgcgacctat tattgccagc agtggagcag caacccgccg     660
acctttggcc agggcaccaa actgcagatt aaacgt                               696
```

<210> SEQ ID NO 85
<211> LENGTH: 232
<212> TYPE: PRT
<213> ORGANISM: artificial
<220> FEATURE:
<223> OTHER INFORMATION: amino acid sequence of modified AVP02-60
anti-MUC1 diabody designated AVP02-105 comprising cysteine
residues in FR1 and a N-terminal serine

<400> SEQUENCE: 85

```
Ser Val Gln Leu Val Glu Ser Gly Gly Gly Val Val Cys Pro Gly Cys
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Asp Lys Gly Leu Glu Leu Val
        35                  40                  45

Ala Thr Ile Asn Ser Asn Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Arg Asp Gly Tyr Asp Glu Gly Phe Asp Tyr Trp Gly Gln
            100                 105                 110

Gly Thr Leu Val Thr Val Ser Ser Gly Gly Gly Gly Ser Gln Ile Gln
        115                 120                 125

Leu Thr Gln Ser Pro Ser Ser Leu Ser Ala Ser Val Gly Asp Arg Val
    130                 135                 140

Thr Ile Thr Cys Ser Ala Ser Ser Ser Val Ser Tyr Met His Trp Tyr
145                 150                 155                 160

Gln Gln Lys Pro Gly Lys Ala Pro Lys Arg Trp Ile Tyr Asp Thr Ser
                165                 170                 175

Lys Leu Ala Ser Gly Val Pro Ser Arg Phe Ser Gly Ser Gly Ser Gly
            180                 185                 190

Thr Asp Tyr Thr Phe Thr Ile Ser Ser Leu Gln Pro Glu Asp Ile Ala
```

```
                195                 200                 205
Thr Tyr Tyr Cys Gln Gln Trp Ser Ser Asn Pro Pro Thr Phe Gly Gln
    210                 215                 220

Gly Thr Lys Leu Gln Ile Lys Arg
225                 230
```

<210> SEQ ID NO 86
<211> LENGTH: 735
<212> TYPE: DNA
<213> ORGANISM: artificial
<220> FEATURE:
<223> OTHER INFORMATION: nucleotide sequence encoding modified AVP07-17 anti-HER2 diabody designated AVP07-88 comprising cysteine residues in FR1, removal of cysteine residues in CDR3H and a N-terminal serine

<400> SEQUENCE: 86

```
agcgtgcagc tggtgcagtg tggggcatgt gtgaaaaagc ccggggagtc tctgaagatc    60
tcctgtaagg ttctggata  cagctttacc agctactgga tcgcctgggt gcgccagatg   120
cccgggaaag gcctggagta catggggctc atctatcctg gtgactctga caccaaatac   180
agcccgtcct tccaaggcca ggtcaccatc tcagtcgaca gtccgtcag  cactgcctac   240
ttgcaatgga gcagtctgaa gccctcggac agcgccgtgt attttgtgc  gagacatgac   300
gtgggatatg cgagtagttc caacgcggca aagtggcctg aatacttcca gcattggggc   360
cagggcaccc tggtcaccgt tcctcaggt  ggaggcggtt cacagtctgt gttgacgcag   420
ccgccctcag tgtctgcggc cccaggacag aaggtcacca tctcctgctc tggaagcagc   480
tccaacattg gaataatta  tgtatcctgg taccagcagc tcccaggaac agtccccaaa   540
ctcctcatct atggtcacac caatcggccc gcagggtcc  ctgaccgatt ctctggctcc   600
aagtctggca cctcagcctc cctggccatc agtgggttcc ggtccgagga tgaggctgat   660
tattactgtg cagcatggga tgacagcctg agtggttggg tgttcggcgg agggaccaag   720
ctgaccgtcc taggt                                                    735
```

<210> SEQ ID NO 87
<211> LENGTH: 245
<212> TYPE: PRT
<213> ORGANISM: artificial
<220> FEATURE:
<223> OTHER INFORMATION: amino acid sequence of modified AVP07-17 anti-HER2 diabody designated AVP07-88 comprising cysteine residues in FR1, removal of cysteine residues in CDR3H and a N-terminal serine

<400> SEQUENCE: 87

```
Ser Val Gln Leu Val Gln Cys Gly Ala Cys Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Ala Trp Val Arg Gln Met Pro Gly Lys Gly Leu Glu Tyr Met
            35                  40                  45

Gly Leu Ile Tyr Pro Gly Asp Ser Asp Thr Lys Tyr Ser Pro Ser Phe
        50                  55                  60

Gln Gly Gln Val Thr Ile Ser Val Asp Lys Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Ala Ser Ser Ser Asn Ala Ala Lys Trp
```

```
            100                 105                 110
Pro Glu Tyr Phe Gln His Trp Gly Gln Gly Thr Leu Val Thr Val Ser
            115                 120                 125

Ser Gly Gly Gly Gly Ser Gln Ser Val Leu Thr Gln Pro Pro Ser Val
            130                 135             140

Ser Ala Ala Pro Gly Gln Lys Val Thr Ile Ser Cys Ser Gly Ser Ser
145                 150                 155                 160

Ser Asn Ile Gly Asn Asn Tyr Val Ser Trp Tyr Gln Gln Leu Pro Gly
                165                 170                 175

Thr Val Pro Lys Leu Leu Ile Tyr Gly His Thr Asn Arg Pro Ala Gly
            180                 185                 190

Val Pro Asp Arg Phe Ser Gly Ser Lys Ser Gly Thr Ser Ala Ser Leu
            195                 200                 205

Ala Ile Ser Gly Phe Arg Ser Glu Asp Glu Ala Asp Tyr Tyr Cys Ala
            210                 215                 220

Ala Trp Asp Asp Ser Leu Ser Gly Trp Val Phe Gly Gly Gly Thr Lys
225                 230                 235                 240

Leu Thr Val Leu Gly
            245

<210> SEQ ID NO 88
<211> LENGTH: 735
<212> TYPE: DNA
<213> ORGANISM: artificial
<220> FEATURE:
<223> OTHER INFORMATION: nucleotide sequence encoding modified AVP07-17
      anti-HER2 diabody designated AVP07-90 comprising cysteine residues
      in FR1, removal of cysteine residues in CDR3H and a N-terminal
      serine

<400> SEQUENCE: 88
agcgtgcagc tggtgcagtg tggggcatgt gtgaaaaagc ccggggagtc tctgaagatc      60
tcctgtaagg gttctggata cagctttacc agctactgga tcgcctgggt gcgccagatg     120
cccgggaaag gcctggagta catggggctc atctatcctg gtgactctga caccaaatac     180
agcccgtcct tccaaggcca ggtcaccatc tcagtcgaca gtccgtcag cactgcctac     240
ttgcaatgga gcagtctgaa gccctcggac agcgccgtgt attttttgtgc gagacatgac     300
gtgggatatg cgagtagttc caacgcggca aagtggcctg aatacttcca gcattggggc     360
cagggcaccc tggtcaccgt tcctcaggt ggaggcggtt cacagtctgt gttgacgcag     420
ccgccctcag tgtctgcggc cccaggacag aaggtcacca tctcctgctc tggaagcagc     480
tccaacattg gaataatta tgtatcctgg taccagcagc tcccaggaac agtccccaaa     540
ctcctcatct atggtcacac caatcggccc gcagggtcc ctgaccgatt ctctggctcc     600
aagtctggca cctcagcctc cctggccatc agtgggttcc ggtccgagga tgaggctgat     660
tattactgtg cagcatggga tgacagcctg agtggttggg tgttcggcgg agggaccaag     720
ctgaccgtcc taggt                                                      735

<210> SEQ ID NO 89
<211> LENGTH: 245
<212> TYPE: PRT
<213> ORGANISM: artificial
<220> FEATURE:
<223> OTHER INFORMATION: amino acid sequence of modified AVP07-17
      anti-HER2 diabody designated AVP07-90 comprising cysteine residues
      in FR1, removal of cysteine residues in CDR3H and a N-terminal
      serine
```

<400> SEQUENCE: 89

| | | | | | | | | | | | | | | |
|---|---|---|---|---|---|---|---|---|---|---|---|---|---|---|
| Ser | Val | Gln | Leu | Val | Gln | Cys | Gly | Ala | Cys | Val | Lys | Lys | Pro | Gly | Glu |
| 1 | | | | 5 | | | | | 10 | | | | | 15 | |
| Ser | Leu | Lys | Ile | Ser | Cys | Lys | Gly | Ser | Gly | Tyr | Ser | Phe | Thr | Ser | Tyr |
| | | | 20 | | | | | 25 | | | | | 30 | | |
| Trp | Ile | Ala | Trp | Val | Arg | Gln | Met | Pro | Gly | Lys | Gly | Leu | Glu | Tyr | Met |
| | | | 35 | | | | 40 | | | | | 45 | | | |
| Gly | Leu | Ile | Tyr | Pro | Gly | Asp | Ser | Asp | Thr | Lys | Tyr | Ser | Pro | Ser | Phe |
| | 50 | | | | | 55 | | | | | 60 | | | | |
| Gln | Gly | Gln | Val | Thr | Ile | Ser | Val | Asp | Lys | Ser | Val | Ser | Thr | Ala | Tyr |
| 65 | | | | | 70 | | | | | 75 | | | | | 80 |
| Leu | Gln | Trp | Ser | Ser | Leu | Lys | Pro | Ser | Asp | Ser | Ala | Val | Tyr | Phe | Cys |
| | | | | 85 | | | | | 90 | | | | | 95 | |
| Ala | Arg | His | Asp | Val | Gly | Tyr | Ala | Ser | Ser | Asn | Ala | Ala | Lys | Trp | |
| | | | 100 | | | | | 105 | | | | | 110 | | |
| Pro | Glu | Tyr | Phe | Gln | His | Trp | Gly | Gln | Gly | Thr | Leu | Val | Thr | Val | Ser |
| | | | 115 | | | | | 120 | | | | | 125 | | |
| Ser | Gly | Gly | Gly | Gly | Ser | Gln | Ser | Val | Leu | Thr | Gln | Pro | Pro | Ser | Val |
| | 130 | | | | | 135 | | | | | 140 | | | | |
| Ser | Ala | Ala | Pro | Gly | Gln | Lys | Val | Thr | Ile | Ser | Cys | Ser | Gly | Ser | Ser |
| 145 | | | | | 150 | | | | | 155 | | | | | 160 |
| Ser | Asn | Ile | Gly | Asn | Asn | Tyr | Val | Ser | Trp | Tyr | Gln | Gln | Leu | Pro | Gly |
| | | | | 165 | | | | | 170 | | | | | 175 | |
| Thr | Val | Pro | Lys | Leu | Leu | Ile | Tyr | Gly | His | Thr | Asn | Arg | Pro | Ala | Gly |
| | | | | 180 | | | | | 185 | | | | | 190 | |
| Val | Pro | Asp | Arg | Phe | Ser | Gly | Ser | Lys | Ser | Gly | Thr | Ser | Ala | Ser | Leu |
| | | | 195 | | | | | 200 | | | | | 205 | | |
| Ala | Ile | Ser | Gly | Phe | Arg | Ser | Glu | Asp | Glu | Ala | Asp | Tyr | Tyr | Cys | Ala |
| | | | 210 | | | | | 215 | | | | | 220 | | |
| Ala | Trp | Asp | Asp | Ser | Leu | Ser | Gly | Trp | Val | Phe | Gly | Gly | Gly | Thr | Lys |
| 225 | | | | | 230 | | | | | 235 | | | | | 240 |
| Leu | Thr | Val | Leu | Gly | | | | | | | | | | | |
| | | | | 245 | | | | | | | | | | | |

<210> SEQ ID NO 90
<211> LENGTH: 735
<212> TYPE: DNA
<213> ORGANISM: artificial
<220> FEATURE:
<223> OTHER INFORMATION: nucleotide sequence encoding modified AVP07-17 anti-HER2 diabody designated AVP07-89 comprising cysteine residues in FR1, removal of cysteine residues in CDR3H and a N-terminal serine

<400> SEQUENCE: 90

```
tctgtgcagc tggtgcagtc tggggcagag gtgaaaaagc ccggggagtc tctgaagatc    60
tcctgtaagg gttctggata cagctttacc agctactgga tcgcctgggt gcgccagatg   120
cccgggaaag gcctggagta catggggctc atctatcctg gtgactctga caccaaatac   180
agcccgtcct tccaaggcca ggtcaccatc tcagtcgaca gtccgtcag cactgcctac   240
ttgcaatgga gcagtctgaa gccctcggac agcgccgtgt attttttgtgc agacatgac   300
gtgggatatg cgagtagttc caacgcggca aagtggcctg aatacttcca gcattggggc   360
cagggcaccc tggtcaccgt ttcctcaggt ggaggcggtt cacagtctgt gttgacgcag   420
ccgccctcag tgtctgcgtg tccaggatgt aaggtcacca tctcctgctc tggaagcagc   480
```

```
tccaacattg ggaataatta tgtatcctgg taccagcagc tcccaggaac agtccccaaa    540
ctcctcatct atggtcacac caatcggccc gcagggtcc ctgaccgatt ctctggctcc     600
aagtctggca cctcagcctc cctggccatc agtgggttcc ggtccgagga tgaggctgat   660
tattactgtg cagcatggga tgacagcctg agtggttggg tgttcggcgg agggaccaag    720
ctgaccgtcc taggt                                                    735
```

<210> SEQ ID NO 91
<211> LENGTH: 245
<212> TYPE: PRT
<213> ORGANISM: artificial
<220> FEATURE:
<223> OTHER INFORMATION: amino acid sequence of modified AVP07-17
      anti-HER2 diabody designated AVP07-89 comprising cysteine residues
      in FR1, removal of cysteine residues in CDR3H and a N-terminal
      serine

<400> SEQUENCE: 91

```
Ser Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Ala Ser Ser Ser Asn Ala Ala Lys Trp
            100                 105                 110

Pro Glu Tyr Phe Gln His Trp Gly Gln Gly Thr Leu Val Thr Val Ser
        115                 120                 125

Ser Gly Gly Gly Gly Ser Gln Ser Val Leu Thr Gln Pro Pro Ser Val
    130                 135                 140

Ser Ala Cys Pro Gly Cys Lys Val Thr Ile Ser Cys Ser Gly Ser Ser
145                 150                 155                 160

Ser Asn Ile Gly Asn Asn Tyr Val Ser Trp Tyr Gln Gln Leu Pro Gly
                165                 170                 175

Thr Val Pro Lys Leu Leu Ile Tyr Gly His Thr Asn Arg Pro Ala Gly
            180                 185                 190

Val Pro Asp Arg Phe Ser Gly Ser Lys Ser Gly Thr Ser Ala Ser Leu
        195                 200                 205

Ala Ile Ser Gly Phe Arg Ser Glu Asp Glu Ala Asp Tyr Tyr Cys Ala
    210                 215                 220

Ala Trp Asp Asp Ser Leu Ser Gly Trp Val Phe Gly Gly Gly Thr Lys
225                 230                 235                 240

Leu Thr Val Leu Gly
                245
```

<210> SEQ ID NO 92
<211> LENGTH: 735
<212> TYPE: DNA
<213> ORGANISM: artificial
<220> FEATURE:
<223> OTHER INFORMATION: nucleotide sequence encoding modified AVP07-17
      anti-HER2 diabody designated AVP07-91 comprising cysteine residues in FR1, removal of cysteine residues in CDR3H and a N-terminal
serine

<400> SEQUENCE: 92

```
agcgtgcagc tggtgcagtc tggggcagag gtgaaatgtc ccgggtgttc tctgaagatc    60
tcctgtaagg gttctggata cagctttacc agctactgga tcgcctgggt gcgccagatg   120
cccgggaaag gcctggagta catggggctc atctatcctg gtgactctga caccaaatac   180
agcccgtcct tccaaggcca ggtcaccatc tcagtcgaca gtccgtcag cactgcctac    240
ttgcaatgga gcagtctgaa gccctcggac agcgccgtgt attttgtgc gagacatgac    300
gtgggatatg cgagtagttc caacgcggca aagtggcctg aatacttcca gcattggggc   360
cagggcaccc tggtcaccgt ttcctcaggt ggaggcggtt cacagtctgt gttgacgcag   420
ccgccctcag tgtctgcggc cccaggacaa aaggtcacca tctcctgctc tggaagcagc   480
tccaacattg gaataatta tgtatcctgg taccagcagc tcccaggaac agtccccaaa    540
ctcctcatct atggtcacac caatcggccc gcagggtcc ctgaccgatt ctctggctcc    600
aagtctggca cctcagcctc cctggccatc agtgggttcc ggtccgagga tgaggctgat   660
tattactgtg cagcatggga tgacagcctg agtggttggg tgttcggcgg agggaccaag   720
ctgaccgtcc taggt                                                    735
```

<210> SEQ ID NO 93
<211> LENGTH: 245
<212> TYPE: PRT
<213> ORGANISM: artificial
<220> FEATURE:
<223> OTHER INFORMATION: amino acid sequence of modified AVP07-17
      anti-HER2 diabody designated AVP07-91 comprising cysteine residues
      in FR1, removal of cysteine residues in CDR3H and a N-terminal
      serine

<400> SEQUENCE: 93

```
Ser Val Gln Leu Val Gln Ser Gly Ala Glu Val Lys Cys Pro Gly Cys
1               5                   10                  15
Ser Leu Lys Ile Ser Cys Lys Gly Ser Gly Tyr Ser Phe Thr Ser Tyr
            20                  25                  30
Trp Ile Ala Trp Val Arg Gln Met Pro Gly Lys Gly Leu Glu Tyr Met
        35                  40                  45
Gly Leu Ile Tyr Pro Gly Asp Ser Asp Thr Lys Tyr Ser Pro Ser Phe
    50                  55                  60
Gln Gly Gln Val Thr Ile Ser Val Asp Lys Ser Val Ser Thr Ala Tyr
65                  70                  75                  80
Leu Gln Trp Ser Ser Leu Lys Pro Ser Asp Ser Ala Val Tyr Phe Cys
                85                  90                  95
Ala Arg His Asp Val Gly Tyr Ala Ser Ser Ser Asn Ala Ala Lys Trp
            100                 105                 110
Pro Glu Tyr Phe Gln His Trp Gly Gln Gly Thr Leu Val Thr Val Ser
        115                 120                 125
Ser Gly Gly Gly Gly Ser Gln Ser Val Leu Thr Gln Pro Pro Ser Val
    130                 135                 140
Ser Ala Ala Pro Gly Gln Lys Val Thr Ile Ser Cys Ser Gly Ser Ser
145                 150                 155                 160
Ser Asn Ile Gly Asn Asn Tyr Val Ser Trp Tyr Gln Gln Leu Pro Gly
                165                 170                 175
Thr Val Pro Lys Leu Leu Ile Tyr Gly His Thr Asn Arg Pro Ala Gly
            180                 185                 190
```

Val Pro Asp Arg Phe Ser Gly Ser Lys Ser Gly Thr Ser Ala Ser Leu
        195                 200                 205

Ala Ile Ser Gly Phe Arg Ser Glu Asp Glu Ala Asp Tyr Tyr Cys Ala
        210                 215                 220

Ala Trp Asp Asp Ser Leu Ser Gly Trp Val Phe Gly Gly Gly Thr Lys
225                 230                 235                 240

Leu Thr Val Leu Gly
            245

<210> SEQ ID NO 94
<211> LENGTH: 696
<212> TYPE: DNA
<213> ORGANISM: artificial
<220> FEATURE:

<223> OTHER INFORMATION: nucleotide sequence encoding modified AVP02-60
      anti-MUC1 diabody designated AVP02-103 comprising cysteine
      residues in FR1 and a N-terminal serine

<400> SEQUENCE: 94
agcgtgcagc tggtttgcag cggttgcgga gtggtgcagc caggtggaag cctgcgtctg      60
agctgcgcag caagcggttt tacctttagc agctatggca tgagctgggt cgtcaggcg     120 ccggataaag gcctggaact ggtggcgacc attaacagca cggtggaag cacctattat     180 ccggatagcg tgaaaggccg ttttaccatt agccgtgata cagcaaaaa caccctgtat     240 ctgcagatga acagcctgcg taccgaagat accgcggtgt attattgcgc gcgtgatcgt     300
gatggctatg atgaaggctt tgattattgg ggccagggca ccctggtgac cgtgagcagc     360 ggtggggggcg gaagccagat tcagctgacc cagagcccga gcagcctgag cgcaagcgtg     420
ggtgatcgtg tgaccattac ctgcagcgcg agcagcagcg tgagctatat gcattggtat     480
cagcagaaac cgggcaaagc gccgaaacgt tggatttatg ataccagcaa actggcgagc     540
ggcgtgccga ccgttttag cggcagcggg agcggcaccg attatacctt taccattagc     600
agcctgcagc cggaagatat tgcgacctat tattgccagc agtggagcag caacccgccg     660 accttggcc agggcaccaa actgcagatt aaacgt                                 696

<210> SEQ ID NO 95
<211> LENGTH: 232
<212> TYPE: PRT
<213> ORGANISM: artificial
<220> FEATURE:
<223> OTHER INFORMATION: amino acid sequence of modified AVP02-60
      anti-MUC1 diabody designated AVP02-103 comprising cysteine
      residues in FR1 and a N-terminal serine

<400> SEQUENCE: 95

Ser Val Gln Leu Val Cys Ser Gly Cys Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Asp Lys Gly Leu Glu Leu Val
        35                  40                  45

Ala Thr Ile Asn Ser Asn Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Asp Arg Asp Gly Tyr Asp Glu Gly Phe Asp Tyr Trp Gly Gln
        100                 105                 110

Gly Thr Leu Val Thr Val Ser Ser Gly Gly Gly Ser Gln Ile Gln
    115                 120                 125

Leu Thr Gln Ser Pro Ser Ser Leu Ser Ala Ser Val Gly Asp Arg Val
130                 135                 140

Thr Ile Thr Cys Ser Ala Ser Ser Val Ser Tyr Met His Trp Tyr
145                 150                 155                 160

Gln Gln Lys Pro Gly Lys Ala Pro Lys Arg Trp Ile Tyr Asp Thr Ser
                165                 170                 175

Lys Leu Ala Ser Gly Val Pro Ser Arg Phe Ser Gly Ser Gly Ser Gly
                180                 185                 190

Thr Asp Tyr Thr Phe Thr Ile Ser Ser Leu Gln Pro Glu Asp Ile Ala
            195                 200                 205

Thr Tyr Tyr Cys Gln Gln Trp Ser Ser Asn Pro Pro Thr Phe Gly Gln
        210                 215                 220

Gly Thr Lys Leu Gln Ile Lys Arg
225                 230

<210> SEQ ID NO 96
<211> LENGTH: 735
<212> TYPE: DNA
<213> ORGANISM: artificial
<220> FEATURE:
<223> OTHER INFORMATION: nucleotide sequence encoding modified AVP07-17
      anti-HER2 diabody designated AVP07-68 comprising cysteine residues
      in FR1, removal of cysteine residues in CDR3H and a N-terminal
      serine

<400> SEQUENCE: 96
agcgtgcagc tggtgcagtc tggggcagag gtgaaaaagc ccggggagtc tctgaagatc      60
tcctgtaagg gttctggata cagctttacc agctactgga tcgcctgggt gcgccagatg     120
cccgggaaag gcctggagta catggggctc atctatcctg gtgactctga caccaaatac     180
agcccgtcct tccaaggcca ggtcaccatc tcagtcgaca gtccgtcag cactgcctac     240 ttgcaatgga gcagtctgaa gccctcggac agcgccgtgt attttgtgc gagacatgac     300 gtgggatatg cgagtagttc caacgcggca agtggcctg aatacttcca gcattggggc     360
cagggcaccc tggtcaccgt ttcctcaggt ggaggcggtt cacagtctgt gttgacgcag     420
ccgtgcagca gctgcgcggc cccaggacag aaggtcacca tctcctgctc tggaagcagc     480
tccaacattg gaataatta tgtatcctgg taccagcagc tcccaggaac agtccccaaa     540
ctcctcatct atggtcacac caatcggccc gcaggggtcc ctgaccgatt ctctggctcc     600
aagtctggca cctcagcctc cctggccatc agtgggttcc ggtccgagga tgaggctgat     660
tattactgtg cagcatggga tgacagcctg agtggttggg tgttcggcgg agggaccaag     720
ctgaccgtcc taggt                                                     735

<210> SEQ ID NO 97
<211> LENGTH: 245
<212> TYPE: PRT
<213> ORGANISM: artificial
<220> FEATURE:
<223> OTHER INFORMATION: amino acid sequence of modified AVP07-17
      anti-HER2 diabody designated AVP07-68 comprising cysteine residues
      in FR1, removal of cysteine residues in CDR3H and a N-terminal
      serine

<400> SEQUENCE: 97

Ser Val Gln Leu Val Gln Ser Gly Ala Glu Val Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Ala Trp Val Arg Gln Met Pro Gly Lys Gly Leu Glu Tyr Met
            35                  40                  45

Gly Leu Ile Tyr Pro Gly Asp Ser Asp Thr Lys Tyr Ser Pro Ser Phe
        50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Ala Ser Ser Ser Asn Ala Ala Lys Trp
            100                 105                 110

Pro Glu Tyr Phe Gln His Trp Gly Gln Gly Thr Leu Val Thr Val Ser
        115                 120                 125

Ser Gly Gly Gly Gly Ser Gln Ser Val Leu Thr Gln Pro Cys Ser Ser
    130                 135                 140

Cys Ala Ala Pro Gly Gln Lys Val Thr Ile Ser Cys Ser Gly Ser Ser
145                 150                 155                 160

Ser Asn Ile Gly Asn Asn Tyr Val Ser Trp Tyr Gln Gln Leu Pro Gly
                165                 170                 175

Thr Val Pro Lys Leu Leu Ile Tyr Gly His Thr Asn Arg Pro Ala Gly
            180                 185                 190

Val Pro Asp Arg Phe Ser Gly Ser Lys Ser Gly Thr Ser Ala Ser Leu
        195                 200                 205

Ala Ile Ser Gly Phe Arg Ser Glu Asp Glu Ala Asp Tyr Tyr Cys Ala
210                 215                 220

Ala Trp Asp Asp Ser Leu Ser Gly Trp Val Phe Gly Gly Gly Thr Lys
225                 230                 235                 240

Leu Thr Val Leu Gly
                245

<210> SEQ ID NO 98
<211> LENGTH: 702
<212> TYPE: DNA
<213> ORGANISM: artificial
<220> FEATURE:
<223> OTHER INFORMATION: nucleotide sequence encoding modified AVP04-07
      anti-TAG72 diabody designated AVP04-51 comprising cysteine
      residues in FR1 and a N-terminal serine

<400> SEQUENCE: 98
agcgtgcagc tgcagcagag cgatgcggaa ctggtgaaac cgggcgcgag cgtgaaaatt      60
agctgcaaag cgagcggcta ccctttacc gatcatgcga ttcattgggt gaaacagaat     120
ccggaacagg gcctggaatg gattggctat tttagcccgg caacgatga ttttaaatat     180 aacgaacgtt ttaaaggcaa agcgaccctg accgcggata aaagcagcag caccgcgtat     240
ctgcagctga acagcctgac cagcgaagat agcgcggtgt atttttgcac ccgtagcctg     300
aatatggcgt attgggtca gggcacctcg gtcaccgtga gcagcggtgg cggcggcagc     360
gatatcgtga tgacccagag cccgagcagc ctgccgtgca gcgtgggcga aaaatgcacc     420
ctgagctgca aaagcagcca gagcctgctg tatagcggaa tcagaaaaa ctatctggcg     480 tggtatcagc agaaaccggg tcagagcccg aaactgctga tttattgggc gagcacccgt     540

-continued

```
gaaagcggcg tgccggatcg ttttaccggc agcggtagcg gcaccgattt taccctgagc    600
attagcagcg tggaaaccga agatctggcg gtgtattatt gccagcagta ttatagctat    660
ccgctgacct ttggtgcggg caccaaactg gtgctgaaac gt                       702
```

<210> SEQ ID NO 99
<211> LENGTH: 234
<212> TYPE: PRT
<213> ORGANISM: artificial
<220> FEATURE:
<223> OTHER INFORMATION: amino acid sequence of modified AVP04-07 anti-TAG72 diabody designated AVP04-51 comprising cysteine residues in FR1 and a N-terminal serine

<400> SEQUENCE: 99

```
Ser Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
                20                  25                  30

Ala Ile His Trp Val Lys Gln Asn Pro Glu Gln Gly Leu Glu Trp Ile
            35                  40                  45

Gly Tyr Phe Ser Pro Gly Asn Asp Asp Phe Lys Tyr Asn Glu Arg Phe
        50                  55                  60

Lys Gly Lys Ala Thr Leu Thr Ala Asp Lys Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
                100                 105                 110

Val Ser Ser Gly Gly Gly Gly Ser Asp Ile Val Met Thr Gln Ser Pro
            115                 120                 125

Ser Ser Leu Pro Cys Ser Val Gly Glu Lys Cys Thr Leu Ser Cys Lys
        130                 135                 140

Ser Ser Gln Ser Leu Leu Tyr Ser Gly Asn Gln Lys Asn Tyr Leu Ala
145                 150                 155                 160

Trp Tyr Gln Gln Lys Pro Gly Gln Ser Pro Lys Leu Leu Ile Tyr Trp
                165                 170                 175

Ala Ser Thr Arg Glu Ser Gly Val Pro Asp Arg Phe Thr Gly Ser Gly
            180                 185                 190

Ser Gly Thr Asp Phe Thr Leu Ser Ile Ser Ser Val Glu Thr Glu Asp
        195                 200                 205

Leu Ala Val Tyr Tyr Cys Gln Gln Tyr Tyr Ser Tyr Pro Leu Thr Phe
    210                 215                 220

Gly Ala Gly Thr Lys Leu Val Leu Lys Arg
225                 230
```

<210> SEQ ID NO 100
<211> LENGTH: 732
<212> TYPE: DNA
<213> ORGANISM: artificial
<220> FEATURE:
<223> OTHER INFORMATION: nucleotide sequence encoding modified AVP04-07 anti-TAG72 scFv designated AVP04-70 comprising cysteine residues in FR1 and a N-terminal serine

<400> SEQUENCE: 100

```
agcgtgcagc tgcagcagag cgatgcggaa ctggtgaaac cgggcgcgag cgtgaaaatt    60
agctgcaaag cgagcggcta tacctttacc gatcatgcga ttcattgggt gaaacagaat    120
```

-continued

```
ccggaacagg gcctggaatg gattggctat tttagcccgg gcaacgatga ttttaaatat    180
aacgaacgtt ttaaaggcaa agcgaccctg accgcggata aaagcagcag caccgcgtat    240
ctgcagctga acagcctgac cagcgaagat agcgcggtgt attttttgcac ccgtagcctg    300 aatatggcgt attggggtca gggcacctcg gtcaccgtga gcagcggtgg cggcggcagc    360
ggtggcggcg gcagcggtgg cggcggcagc gatatcgtga tgacccagag ctgcagcagc    420
tgcccggtga gcgtgggcga aaaagtgacc ctgagctgca aaagcagcca gagcctgctg    480
tatagcggca atcagaaaaa ctatctggcg tggtatcagc agaaaccggg tcagagcccg    540
aaactgctga tttattgggc gagcacccgt gaaagcggcg tgccggatcg ttttaccggc    600
agcggtagcg gcaccgattt taccctgagc attagcagcg tggaaaccga agatctggcg    660
gtgtattatt gccagcagta ttatagctat ccgctgaccct ttggtgcggg caccaaactg    720
gtgctgaaac gt                                                         732
```

<210> SEQ ID NO 101
<211> LENGTH: 244
<212> TYPE: PRT
<213> ORGANISM: artificial
<220> FEATURE:
<223> OTHER INFORMATION: amino acid sequence of modified AVP04-07
    anti-TAG72 scFv designated AVP04-70 comprising cysteine residues
    in FR1 and a N-terminal serine

<400> SEQUENCE: 101

```
Ser Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Gly Gly Gly Gly Ser Gly Gly Gly
        115                 120                 125

Gly Ser Asp Ile Val Met Thr Gln Ser Cys Ser Ser Cys Pro Val Ser
    130                 135                 140

Val Gly Glu Lys Val Thr Leu Ser Cys Lys Ser Ser Gln Ser Leu Leu
145                 150                 155                 160

Tyr Ser Gly Asn Gln Lys Asn Tyr Leu Ala Trp Tyr Gln Gln Lys Pro
                165                 170                 175

Gly Gln Ser Pro Lys Leu Leu Ile Tyr Trp Ala Ser Thr Arg Glu Ser
            180                 185                 190

Gly Val Pro Asp Arg Phe Thr Gly Ser Gly Ser Gly Thr Asp Phe Thr
        195                 200                 205

Leu Ser Ile Ser Ser Val Glu Thr Glu Asp Leu Ala Val Tyr Tyr Cys
    210                 215                 220

Gln Gln Tyr Tyr Ser Tyr Pro Leu Thr Phe Gly Ala Gly Thr Lys Leu
225                 230                 235                 240
```

Val Leu Lys Arg

<210> SEQ ID NO 102
<211> LENGTH: 687
<212> TYPE: DNA
<213> ORGANISM: artificial
<220> FEATURE:
<223> OTHER INFORMATION: nucleotide sequence encoding modified AVP04-07
anti-TAG72 triabody designated AVP04-74 comprising cysteine
residues in FR1 and a N-terminal serine

<400> SEQUENCE: 102

| | | | |
|---|---|---|---|
| agcgtgcagc tgcagcagag cgatgcggaa ctggtgaaac cgggcgcgag cgtgaaaatt | | | 60 |
| agctgcaaag cgagcggcta cctttacc gatcatgcga ttcattgggt gaaacagaat | | | 120 |
| ccggaacagg gcctggaatg gattggctat tttagcccgg gcaacgatga tttaaatat | | | 180 |
| aacgaacgtt ttaaaggcaa agcgaccctg accgcggata aaagcagcag caccgcgtat | | | 240 |
| ctgcagctga acagcctgac cagcgaagat agcgcggtgt atttttgcac ccgtagcctg | | | 300 |
| aatatggcgt attggggtca gggcacctcg gtcaccgtga gcagcgatat cgtgatgacc | | | 360 |
| cagagctgca gcagctgccc ggtgagcgtg ggcgaaaaag tgaccctgag ctgcaaaagc | | | 420 |
| agccagagcc tgctgtatag cggcaatcag aaaaactatc tggcgtggta tcagcagaaa | | | 480 |
| ccgggtcaga gcccgaaact gctgatttat tgggcgagca cccgtgaaag cggcgtgccg | | | 540 |
| gatcgtttta ccggcagcgg tagcggcacc gattttaccc tgagcattag cagcgtggaa | | | 600 |
| accgaagatc tggcggtgta ttattgccag cagtattata gctatccgct gacctttggt | | | 660 |
| gcgggcacca aactggtgct gaaacgt | | | 687 |

<210> SEQ ID NO 103
<211> LENGTH: 229
<212> TYPE: PRT
<213> ORGANISM: artificial
<220> FEATURE:
<223> OTHER INFORMATION: amino acid sequence of modified AVP04-07
anti-TAG72 triabody designated AVP04-74 comprising cysteine
residues in FR1 and a N-terminal serine

<400> SEQUENCE: 103

Ser Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Asp Ile Val Met Thr Gln Ser Cys Ser Ser Cys Pro Val
        115                 120                 125

Ser Val Gly Glu Lys Val Thr Leu Ser Cys Lys Ser Ser Gln Ser Leu
    130                 135                 140

Leu Tyr Ser Gly Asn Gln Lys Asn Tyr Leu Ala Trp Tyr Gln Gln Lys
145                 150                 155                 160

Pro Gly Gln Ser Pro Lys Leu Leu Ile Tyr Trp Ala Ser Thr Arg Glu
             165                 170                 175

Ser Gly Val Pro Asp Arg Phe Thr Gly Ser Gly Ser Gly Thr Asp Phe
         180                 185                 190

Thr Leu Ser Ile Ser Ser Val Glu Thr Glu Asp Leu Ala Val Tyr Tyr
     195                 200                 205

Cys Gln Gln Tyr Tyr Ser Tyr Pro Leu Thr Phe Gly Ala Gly Thr Lys
    210                 215                 220

Leu Val Leu Lys Arg
225

<210> SEQ ID NO 104
<211> LENGTH: 765
<212> TYPE: DNA
<213> ORGANISM: artificial
<220> FEATURE:
<223> OTHER INFORMATION: nucleotide sequence encoding modified AVP07-17
      anti-HER2 scFv designated AVP07-71 comprising cysteine residues in
      FR1, removal of cysteine residues in CDR3H and a N-terminal serine

<400> SEQUENCE: 104
agcgtgcagc tggtgcagtc tggggcagag gtgaaaaagc ccggggagtc tctgaagatc    60
tcctgtaagg gttctggata cagctttacc agctactgga tcgcctgggt gcgccagatg   120
cccgggaaag gcctggagta catggggctc atctatcctg gtgactctga caccaaatac   180
agcccgtcct tccaaggcca ggtcaccatc tcagtcgaca agtccgtcag cactgcctac   240
ttgcaatgga gcagtctgaa gccctcggac agcgccgtgt attttgtgc gagacatgac   300 gtgggatatg cgagtagttc caacgcggca agtggcctg aatacttcca gcattggggc   360
cagggcaccc tggtcaccgt ttcctcaggt ggaggcggtt caggtggagg cggttcaggt   420
ggaggcggtt cacagtctgt gttgacgcag ccgtgcagca gctgcgcggc cccaggacag   480
aaggtcacca tctcctgctc tggaagcagc tccaacattg gaataatta tgtatcctgg   540 taccagcagc tcccaggaac agtccccaaa ctcctcatct atggtcacac caatcggccc   600
gcaggggtcc ctgaccgatt ctctggctcc aagtctggca cctcagcctc cctggccatc   660
agtgggttcc ggtccgagga tgaggctgat tattactgtg cagcatggga tgacagcctg   720
agtggttggg tgttcggcgg agggaccaag ctgaccgtcc taggt                   765

<210> SEQ ID NO 105
<211> LENGTH: 255
<212> TYPE: PRT
<213> ORGANISM: artificial
<220> FEATURE:
<223> OTHER INFORMATION: amino acid sequence of modified AVP07-17
      anti-HER2 scFv designated AVP07-71 comprising cysteine residues in
      FR1, removal of cysteine residues in CDR3H and a N-terminal serine

<400> SEQUENCE: 105

Ser Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr

```
                 65                  70                  75                  80
Leu Gln Trp Ser Ser Leu Lys Pro Ser Asp Ser Ala Val Tyr Phe Cys
                85                  90                  95

Ala Arg His Asp Val Gly Tyr Ala Ser Ser Ser Asn Ala Ala Lys Trp
            100                 105                 110

Pro Glu Tyr Phe Gln His Trp Gly Gln Gly Thr Leu Val Thr Val Ser
        115                 120                 125

Ser Gly Gly Gly Ser Gly Gly Gly Ser Gly Gly Gly Ser
    130                 135                 140

Gln Ser Val Leu Thr Gln Pro Cys Ser Cys Ala Ala Pro Gly Gln
145                 150                 155                 160

Lys Val Thr Ile Ser Cys Ser Gly Ser Ser Asn Ile Gly Asn Asn
                165                 170                 175

Tyr Val Ser Trp Tyr Gln Gln Leu Pro Gly Thr Val Pro Lys Leu Leu
            180                 185                 190

Ile Tyr Gly His Thr Asn Arg Pro Ala Gly Val Pro Asp Arg Phe Ser
        195                 200                 205

Gly Ser Lys Ser Gly Thr Ser Ala Ser Leu Ala Ile Ser Gly Phe Arg
    210                 215                 220

Ser Glu Asp Glu Ala Asp Tyr Tyr Cys Ala Ala Trp Asp Asp Ser Leu
225                 230                 235                 240

Ser Gly Trp Val Phe Gly Gly Gly Thr Lys Leu Thr Val Leu Gly
                245                 250                 255

<210> SEQ ID NO 106
<211> LENGTH: 55
<212> TYPE: DNA
<213> ORGANISM: artificial
<220> FEATURE:
<223> OTHER INFORMATION: nucleotide sequence of mutagenic primer for
      introducing cysteine residues at Kabat positions L8 and L11 of
      the FR1 region of the VL chain in AVP04-07

<400> SEQUENCE: 106
gatatcgtga tgacccagag ctgcagcagc tgcccggtga gcgtgggcga aaaag          55

<210> SEQ ID NO 107
<211> LENGTH: 55
<212> TYPE: DNA
<213> ORGANISM: artificial
<220> FEATURE:
<223> OTHER INFORMATION: nucleotide sequence of mutagenic primer for
      introducing cysteine residues at Kabat positions L8 and L11 of
      the FR1 region of the VL chain in AVP04-07

<400> SEQUENCE: 107 cttttttcgcc cacgctcacc gggcagctgc tgcagctctg ggtcatcacg atatc          55

<210> SEQ ID NO 108
<211> LENGTH: 735
<212> TYPE: DNA
<213> ORGANISM: artificial
<220> FEATURE:
<223> OTHER INFORMATION: nucleotide sequence encoding modified AVP07-17
      anti-HER2 diabody designated AVP07-86 replacing CDR3H Cysteine
      residues Cys104 (Kabat numbering H100) and Cys109 (H100E) with
      Alanines and comprising a N-terminal serine

<400> SEQUENCE: 108
agcgtgcagc tggtgcagtc tggggcagag gtgaaaaagc ccggggagtc tctgaagatc       60
tcctgtaagg gttctggata cagctttacc agctactgga tcgcctgggt gcgccagatg     120
```

```
cccgggaaag gcctggagta catgggctc atctatcctg gtgactctga caccaaatac    180
agcccgtcct tccaaggcca ggtcaccatc tcagtcgaca gtccgtcag cactgcctac     240 ttgcaatgga gcagtctgaa gccctcggac agcgccgtgt attttgtgc gagacatgac     300 gtgggatatg cgagtagttc caacgcggca aagtggcctg aatacttcca gcattggggc    360
cagggcaccc tggtcaccgt ttcctcaggt ggaggcggtt cacagtctgt gttgacgcag    420
ccgccctcag tgtctgcggc cccaggacag aaggtcacca tctcctgctc tggaagcagc    480
tccaacattg gaataatta tgtatcctgg taccagcagc tcccaggaac agtccccaaa    540
ctcctcatct atggtcacac caatcggccc gcagggtcc ctgaccgatt ctctggctcc    600
aagtctggca cctcagcctc cctggccatc agtgggttcc ggtccgagga tgaggctgat    660
tattactgtg cagcatggga tgacagcctg agtggttggg tgttcggcgg agggaccaag    720
ctgaccgtcc taggt                                                      735
```

<210> SEQ ID NO 109
<211> LENGTH: 245
<212> TYPE: PRT
<213> ORGANISM: artificial
<220> FEATURE:
<223> OTHER INFORMATION: amino acid sequence of modified AVP07-17
      anti-HER2 diabody designated AVP07-86 replacing CDR3H Cysteine
      residues Cys104 (Kabat numbering H100) and Cys109 (H100E) with
      Alanines and comprising a N-terminal serine

<400> SEQUENCE: 109

```
Ser Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Ala Trp Val Arg Gln Met Pro Gly Lys Gly Leu Glu Tyr Met
            35                  40                  45

Gly Leu Ile Tyr Pro Gly Asp Ser Asp Thr Lys Tyr Ser Pro Ser Phe
        50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Ala Ser Ser Asn Ala Ala Lys Trp
                100                 105                 110

Pro Glu Tyr Phe Gln His Trp Gly Gln Gly Thr Leu Val Thr Val Ser
            115                 120                 125

Ser Gly Gly Gly Gly Ser Gln Ser Val Leu Thr Gln Pro Pro Ser Val
        130                 135                 140

Ser Ala Ala Pro Gly Gln Lys Val Thr Ile Ser Cys Ser Gly Ser Ser
145                 150                 155                 160

Ser Asn Ile Gly Asn Asn Tyr Val Ser Trp Tyr Gln Gln Leu Pro Gly
                165                 170                 175

Thr Val Pro Lys Leu Leu Ile Tyr Gly His Thr Asn Arg Pro Ala Gly
            180                 185                 190

Val Pro Asp Arg Phe Ser Gly Ser Lys Ser Gly Thr Ser Ala Ser Leu
        195                 200                 205

Ala Ile Ser Gly Phe Arg Ser Glu Asp Glu Ala Asp Tyr Tyr Cys Ala
    210                 215                 220

Ala Trp Asp Asp Ser Leu Ser Gly Trp Val Phe Gly Gly Gly Thr Lys
```

Leu Thr Val Leu Gly
            245

<210> SEQ ID NO 110
<211> LENGTH: 345
<212> TYPE: DNA
<213> ORGANISM: Artificial
<220> FEATURE:
<223> OTHER INFORMATION: Nucleotide sequence encoding VH of AVP04-07
      anti-TAG-72

<400> SEQUENCE: 110
caggtgcagc tgcagcagag cgatgcggaa ctggtgaaac cgggcgcgag cgtgaaaatt      60
agctgcaaag cgagcggcta cctttacc gatcatgcga ttcattgggt gaaacagaat       120
ccggaacagg gcctggaatg gattggctat ttttagcccgg gcaacgatga ttttaaatat    180
aacgaacgtt ttaaaggcaa agcgacccct accgcggata aaagcagcag caccgcgtat    240
ctgcagctga cagcctgac cagcgaagat agcgcggtgt atttttgcac ccgtagcctg     300
aatatggcgt attggggtca gggcacctcg gtcaccgtga gcagc                    345

<210> SEQ ID NO 111
<211> LENGTH: 115
<212> TYPE: PRT
<213> ORGANISM: artificial
<220> FEATURE:
<223> OTHER INFORMATION: Amino acid sequence encoding VH of AVP04-07
      anti-TAG-72

<400> SEQUENCE: 111

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser
        115

<210> SEQ ID NO 112
<211> LENGTH: 342
<212> TYPE: DNA
<213> ORGANISM: artificial
<220> FEATURE:
<223> OTHER INFORMATION: nucleotide sequence encoding VL of AVP04-07
      anti-TAG72

<400> SEQUENCE: 112
gatatcgtga tgacccagag cccgagcagc ctgccggtga gcgtgggcga aaaagtgacc      60
ctgagctgca aaagcagcca gagcctgctg tatagcggaa tcagaaaaa ctatctggcg     120 tggtatcagc agaaaccggg tcagagcccg aaactgctga tttattgggc gagcacccgt    180

```
gaaagcggcg tgccggatcg ttttaccggc agcggtagcg gcaccgattt taccctgagc    240
attagcagcg tggaaaccga agatctggcg gtgtattatt gccagcagta ttatagctat    300
ccgctgacct ttggtgcggg caccaaactg gtgctgaaac gt                       342
```

<210> SEQ ID NO 113
<211> LENGTH: 114
<212> TYPE: PRT
<213> ORGANISM: artificial
<220> FEATURE:
<223> OTHER INFORMATION: amino acid sequence of VL of AVP04-07 anti-TAG72

<400> SEQUENCE: 113

```
Asp Ile Val Met Thr Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
            20                  25                  30

Gly Asn Gln Lys Asn Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Ser Val Glu Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys Arg
```

<210> SEQ ID NO 114
<211> LENGTH: 714
<212> TYPE: DNA
<213> ORGANISM: artificial
<220> FEATURE:
<223> OTHER INFORMATION: nucleotide sequence encoding AVP04-07 anti-TAG72 diabody lacking a linker sequence

<400> SEQUENCE: 114

```
caggtgcagc tgcagcagag cgatgcggaa ctggtgaaac cgggcgcgag cgtgaaaatt    60
agctgcaaag cgagcggcta ccctttacc gatcatgcga ttcattgggt gaaacagaat    120
ccggaacagg gcctggaatg gattggctat tttagcccgg caacgatga ttttaaatat    180 aacgaacgtt ttaaaggcaa agcgaccctg accgcggata aaagcagcag caccgcgtat    240
ctgcagctga acagcctgac cagcgaagat agcgcggtgt attttttgcac ccgtagcctg    300 aatatggcgt attggggtca gggcaccctcg gtcaccgtga gcagcgatat cgtgatgacc    360
cagagcccga gcagcctgcc ggtgagcgtg ggcgaaaaag tgaccctgag ctgcaaaagc    420
agccagagcc tgctgtatag cggcaatcag aaaaactatc tggcgtggta tcagcagaaa    480
ccgggtcaga gcccgaaact gctgatttat tgggcgagca cccgtgaaag cggcgtgccg    540
gatcgtttta ccggcagcgg tagcggcacc gattttaccc tgagcattag cagcgtggaa    600
accgaagatc tggcggtgta ttattgccag cagtattata gctatccgct gacctttggt    660
gcgggcacca aactggtgct gaaacgtgcg ggcaccaaac tggtgctgaa acgt          714
```

<210> SEQ ID NO 115
<211> LENGTH: 229

```
<212> TYPE: PRT
<213> ORGANISM: artificial
<220> FEATURE:
<223> OTHER INFORMATION: amino acid sequence of AVP04-07 anti-TAG72
      diabody lacking a linker sequence

<400> SEQUENCE: 115

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Asp Ile Val Met Thr Gln Ser Pro Ser Ser Leu Pro Val
        115                 120                 125

Ser Val Gly Glu Lys Val Thr Leu Ser Cys Lys Ser Ser Gln Ser Leu
    130                 135                 140

Leu Tyr Ser Gly Asn Gln Lys Asn Tyr Leu Ala Trp Tyr Gln Gln Lys
145                 150                 155                 160

Pro Gly Gln Ser Pro Lys Leu Leu Ile Tyr Trp Ala Ser Thr Arg Glu
                165                 170                 175

Ser Gly Val Pro Asp Arg Phe Thr Gly Ser Gly Ser Gly Thr Asp Phe
            180                 185                 190

Thr Leu Ser Ile Ser Ser Val Glu Thr Glu Asp Leu Ala Val Tyr Tyr
        195                 200                 205

Cys Gln Gln Tyr Tyr Ser Tyr Pro Leu Thr Phe Gly Ala Gly Thr Lys
    210                 215                 220

Leu Val Leu Lys Arg
225

<210> SEQ ID NO 116
<211> LENGTH: 684
<212> TYPE: DNA
<213> ORGANISM: artificial
<220> FEATURE:
<223> OTHER INFORMATION: nucleotide sequence encoding anti-TAG72 diabody
      lacking a linker sequence and amino acid N-terminal to linker
      (designated AVP04-09)

<400> SEQUENCE: 116
caggtgcagc tgcagcagag cgatgcggaa ctggtgaaac cgggcgcgag cgtgaaaatt     60
agctgcaaag cgagcggcta ccctttacc gatcatgcga ttcattgggt gaaacagaat    120
ccggaacagg gcctggaatg gattggctat tttagcccgg gcaacgatga ttttaaatat    180
aacgaacgtt ttaaaggcaa agcgaccctg accgcggata aaagcagcag caccgcgtat    240
ctgcagctga acagcctgac cagcgaagat agcgcggtgt attttttgcac ccgtagcctg    300 aatatggcgt attgggggtca gggcacctcg gtcaccgtga gcgatatcgt gatgacccag    360
agcccgagca gcctgccggt gagcgtgggc gaaaaagtga ccctgagctg caaaagcagc    420
```

```
cagagcctgc tgtatagcgg caatcagaaa aactatctgg cgtggtatca gcagaaaccg      480
ggtcagagcc cgaaactgct gatttattgg gcgagcaccc gtgaaagcgg cgtgccggat      540
cgttttaccg gcagcggtag cggcaccgat tttaccctga gcattagcag cgtggaaacc      600
gaagatctgg cggtgtatta ttgccagcag tattatagct atccgctgac ctttggtgcg      660
ggcaccaaac tggtgctgaa acgt                                             684
```

<210> SEQ ID NO 117
<211> LENGTH: 228
<212> TYPE: PRT
<213> ORGANISM: artificial
<220> FEATURE:
<223> OTHER INFORMATION: amino acid sequence of AVP04-07 anti-TAG72
      diabody lacking a linker sequence (designated AVP04-69)

<400> SEQUENCE: 117

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Asp Ile Val Met Thr Gln Ser Pro Ser Ser Leu Pro Val Ser
        115                 120                 125

Val Gly Glu Lys Val Thr Leu Ser Cys Lys Ser Ser Gln Ser Leu Leu
    130                 135                 140

Tyr Ser Gly Asn Gln Lys Asn Tyr Leu Ala Trp Tyr Gln Gln Lys Pro
145                 150                 155                 160

Gly Gln Ser Pro Lys Leu Leu Ile Tyr Trp Ala Ser Thr Arg Glu Ser
                165                 170                 175

Gly Val Pro Asp Arg Phe Thr Gly Ser Gly Ser Gly Thr Asp Phe Thr
            180                 185                 190

Leu Ser Ile Ser Ser Val Glu Thr Glu Asp Leu Ala Val Tyr Tyr Cys
        195                 200                 205

Gln Gln Tyr Tyr Ser Tyr Pro Leu Thr Phe Gly Ala Gly Thr Lys Leu
    210                 215                 220

Val Leu Lys Arg
225
```

<210> SEQ ID NO 118
<211> LENGTH: 702
<212> TYPE: DNA
<213> ORGANISM: artificial
<220> FEATURE:
<223> OTHER INFORMATION: nucleotide sequence encoding modified AVP04-07
      anti-TAG72 diabody designated AVP04-50 comprising cysteine
      residues in FR1

<400> SEQUENCE: 118

```
caggtgcagc tgcagcagag cgatgcggaa ctggtgaaac cgggcgcgag cgtgaaaatt       60
```

-continued

```
agctgcaaag cgagcggcta tacctttacc gatcatgcga ttcattgggt gaaacagaat    120
ccggaacagg gcctggaatg gattggctat tttagcccgg gcaacgatga ttttaaatat    180
aacgaacgtt ttaaaggcaa agcgaccctg accgcggata aaagcagcag caccgcgtat    240
ctgcagctga acagcctgac cagcgaagat agcgcggtgt attttttgcac ccgtagcctg    300 aatatggcgt attggggtca gggcacctcg gtcaccgtga gcagcggtgg cggcggcagc    360
gatatcgtga tgacccagag ctgcagcagc tgcccggtga gcgtgggcga aaaagtgacc    420
ctgagctgca aaagcagcca gagcctgctg tatagcggca tcagaaaaa ctatctggcg    480 tggtatcagc agaaaccggg tcagagcccg aaactgctga tttattgggc gagcacccgt    540
gaaagcggcg tgccggatcg tttaccggc agcggtagcg gcaccgattt taccctgagc    600
attagcagcg tggaaaccga agatctggcg gtgtattatt gccagcagta ttatagctat    660
ccgctgacct ttggtgcggg caccaaactg gtgctgaaac gt    702
```

<210> SEQ ID NO 119
<211> LENGTH: 234
<212> TYPE: PRT
<213> ORGANISM: artificial
<220> FEATURE:
<223> OTHER INFORMATION: amino acid sequence of modified AVP04-07 anti-TAG72 diabody designated AVP04-50 comprising cysteine residues in FR1

<400> SEQUENCE: 119

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Gly Gly Gly Gly Ser Asp Ile Val Met Thr Gln Ser Cys
        115                 120                 125

Ser Ser Cys Pro Val Ser Val Gly Glu Lys Val Thr Leu Ser Cys Lys
    130                 135                 140

Ser Ser Gln Ser Leu Leu Tyr Ser Gly Asn Gln Lys Asn Tyr Leu Ala
145                 150                 155                 160

Trp Tyr Gln Gln Lys Pro Gly Gln Ser Pro Lys Leu Leu Ile Tyr Trp
                165                 170                 175

Ala Ser Thr Arg Glu Ser Gly Val Pro Asp Arg Phe Thr Gly Ser Gly
            180                 185                 190

Ser Gly Thr Asp Phe Thr Leu Ser Ile Ser Ser Val Glu Thr Glu Asp
        195                 200                 205

Leu Ala Val Tyr Tyr Cys Gln Gln Tyr Tyr Ser Tyr Pro Leu Thr Phe
    210                 215                 220

Gly Ala Gly Thr Lys Leu Val Leu Lys Arg
225                 230
```

<210> SEQ ID NO 120
<211> LENGTH: 687
<212> TYPE: DNA
<213> ORGANISM: artificial
<220> FEATURE:
<223> OTHER INFORMATION: nucleotide sequence encoding modified AVP04-69 anti-TAG72 diabody designated AVP04-50 comprising cysteine residues in FR1 and lacking a linker sequence

<400> SEQUENCE: 120

```
caggtgcagc tgcagcagag cgatgcggaa ctggtgaaac cgggcgcgag cgtgaaaatt      60
agctgcaaag cgagcggcta cctttacc gatcatgcga ttcattgggt gaaacagaat      120
ccggaacagg gcctggaatg gattggctat tttagcccgg caacgatga ttttaaatat      180
aacgaacgtt ttaaaggcaa agcgaccctg accgcggata aagcagcag caccgcgtat      240
ctgcagctga acagcctgac cagcgaagat agcgcggtgt attttttgcac ccgtagcctg      300
aatatggcgt attggggtca gggcacctcg gtcaccgtga gcagcgatat cgtgatgacc      360
cagagctgca gcagctgccc ggtgagcgtg ggcgaaaaag tgaccctgag ctgcaaaagc      420
agccagagcc tgctgtatag cggcaatcag aaaaactatc tggcgtggta tcagcagaaa      480
ccgggtcaga gcccgaaact gctgatttat tgggcgagca cccgtgaaag cggcgtgccg      540
gatcgtttta ccggcagcgg tagcggcacc gattttaccc tgagcattag cagcgtggaa      600
accgaagatc tggcggtgta ttattgccag cagtattata gctatccgct gacctttggt      660
gcgggcacca aactggtgct gaaacgt                                         687
```

<210> SEQ ID NO 121
<211> LENGTH: 229
<212> TYPE: PRT
<213> ORGANISM: artificial
<220> FEATURE:
<223> OTHER INFORMATION: amino acid sequence of modified modified AVP04-69 anti-TAG72 diabody designated AVP04-50 comprising cysteine residues in FR1 and lacking a linker sequence

<400> SEQUENCE: 121

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Phe Lys Tyr Asn Glu Arg Phe
    50                  55                  60

Lys Gly Lys Ala Thr Leu Thr Ala Asp Lys Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Asp Ile Val Met Thr Gln Ser Cys Ser Ser Cys Pro Val
        115                 120                 125

Ser Val Gly Glu Lys Val Thr Leu Ser Cys Lys Ser Ser Gln Ser Leu
    130                 135                 140

Leu Tyr Ser Gly Asn Gln Lys Asn Tyr Leu Ala Trp Tyr Gln Gln Lys
145                 150                 155                 160
```

```
Pro Gly Gln Ser Pro Lys Leu Leu Ile Tyr Trp Ala Ser Thr Arg Glu
            165                 170                 175

Ser Gly Val Pro Asp Arg Phe Thr Gly Ser Gly Ser Gly Thr Asp Phe
        180                 185                 190

Thr Leu Ser Ile Ser Ser Val Glu Thr Glu Asp Leu Ala Val Tyr Tyr
        195                 200                 205

Cys Gln Gln Tyr Tyr Ser Tyr Pro Leu Thr Phe Gly Ala Gly Thr Lys
    210                 215                 220

Leu Val Leu Lys Arg
225
```

<210> SEQ ID NO 122
<211> LENGTH: 684
<212> TYPE: DNA
<213> ORGANISM: artificial
<220> FEATURE:
<223> OTHER INFORMATION: nucleotide sequence encoding modified AVP04-09 anti-TAG72 diabody designated AVP04-50 comprising cysteine residues in FR1 and lacking a linker sequence and amino acid N-terminal to linker

<400> SEQUENCE: 122

```
caggtgcagc tgcagcagag cgatgcggaa ctggtgaaac cgggcgcgag cgtgaaaatt     60
agctgcaaag cgagcggcta ccctttacc gatcatgcga ttcattgggt gaaacagaat    120
ccggaacagg gcctggaatg gattggctat tttagcccgg caacgatga ttttaaatat     180
aacgaacgtt ttaaaggcaa agcgaccctg accgcggata aaagcagcag caccgcgtat    240
ctgcagctga acagcctgac cagcgaagat agcgcggtgt attttttgcac ccgtagcctg    300
aatatggcgt attggggtca gggcaccctcg gtcaccgtga gcgatatcgt gatgacccag    360
agctgcagca gctgcccggt gagcgtgggc gaaaaagtga ccctgagctg caaaagcagc    420
cagagcctgc tgtatagcgg caatcagaaa aactatctgg cgtggtatca gcagaaaccg    480
ggtcagagcc cgaaactgct gatttattgg gcgagcaccc gtgaaagcgg cgtgccggat    540
cgttttaccg gcagcggtag cggcaccgat tttaccctga gcattagcag cgtggaaacc    600
gaagatctgg cggtgtatta ttgccagcag tattatagct atccgctgac ctttggtgcg    660
ggcaccaaac tggtgctgaa acgt                                            684
```

<210> SEQ ID NO 123
<211> LENGTH: 228
<212> TYPE: PRT
<213> ORGANISM: artificial
<220> FEATURE:
<223> OTHER INFORMATION: amino acid sequence of modified modified AVP04-09 anti-TAG72 diabody designated AVP04-50 comprising cysteine residues in FR1 and lacking a linker sequence and amino acid N-terminal to linker

<400> SEQUENCE: 123

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80
```

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Asp Ile Val Met Thr Gln Ser Cys Ser Cys Pro Val Ser
        115                 120                 125

Val Gly Glu Lys Val Thr Leu Ser Cys Lys Ser Ser Gln Ser Leu Leu
    130                 135                 140

Tyr Ser Gly Asn Gln Lys Asn Tyr Leu Ala Trp Tyr Gln Gln Lys Pro
145                 150                 155                 160

Gly Gln Ser Pro Lys Leu Leu Ile Tyr Trp Ala Ser Thr Arg Glu Ser
                165                 170                 175

Gly Val Pro Asp Arg Phe Thr Gly Ser Gly Ser Gly Thr Asp Phe Thr
            180                 185                 190

Leu Ser Ile Ser Ser Val Glu Thr Glu Asp Leu Ala Val Tyr Tyr Cys
            195                 200                 205

Gln Gln Tyr Tyr Ser Tyr Pro Leu Thr Phe Gly Ala Gly Thr Lys Leu
    210                 215                 220

Val Leu Lys Arg
225

<210> SEQ ID NO 124
<211> LENGTH: 702
<212> TYPE: DNA
<213> ORGANISM: artificial
<220> FEATURE:
<223> OTHER INFORMATION: nucleotide sequence encoding modified AVP04-07
      anti-TAG72 diabody with a N-terminal serine residue

<400> SEQUENCE: 124
agcgtgcagc tgcagcagag cgatgcggaa ctggtgaaac cgggcgcgag cgtgaaaatt    60
agctgcaaag cgagcggcta cctttacc gatcatgcga ttcattgggt gaaacagaat    120
ccggaacagg gcctggaatg gattggctat tttagcccgg caacgatga ttttaaatat    180
aacgaacgtt taaaggcaa agcgaccctg accgcggata aaagcagcag caccgcgtat    240
ctgcagctga acagcctgac cagcgaagat agcgcggtgt attttttgcac ccgtagcctg    300
aatatggcgt attggggtca gggcacctcg gtcaccgtga gcagcggtgg cggcggcagc    360
gatatcgtga tgacccagag cccgagcagc ctgccggtga gcgtgggcga aaaagtgacc    420
ctgagctgca aaagcagcca gagcctgctg tatagcggca atcagaaaaa ctatctggcg    480
tggtatcagc agaaaccggg tcagagcccg aaactgctga tttattgggc gagcacccgt    540
gaaagcggcg tgccggatcg tttttaccggc agcggtagcg gcaccgattt tacgctgagc    600
attagcagcg tggaaaccga agatctggcg gtgtattatt gccagcagta ttatagctat    660
ccgctgacct tggtgcggg caccaaactg gtgctgaaac gt                         702

<210> SEQ ID NO 125
<211> LENGTH: 234
<212> TYPE: PRT
<213> ORGANISM: artificial
<220> FEATURE:
<223> OTHER INFORMATION: amino acid sequence of modified AVP04-07
      anti-TAG72 diabody with a N-terminal serine residue

<400> SEQUENCE: 125

Ser Val Gln Leu Gln Gln Ser Asp Ala Glu Leu Val Lys Pro Gly Ala
1               5                   10                  15

```
Ser Val Lys Ile Ser Cys Lys Ala Ser Gly Tyr Thr Phe Thr Asp His
             20                  25                  30

Ala Ile His Trp Val Lys Gln Asn Pro Glu Gln Gly Leu Glu Trp Ile
         35                  40                  45

Gly Tyr Phe Ser Pro Gly Asn Asp Asp Phe Lys Tyr Asn Glu Arg Phe
 50                  55                  60

Lys Gly Lys Ala Thr Leu Thr Ala Asp Lys Ser Ser Ser Thr Ala Tyr
 65                  70                  75                  80

Leu Gln Leu Asn Ser Leu Thr Ser Glu Asp Ser Ala Val Tyr Phe Cys
             85                  90                  95

Thr Arg Ser Leu Asn Met Ala Tyr Trp Gly Gln Gly Ser Val Thr
            100                 105                 110

Val Ser Ser Gly Gly Gly Gly Ser Asp Ile Val Met Thr Gln Ser Pro
            115                 120                 125

Ser Ser Leu Pro Val Ser Val Gly Glu Lys Val Thr Leu Ser Cys Lys
130                 135                 140

Ser Ser Gln Ser Leu Leu Tyr Ser Gly Asn Gln Lys Asn Tyr Leu Ala
145                 150                 155                 160

Trp Tyr Gln Gln Lys Pro Gly Gln Ser Pro Lys Leu Leu Ile Tyr Trp
                165                 170                 175

Ala Ser Thr Arg Glu Ser Gly Val Pro Asp Arg Phe Thr Gly Ser Gly
            180                 185                 190

Ser Gly Thr Asp Phe Thr Leu Ser Ile Ser Ser Val Glu Thr Glu Asp
            195                 200                 205

Leu Ala Val Tyr Tyr Cys Gln Gln Tyr Tyr Ser Tyr Pro Leu Thr Phe
            210                 215                 220

Gly Ala Gly Thr Lys Leu Val Leu Lys Arg
225                 230

<210> SEQ ID NO 126
<211> LENGTH: 687
<212> TYPE: DNA
<213> ORGANISM: artificial
<220> FEATURE:
<223> OTHER INFORMATION: nucleotide sequence encoding modified AVP04-69
      anti-TAG72 diabody lacking a linker sequence and comprising a
      N-terminal serine residue

<400> SEQUENCE: 126
agcgtgcagc tgcagcagag cgatgcggaa ctggtgaaac cgggcgcgag cgtgaaaatt      60
agctgcaaag cgagcggcta cctttacc gatcatgcga ttcattgggt gaaacagaat     120
ccggaacagg gcctggaatg gattggctat tttagcccgg gcaacgatga ttttaaatat     180
aacgaacgtt ttaaaggcaa agcgaccctg accgcggata aaagcagcag caccgcgtat     240
ctgcagctga acagcctgac cagcgaagat agcgcggtgt attttgcac ccgtagcctg     300 aatatggcgt attgggtca gggcaccctcg gtcaccgtga gcagcgatat cgtgatgacc     360
cagagcccga gcagcctgcc ggtgagcgtg ggcgaaaaag tgaccctgag ctgcaaaagc     420
agccagagcc tgctgtatag cggcaatcag aaaaactatc tggcgtggta tcagcagaaa     480
ccgggtcaga gcccgaaact gctgatttat tgggcgagca cccgtgaaag cggcgtgccg     540 gatcgttta ccggcagcgg tagcggcacc gattttaccc tgagcattag cagcgtggaa     600
accgaagatc tggcggtgta ttattgccag cagtattata gctatccgct gacctttggt     660
gcgggcacca aactggtgct gaaacgt                                          687
```

<210> SEQ ID NO 127
<211> LENGTH: 229
<212> TYPE: PRT
<213> ORGANISM: artificial
<220> FEATURE:
<223> OTHER INFORMATION: amino acid sequence of modified AVP04-69 anti-TAG72 diabody lacking a linker sequence and comprising a N-terminal serine residue

<400> SEQUENCE: 127

```
Ser Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Asp Ile Val Met Thr Gln Ser Pro Ser Ser Leu Pro Val
        115                 120                 125

Ser Val Gly Glu Lys Val Thr Leu Ser Cys Lys Ser Ser Gln Ser Leu
    130                 135                 140

Leu Tyr Ser Gly Asn Gln Lys Asn Tyr Leu Ala Trp Tyr Gln Gln Lys
145                 150                 155                 160

Pro Gly Gln Ser Pro Lys Leu Leu Ile Tyr Trp Ala Ser Thr Arg Glu
                165                 170                 175

Ser Gly Val Pro Asp Arg Phe Thr Gly Ser Gly Ser Gly Thr Asp Phe
            180                 185                 190

Thr Leu Ser Ile Ser Ser Val Glu Thr Glu Asp Leu Ala Val Tyr Tyr
        195                 200                 205

Cys Gln Gln Tyr Tyr Ser Tyr Pro Leu Thr Phe Gly Ala Gly Thr Lys
    210                 215                 220

Leu Val Leu Lys Arg
225
```

<210> SEQ ID NO 128
<211> LENGTH: 684
<212> TYPE: DNA
<213> ORGANISM: artificial
<220> FEATURE:
<223> OTHER INFORMATION: nucleotide sequence encoding modified AVP04-09 anti-TAG72 diabody lacking a linker sequence and amino acid N-terminal to linker and comprising a N terminal serine residue

<400> SEQUENCE: 128

```
agcgtgcagc tgcagcagag cgatgcggaa ctggtgaaac cgggcgcgag cgtgaaaatt      60
agctgcaaag cgagcggcta cctttacc gatcatgcga ttcattgggt gaaacagaat     120
ccggaacagg gcctggaatg gattggctat tttagcccgg caacgatga ttttaaatat     180 aacgaacgtt ttaaaggcaa agcgacccctg accgcggata aaagcagcag caccgcgtat     240
ctgcagctga acagcctgac cagcgaagat agcgcggtgt attttgcac ccgtagcctg     300
```

```
aatatggcgt attggggtca gggcacctcg gtcaccgtga gcgatatcgt gatgacccag    360
agcccgagca gcctgccggt gagcgtgggc gaaaaagtga ccctgagctg caaaagcagc    420
cagagcctgc tgtatagcgg caatcagaaa aactatctgg cgtggtatca gcagaaaccg    480
ggtcagagcc cgaaactgct gatttattgg gcgagcaccc gtgaaagcgg cgtgccggat    540
cgttttaccg gcagcggtag cggcaccgat tttaccctga gcattagcag cgtggaaacc    600
gaagatctgg cggtgtatta ttgccagcag tattatagct atccgctgac ctttggtgcg    660
ggcaccaaac tggtgctgaa acgt                                          684
```

<210> SEQ ID NO 129
<211> LENGTH: 228
<212> TYPE: PRT
<213> ORGANISM: artificial
<220> FEATURE:
<223> OTHER INFORMATION: amino acid sequence of modified AVP04-09
      anti-TAG72 diabody lacking a linker sequence and amino acid
      N-terminal to linker and comprising a N terminal serine residue

<400> SEQUENCE: 129

```
Ser Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Asp Ile Val Met Thr Gln Ser Pro Ser Ser Leu Pro Val Ser
        115                 120                 125

Val Gly Glu Lys Val Thr Leu Ser Cys Lys Ser Ser Gln Ser Leu Leu
    130                 135                 140

Tyr Ser Gly Asn Gln Lys Asn Tyr Leu Ala Trp Tyr Gln Gln Lys Pro
145                 150                 155                 160

Gly Gln Ser Pro Lys Leu Leu Ile Tyr Trp Ala Ser Thr Arg Glu Ser
                165                 170                 175

Gly Val Pro Asp Arg Phe Thr Gly Ser Gly Ser Gly Thr Asp Phe Thr
            180                 185                 190

Leu Ser Ile Ser Ser Val Glu Thr Glu Asp Leu Ala Val Tyr Tyr Cys
        195                 200                 205

Gln Gln Tyr Tyr Ser Tyr Pro Leu Thr Phe Gly Ala Gly Thr Lys Leu
    210                 215                 220

Val Leu Lys Arg
225
```

<210> SEQ ID NO 130
<211> LENGTH: 687
<212> TYPE: DNA
<213> ORGANISM: artificial
<220> FEATURE:
<223> OTHER INFORMATION: nucleotide sequence encoding modified AVP04-50
      anti-TAG72 diabody comprising cysteine residues in FR1 and a N-terminal serine residue and lacking a linker sequence

<400> SEQUENCE: 130

```
agcgtgcagc tgcagcagag cgatgcggaa ctggtgaaac cgggcgcgag cgtgaaaatt      60
agctgcaaag cgagcggcta cctttacc gatcatgcga ttcattgggt gaaacagaat       120
ccggaacagg gcctggaatg gattggctat tttagcccgg caacgatga ttttaaatat      180
aacgaacgtt ttaaaggcaa agcgaccctg accgcggata aaagcagcag caccgcgtat      240
ctgcagctga acagcctgac cagcgaagat agcgcggtgt attttttgcac ccgtagcctg      300
aatatggcgt attggggtca gggcacctcg gtcaccgtga gcagcgatat cgtgatgacc      360
cagagctgca gcagctgccc ggtgagcgtg ggcgaaaaag tgaccctgag ctgcaaaagc      420
agccagagcc tgctgtatag cggcaatcag aaaaactatc tggcgtggta tcagcagaaa      480
ccgggtcaga gcccgaaact gctgatttat tgggcgagca cccgtgaaag cggcgtgccg      540
gatcgtttta ccggcagcgg tagcggcacc gattttaccc tgagcattag cagcgtggaa      600
accgaagatc tggcggtgta ttattgccag cagtattata gctatccgct gacctttggt      660
gcgggcacca aactggtgct gaaacgt                                          687
```

<210> SEQ ID NO 131
<211> LENGTH: 229
<212> TYPE: PRT
<213> ORGANISM: artificial
<220> FEATURE:
<223> OTHER INFORMATION: amino acid sequence of modified AVP04-50
      anti-TAG72 diabody comprising cysteine residues in FR1 and a
      N-terminal serine residue and lacking a linker sequence

<400> SEQUENCE: 131

```
Ser Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
                20                  25                  30

Ala Ile His Trp Val Lys Gln Asn Pro Glu Gln Gly Leu Glu Trp Ile
            35                  40                  45

Gly Tyr Phe Ser Pro Gly Asn Asp Asp Phe Lys Tyr Asn Glu Arg Phe
        50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser Asp Ile Val Met Thr Gln Ser Cys Ser Ser Cys Pro Val
        115                 120                 125

Ser Val Gly Glu Lys Val Thr Leu Ser Cys Lys Ser Ser Gln Ser Leu
    130                 135                 140

Leu Tyr Ser Gly Asn Gln Lys Asn Tyr Leu Ala Trp Tyr Gln Gln Lys
145                 150                 155                 160

Pro Gly Gln Ser Pro Lys Leu Leu Ile Tyr Trp Ala Ser Thr Arg Glu
                165                 170                 175

Ser Gly Val Pro Asp Arg Phe Thr Gly Ser Gly Ser Gly Thr Asp Phe
            180                 185                 190

Thr Leu Ser Ile Ser Ser Val Glu Thr Glu Asp Leu Ala Val Tyr Tyr
        195                 200                 205
```

```
Cys Gln Gln Tyr Tyr Ser Tyr Pro Leu Thr Phe Gly Ala Gly Thr Lys
    210                 215                 220

Leu Val Leu Lys Arg
225
```

<210> SEQ ID NO 132
<211> LENGTH: 684
<212> TYPE: DNA
<213> ORGANISM: artificial
<220> FEATURE:
<223> OTHER INFORMATION: nucleotide sequence encoding modified AVP04-50 anti-TAG72 diabody comprising cysteine residues in FR1 and a N-terminal serine residue and lacking a linker sequence and amino acid N-terminal to linker

<400> SEQUENCE: 132

```
agcgtgcagc tgcagcagag cgatgcggaa ctggtgaaac cgggcgcgag cgtgaaaatt    60
agctgcaaag cgagcggcta cctttacc gatcatgcga ttcattgggt gaaacagaat    120
ccggaacagg gcctggaatg gattggctat tttagcccgg caacgatga ttttaaatat    180
aacgaacgtt ttaaaggcaa agcgaccctg accgcggata aaagcagcag caccgcgtat    240
ctgcagctga acagcctgac cagcgaagat agcgcggtgt atttttgcac ccgtagcctg    300
aatatggcgt attggggtca gggcaccctcg gtcaccgtga gcgatatcgt gatgacccag    360
agctgcagca gctgcccggt gagcgtgggc gaaaaagtga ccctgagctg caaaagcagc    420
cagagcctgc tgtatagcgg caatcagaaa aactatctgg cgtggtatca gcagaaaccg    480
ggtcagagcc cgaaactgct gatttattgg gcgagcaccc gtgaaagcgg cgtgccggat    540
cgttttaccg gcagcggtag cggcaccgat tttaccctga gcattagcag cgtggaaacc    600
gaagatctgg cggtgtatta ttgccagcag tattatagct atccgctgac ctttggtgcg    660
ggcaccaaac tggtgctgaa acgt                                          684
```

<210> SEQ ID NO 133
<211> LENGTH: 228
<212> TYPE: PRT
<213> ORGANISM: artificial
<220> FEATURE:
<223> OTHER INFORMATION: amino acid sequence of modified AVP04-50 anti-TAG72 diabody comprising cysteine residues in FR1 and a N-terminal serine residue and lacking a linker sequence and amino acid N-terminal to linker

<400> SEQUENCE: 133

```
Ser Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Leu Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Asp Ile Val Met Thr Gln Ser Cys Ser Ser Cys Pro Val Ser
        115                 120                 125
```

```
Val Gly Glu Lys Val Thr Leu Ser Cys Lys Ser Ser Gln Ser Leu Leu
    130                 135                 140

Tyr Ser Gly Asn Gln Lys Asn Tyr Leu Ala Trp Tyr Gln Gln Lys Pro
145                 150                 155                 160

Gly Gln Ser Pro Lys Leu Leu Ile Tyr Trp Ala Ser Thr Arg Glu Ser
                165                 170                 175

Gly Val Pro Asp Arg Phe Thr Gly Ser Gly Ser Gly Thr Asp Phe Thr
            180                 185                 190

Leu Ser Ile Ser Ser Val Glu Thr Glu Asp Leu Ala Val Tyr Tyr Cys
        195                 200                 205

Gln Gln Tyr Tyr Ser Tyr Pro Leu Thr Phe Gly Ala Gly Thr Lys Leu
    210                 215                 220

Val Leu Lys Arg
225

<210> SEQ ID NO 134
<211> LENGTH: 5
<212> TYPE: PRT
<213> ORGANISM: artificial
<220> FEATURE:
<223> OTHER INFORMATION: Linker

<400> SEQUENCE: 134

Gly Gly Gly Gly Ser
1               5

<210> SEQ ID NO 135
<211> LENGTH: 4
<212> TYPE: PRT
<213> ORGANISM: artificial
<220> FEATURE:
<223> OTHER INFORMATION: Linker

<400> SEQUENCE: 135

Gly Gly Gly Gly
1
```